United States Patent
Ericsson et al.

(10) Patent No.: US 12,071,440 B2
(45) Date of Patent: Aug. 27, 2024

(54) PYRROLOPYRROLE COMPOSITIONS AS PYRUVATE KINASE (PKR) ACTIVATORS

(71) Applicant: Novo Nordisk Health Care AG, Zurich (CH)

(72) Inventors: Anna Ericsson, Shrewsbury, MA (US); Neal Green, Newton, MA (US); Gary Gustafson, Ridgefield, CT (US); Bingsong Han, Westwood, MA (US); David R. Lancia, Jr., Boston, MA (US); Lorna Mitchell, West Beach (AU); David Richard, Littleton, MA (US); Tatiana Shelekhin, Ridgefield, CT (US); Chase C. Smith, Rutland, MA (US); Zhongguo Wang, Lexington, MA (US); Xiaozhang Zheng, Lexington, MA (US)

(73) Assignee: Novo Nordisk Health Care AG, Zurich (CH)

( * ) Notice: Subject to any disclaimer, the term of this patent is extended or adjusted under 35 U.S.C. 154(b) by 0 days.

(21) Appl. No.: 18/124,071

(22) Filed: Mar. 21, 2023

(65) Prior Publication Data

US 2024/0083901 A1    Mar. 14, 2024

Related U.S. Application Data

(63) Continuation of application No. 17/239,364, filed on Apr. 23, 2021, now Pat. No. 11,649,242, which is a
(Continued)

(51) Int. Cl.
*A61K 31/407* (2006.01)
*A61K 9/00* (2006.01)
(Continued)

(52) U.S. Cl.
CPC ........... *C07D 487/04* (2013.01); *A61K 9/0053* (2013.01); *A61K 31/407* (2013.01); *A61P 7/00* (2018.01); *C07D 519/00* (2013.01)

(58) Field of Classification Search
CPC .. C07D 487/04; C07D 519/00; A61K 9/0053; A61K 31/407; A61P 7/00
(Continued)

(56) References Cited

U.S. PATENT DOCUMENTS

| 4,602,093 A | 7/1986 | Baldwin et al. |
| 4,918,073 A | 4/1990 | Ruger et al. |

(Continued)

FOREIGN PATENT DOCUMENTS

| CN | 101812063 A | 8/2010 |
| CN | 102206217 A | 10/2011 |

(Continued)

OTHER PUBLICATIONS

Abbady M.A., et al., Synthesis and biological activity of some new 4-(2-pyrazolin-3-yl)-, 4-(2-isoxazolin-e-yl)- and 4-(1,2,5,6-tetrahydro-2-thioxopyrimidin-4-yl)phenyl aminophenyl sulfides and sulfones., *Egyptian Journal of Pharmaceutical Sciences*, vol. 27, No. 1-4, (1986), Abstract Only.

(Continued)

*Primary Examiner* — Taylor V Oh
(74) *Attorney, Agent, or Firm* — Jianjie Hu

(57) ABSTRACT

The disclosure relates to modulating pyruvate kinase and provides novel chemical compounds useful as activators of PKR, as well as various uses of these compounds. PKR activating compounds are useful in the treatment of diseases and disorders associated with PKR and/or PKM2, such as pyruvate kinase deficiency (PKD), sickle cell disease (SCD), and thalassemia.

4 Claims, 1 Drawing Sheet

Related U.S. Application Data continuation of application No. 16/496,279, filed as application No. PCT/US2018/023405 on Mar. 20, 2018, now Pat. No. 11,014,927.

(60) Provisional application No. 62/473,751, filed on Mar. 20, 2017.

(51) Int. Cl.
*A61P 7/00* (2006.01)
*C07D 487/04* (2006.01)
*C07D 519/00* (2006.01)

(58) Field of Classification Search
USPC .......................................................... 514/410
See application file for complete search history.

(56) References Cited

U.S. PATENT DOCUMENTS

| | | |
|---|---|---|
| 5,030,631 A | 7/1991 | Bauer |
| 5,037,467 A | 8/1991 | Cho et al. |
| 5,059,605 A | 10/1991 | Clough et al. |
| 5,089,621 A | 2/1992 | Kim et al. |
| 5,091,384 A | 2/1992 | Kim et al. |
| 5,180,719 A | 1/1993 | White et al. |
| 5,250,544 A | 10/1993 | Lavielle et al. |
| 5,336,772 A | 8/1994 | Saiki et al. |
| 5,480,899 A | 1/1996 | Yano et al. |
| 5,672,601 A | 9/1997 | Cignarella |
| 5,714,625 A | 2/1998 | Hada et al. |
| 5,747,502 A | 5/1998 | Hanaoka et al. |
| 5,962,703 A | 10/1999 | Moszner et al. |
| 6,214,879 B1 | 4/2001 | Abraham et al. |
| 6,534,501 B2 | 3/2003 | Abraham et al. |
| 6,710,052 B2 | 3/2004 | Pease et al. |
| 6,878,715 B1 | 4/2005 | Klein et al. |
| 7,138,401 B2 | 11/2006 | Kasibhatla et al. |
| 7,160,885 B2 | 1/2007 | Currie et al. |
| 7,875,603 B2 | 1/2011 | Rathinavelu et al. |
| 8,501,953 B2 | 8/2013 | Salituro et al. |
| 8,552,050 B2 | 10/2013 | Cantley et al. |
| 8,692,001 B2 | 4/2014 | Becker et al. |
| 8,742,119 B2 | 6/2014 | Salituro et al. |
| 8,785,450 B2 | 7/2014 | Salituro et al. |
| 8,841,305 B2 | 9/2014 | Thomas et al. |
| 8,877,791 B2 | 11/2014 | Cantley et al. |
| 8,889,667 B2 | 11/2014 | Salituro et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,108,921 B2 | 8/2015 | Cianchetta et al. |
| 9,181,231 B2 | 11/2015 | Su |
| 9,221,792 B2 | 12/2015 | Salituro et al. |
| 9,248,199 B2 | 2/2016 | Metcalf |
| 9,328,077 B2 | 5/2016 | Salituro et al. |
| 9,394,257 B2 | 7/2016 | Ho et al. |
| 9,422,279 B2 | 8/2016 | Metcalf et al. |
| 9,458,132 B2 | 10/2016 | Cianchetta et al. |
| 9,458,139 B2 | 10/2016 | Xu et al. |
| 9,604,999 B2 | 3/2017 | Harris et al. |
| 9,708,267 B2 | 7/2017 | Boxer et al. |
| 9,744,145 B1 | 8/2017 | Liu et al. |
| 9,776,960 B2 | 10/2017 | Xu et al. |
| 9,802,900 B2 | 10/2017 | Li et al. |
| 9,957,250 B2 | 5/2018 | Metcalf et al. |
| 9,981,939 B2 | 5/2018 | Metcalf et al. |
| 10,004,725 B2 | 6/2018 | Dufu et al. |
| 10,017,491 B2 | 7/2018 | Metcalf et al. |
| 10,034,879 B2 | 7/2018 | Metcalf et al. |
| 10,077,249 B2 | 9/2018 | Li et al. |
| 10,100,040 B2 | 10/2018 | Li et al. |
| 10,100,043 B2 | 10/2018 | Metcalf et al. |
| 10,208,052 B1 | 2/2019 | Zheng et al. |
| 10,266,551 B2 | 4/2019 | Li et al. |
| 10,315,991 B2 | 6/2019 | Xu et al. |
| 10,377,741 B2 | 8/2019 | Metcalf et al. |
| 10,435,393 B2 | 10/2019 | Xu et al. |
| 10,450,269 B1 | 10/2019 | Xu et al. |
| 10,472,371 B2 | 11/2019 | Zheng et al. |
| 10,493,035 B2 | 12/2019 | Dalziel et al. |
| 10,577,345 B2 | 3/2020 | Li et al. |
| 10,675,274 B2 | 6/2020 | Ericsson et al. |
| 10,683,285 B2 | 6/2020 | Li |
| 10,695,330 B2 | 6/2020 | Li et al. |
| 10,836,771 B2 | 11/2020 | Zheng et al. |
| 11,014,927 B2 | 5/2021 | Ericsson et al. |
| 11,071,725 B2 | 7/2021 | Ericsson et al. |
| 11,396,513 B2 | 7/2022 | Zheng et al. |
| 11,649,242 B2 | 5/2023 | Ericsson et al. |
| 11,844,787 B2 | 12/2023 | Ericsson et al. |
| 2004/0077648 A1 | 4/2004 | Timmer et al. |
| 2004/0102458 A1 | 5/2004 | Chiosis et al. |
| 2005/0002861 A1 | 1/2005 | Krause et al. |
| 2005/0049263 A1 | 3/2005 | Kasibhatla et al. |
| 2005/0059663 A1 | 3/2005 | Martin et al. |
| 2005/0181305 A1 | 8/2005 | Shibuya |
| 2005/0256103 A1 | 11/2005 | Suzuki et al. |
| 2006/0074121 A1 | 4/2006 | Chen et al. |
| 2006/0211737 A1 | 9/2006 | Huang et al. |
| 2007/0015752 A1 | 1/2007 | Hangauer, Jr. |
| 2007/0270433 A1 | 11/2007 | Brinkman et al. |
| 2008/0058315 A1 | 3/2008 | Cai et al. |
| 2008/0184495 A1 | 8/2008 | Brun et al. |
| 2008/0253965 A1 | 10/2008 | Chiosis et al. |
| 2008/0269234 A1 | 10/2008 | Gandhi et al. |
| 2009/0042966 A1 | 2/2009 | Coleman et al. |
| 2009/0163545 A1 | 6/2009 | Goldfarb |
| 2009/0291921 A1 | 11/2009 | Jabri et al. |
| 2010/0029575 A1 | 2/2010 | Junien et al. |
| 2010/0120863 A1 | 5/2010 | Biftu et al. |
| 2010/0144594 A1 | 6/2010 | Zoller et al. |
| 2010/0144722 A1 | 6/2010 | Alexander et al. |
| 2010/0152157 A1 | 6/2010 | Puech et al. |
| 2010/0179154 A1 | 7/2010 | Almario Garcia et al. |
| 2010/0216774 A1 | 8/2010 | Bender et al. |
| 2010/0324030 A1 | 12/2010 | Dale et al. |
| 2011/0059089 A1 | 3/2011 | Swagemakers et al. |
| 2011/0085969 A1 | 4/2011 | Rollo et al. |
| 2011/0104054 A1 | 5/2011 | Chiosis et al. |
| 2012/0134979 A1 | 5/2012 | Xia et al. |
| 2012/0252818 A1 | 10/2012 | Chiosis et al. |
| 2013/0109684 A1 | 5/2013 | Blagg et al. |
| 2013/0116430 A1 | 5/2013 | Fujiwara et al. |
| 2013/0155489 A1 | 6/2013 | Kato et al. |
| 2013/0190315 A1 | 7/2013 | Metcalf et al. |
| 2013/0190316 A1 | 7/2013 | Metcalf et al. |
| 2014/0228360 A1 | 8/2014 | Duncan et al. |
| 2014/0242602 A1 | 8/2014 | Chiosis et al. |
| 2015/0246025 A1 | 9/2015 | Desai et al. |
| 2016/0106728 A1 | 4/2016 | Shen et al. |
| 2016/0200681 A1 | 7/2016 | Yu et al. |
| 2017/0121338 A1 | 5/2017 | Zhang et al. |
| 2017/0216434 A1 | 8/2017 | Hines et al. |
| 2017/0217964 A1 | 8/2017 | Li |
| 2018/0215765 A1 | 8/2018 | Di Giorgio et al. |
| 2018/0282369 A1 | 10/2018 | Desai et al. |
| 2019/0218221 A1 | 7/2019 | Zheng et al. |
| 2020/0031839 A1 | 1/2020 | Zheng et al. |
| 2020/0069643 A1 | 3/2020 | Ericsson |
| 2020/0085798 A1 | 3/2020 | Ericsson |
| 2020/0087309 A1 | 3/2020 | Lancia, Jr. |
| 2020/0129485 A1 | 4/2020 | Ericsson et al. |
| 2020/0253939 A1 | 8/2020 | Ericsson et al. |
| 2021/0017184 A1 | 1/2021 | Zheng et al. |
| 2021/0246143 A1 | 8/2021 | Ericsson et al. |
| 2022/0031671 A1 | 2/2022 | Ericsson et al. |
| 2022/0304987 A1 | 9/2022 | Ericsson et al. |
| 2022/0378755 A1 | 12/2022 | Luke et al. |
| 2022/0378756 A1 | 12/2022 | Ericsson et al. |

FOREIGN PATENT DOCUMENTS

| | | |
|---|---|---|
| CN | 102952139 A | 3/2013 |
| CN | 103570722 A | 2/2014 |

(56) References Cited

FOREIGN PATENT DOCUMENTS

| | | |
|---|---|---|
| CN | 104736534 A | 6/2015 |
| CN | 105037367 A | 11/2015 |
| CN | 105085528 A | 11/2015 |
| CN | 105153119 A | 12/2015 |
| CN | 105254628 A | 1/2016 |
| CN | 105294694 A | 2/2016 |
| CN | 105348286 A | 2/2016 |
| CN | 106928222 A | 7/2017 |
| CN | 109912610 A | 6/2019 |
| DE | 102008010661 A1 | 9/2009 |
| EP | 0007529 A1 | 2/1980 |
| EP | 0036711 A2 | 9/1981 |
| EP | 0264883 A2 | 4/1988 |
| EP | 0273534 A2 | 7/1988 |
| EP | 0338372 A2 | 10/1988 |
| EP | 0363212 A2 | 4/1990 |
| EP | 0378255 A2 | 7/1990 |
| EP | 0424850 A1 | 5/1991 |
| EP | 0424851 A1 | 5/1991 |
| EP | 0424852 A1 | 5/1991 |
| EP | 0486022 A2 | 5/1992 |
| EP | 0520277 A2 | 12/1992 |
| EP | 0590415 A2 | 4/1994 |
| EP | 0737670 A1 | 10/1996 |
| EP | 1096310 A2 | 5/2001 |
| EP | 1099692 A1 | 5/2001 |
| EP | 1249233 A1 | 10/2002 |
| EP | 1952800 A2 | 8/2008 |
| EP | 3141542 A1 | 3/2017 |
| EP | 2797416 B1 | 8/2017 |
| EP | 3483164 A1 | 5/2019 |
| IN | 1809/MUM/2013 | 5/2013 |
| IN | 2013/MU01809 | 3/2015 |
| JP | S 61 200544 | 9/1986 |
| JP | 3 13040 B2 | 2/1991 |
| JP | 3 275666 | 12/1991 |
| JP | 04 054181 A | 2/1992 |
| JP | 05125050 A | 5/1993 |
| JP | 05 196976 | 8/1993 |
| JP | 7 164400 | 6/1995 |
| JP | 1 110376 | 1/1999 |
| JP | 2001261653 A | 9/2001 |
| JP | 2003514673 | 4/2003 |
| JP | 2004175674 A | 6/2004 |
| JP | 2007246885 A | 9/2007 |
| JP | 2007328090 A | 12/2007 |
| JP | 2008031064 A | 2/2008 |
| JP | 2008063256 A | 3/2008 |
| JP | 2009149707 A | 7/2009 |
| JP | 2009212473 A | 9/2009 |
| JP | 2010192782 A | 9/2010 |
| JP | 2011246649 A | 12/2011 |
| JP | 2012188474 A | 10/2012 |
| JP | 2012188475 A | 10/2012 |
| JP | 2013171968 A | 9/2013 |
| KR | 20110096442 A | 8/2011 |
| LB | 11379 | 7/2018 |
| RU | 2517693 C2 | 4/2011 |
| RU | 2472794 C1 | 11/2012 |
| WO | WO 1993/011106 | 6/1993 |
| WO | WO 1993/022298 A1 | 11/1993 |
| WO | WO 1995/019353 A1 | 7/1995 |
| WO | WO 1998/038239 | 9/1998 |
| WO | WO 1998/050364 A1 | 11/1998 |
| WO | WO 1999/001442 A1 | 1/1999 |
| WO | WO 1999/002493 A1 | 1/1999 |
| WO | WO 1999/047489 A1 | 9/1999 |
| WO | WO 1999/047516 A1 | 9/1999 |
| WO | WO 1999/048461 A2 | 9/1999 |
| WO | WO 1999/048490 A1 | 9/1999 |
| WO | WO 1999/065895 A1 | 12/1999 |
| WO | WO 1999/065901 | 12/1999 |
| WO | WO 2000/004023 A1 | 1/2000 |
| WO | WO 2000/021951 A1 | 4/2000 |
| WO | WO 2000/053591 A1 | 9/2000 |
| WO | WO 2001/010842 A2 | 2/2001 |
| WO | WO 2001/032764 | 5/2001 |
| WO | WO 2001/043744 A1 | 6/2001 |
| WO | WO 2001/053288 A2 | 7/2001 |
| WO | WO 2001/057037 A2 | 8/2001 |
| WO | WO 2001/085728 A2 | 11/2001 |
| WO | WO 2002/030358 | 4/2002 |
| WO | WO 2002/034754 A1 | 5/2002 |
| WO | WO 2002/060902 A1 | 8/2002 |
| WO | WO 2002/076989 A1 | 10/2002 |
| WO | WO 2002/095063 A1 | 11/2002 |
| WO | WO 2003/015769 A1 | 2/2003 |
| WO | WO 2003/037860 A2 | 5/2003 |
| WO | WO 2003/063794 | 8/2003 |
| WO | WO 2003/067332 A2 | 8/2003 |
| WO | WO 2003/084948 A1 | 10/2003 |
| WO | WO 2004/002490 A2 | 1/2004 |
| WO | WO 2004/007770 A2 | 1/2004 |
| WO | WO 2004/009600 A1 | 1/2004 |
| WO | WO 2004/013144 A1 | 2/2004 |
| WO | WO 2004/014374 A1 | 2/2004 |
| WO | WO 2004/014382 | 2/2004 |
| WO | WO 2004/024676 A1 | 3/2004 |
| WO | WO 2004/080457 A1 | 9/2004 |
| WO | WO 2004/089470 A1 | 10/2004 |
| WO | WO 2004/089947 A2 | 10/2004 |
| WO | WO 2004/104000 A1 | 12/2004 |
| WO | WO 2005/000098 A2 | 1/2005 |
| WO | WO 2005/002577 A1 | 1/2005 |
| WO | WO 2005/009965 A1 | 2/2005 |
| WO | WO 2005/011653 A2 | 2/2005 |
| WO | WO 2005/011656 A2 | 2/2005 |
| WO | WO 2005/016915 A1 | 2/2005 |
| WO | WO 2005/023761 A2 | 3/2005 |
| WO | WO 2005/049570 | 6/2005 |
| WO | WO 2005/058869 | 6/2005 |
| WO | WO 2005/058870 | 6/2005 |
| WO | WO 2005/058871 | 6/2005 |
| WO | WO 2005/058873 | 6/2005 |
| WO | WO 2005/058874 | 6/2005 |
| WO | WO 2005/084667 A1 | 9/2005 |
| WO | WO 2005/094251 A2 | 10/2005 |
| WO | WO 2005/094834 A1 | 10/2005 |
| WO | WO 2005/103015 A1 | 11/2005 |
| WO | 2006/009886 A1 | 1/2006 |
| WO | WO 2006/002100 A2 | 1/2006 |
| WO | 2006/018279 A2 | 2/2006 |
| WO | 2006/018280 A2 | 2/2006 |
| WO | 2006/021448 A1 | 3/2006 |
| WO | 2006/023608 A2 | 3/2006 |
| WO | 2006/034315 A2 | 3/2006 |
| WO | 2006/038172 A1 | 4/2006 |
| WO | 2006/060122 A2 | 6/2006 |
| WO | 2006/084030 A2 | 8/2006 |
| WO | 2006/086445 A2 | 8/2006 |
| WO | 2006/099884 A1 | 9/2006 |
| WO | 2006/101521 A2 | 9/2006 |
| WO | 2006/110390 A1 | 10/2006 |
| WO | 2006/123121 A1 | 11/2006 |
| WO | 2006/130469 A1 | 12/2006 |
| WO | 2006/137485 A1 | 12/2006 |
| WO | 2007/006926 A1 | 1/2007 |
| WO | WO 2007/007069 A1 | 1/2007 |
| WO | 2007/019344 A1 | 2/2007 |
| WO | WO 2007/027734 A2 | 3/2007 |
| WO | WO 2007/042325 A1 | 4/2007 |
| WO | WO 2007/083119 A2 | 7/2007 |
| WO | WO 2007/087231 A2 | 8/2007 |
| WO | WO 2007/088123 A2 | 8/2007 |
| WO | WO 2007/097931 A2 | 8/2007 |
| WO | WO 2007/098418 A1 | 8/2007 |
| WO | WO 2007/126745 A2 | 11/2007 |
| WO | WO 2007/136603 A2 | 11/2007 |
| WO | WO 2007/138351 A2 | 12/2007 |
| WO | WO 2008/005937 A2 | 1/2008 |
| WO | WO 2008/019139 A2 | 2/2008 |
| WO | WO 2008/032905 A1 | 3/2008 |
| WO | WO 2008/057608 A2 | 5/2008 |
| WO | WO 2008/083027 A1 | 7/2008 |

(56) References Cited

FOREIGN PATENT DOCUMENTS

| | | |
|---|---|---|
| WO | WO 2008/094203 A2 | 8/2008 |
| WO | WO 2008/115719 A1 | 9/2008 |
| WO | WO 2008/120003 A1 | 10/2008 |
| WO | WO 2008/135141 A1 | 11/2008 |
| WO | WO 2008/139585 A1 | 11/2008 |
| WO | WO 2009/001126 A1 | 12/2008 |
| WO | WO 2009/004356 A1 | 1/2009 |
| WO | WO 2009/025781 A1 | 2/2009 |
| WO | WO 2009/025784 A1 | 2/2009 |
| WO | WO 2009/063244 A1 | 5/2009 |
| WO | WO 2009/077527 A1 | 6/2009 |
| WO | WO 2009/093032 A1 | 7/2009 |
| WO | WO 2009/112677 | 9/2009 |
| WO | WO 2009/121623 A2 | 10/2009 |
| WO | WO 2009/136889 A1 | 11/2009 |
| WO | WO 2009/153554 A1 | 12/2009 |
| WO | WO 2010/002802 A1 | 1/2010 |
| WO | WO 2010/021717 A2 | 2/2010 |
| WO | WO 2010/028761 A1 | 3/2010 |
| WO | WO 2010/042867 A2 | 4/2010 |
| WO | WO 2010/058318 A1 | 5/2010 |
| WO | WO 2010/092181 A1 | 8/2010 |
| WO | WO 2010/105243 A1 | 9/2010 |
| WO | WO 2010/108268 A1 | 9/2010 |
| WO | WO 2010/115688 A1 | 10/2010 |
| WO | WO 2010/118063 | 10/2010 |
| WO | WO 2010/129596 | 11/2010 |
| WO | WO 2010/132599 A1 | 11/2010 |
| WO | WO 2010/135524 A1 | 11/2010 |
| WO | WO 2010/151797 | 12/2010 |
| WO | WO 2011/002816 | 1/2011 |
| WO | WO 2011/002817 | 1/2011 |
| WO | WO 2011/025690 A1 | 3/2011 |
| WO | WO 2011/037793 A1 | 3/2011 |
| WO | WO 2011/050210 | 4/2011 |
| WO | WO 2011/050211 | 4/2011 |
| WO | WO 2011/060321 A1 | 5/2011 |
| WO | WO 2011/063055 A2 | 5/2011 |
| WO | WO 2011/103256 A1 | 8/2011 |
| WO | WO 2011/116282 A2 | 9/2011 |
| WO | WO 2011/137089 A1 | 11/2011 |
| WO | WO 2011/146358 A1 | 11/2011 |
| WO | WO 2012/002577 A1 | 1/2012 |
| WO | WO 2012/007861 A1 | 1/2012 |
| WO | WO 2012/007868 A2 | 1/2012 |
| WO | WO 2012/007877 A2 | 1/2012 |
| WO | WO 2012/019426 A1 | 2/2012 |
| WO | WO 2012/019427 A1 | 2/2012 |
| WO | WO 2012/056319 A1 | 5/2012 |
| WO | WO 2012/068096 A2 | 5/2012 |
| WO | WO 2012/071519 A1 | 5/2012 |
| WO | WO 2012/071684 A1 | 6/2012 |
| WO | WO 2012/080729 A2 | 6/2012 |
| WO | WO 2012/083246 | 6/2012 |
| WO | WO 2012/088314 | 6/2012 |
| WO | WO 2012/092426 A1 | 7/2012 |
| WO | WO 2012/092442 | 7/2012 |
| WO | WO 2012/092485 A1 | 7/2012 |
| WO | WO 2012/151440 A1 | 11/2012 |
| WO | WO 2012/151448 A1 | 11/2012 |
| WO | WO 2012/151450 A1 | 11/2012 |
| WO | WO 2012/151451 A1 | 11/2012 |
| WO | WO 2012/151452 A1 | 11/2012 |
| WO | WO 2012/160392 | 11/2012 |
| WO | WO 2012/160447 A1 | 11/2012 |
| WO | WO 2012/174126 | 12/2012 |
| WO | WO 2013/003249 A1 | 1/2013 |
| WO | WO 2013/003250 A1 | 1/2013 |
| WO | WO 2013/021054 A1 | 2/2013 |
| WO | WO 2013/038390 A1 | 3/2013 |
| WO | 2013/056153 | 4/2013 |
| WO | WO 2013/102142 A1 | 7/2013 |
| WO | WO 2013/102826 A1 | 7/2013 |
| WO | WO 2013/118805 A1 | 8/2013 |
| WO | WO 2013/126856 A1 | 8/2013 |
| WO | WO 2013/127266 A1 | 9/2013 |
| WO | WO 2013/155223 A1 | 10/2013 |
| WO | WO 2013/177224 A1 | 11/2013 |
| WO | WO 2013/184794 A2 | 12/2013 |
| WO | WO 2014/008458 A2 | 1/2014 |
| WO | WO 2014/014050 A1 | 1/2014 |
| WO | WO 2014/018355 A1 | 1/2014 |
| WO | WO 2014/023814 A1 | 2/2014 |
| WO | WO 2014/044356 A1 | 3/2014 |
| WO | WO 2014/048865 A1 | 4/2014 |
| WO | WO 2014/061031 A1 | 4/2014 |
| WO | WO 2014/062838 A2 | 4/2014 |
| WO | WO 2014/074848 | 5/2014 |
| WO | WO 2014/102817 A1 | 7/2014 |
| WO | WO 2014/118634 A1 | 8/2014 |
| WO | WO 2014/130890 A1 | 8/2014 |
| WO | WO 2014/139144 A1 | 9/2014 |
| WO | WO 2014/139325 A1 | 9/2014 |
| WO | WO 2014/139978 A1 | 9/2014 |
| WO | WO 2014/144715 A1 | 9/2014 |
| WO | WO 2014/150276 A1 | 9/2014 |
| WO | WO 2014/152588 A1 | 9/2014 |
| WO | WO 2014/172638 A2 | 10/2014 |
| WO | WO 2015/030514 A1 | 3/2015 |
| WO | WO 2015/036078 | 3/2015 |
| WO | WO 2015/042397 A1 | 3/2015 |
| WO | WO 2015/048336 A2 | 4/2015 |
| WO | WO 2015/051230 A1 | 4/2015 |
| WO | WO 2015/054555 A1 | 4/2015 |
| WO | WO 2015/078374 A1 | 6/2015 |
| WO | WO 2015/093948 A2 | 6/2015 |
| WO | WO 2015/116061 A1 | 8/2015 |
| WO | WO 2015/130915 A1 | 9/2015 |
| WO | WO 2015/144605 A1 | 10/2015 |
| WO | WO 2015/172732 A1 | 11/2015 |
| WO | WO 2015/183173 A1 | 12/2015 |
| WO | WO 2015/192701 A1 | 12/2015 |
| WO | WO 2016/005576 A1 | 1/2016 |
| WO | WO 2016/005577 A1 | 1/2016 |
| WO | WO 2016/014324 A1 | 1/2016 |
| WO | WO 2016/014522 A1 | 1/2016 |
| WO | WO 2016/021815 | 2/2016 |
| WO | WO 2016/044604 A1 | 3/2016 |
| WO | WO 2016/044629 A1 | 3/2016 |
| WO | WO 2016/044650 A1 | 3/2016 |
| WO | WO 2016/046837 A1 | 3/2016 |
| WO | WO 2016/047592 A1 | 3/2016 |
| WO | WO 2016/168647 A1 | 10/2016 |
| WO | WO 2016/181408 A2 | 11/2016 |
| WO | WO 2016/196816 | 12/2016 |
| WO | WO 2016/201227 A1 | 12/2016 |
| WO | WO 2017/006270 | 1/2017 |
| WO | WO 2017/050791 A1 | 3/2017 |
| WO | WO 2017/050792 A1 | 3/2017 |
| WO | WO 2017/191274 A2 | 11/2017 |
| WO | WO 2017/214002 A1 | 12/2017 |
| WO | WO 2018/049263 A1 | 3/2018 |
| WO | WO 2018/109277 A1 | 6/2018 |
| WO | WO 2018/175474 A1 | 9/2018 |
| WO | WO 2019/035863 A1 | 2/2019 |
| WO | WO 2019/035864 A1 | 2/2019 |
| WO | WO 2019/035865 A1 | 2/2019 |
| WO | WO 2019/099651 A1 | 5/2019 |
| WO | WO 2019/104134 | 5/2019 |
| WO | WO 2019/113359 | 6/2019 |
| WO | WO 2020/061252 | 3/2020 |
| WO | WO 2020/061255 | 3/2020 |
| WO | WO 2020/061261 | 3/2020 |
| WO | WO 2020/061378 | 3/2020 |
| WO | 2020139916 A1 | 7/2020 |
| WO | WO 2020/191022 | 9/2020 |

OTHER PUBLICATIONS

Abraham DJ, Mehanna AS, Wireko FC, et al. "Vanillin, a potential agent for the treatment of sickle cell anemia." *Blood6*. 1991;77(6):1334-41.

(56) References Cited

OTHER PUBLICATIONS

Adakveo [package insert]. East Hanover, New Jersey, Novartis Pharmaceuticals Corporation (Nov. 2019), 10 pgs.
Agios First Quarter 2020 Financial Results (Apr. 30, 2020), pp. 1-22.
Agrawal RK, Patel RK, Shah V, Nainiwal L, Trivedi B. "Hydroxyurea in sickle cell disease: drug review." *Indian J Hematol Blood Transfus.* Jun. 2014, 30(2):91-96.
Agrawal, R. K. et al., "Hydroxyurea in Sickle Cell Disease: Drug Review", *Indian J. Hematol Blood Transfus*, 30(2), pp. 91-96, (Apr.-Jun. 2014).
Aiuti, A. et al, Progress and prospects: gene therapy clinical trials (part 2), *Gene Ther*, 14(22):1555-1563 (2007).
Al-Hakim, A.K. et al., 14-3-3 cooperates with LKB1 to regulate the activity and localization of QSK and SIK, *Journal of Cell Science* 118 (23), pp. 5661-5673 (Aug. 2005).
Al-Hakim, A.K. et al., "Control of AMPK-related kinases by USP9X and atypical Lys29/Lys33-linked polyubiquitin chains", *Biochemical Journal*, 411 (2), pp. 249-260, (Feb. 2008).
Alves-Filho, J.C. & Palsson-Mcdermott, E.M., Pyruvate Kinase M2: A Potential Target for Regulating Inflammation, *Frontiers in Immunology*, 7(145): Article 145 (2016).
Ambrus, J. et al., Studies on the vasoocclusive crisis of sickle cell disease. III. In vitro and in vivo effect of the pyrimido-pyrimidine derivative, RA-233: studies on its mechanism of action, *J Med*, 18(3-4):165-198 (1987).
Amer, J. et al., Red blood cells, platelets and polymorphonuclear neutrophils of patients with sickle cell disease exhibit oxidative stress that can be ameliorated by antioxidants, *British Journal of Haematology*, 132(1):108-113 (2006).
Andresen, C.A. et al., "Protein Interaction Screening for the Ankyrin Repeats and Suppressor of Cytokine Signaling (SOCS) Box (ASB) Family Identify Asb11 as a Novel Endoplasmic Reticulum Resident Ubiquitin Ligase", *The Journal of Biological Chemistry*, vol. 289, No. 4, pp. 2043-2054, (Jan. 24, 2014).
Ataga KI, Kutlar A, Kanter J, Liles D, Cancado R, Friedrisch J, Guthrie TH, Knight- Madden J, Alvarez OA, Gordeuk VR, Gualandro S, Colella MP, Smith WR, Rollins SA, Stocker JW, Rother RP. "Crizanlizumab for the prevention of pain crises in sickle cell disease." *N Engl J Med*. Feb. 2, 2017, 376(5):429-439.
Atkinson, Peter J., et al., 3,4-Dihydro-2H-benzoxazinones are 5-HT1A receptor antagonists with potent 5-HT reuptake inhibitory activity, *BioOrganic & Medicinal Chemistry Letters*, 15(3), pp. 737-741 (2005).
Austin, Nigel E., et al., "Novel 2,3,4,5-tetrahydro-1H-3-benzazepines with high affinity and selectivity for the dopamine D3 receptor", *BioOrganic & Medicinal Chemistry Letters*, 10(22), pp. 2553-2555, (2000).
Bailey, S.D. et al., "Variation at the NFATC2 Locus Increases the Risk of Thiazolidinedione-Induced Edema in the Diabetes Reduction Assessment with Ramipril and rosiglitazone Medication (DREAM) Study", *Diabetes Care*, vol. 33, No. 10, pp. 2250-2254, (Oct. 2010).
Bakshi N, Sinha CB, Ross D, Khemani K, Loewenstein G, Krishnamurti L. "Proponent or collaborative: Physician perspectives and approaches to disease modifying therapies in sickle cell disease." *PLoS One*. Jul. 20, 2017, 12(7):e0178413.
Balakin, Konstantin V. et al., Comprehensive Computational Assessment of ADME Properties using Mapping Techniques, *Current Drug Discovery Technologies*, 2(2), pp. 99-113 (2005).
Banerjee, S. et al., "Interplay between Polo kinase, LKB1-activated NUAK1 kinase, PP1β phosphatase complex and the SCF$β^{TrCP}$ E3 ubiquitin ligase", *Biochem. J.* 461, pp. 233-245, (2014).
Banerjee, T. and Kuypers F.A., Reactive oxygen species and phosphatidylserine externalization in murine sickle red cells, *British Journal of Haematology*, 124:391-402 (2004).
Barbier AJ, Bodie S, Connor G, et al. "Safety, tolerability, pharmacokinetics and pharmacodynamics of multiple doses of AG-519, an allosteric activator of pyruvate kinase-R, in healthy subjects." *Blood*. 2016, 128:1264.

Barua, A.K., et al., Chemistry and Industry Communications to the Editor 1376 24 (Oct. 1970).
Bennett, Eric J., et al., "Dynamics of Cullin-RING Ubiquitin Ligase Network Revealed by Systematic Quantitative Proteomics", *Cell* 143, pp. 951-965, (Dec. 10, 2010).
Betz T, Lenz M, Joanny JF, Sykes C. "ATP-dependent mechanics of red blood cells." *Proc Natl Acad Sci USA*. 2009;106(36):15320-5.
Beutler, E. and Gelbart, T., "Estimating the prevalence of pyruvate kinase deficiency from the gene frequency in the general white population", *Blood*, 95(11): 3585-3588 (2000).
Bianchi, P. and Zanella, A., "Hematologically important mutations: red cell pyruvate kinase", (Third update), *Blood Cells Mol Dis.*, 26(1): 47-53 (2000).
Biftu, T. et al., "Omarigliptin (MK-3102): A Novel Long-Acting DPP-4 Inhibitor for Once-Weekly Treatment of Type 2 Diabetes", *Journal of Medicinal Chemistry*, 57, pp. 3205-3212, (2014).
Bouwmeester, T. et al., "A physical and functional map of the human TNF-α/NF-κB signal transduction pathway", *Nature Cell Biology*, vol. 6, No. 2, pp. 97-105, (Feb. 2004).
Boxer, M.B. et al., "Evaluation of Substituted N,N$^1$-Diarylsulfonamides as Activators of the Tumor Cell Specific M2 Isoform of Pyruvate Kinase", *J. Med. Chem.*, 53: pp. 1048-1055 (2010).
Brajenovic, M. et al., "Comprehensive Proteomic Analysis of Human Par Protein Complexes Reveals an Interconnected Protein Network", *The Journal of Biological Chemistry*, vol. 275, No. 13, pp. 12804-12811 (Mar. 2004).
Brehme, M. et al., "Charting the molecular network of the drug target Bcr-Abl", *PNAS*, vol. 106, No. 18, pp. 7414-7419, (May 2009).
Bridges, C.R., et al., "USP9X deubiquitylating enzyme maintains RAPTOR protein levels, mTORC1 signalling and proliferation in neural progenitors", *Scientific Reports* 7:391, pp. 1-15, (Mar. 2017).
Brown, R. Clark, et al., "FT-4202, an Allosteric Activator of Pyruvate Kinase-R, Demonstrates Proof of Mechanism and Proof of Concept after a Single Dose and after Multiple Daily Doses in a Phase 1 Study of Patients with Sickle Cell Disease," *Blood* (2020) 136 (Supplement 1):19-20, Nov. 4, 2020.
Brown, R. Clark, et al., "FT-4202, an Allosteric Activator of Pyruvate Kinase-R, Demonstrates Proof of Mechanism and Proof of Concept after a Single Dose and after Multiple Daily Doses in a Phase 1 Study of Patients with Sickle Cell Disease," *ASH* 2020, Dec. 7, 2020.
Budzikiewicz, Herbert et al., "Vincetene, a benzopyrroloisoquinoline alkaloid, from *Cynanchum vincetoxicum* (L.) Pers. (Asclepiadaceae)", Liebigs Annalen Der Chemie, (8), pp. 1212-1231 (1979).
Buontempo P, Jubin RG, Buontempo C, Real R, Kazo F, O'Brien S, Adeel F, Abuchowski A. "Pegylated carboxyhemoglobin bovine (SANGUINATE) restores RBCs roundness and reduces pain during a sickle cell vaso-occlusive crisis." *Blood*.2017, 130:969.
Cabrales, P. et al., "A look inside the mechanistic black box: Are red blood cells the critical effectors of RRx-001 cytotoxicity?", *Med Oncol.*, 33(7):63 (2016).
CAS Registry No. 1208929-16-1, Tert-Butyl 1H,2H,3H,4H,5H,6H-Pyrrolo[3,4-C]Pyrrole-2-Carboxylate Hydrochloride (Mar. 11, 2010).
Castilhos, L. et al., "Altered E-NTPDase/E-ADA activities and CD39 expression in platelets of sickle cell anemia patients", *Biomed Pharmacother.*, 79:241-246 (2016).
Castilhos, L. et al., "Increased oxidative stress alters nucleosides metabolite levels in sickle cell anemia", *Redox Rep.*, 22(6):451-459 (2017).
Castilhos, L. et al., "Sickle cell anemia induces changes in peripheral lymphocytes E-NTPDase/E-ADA activities and cytokines secretion in patients under treatment", *Biomedicine & Pharmacotherapy* 73 (2015), pp. 102-108.
Castro, O., Viability and function of stored sickle erythrocytes, *Transfusion*, 20(6):695-703 (1980).
Cazzola, M., Pyruvate kinase deficiency, Haematologica, 90(1):1-2 (2005).
Charache, S. et al., Effect of 2,3-Diphosphateglycerate on oxygen affinity of blood in sickle, Cell Anemia, Journal of Clinical Investigation, 49(4):806-812 (1970).

(56) References Cited

OTHER PUBLICATIONS

Chaudhary, Neelam & Maddika, Subbareddy, "WWP2-WWP1 Ubiquitin Ligase Complex Coordinated by PPM1G Maintains the Balance Between Cellular p73 and ΔNp73 Levels", Mol. Cell. Biol. (Oct. 2014).
Chen, Yue et al.—Preclinical Pharmacokinetic/Pharmacodynamic Relationships for AG-348, An Investigational Small-Molecule Activator of Pyruvate Kinase, European Hematology Association, Jun. 13, 2015.
Cheung, Yiu-Yin et al., Solution-Phase Parallel Synthesis and SAR of Homopiperazinyl Analogs as Positive Allosteric Modulators of MGlu$_4$, ACS Comb Sci. 13(2), pp. 159-165, (Mar. 2011).
Chiosis et al., Development of a Purine-Scaffold Novel Class of Hsp90 Binders that Inhibit the Proliferation of Cancer Cells and Induce the Degradation of Her2 Tyrosine Kinase, BioOrganic & Medicinal Chemistry, vol. 10, Iss 11, (Nov. 2002), pp. 3555-3564.
Chiou WL, Barve A. "Linear correlation of the fraction of oral dose absorbed of 64 drugs between humans and rats." Pharm Res. Nov. 1998, 15(11):1792-5.
Chonat, S. et al.,—Improvement in Red Blood Cell Physiology in Children With Sickle Cell Anemia Receiving Voxelotor—Childrens Healthcare of Atlanta (Dec. 2019).
Choudhury, N.R., et al., "RNA-binding activity of TRIM25 is mediated by its PRY/SPRY domain and is required for ubiquitination", BMC Biology 15:105, pp. 1-20, (2017).
Christensen, R.D. et al., Siblings with Severe Pyruvate Kinase Deficiency and a Complex Genotype, American Journal of Medical Genetics, Part A, (2016), pp. 2449-2452.
Chubukov V, Johnson K, Kosinski PA, et al. "Characterization of metabolic response to AG-348, an allosteric activator of red cell pyruvate kinase, in healthy volunteers and pyruvate kinase deficiency patients." Poster presented at: 58th American Society of Hematology Annual Meeting and Exposition; Dec. 4, 2016; San Diego, California. http://investor.agios.com/staticfiles/e1e9fd70-c84b-4472-bff3-bef0ecf05482 Accessed Jul. 28, 2017.
Chung, J.Y.L. et al., "Evolution of a Manufacturing Route to Omarigliptin, A Long-Acting DPP-4 Inhibitor for the Treatment of Type 2 Diabetes", Organic Process Research & Development, 19, pp. 1760-1768, (2015).
Clinical Trial Study—NCT02604433—U.S. National Library of Medicine, An Efficacy and Safety Study of Luspatercept (ACE-536) Versus Placebo in Adults Who Require Regular Red Blood Cell Transfusions Due to Beta (β) Thalassemia (BELIEVE), Submitted Date: Nov. 13, 2015, 24 pgs.
ClinicalTrials.gov, NCT03815695, (v1)—U.S. National Library of Medicine, "A SAD/MAD to Assess the Safety, Pharmacokinetics and Pharmacodynamics of FT-4202 in Healthy Volunteers and Sickle Cell Disease Patients" (Jan. 22, 2019).
Clinical Trials Study, NCT03815695, (v2)—U.S. National Library of Medicine, "A SAD/MAD to Assess the Safety, Pharmacokinetics and Pharmacodynamics of FT-4202 in Healthy Volunteers and Sickle Cell Disease Patients," (Mar. 13, 2019) pp. 1-5.
ClinicalTrials.gov, NCT03815695, (v3)—U.S. National Library of Medicine, "A SAD/MAD to Assess the Safety, Pharmacokinetics and Pharmacodynamics of FT-4202 in Healthy Volunteers and Sickle Cell Disease Patients" (Sep. 16, 2019).
Clinical Trial Study—NCT03815695, (v4)—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Sep. 19, 2019 (v4), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Sep. 23, 2019 (v5), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Oct. 9, 2019 (v6), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Oct. 10, 2019 (v7), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Nov. 27, 2019 (v8), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Jan. 15, 2020 (v9 ), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Jan. 16, 2020 (v10), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Feb. 21, 2020 (v11), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Apr. 1, 2020, (v12), 12 pgs.
ClinicalTrials.gov, NCT03815695 (v13), "A SAD/MAD to Assess the Safety, Pharmacokinetics and Pharmacodynamics of FT-4202 in Healthy Volunteers and Sickle Cell Patients," Jun. 15, 2020.
ClinicalTrials.gov, NCT03815695 (v14), "A SAD/MAD to Assess the Safety, Pharmacokinetics and Pharmacodynamics of FT-4202 in Healthy Volunteers and Sickle Cell Patients," Jul. 17, 2020.
ClinicalTrials.gov, NCT03815695 (v15), "A SAD/MAD to Assess the Safety, Pharmacokinetics and Pharmacodynamics of FT-4202 in Healthy Volunteers and Sickle Cell Patients," Aug. 19, 2020.
ClinicalTrials.gov, NCT03815695 (v16), "A SAD/MAD to Assess the Safety, Pharmacokinetics and Pharmacodynamics of FT-4202 in Healthy Volunteers and Sickle Cell Patients," Sep. 1, 2020.
ClinicalTrials.gov, NCT03815695 (v17), "A SAD/MAD to Assess the Safety, Pharmacokinetics and Pharmacodynamics of FT-4202 in Healthy Volunteers and Sickle Cell Patients," Sep. 18, 2020.
ClinicalTrials.gov, NCT03815695 (v18), "A SAD/MAD to Assess the Safety, Pharmacokinetics and Pharmacodynamics of FT-4202 in Healthy Volunteers and Sickle Cell Patients," Oct. 15, 2020.
ClinicalTrials.gov, NCT03815695 (v19), "A SAD/MAD to Assess the Safety, Pharmacokinetics and Pharmacodynamices of FT-4202 in Healthy Volunteers and Sickle Cell Patients," Study Record Versions 19—Dec. 24, 2020.
ClinicalTrials.gov, NCT03815695 (v20), "A SAD/MAD to Assess the Safety, Pharmacokinetics and Pharmacodynamices of FT-4202 in Healthy Volunteers and Sickle Cell Patients," Study Record Versions 20, Jan. 8, 2021.
ClinicalTrials.gov, NCT04624659 (v1), "A Study of FT-4202 in Adults and Adolescents With Sickle Cell Disease," Study Record Version 1—Nov. 5, 2020.
ClinicalTrials.gov, NCT04624659 (v2), "A Study of FT-4202 in Adults and Adolescents With Sickle Cell Disease," Study Record Version 2—Nov. 10, 2020.
ClinicalTrials.gov, NCT04624659 (v3), "A Study of FT-4202 in Adults and Adolescents With Sickle Cell Disease," Study Record Versions 3—Dec. 10, 2020.
ClinicalTrials.gov, NCT04624659 (v4), "A Study of FT-4202 in Adults and Adolescents With Sickle Cell Disease," Study Record Versions 4, Dec. 28, 2020.
ClinicalTrials.gov, NCT04624659 (v5), "A Study of FT-4202 in Adults and Adolescents With Sickle Cell Disease," Study Record Versions 5, Jan. 7, 2021.

(56) References Cited

OTHER PUBLICATIONS

ClinicalTrials.gov, NCT04624659 (v6), "A Study of FT-4202 in Adults and Adolescents With Sickle Cell Disease," Study Record Versions 6, Jan. 14, 2021.
ClinicalTrials.gov, NCT04624659 (v7), "A Study of FT-4202 in Adults and Adolescents With Sickle Cell Disease," Study Record Versions 7, Feb. 8, 2021.
Cloutier, P. et al., "R2TP/Prefoldin-like component RUVBL1/RUVBL2 directly interacts with ZNHIT2 to regulate assembly of U5 small nuclear ribonucleoprotein", Nature Communications, pp.1-14 (May 2017).
Cole, D.C. et al., Conformationally Constrained N1-arylsulfonyltryptamine derivatives as 5-HT6 receptor antagonists, BioOrganic & Medicinal Chemistry Letters, Vol. 15, No. 21, (Nov. 1, 2005), pp. 4780-4785.
Cox, J.L., et al., "The SOX2-Interactome in Brain Cancer Cell Identifies the Requirement of MSI2 and USP9X for the Growth of Brain Tumor Cell", Plos One, vol. 8, Issue 5, pp. 1-13, (May 2013).
Croasdell, G., European Hematology Association—20th Annual Congress (Jun. 11-14, 201—Vienna, Austria) Meeting Report, Drugs of Today (2015), 51(7),l pp. 441-445.
Das, A. et al., "USP9X counteracts differential ubiquitination of NPHP5 by MARCH7 and BBS11 to regulate ciliogenesis", PLOS Genetics, pp. 1-24, (May 12, 2017).
Davis, Z.H., et al., "Global Mapping of Herpesvirus-Host Protein Complexes Reveals a Transcription Strategy for Late Genes", Molecular Cell 57, pp. 349-360; (Jan. 22, 2015).
De Furia, F. et al., The effects of cyanate in vitro on red blood cell metabolism and function in sickle cell anemia, J Clin Invest., 51(3):566-574 (1972).
De Jong, K. and Kuypers, F., Sulphydryl modifications alter scramblase activity in murine sickle cell disease, British Journal of Haematology, 133(4):427-432 (2006).
De Rosa MC, Carelli Alinovi C, Galtieri A, Russo A, Giardina B. "Allosteric properties of hemoglobin and the plasma membrane of the erythrocyte: New insights in gas transport and metabolic modulation." IUBMB Life. 2008, 60(2):87-93.
Diez, A. et al., Life-threatening nonspherocytic hemolytic anemia in a patient with a null mutation in the PKLR gene and no compensatory PKM gene expression, Blood, 106:1851 (2005).
Diez-Silva M, Dao M, Han J, Lim CT, Suresh S. "Shape and biomechanical characteristics of human red blood cells in health and disease." MRS Bull. May 2010, 35(5):382-8.
Drissi, R. et al., "Quantitative Proteomics Reveals Dynamic Interactions of the Mini chromosome Maintenance Complex (MCM) in the Cellular Response to Etoposide Induced DNA Damage", Molecular & Cellular Proteomics, pp. 2002-2013, (2015).
DROXIA [package insert]. Princeton, New Jersey, Bristol-Myers Squibb Company, (Dec. 2017), 28 pgs.
DROXIA [package insert]. Princeton, New Jersey, Bristol-Myers Squibb Company (Dec. 2019), 25 pgs.
Dupont, S. et al., "FAM/USP9x, a Deubiquitinating Enzyme Essential for TGFβ Signaling, Controls Smad4 Monoubiquitination", Cell, 136, pp. 123-135, (Jan. 9, 2009).
Dzandu JK, Johnson RM. "Membrane protein phosphorylation in intact normal and sickle cell erythrocytes." J Biol Chem. Jul. 10, 1980, 255(13):6382-6.
El-Sharief, A.M., et al., Some halogenated sulfonamides with biological interest, Journal of the Indian Chemical Society, vol. 61, No. 6, (1984), pp. 537-543.
Emam, H.A., et al., Heterocyclization of sulfamido chalcones to pyrazoline, cyanopyridone, nicotinonitrile and hydrobenzo [1,2-c] pyrazole derivatives, Journal of the Serbian Chemical Society, Vol. 62, No. 7, (1997), Abstract only.
ENDARI [package insert]. Torrance, California: Emmaus Medical, Inc., (Jul. 2017), 8 pgs.
ENDARI [package insert]. Torrance, California, Emmaus Medical, Inc., (Nov. 2019), 10 pgs.
Ernst, A. et al., "A Strategy for Modulation of Enzymes in the Ubiquitin System", Science, 339, pp. 1-15, (Feb. 2013).

Estepp, et al., Phase 1 Single (SAD) and Multiple Ascending Dose (MAD) Study of the Safety, Pharmacokinetics (PK) and Pharmacodynamics (PD) of FT-4202, A PKR-Activator, In Healthy and Sickle Cell Disease Subjects, Abstract, e-Poster, European Hematology Association Open Access Library, Presentation EHA25, (May 14, 2020), 2 pgs.
Estepp, et al., Phase 1 Single (SAD) and Multiple Ascending Dose (MAD) Study of the Safety, Phyarmacokinetics (PK) and Pharmacodynamics (PD) of FT-4202, a PKR Activator, in Healthy and Sickle Cell Disease Subjects, Poster, EP1531, (Jun. 12, 2020), 1 pg.
Estepp, J.H. et al., A clinically meaningful fetal hemoglobin threshold for children with sickle cell anemia during hydroxyurea therapy, Am J Hematol., 92:1333-1339 (2017).
Estepp, Jeremie H., et al., "Phase 1 Single (SAD) and Multiple Ascending Dose (MAD) Study of the Safety, Pharmacokinetics (PK) and Pharmacodynamics (PD) of FT-4202, a PKR Activator, in Healthy Volunteers and Patients with Sickle Cell Disease," Virtual meeting [poster EP1531] presented at the $25^{th}$ Congress of the European Hematology Association; Jul. 11-21, 2020.
European Hematology Association HemaSphere Abstract Book, $15^{th}$ Annual Sickle Cell & Thalassaemia & 1st EHA European Sickle Cell Conference, Oct. 26-31, 2020.
Fioravanti, R., et al., Synthesis and Biological Evaluation of N-substituted -3, 5-diphenyl-2-pyrazoline derivatives as cyclooxygenase (COX-2) inhibitors, European Journal of Medicinal Chemistry, vol. 45, No. 12, (Dec. 1, 2010), pp. 6135-6138, XP027526583.
Fitch, R. W. et al., Phantasmidine: An Epibatidine Congener from the Ecuadorian Poison Frog *Epipedobates anthonyi*, Journal of Natural Products (2010), vol. 73, No. 3, pp. 331-337.
Fleischhacker, W., et al., "Heterocyclic fused naphthalene systems from thebaine. 1", Liebigs Annalen Der Chemie, (5), pp. 844-851, (1983).
Fogeron, M.L. et al., "LGALS3BP regulates centriole biogenesis and centrosome hypertrophy in cancer cells", Nature Communications, 4:1531, pp. 1-14; (2013).
Forma Therapeutics, Press Release, "Forma Therapeutics Presents Clinical Proof-of-Concept Data at the $62^{nd}$ Annual ASH Meeting Supporting the Potential of its Novel Investigational PKR Activator, FT-4202, to Treat Sickle Cell Disease (SCD)" (Dec. 7, 2020).
Forma Therapeutics, Inc., Press Release—"Forma Therapeutics Announces Positive FT-4202 600 mg Multiple Ascending Dose Cohort Data Supporting the Doses Being Evaluated in Phase 2/3 Registrational Trial, Called the Hibiscus Study", Mar. 30, 2021—2 pgs.
Frost, David A., et al., "Naturally occurring compounds related to phenalenone. V. Synthetic approaches to structures based on 8,9-dihydro-8,8,9-trimethylphenaleno [1,2-b]furan-7-one", Journal of the Chemical Society, Perkin Transactions 1: Organic and Bio-Organic Chemistry (1972-1999), pp. 2159-2169.
Gaudet, P. et al., "Phylogenetic-based propagation of functional annotations within the Gene Ontology consortium", vol. 12, No. 5, pp. 449-462; (Aug. 2011).
Giannone, R.J., et al., "The Protein Network Surrounding the Human Telomere Repeat Binding Factors TRF1, TRF2, and POT1", PLOS One, vol. 5, Issue 8, pp. 1-10, (Aug. 2010).
Gizi, A. et al., Assessment of oxidative stress in patients with sickle cell disease: The glutathione system and the oxidant-antioxidant status, Blood Cells Mol Dis., 46(3):220-225 (2011).
Gladwin, M., Adenosine recepter crossroads in sickle cell disease, Nature Medicine, 17(1):38-40, (2011).
Glombitza, S. et al., Adenosine causes cAMP-dependent activation of chick embryo red cell carbonic anhydrase and 2,3-DPG synthesis, American Journal of Physiology, 271(4):973-81 (1996).
Gomez-Bougie, P. et al., "Noxa controls Mule-dependent Mcl-1 ubiquitination through the regulation of the Mcl-1/USP9X interaction", Biochemical and Biophysical Research Communications 413, pp. 460-464, (2011).
Goncharov, T. et al., "OTUB1 modulates c-IAP1 stability to regulate signaling pathways", The EMBO Journal 32, No. 8, pp. 1103-1114, (2013).
Grace RF, Rose C, Layton DM, Yaish HM, Barcellini W, Galactéros F, Morton DH, Ravindranath Y, Kuo KHM, van Beers EJ, Kwiatkowski

(56) References Cited

OTHER PUBLICATIONS

JL, Silver BA, Merica E, Kung C, Cohen M, Yang H, Hixon J, Kosinski PA, Silver L, Dang L, Yuan Z, Barbier AJ, Glader B. "Effects of AG_348, a pyruvate kinase activator, on anemia and hemolysis in patients with pyruvate kinase deficiency: Data from the DRIVE PK study". Blood. 2016, 128:402.

Grace, et al., Safety and Efficacy of Mitapivat in Pyruvate Kinase Deficiency, N. Engl. J. Med. 381, 10, (Sep.. 5, 2019), p. 933-944.

Grasso, D. et al., "Zymophagy, a Novel Selective Autophagy Pathway Mediated by VMP1-USP9x-p62, Prevents Pancreatic Cell Death", The Journal of Biological Chemistry, vol. 286, No. 10, pp. 8308-8324, (Mar. 2011).

Greco, T.M. et al., "Nuclear Import of Histone Deacetylase 5 by Requisite Nuclear Localization Signal Phosphorylation", Molecular & Cellular Proteomics 10: , pp. 1-15, (2011).

Grou, C.P., et al., "Identification of ubiquitin-specific protease 9X (USP9X) as a deubiquitinase acting on the ubiquitin-peroxin 5 (PEX5) thioester conjugate", J. Biol. Chem., pp. 1-24; (Feb. 27, 2012).

Habata, S. et al., "BAG3-mediated Mcl-1 stabilization contributes to drug resistance via interaction with USP9X in ovarian cancer", International Journal of Oncology 49: pp. 402-410, (2016).

Han, K.J. et al., "Ubiquitin-specific Protease 9x Deubiquitinates and Stabilizes the Spinal Muscular Atrophy Protein—Survival Motor Neuron", J. Biol. Chem., pp. 1-22, (Oct. 2012).

Hanson, D. et al., "Identifying biological pathways that underlie primordial short stature using network analysis", Journal of Molecular Endocrinology, pp. 333-344, (2014).

Harada, R. et al., "Structure of pristimerine, a quinonoid triterpene", Tetrahedron Letters, pp. 603-607, (1962).

Harayama, Takashi et al., "Novel synthesis of naphthobenzazepines from N-bromobenzylnaphthylamines by regioselective C—H activation utilizing the intramolecular coordination of an amine to Pd", Synlett, (8), pp. 1141-1144, (2003).

Hauri, S. et al., "Interaction proteome of human Hippo signaling: modular control of the co-activator YAP1", Molecular Systems Biology, 9: 713, pp. 1-16 (Nov. 2013).

Havugimana, P. et al., "A Census of Human Soluble Protein Complexes", Cell 150, pp. 1068-1081, (Aug. 2012).

Hebbel RP, Eaton JW, Balasingam M, Steinberg MH. "Spontaneous oxygen radical generation by sickle erythrocytes." J Clin Invest. 1982, 70(6):1253-9.

Hein, M.Y., et al., "A Human Interactome in Three Quantitative Dimensions Organized by Stoichiometries and Abundances", Cell 163, pp. 712-723, (Oct. 2015).

Hierso, R. et al., Effects of oxidative stress on red blood cell rheology in sickle cell patients, British Journal of Haematology, 166(4):601-606 (2014).

Homan, C.C. et al., "Mutations in USP9X Are Associated with X-linked Intellectual Disability and Disrupt Neuronal Cell Migration and Growth", The American Journal of Human Genetics 94, pp. 470-478, (Mar. 2014).

Hoppe CC, Inati AC, Brown C, et al. "Initial results from a cohort in a phase 2a study (GBT440-007) evaluating adolescents with sickle cell disease treated with multiple doses of GBT440, a HbS polymerization inhibitor." Blood. 2017:130(Suppl 1): 689.

Husain, M.I., et al., Synthesis of some new N-[4-(acetyl/phenyl-5-arylpyrazolin-3-yl)phenyl]arylsulfonamides as oral hypoglycemic agents, Indian Drugs, vol. 24, No. 4, (1987), Abstract only.

Huttlin, E. L., et al., "The BioPlex Network: A Systematic Exploration of the Human Interactome", Cell 162, pp. 425-440, (Jul. 2015).

Huttlin, E.L., et al., "Architecture of the human interactome defines protein communities and disease networks", Nature, pp. 1-35, (May 2017).

Hydrea [package insert]. Princeton, New Jersey, Bristol-Myers Squibb Company (Jul. 2019), 29 pgs.

Imamura K, Tanaka T. "Multimolecular forms of pyruvate kinase from rat and other mammalian tissues. I Electrophoretic studies." J Biochem. 1972, 71:1043-51.

Imamura K, Tanaka T. "Pyruvate kinase isozymes from rat." Methods Enzymol. 1982, 90:150-65.

International Search Report and Written Opinion for PCT/US2019/051831, dated Dec. 6, 2019 (Dec. 6, 2019).

International Search Report and Written Opinion for PCT/US2020/051645, dated Dec. 7, 2020 (Dec. 7, 2020).

International Search Report and Written Opinion for PCT/US2020/051579, dated Dec. 10, 2020 (Dec. 10, 2020).

International Search Report and Written Opinion for PCT/US2019/052024, dated Dec. 23, 2019 (Dec. 23, 2019).

International Search Report and Written Opinion for PCT/US2018/023405, dated Jun. 5, 2018 (Jun. 5, 2018).

Iwasaki, Tameo et al., "Novel Selective PDE IV Inhibitors as Antiasthmatic Agents. Synthesis and Biological Activities of a Series of 1-Aryl-2,3-bis (hydroxymethyl) naphthalene Lignans", Journal of Medicinal Chemistry (1996), pp. 2696-2704.

Jendralla, H. et al., Synthesis of 1,2,3,4,5,6-Hexahydropyrrolo[3,4-c]pyrrole dihydrobromide and 1,2,3,5-Tetrahydro-2-[(4-Methyl-Phenyl) Sulfonyl]Pyrrolo[3,4-c]Pyrrole, Heterocycles, 41(6): 1291-1298 (1995).

Jin, Y. et al., Effects of gamma irradiation on red cells from donors with sickle cell trait, Transfusion, 37(8): 804-808 (1997).

Johansen, L.D., et al., "IKAP localizes to membrane ruffles with filamin A and regulates actin cytoskeleton organization and cell migration", Journal of Cell Science 121, pp. 854-864, (Dec. 2007).

Jones, M.H., et al., "The *Drosophila* developmental gene fat facets has a human homologue in Xp11.4 which escapes X-inactivation and has related sequences on Yq11.2", Human Molecular Genetics, vol. 5, No. 11, pp. 1695-1701, (Aug. 1996).

Jorgensen, Eugene C., et al., "Thyroxine analogs. 20. Substituted 1-and 2-naphthyl ethers of 3,5-diiodotyrosine", Journal of Medicinal Chemistry 14(11), pp. 1023-1026, (1971).

Joshi, B., et al., Indian J. Chem., Sect. B (1983), 22B(2), Abstract only. Chemical Abstract No. 99:105146

Joshi, P., et al., "The functional interactome landscape of the human histone deacetylase family", Molecular Systems Biology 9, 672, (2013).

Kalai, T. et al., Synthesis of Pyrroline Nitroxide Annulated Carbocycles and Heterocycles, Synthesis No. 6, pp. 831-837 (2000).

Kalfa, et al., FORMA Therapeutics, Inc., Watertown, MA, Power Pointe Presentation, Dated Nov. 6, 2019 , Phase 1 Single and Multiple Ascending Dose Study of the Safety, Tolerability, Pharmacokinetics and Pharmacodynamics of FT-4202, an Allosteric activator of Pyruvate Kinase-R, in Healthy and Sickle Cell Disease Subjects, 15 pgs.

Kalfa, T. A. et al., "Phase 1 Single (SAD) and Multiple Ascending Dose (MAD) Study of the Safety, Pharmacokinetics (PK) and Pharmacodynamics (PD) of FT-4202, a PKR Activator, in Healthy and Sickle Cell Diseases Subjects", JSCDH-D-20-0053, vol. VII, Pub. Date: June 12, 2020; pp. 83-84.

Kalfa, T. et al., "Phase 1 Single (SAD) and Multiple Ascending Dose (MAD) Study of the Safety, Pharmacokinetics (PK) and Pharmacodynamics (PD) of FT-4202, a PKR Activator, in Healthy and Sickle Cell Diseases Subjects", 14th Annual Sickle Cell Disease Research and Educational Symposium/43rd National Sickle Cell Disease Scientific Meeting (Sep. 23-25, 2020).

Kalfa, T.A. et al., "616 Phase 1 Single (SAD) and Julotiple Ascending Dose (MAD) Studies of the Safety, Tolerability, Pharmacokinetics (PK) and Pharmacodynamics (PD) of FT-4202, an Allosteric Activator of Pyruvate Kinase-R, in Healthy and Sickle Cell Disease Subjects", (Nov. 2019).

Kaltenbach, L.S., et al., "Huntingtin Interacting Proteins Are Genetic Modifiers of Neurodegeneration", PLOS Genetics, vol. 3, Issue 5, pp. 689-708, (May 2007).

Kasturi, Tirumalai R., et al., "Reactions of tetrahalo-1,2-benzoquinones. III. Reaction of tetrachloro-1,2-benzoquinone withtetralones and naphthols: pathway to the condensates", Journal of the Chemical Society C: Organic, (9), pp. 1257-1259, (1970).

Katzenellenbogen, R.A., et al., "NFX1-123 and Poly(A) Binding Proteins Synergistically Augment Activation of Telomerase in Human Papillomavirus Type 16 E6-Expressing Cells", Journal of Virology, vol. 81, pp. 3786-3796, (Apr. 2007).

(56) References Cited

OTHER PUBLICATIONS

Khafagy, M.M., Synthesis of some pyrimidine and pyrazoline derivatives, Al-Azhar Bulletin of Science, vol. 3, No. 1, (1992), Abstract only.

Kharalkar, S.S. et al., Identification of Novel Allosteric Regulators of Human-Erythrocyte Pyruvate Kinase, Chemistry & Biodiversity, Vol. 4, pp. 2603-2617 (Feb. 2007).

Kim H, Kosinski P, Kung C, Dang L, Chen Y, Yang H, Chen YS, Kramer J, Liu G. "A fit-for-purpose LC-MS/MS method for the simultaneous quantitation of ATP and 2,3-DPG in human K2EDTA whole blood." J Chromatogr B Analyt Technol Biomed Life Sci. Sep. 1, 2017, 1061-1062:89-96.

Kim J, Lee H, Shin S. "Advances in the measurement of red blood cell deformability: A brief review." J Cell Biotech. 2015;1:63-79.

Kim, M., et al., "Role of Angiomotin-like 2 mono-ubiquitination on YAP inhibition", EMBO reports, vol. 17, No. 1., pp. 64-78, (Nov. 23, 2015).

Kimura, K., et al., "Diversification of transcriptional modulation: Large-scale identification and characterization of putative alternative promoters of human genes", Genome Research 16, pp. 55-65, (2006).

Kirli, K., et al., "A deep proteomics perspective on CRM1-mediated nuclear export and nucleocytoplasmic partitioning", eLife, pp. 1-28; (2015).

Knauff, E.A.H., et al., "Genome-wide association study in premature ovarian failure patients suggests ADAMTS19 as a possible candidate gene", Human Reproduction, vol. 24, No. 9, pp. 2372-2379, (2009).

Kodama, K. et al., Solvent-induced dual chirality switching in the optical resolution of tropic acid via diastereomeric salt formation with (1R,2S)-2-amino-1,2-diphenylethanol, Tetrahedron 70:7923-7928 (2014).

Konstantinidis, Diamantis G., et al., "Ex-Vivo FT-4202 Treatment Improves Hemoglobin Oxygen Affinity and Membrane Health in Red Blood Cells of Patients with Hemoglobin SS and Hemoglobin SC Disease Irrespective of Prior Hydroxyurea Use," Blood (2020) 136 (Supplement1):23-24, Nov. 4, 2020.

Konstantinidis, Diamantis G., et al., "Ex-Vivo FT-4202 Treatment Improves Hemoglobin Oxygen Affinity and Membrane Health in Red Blood Cells of Patients with Hemoglobin SS and Hemoglobin SC Disease Irrespective of Prior Hydroxyurea Use," Presented at the 62$^{nd}$ American Society of Hematology (ASH) Annual Meeting, Dec. 5, 2020.

Kristensen, A.R., Gsponer, J. and Foster, L.J., "A high-throughput approach for measuring temporal changes in the interactome", Nat Methods, 9(9), pp. 1-12, (2012).

Kuehl, G. et al., In vitro interactions of 51Cr in human red blood cells and hemolysates, Vox Sang., 40(4):260-272 (1981).

Kung C, Hixon J, Kosinski PA, et al. "AG-348 enhances pyruvate kinase activity in red blood cells from patients with pyruvate kinase deficiency." Blood. 2017;130(11):1347-1356.

Kurita, R. et al., Establishment of Immortalized Human Erythroid Progenitor Cell Lines Able to Produce Enucleated Red Blood Cells, PLOS ONE, vol. 8, Iss.3, pp. 1-15 (Mar. 2013).

Kushwaha, D., et al., "USP9X inhibition promotes radiation-induced apoptosis in non-small cell lung cancer cells expressing mid-to-high MCL1", Cancer Biology & Therapy 16:3, pp. 392-401, (Mar. 2015).

Kwasna, D., et al., "Discovery and Characterization of ZUFSP/ZUP1, a Distinct Deubiquitinase Class Important for Genome Stability", Molecular Cell 70, pp. 150-164, (2018).

Le Quesne, P.W. et al., One-Step Preparation of Tetrakis(bromomethyl)ethylene from Pinacolyl Alcohol, J. Org. Chem., 40(1): 142-143 (1975).

Le, Kha et al., Population pharmacokinetics and pharmacodynamics of AG-519, a pyruvate kinase activator for the treatment of pyruvate kinase deficiency, in human healthy volunteers, Agios Pharma—1263 Poster,—58th American Society of Hematology Annual Meeting and Exposition, Dec. 3-6, 2016—San Diego, CA.

Le, Kha et al., Population pharmacokinetics and pharmacodynamics of AG-348 in healthy human volunteers guide dose selection for the treatment of pyruvate kinase deficiency, Agios Pharma—3336 Poster,—57th American Society of Hematology Annual Meeting and Exposition, Dec. 5-8, 2015—Orlando, FL.

Lehrer-Graiwer J, Howard J, Hemmaway CJ, et al. "Long-term dosing in sickle cell disease subjects with GBT440, a novel HbS polymerization inhibitor." Blood, 2016:128(22): 2488.

Lehrer-Graiwer, Josh et al., Long-Term Dosinig in Sickle Cell Disease Subjects with GBT440, a Novel HbS Polymerization Inhibitor, blood, 114, Hemoglobinopathies, Excluding Thalassemia- Clinical Poster II, Dec. 2, 2016.

Lenihan, J.A., Saha, Orthis, and Young P.W., "Proteomic analysis reveals novel ligands and substrates for LNX1 E3 ubiquitin ligase", PLOS ONE, pp. 1-18; (Nov. 2017).

Li, X., et al., "Defining the protein-protein interaction network of the human protein tyrosine phosphatase family", The American Society for Biochemistry and Molecular Biology, Inc., pp. 1-54, (2016).

Litinov RI, Weisel JW. "Role of red blood cells in haemostasis and thrombosis." ISBT Sci Ser. Feb. 2017, 12(1):176-183.

Liu, X.H., et al., European Journal of Cancer, vol. 31A, No. 6, pp. 953-963, (1995).

Llauger et al., "Evaluation of 8-Arylsulfanyl, 8-Arylsulfoxyl, and 8-Arylsulfonyl Adenine Derivatives as Inhibitors of the Heat Shock Protein 90", J. Med. Chem., 48 (8), pp. 2892-2905, (Mar. 25 2005).

Llauger et al., "Synthesis of 8-arylsulfoxyl/sulfonyl adenines", Tetrahedron Letters, vol. 45, Issue 52, (Dec. 20, 2004), pp. 9549-9552.

Lochmatter, C. et al., Integrative phosphoproteomics links IL-23R signalling with metabolic adaption in lymphocytes, Scientific Reports, 6:24491 (2016).

Lockwood, S. et al., Endothelium-derived nitric oxide production is increased by ATP released from red blood cells incubated with hydroxyurea, Nitric Oxide, 38:1-7 (2014).

Loriga G. et al., Synthesis of 3,6-diazabicyclo [3.1.1]heptanes as novel ligands for the opioid receptors, Bioorganic & Medicinal Chemistry, Pergamon, GB, vol. 14, No. 3, pp. 676-691, (Feb. 1, 2006).

Lu, L., et al., "The HECT Type Ubiquitin Ligase NEDL2 Is Degraded by Anaphase—promoting Complex/Cyclosome (APC/C)-Cdh1, and Its Tight Regulation Maintains the Metaphase to Anaphase Transition", The Journal of Biological Chemistry, vol. 288, No. 50, pp. 35637-35650; (Dec. 2013).

Lucas, et al., "Facile Synthesis of a Library of 9-Alkyl-8-benzyl-9H-purin-6-ylamine Derivatives", J. Comb. Chem., 3 (6), pp. 518-520, (Sep. 21, 2001).

MacDonald, Gregor J., et al, "Design and Synthesis of trans-3-(2-(4-((3-(3-(5-Methyl-1,2,4-oxadiazolyl))-phenyl(carboxamido)cyclohexy1)ethyl)-7-methylsulfonyl-2,3,4,5-tetrahydro-1H-3-benzazepine (SB-414796): A Potent and Selective Dopamine D3 Receptor Antagonist", Journal of Medicinal Chemistry, 46(23), pp. 4952-4964 (2003).

Macdonald, Rosemary, Red cell 2,3-diphosphoglycerate and oxygen affinity, Anaesthesia, vol. 32, pp. 544-553, (1977).

Martinez-Mayorga Karina et al, Ligand/kappa-opioid receptor interactions: Insights from the X-ray crystal structure, European Journal of Medicinal Chemistry, vol. 66, pp. 114-121 (May 30, 2013).

Mathe-Allainmat, Monique et al., "Synthesis of 2-Amido-2, 3-dihydro-1H-phanalene Derivatives as New Conformationally Restricted Ligands for Melatonin Receptors", Journal of Medicinal Chemistry, 39(16), pp. 3089-3095, (1996).

McCluskey A., et al., BioOrganic & Medicinal Chemistry Letters 10 (2000), pp. 1687-1690.

McCluskey A., et al., Bioorganic & Medicinal Chemistry Letters 11 (2001), pp. 2941-2946.

McGarry, E., et al., "The deubiquitinase USP9X maintains DNA replication fork stability and DNA damage checkpoint responses by regulating CLASPIN during S-phase", Cancerres.aacrjournals.org, pp. 1-39; (2016).

Metcalf B, Chuang C, Dufu K, et al. "Discovery of GBT440, an orally bioavailable R-state stabilizer of sickle cell hemoglobin." ACS Med Chem Lett. 2017; 8(3):321-326.

(56) References Cited

OTHER PUBLICATIONS

Meza, N.W. et al, In vitro and in vivo expression of human erythrocyte pyruvate kinase in erythroid cells: a gene therapy approach, Hum Gene Ther, 18(6):502-514 (2007).

Middelkoop, E. et al., Studies on sickled erythrocytes provide evidence that the asymmetric distribution of phosphatidylserine in the red cell membrane is maintained by both ATP—dependent translocation and interaction with membrane skeletal proteins, Biochimica et Biophysica Acta, 937:281-288 (1988).

Misra H. Bainbridge J, Berryman J, Abuchowski A, Galvez KM, Uribe LF, Hernandez AL, Sosa NR. "A phase 1b open label, randomized, safety study of SANGUINATE™ in patients with sickle cell anemia." Rev Bras Hematol Hemoter. Jan.-Mar. 2017, 39(1):20-7.

Miwa, S. and Fujii, H., Molecular basis of erythroenzymopathies associated with hereditary hemolytic anemia: tabulation of mutant enzymes, Am J Hematol., 51(2): 122-132 (1996).

Moehrle, H., et al., "1,2,3,4-Tetrahydroquinolines as substrates for Mannich compounds", Chemical Sciences, 53(7), pp. 742-752; (1998).

Moriyama R, Lombardo CR, Workman RF, Low PS. "Regulation of linkages between the erythrocyte membrane and its skeleton by 2,3-diphosphoglycerate." J Biol Chem. May 25, 1993, 268(15):10990-6.

Mouchantaf, R., et al., "The Ubiquitin Ligase Itch is Auto-ubiquitylated in Vivo and in Vitro but is Protected from Degradation by Interacting with the Deubiquitylating Enzyme FAM/USP9X", The Journal of Biological Chemistry, Vol. 281, No. 50, pp. 38738-38747, (Dec. 2006).

Murn, J. et al., "Control of a neuronal morphology program by an RNA-binding zinc finger protein, Unkempt", Genes & Development 29, pp. 501-512, (2015).

Murray, R.Z., Jolly, L.A., Wood, S.A., "The FAM Deubiquitylating Enzyme Localizes to Multiple Points of Protein Trafficking in Epithelia, where it Associates with E-cadherin and β-catenin", Molecular Biology of the Cell, vol. 15, pp. 1591-1599; (Apr. 2004).

Muzyamba, M. and Gibson, J., Effect of 1-chloro-2,4-dinitrobenzene on K+ transport in normal and sickle human red blood cells, Journal of Physiology, 547(3):903-911 (2003).

Nagai, H., et al., "Ubiquitine-like Sequence in ASK1 Plays Critical Roles in the Recognition and Stabilization by USP9X and Oxidative Stress-Induced Cell Death", Molecular Cell 36, pp. 805-818, (Dec. 2009).

Nagy, Peter I., et al., "Theoretical and Experimental Study on Ion-Pair Formation and Partitioning of Organic Salts in Octanol/Water and Dichloromethane/Water Sytems", Journal of the American Chemical Society, 122 (28), pp. 6583-6593 (2000).

Nam, Keun-Soo et al., "Synthesis of quinolone antimicrobial agents and their antibacterial activities," 5 Korean J. Med. Chem. (1995), pp. 2-5.

Narayanan, N., Wang, Z., Li, L., and Yang, Y., "Arginine methylation of USP9X promotes its interaction with TDRD3 and its anti-apoptotic activities in breast cancer cells", Cell Discovery 3, pp. 1-17, (2017).

Nathan, J.A., et al., "The Ubiquitin E3 Ligase MARCH7 is Differentially Regulated by the Deubiquitylating Enzymes USP7 and USP9X", Traffic, 9, pp. 1130-1145, (2008).

Neto, E.D. et al., "Shotgun sequencing of the human transcriptome with ORF expressed sequence tags", PNAS, vol. 97, No. 7, pp. 3491-3496, (Mar. 2000).

Noma, T., et al., "Stage- and sex-dependent expressions of Usp9x, an X-linked mouse ortholog of Drosophila Fat facets, during gonadal development and oogenesis in mice", Gene Expression Patters 2, pp. 87-91, (2002).

O'Connor, H.F., et al., "Ubiquitin-Activated Interaction Traps (UBAITs) identify E3 ligase binding partners", EMBO reports, vol. 16, No. 12., (2015).

Obach RS. "Prediction of human clearance of twenty-nine drugs from hepatic microsomal intrinsic clearance data: An examination of in vitro half-life approach and nonspecific binding to microsomes." Drug Metab Dispos. Nov. 1999, 27(11):1350-9.

Oksenberg D, Dufu K, Patel MP, Chuang C, Li Z, Xu Q, Silva-Garcia A, Zhou C, Hutchaleelaha A, Patskovska L, Patskovsky Y, Almo SC, Sinha U, Metcalf BW, Archer DR. "GBT440 increases haemoglobin oxygen affinity, reduces sickling and prolongs RBC half-life in a murine model of sickle cell disease." Br J Haematol. Oct. 2016, 175(1):141-53.

Oliviero, G., et al., "The variant Polycomb Repressor Complex 1 component PCGF1 interacts with a pluripotency sub-network that includes DPPA4, a regulator of embryogenesis", pp. 1-11, (2015).

Olsen, J.V., et al., "Global, In Vivo, and Site-Specific Phosphorylation Dynamics in Signaling Networks", Cell 127, pp. 635-648, (Nov. 2006).

Oski, M.D., Frank A., "The Role of Organic Phosphates in Erythrocytes on the Oxygen Dissociation of Hemoglobin," Annals of Clinical Laboratory Science, vol. 1, No. 2 (Nov. 1970), pp. 162-176.

Ould Amar, A.K. et al., Assessment of qualitative functional parameters of stored red blood cells from donors with sickle cell trait (AS) or with heterozygote (AC) status, Transfus Clin Biol., 3(4):225-233 (1996).

Ouyang, W., et al., "β-catenin is regulated by USP9x and mediates resistance to TRAIL-induced apoptosis in breast cancer", Oncology Reports 35, pp. 717-724, (2016).

OXBRYTA [package insert]. San Francisco, California, Global Blood Therapeutics, Inc. (Nov. 2019), 15 pgs.

OXBRYTA Slide Show—Jan. 2020.

Paemka, L., et al., "Seizures Are Regulated by Ubiquitin-specific Peptidase 9 X-linked (USP9X), a De-Ubiquitinase", PLOS Genetics, 11(3): pp. 1-16, (Mar. 2015).

Palsson-Mcdermott, EM et al., Pyruvate kinase M2 regulates Hif-1a activity and IL-1β induction and is a critical determinant of the Warburg Effect in LPS-activated macrophages, Cell Metabolism, 21:65-80 (2015).

Papp, S.J., et al., "DNA damage shifts circadian clock time via Hausp-dependent Cry1 stabilization", eLIFE, pp. 1-19, (2015).

Park, Yoon, Jin, Hyung-seung, and Liu, Yun-Cai, "Regulation of T cell function by the ubiquitin-specific protease USP9X via modulating the Carma 1-Bcl10-Malt1 complex", PNAS, vol. 110, No. 23, pp. 9433-9438, (Jun. 2013).

Pászty C. "Transgenic and gene knock-out mouse models of sickle cell anemia and the thalassemias." Curr Opin Hematol. 1997, 4(2):88-93.

Patel, P., et al., Synthesis of some novel pyrazoline and cyanopyridine derivatives as antimicrobial agents, II Farmaco, vol. 51, No. 1, (1996), Abstract only.

Pavagadhi, T.H., et al., 3-(3'-phenoxyphenylmethyl)-5-aryl-1-acetylpyrazolines, Journal of the Institution of Chemists (India), vol. 73, No. 3, (2001), Abstract only.

Peddaboina, C. et al., "The downregulation of Mcl-1 via USP9X inhibition sensitizes solid tumors to Bcl-xl inhibition", BMC Cancer, 12:541, pp. 1-12, (2012).

Perez-Mancera, P.A., et al., "The deubiquitinase USP9X suppresses pancreatic ductal adenocarcinoma", Nature, 486(7402): pp. 266-270; (Dec. 2012).

Platt OS. "Hydroxyurea for the treatment of sickle cell anemia." N Engl J Med. 2008;358(13):1362-9.

Poillon W., & Kim, B., 2,3-Diphosphoglycerate and intracellular pH as interdependent determinants of the physiologic solubility of deoxyhemoglobin S, Blood, 76:1028-1036 (1990).

Poillon, W. et al., Antisickling effects of 2,3-Diphosphoglycerate Depletion, Blood, 85(11):3289-3296 (1995).

Poillon, W. et al., Intracellular hemoglobin S polymerization and the clinical severity of sickle cell anemia, Blood, 91:1777-1783 (1998).

Poillon, W. et al., The Effect of 2,3-Diphosphoglycerate on the Solubility of Deoxyhemoglobin S1, Archives of Biochemistry and Biophysics, vol. 249, No. 2, pp. 301-305, (Sep. 1986).

Press Release—"Agios Announces New Data from AG-348 and AG-519 Demonstrating Potential for First Disease-modifying Treatment for Patients with PK Deficiency" Dec. 4 2016—Globe Newswire Press Release—"Agios Presents Updated Data from DRIVE PK Study Demonstrating AG-348 is Well-Tolerated and Results in

(56) References Cited

OTHER PUBLICATIONS

Clinically Relevant, Rapid and Sustained Hemoglobin Increases in Patients with Pyruvate Kinase Deficiency" Dec. 10, 2017—Globe Newswire.
PubChem SID: 440235168, modify date Feb. 25, 2021 (Feb. 25, 2021), Version 2, p. 1-7, Structure.
PubChem SID: 440235168, date Feb. 18, 2021 (Feb. 18, 2021), Version 1 of 2, p. 1- 7, Structure.
PubChem CID: 135338361, create date: Dec. 15, 2018 (Dec. 15, 2018), p. 1, formula.
PubChem CID: 135338378, create date: Dec. 15 2018 (Dec. 15 2018), p. 1, formula.
PubChem CID: 69203074, create date: Nov. 30, 2012 (Nov. 30, 2012), pp. 1-20, compound summary.
PubChem CID: 69203505, create date: Nov. 30, 2012 (Nov. 30, 2012), pp. 1-20, compound summary.
Rab, et al., AG-348 (Mitapivat), an allosteric activator of red blood cell pyruvate kinase, increases enzymatic activity, protein stability, and ATP levels over a broad range of PKLR genotypes, Haematologica, 105:xxx, (Jan. 23, 2020).
Rab, M.A.E. et al., Rapid and reproducible characterization of sickling during automated deoxygenation in sickle cell disease patients, Am. J. Hematol. (2019; 94; pp. 575-584.
Rabai M, Detterich JA, Wenby RB, et al. "Deformability analysis of sickle blood using ektacytometry." Biorheology. 2014;51(2-3):159-70.
Ramdani, G. and Langsley, G., ATP, an Extracellular Signaling Molecule in Red Blood Cells: A Messenger for Malaria?, Biomed Journal, 37(5):284-292 (2014).
Raththagala, M. et al., Hydroxyurea stimulates the release of ATP from rabbit erythrocytes through an increase in calcium and nitric oxide production, European Journal of Pharmacology, 645(1-3):32-38 (2010).
REBLOZYL [package insert]. Cambridge, Massachusetts, Acceleron Pharma, Inc. (2020), 27 pgs.
REBLOZYL [package insert]. Summit, New Jersey, Celgene Corporation (Nov. 2019), 16 pgs.
Rice-Evans C, Omorphos SC, Baysal E. "Cell membranes and oxidative damage." Biochem J. Jul. 1, 1986, 237(1):265-9.
Rosa, M. et al., Allosteric properties of hemoglobin and the plasma membrane of the erythrocyte: New insights in gas transport and metabolic modulation, Life, 60(2):87-93 (2008).
Ross, M.T., et al., "The DNA sequence of the human X chromosome", Nature, 434, pp. 325-337; (Mar. 2005).
Rott, Ruth, et al., "α-Synuclein fate is determined by USP9X-regulated monoubiquitination", PNAS, (2011).
Roy, R., et al., "hnRNPA1 couples nuclear export and translation of specific mRNAs downstream of FGF-2/S6K2 signalling", Nucleic Acids Research, vol. 42, No. 20, pp. 12483-12497, (Oct. 2014).
Rush, J., et al., "Immunoaffinity profiling of tyrosine phosphorylation in cancer cells", Nature Biotechnology, vol. 23, No. 1, pp. 94-101, (2005).
Sampson M, Archibong AE, Powell A, et al. "Perturbation of the developmental potential of preimplantation mouse embryos by hydroxyurea." Int J Environ Res Public Health. 2010;7(5):2033-44.
Sato, Y., et al., "Ubiquitin-specific protease 9X in host cells interacts with herpes simplex virus 1 ICP0", J. Vet. Med. Sci. 78(3), pp. 405-410; (2016).
Savio et al., "USP9X Controls EGFR Fate by Deubiquitinating the Endocytic Adaptor Eps15", Current Biology 26, pp. 173-183, (Jan. 2016).
Schwartz, R. et al., Two distinct pathways mediate the formation of intermediate density cells and hyperdense cells from normal density sickle red blood cells, Blood, 92(12):4844-4855 (1998).
Schwickart, M., et al., "Deubiquitinase USP9X stabilizes MCL1 and promotes tumour cell survival", Nature vol. 463, pp. 103-108; (Jan. 2010).
Sega, M. et al., Fluorescence assay of the interaction between hemoglobin and the cytoplasmic domain of erythrocyte membrane band 3, Blood Cells Mol Dis., 55(3):266-271 (2015).
Shen, G., et al., "MicroRNA-26b inhibits epithelial-mesenchymal transition in hepatocellular carcinoma by targeting USP9X," BMC Cancer 14:393, pp. 1-11, (2014).
Shrestha, Archana, et al., "Oral Administration of FT-4202, an Allosteric Activator of Pyruvate Kinase-R, Has Potent Anti-Sickling Effects in a Sickle Cell Anemia (SCA) Mouse Model, Resulting in Improved RBC Survival and Hemoglobin Levels," Blood (2020) 136 (Supplement 1):21-22, Nov. 4, 2020.
Shrestha, Archana, et al., "Oral Administration of FT-4202, an Allosteric Activator of Pyruvate Kinase-R, Has Potent Anti-Sickling Effects in a Sickle Cell Anemia (SCA) Mouse Model, Resulting in Improved RBC Survival and Hemoglobin Levels," Presented at the $62^{nd}$ American Society of Hematology (ASH) Annual Meeting, Dec. 5, 2020.
SIKLOS [package insert]. Lannoy, France, Delpharm Lille, (May 2019), 24 pgs.
SIKLOS [package insert]. Paris, France, Addmedica, (Dec. 2017), 25 pgs.
SIKLOS [package insert]. Paris, France, Addmedica, (May 2018), 23 pgs.
Smidrkal, Jan., "Synthesis of fagaronine", Collection of Czechoslovak Chemical Communications, 53(12), pp. 3184-3192, (1988).
Sorathiya, S.D., et al., Preparation and antimicrobial activity of 3-(p-(2',5'- dibromobenzenesulfonamido)phenyl)-5-aryl-1H/acetyl/phenyl-2-pyrazolines, Indian Journal of Chemistry, Section B: Organic, Incl. Medicinal Chemistry, vol. 36B, No. 7, (1997), Abstract only.
Soupene, E. and Kuypers, F., Identification of an erythroid ATP-dependent aminophospholipid transporter, British Journal of Haematology, 133(4):436-438 (2006).
Space SL, Lane PA, Pickett CK, Weil JV. "Nitric oxide attenuates normal and sickle red blood cell adherence to pulmonary endothelium." Am J Hematol. Apr. 2000, 63(4):200-4.
Spinella, J.F., et al., "Genomic characterization of pediatric T-cell acute lymphoblastic leukemia reveals novel recurrent driver mutations", Oncotarget, vol. 7, No. 40, pp. 65485-65503, (Sep. 2016).
Stasiuk, M. et al., Transformations of erythrocytes shape and its regulation, Postepy Biochem., 55(4):425-33 (2009). English Abstract.
St-Denis, N., et al., "Phenotypic and Interaction Profiling of the Human Phosphatases Identifies Diverse Mitotic Regulators", Cell Reports 17, pp. 2488- 2501, (Nov. 2016).
Stebbins et al., Crystal Structure of an Hsp90-Geldanamycin Complex: Targeting of a Protein Chaperone by an Antitumor Agent, Cell, (Apr. 1997), 89, p. 241.
Steinberg, Martin H., Pathophysiologically based drug treatment of sickle cell disease, TRENDS in Pharmacological Sciences, vol. 27, No. 4, (Apr. 2006).
Strausberg, R.L., et al., "Generation and initial analysis of more than 15,000 full-length human and mouse cDNA sequences", PNAS vol. 99, No. 26, pp. 16899-16903, (Dec. 2002).
Sun, H., et al., "Bcr-Abl ubiquitination and Usp9x inhibition block kinase signaling and promote CML cell apoptosis", Blood, (Jan. 2011).
Sundd, Prithu et al., Pathophysiology of Sickle Cell Disease, Annual Review of Pathology: Mechanisms of Disease, (Oct. 9, 2018), pp. 261-290.
Swanson, Devin M. et al., "Identification and biological evaluation of 4-(3-trifluoromethylpyridine-2-yl) piperazine-1-c arboxylic acid (5-trifluoromethylpyridin-2-yl) amide, a high affinity TRPV1 (VR1) vanilloid receptor antagonist", Journal of Medicinal Chemistry, 48(6), pp. 1857-1872 (2005).
Taipale, M., et al., "A Quantitative Chaperone Interaction Network Reveals the Architecture of Cellular Protein Homeostasis Pathways", Cell 158, pp. 434-448, (Jul. 2014).
Takenaka, M. et al, Isolation and characterization of the human pyruvate kinase M gene, Eur J Biochem, 198(1):101-106 (1991).
Talmud, P.J., et al., "Gene-centric Association Signals for Lipids and Apolipoproteins Identified via the Human CVD Bead Chip", The American Journal of Human Genetics 85, pp. 628-642, (Nov. 2009).
Tanphaichitr, V.S. et al, Successful bone marrow transplantation in a child with red blood cell pyruvate kinase deficiency, Bone Marrow Transplant, 26(6):689-690 (2000).
Taya, S., et al., "The deubiquitinating enzyme Fam interacts with and stabilizes β-catenin", Genes to Cells 4, pp. 757-767, (1999).

(56) References Cited

OTHER PUBLICATIONS

Taya, S., et al., "The Ras Target AF-6 is a Substrate of the Fam Deubiquitinating Enzyme", The Journal of Cell Biology, vol. 142, No. 4, pp. 1053-1062, (Aug. 1998).
Telen, Marilyn, Malik, Punam, and Vercellotti, Gregory M., Therapeutic strategies for sickle cell disease: towards a multi-agent approach, Nature Reviews/Drug Discovery; (Dec. 4, 2018).
Terao, Y., et al., "Trifluoroacetic Acid-Catalyzed 1,3-Cycloaddition of the Simplest Iminium Ylide Leading to 3- or 3,4-Substituted Pyrrolidines and 2,5-Dihydropyrroles", Chem. Pharm. Bull., 33(7), pp. 2762-2766, (1985).
Théard, D., et al., "USP9x-mediated deubiquitination of EFA6 regulates de novo tight junction assembly", The EMBO Journal, vol. 29, No. 9, pp. 1499-1509, (2010).
Thein, Swee Lay, The Molecular Basis of β-Thalassemia, Cold Spring Harb Perspect Med. (2013).
Thompson, Alexis, M.D., M.P.H., "A Targeted Agent for Sickle Cell Disease—Changing the Protein but Not the Gene," The New England Journal of Medicine, (Jun. 14, 2019).
Tian, S., et al., Yaoxue Xueba (1993), 28(11), pp. 870-875. Chemical Abstract No. 120:299229.
Toloczko, A., et al., "Deubiquitinating Enzyme USP9X Suppresses Tumor Growth via LATS kinase and Core Components of the Hippo pathway", Cancer Research, pp. 1-37, (Jul. 2017).
Tripathi, Ashutoshi and Safo, Martin K., In Silico-Screening Approaches for Lead Generation: Identification of Novel Allosteric Modulators of Human-Erythrocyte Pyruvate Kinase, Allostery: Methods and Protocols, Methods in Molecular Biology, Chpt. 19, vol. 796, pp. 351-367 (2012).
Trivigno, D., et al., "Deubiquitinase USP9x Confers Radioresistance through Stabilization of Mcl-1 1,2", NEO Plasia, vol. 14, No. 10, pp. 893-904, (Oct. 2012).
Tsai, Y.C., et al., "Functional Proteomics Establishes the Interaction of SIRT7 with Chromatin Remodeling Complexes and Expands Its Role in Regulation of RNA Polymerase I Transcription", Molecular & Cellular Proteomics 11.5, pp. 60-76, (2012).
Tsutsumi H, Tani K, Fujii H, Miwa S. "Expression of L- and M-type pyruvate kinase in human tissues. Genomics." 1988, 2(1):86-9.
United States Securities and Exchange Commission, Form S-1 Registration Statement, Forma Therapeutics Holdings, Inc., dated Dec. 8, 2020, 374 pages.
United States Securities and Exchange Commission, Form S-1, Registration Statement—Forma Therapeutics Holdings, Inc., May 29, 2020.
Upadhyay J., et al., Studies on pyrazolines. Part III. Preparation and antimicrobial activity of 3-(4-phenylsulfonamidophenyl)-5-aryl-1-ace tyl/phenyl-4,5-dihydropyrazoles, Journal of the Indian Chemical Society, vol. 68, No. 7, (1991), pp. 413-414.
Van Zweiten, R. et al., Inborn defects in the antioxidant systems of human red blood cells, Free Radio Biol Med., 67:377-386 (2014).
Vanderah et al, Novel d-amino acid tetrapeptides produce potent antinociception by selectively acting at peripheral kappa-opioid receptors, European Journal of Pharmacology, Elsevier Science, vol. 583, No. 1, pp. 62-72 (Jan. 24, 2008).
Varjosalo, M., et al., The Protein Interaction Landscape of the Human CMGC Kinase Group, Cell Reports 3, pp. 1306-1320, (Apr. 2013).
Verma, S.K. et al., Imidazole-Catalyzed Monoacylation of Symmetrical Diamines, Organic Letters, 12(19): 4232-4235 (201).
Vichinsky, E. et al., "A Phase 3 Randomized Trial of Voxelotor in Sickle Cell Disease," N Engl J Med. DOI: 10.1056/NEJMoa1903212 (Jun. 2019).
Vichinsky, E. et al., Protocol to A Phase 3 Randomized Trial of Voxelotor in Sickle Cell Disease, (Jun. 14, 2019).
Vichinsky, E. et al., Supplementary Appendix to a Phase 3 Randomized Trial of Voxelotor in Sickle Cell Disease, (Jun. 14, 2019).
Vong, Q. P., et al., "Chromosome Alignment and Segregation Regulated by Ubiquitination of Survivin", Science, vol. 310, pp. 1499-1504, (Dec. 2, 2005).
Voskou S, Aslan M, Fanis P, Phylactides M, Kleanthous M. "Oxidative stress in β-thalassaemia and sickle cell disease." Redox Biol. Dec. 2015, 6:226-39.
Wagner, G. et al., Red cell vesiculation—a common membrane physiologic event, J Lab Clin., 108(4):315-324 (1986).
Wan, C., et al., "Panorama of ancient metazoan macromolecular complexes", Nature 525(7569), pp. 339-344, (Sep. 2015).
Wang, G.S., et al., Journal of Ethnopharmacology, 26 (1989), pp. 147-162.
Wang, H. et al., JMJD5 regulates PKM2 nuclear translocation and reprograms HIF-1a-mediated glucose metabolism, PNAS, 111(1):279-284 (2014).
Wang, J., et al, "TopBP1 Controls BLM Protein Level to Maintain Genome Stability", Molecular Cell 52, pp. 667-678, (Dec. 2013).
Wang, Q., et al., "The X-linked Deubiquitinase USP9X Is an Integral Component of Centrosome", The American Society for Biochemistry and Molecular Biology, Inc., pp. 1-33, (2017).
Wang, S. et al., "Ablation of the oncogenic transcription factor ERG by deubiquitinase inhibition in prostate cancer", PNAS, vol. 111, No. 11, pp. 4251-4256, (Mar. 2014).
Wang, S., et al., "The ubiquitin ligase TRIM25 targets ERG for degradation in prostate cancer", Oncotarget, vol. 7, No. 40, pp. 64921-64931, (2016).
Wang, X, et al., "Hsp90 Cochaperone Aha1 Downregulation Rescues Misfolding of CFTR in Cystic Fibrosis", Cell 127, pp. 803-815, (Nov. 2006).
Waza et al., Nature, 11, No. 10, (Oct. 2005), pp. 1088-1095.
Weatherall, D., The inherited diseases of hemoglobin are an emerging global health burden, Blood, 115(22):4331-43336 (2010).
Wei, Wan-Guo et al., "A practical procedure for multisubstituted .beta.-naphthols and their derivatives", Tetrahedron, 59(34), pp. 6621-6625, (2003).
Willcocks, J. et al., Simultaneous determination of low free Mg2+ and pH in human sickle cells using P NMR spectroscopy, The Journal of Biological Chemistry, 277(51):49911-49920 (2002).
Wood BL, Gibson DF, Tait JF. "Increased erythrocyte phosphatidylserine exposure in sickle cell disease: flow-cytometric measurement and clinical associations." Blood., 88(5):1873-80 (Sep. 1, 1996).
Wood, Kenneth W., et al., "An Adaptive, Randomized, Placebo-Controlled, Double-Blind, Multi-Center Study of Oral FT-4202, a Pyruvate Kinase Activator in Patients with Sickle Cell Disease (PRAISE)," Blood (2020) 136 (Supplement 1):19-20, Nov. 4, 2020.
Wood, Kenneth W., et al., "An Adaptive, Randomized, Placebo-Controlled, Double-Blind, Multi-Center Study of Oral FT-4202, a Pyruvate Kinase Activator in Patients with Sickle Cell Disease," Presented at the 62$^{nd}$ American Society of Hematology (ASH) Annual Meeting, Dec. 7, 2020.
Woods, N.T., et al., "Charting the Landscape of Tandem BRCT Domain-Mediated Protein Interactions", Sci Signal, 5(242), pp. 1-35, (2014).
Wright, S.W. et al., A Convenient Preparation of Heteroaryl Sulfonamides and Sulfonyl Fluorides from Heteroaryl Thiols, J. Org. Chem., 71: 1080-1084 (2006).
Wu, Y., et al., "Aberrant phosphorylation of SMAD4 Thr277-mediated USP9x-SMAD4 interaction by free fatty acids promotes breast cancer matastasis", Cancer Research, pp. 1-34, (2017).
Wu, Z., et al., "Targeted Ubiquitination and Degradation of G-Protein-Coupled Receptor Kinase 5 by the DDB1-CUL4 Ubiquitin Ligase Complex", PLOS One, vol. 7, Issue 8, pp. 1-11, (Aug. 2012).
Xie, Y., et al., "Deubiquitinase FAM/USP9X Interacts with the E3 Ubiquitin Ligase SMURF1 Protein and Protects It from Ligase Activity-dependent Self-degradation", The Journal of Biological Chemistry., vol. 288, No. 5, pp. 2976-2985, (Feb. 2013).
Xu, Z., et al., "Identification of a Deubiquitinating Enzyme as a Novel AGS3-Interacting Protein", PLOS One, vol. 5, Issue 3, pp. 1-12, (Mar. 2010).
Yan, J., et al., "Usp9x- and Noxa-mediated Mcl-1 downregulation contributes to pemetrexed-induced apoptosis in human non-small-cell lung cancer cells", Cell Death and Disease 5, pp. 1-7, (2014).
Yang H, Merica E, Chen Y, Cohen M, Goldwater R, Hill C, et al. "Phase I single (SAD) and multiple ascending dose (MAD) studies of the safety, tolerability, pharmacokinetics (PK) and pharmacodynam-

(56) References Cited

OTHER PUBLICATIONS ics (PD) of AG-348, a first-in-class allosteric activator of pyruvate kinase-R, in healthy subjects." Blood. 2014, 124:4007.

Yang H, Merica E, Chen Y, et al. "Phase 1 Single- and Multiple-Ascending-Dose Randomized Studies of the Safety, Pharmacokinetics, and Pharmacodynamics of AG-348, a First-in-Class Allosteric Activator of Pyruvate Kinase R, in Healthy Volunteers." Clin Pharmacol Drug Dev. Aug. 9, 2018.

Yang, H. et al., Phase 1 Single- and Multiple-Ascending-Dose Randomized Studies of the Safety, Pharmacokinetics, and Pharmacodynamics of AG-348, a First-in-Class Allosteric Activator of Pyruvate Kinase R, in Healthy Volunteers, 8 Clin. Pharmacol. Drug Dev. 246-259 (2019).

Yi, S., et al., Leukemia Research, vol. 15(10), (1991), pp. 883-886.

You, J. and Pickart, C.M., "A HECT Domain E3 Enzyme Assembles Novel Polyubiquitin Chains", vol. 276, No. 23, pp. 19871-19878, (2001).

Yu, W., et al., "Large-Scale Concatenation cDNA Sequencing", Genome Research 7, pp. 353-358, (1997).

Zanella A, Fermo E, Bianchi P, Chiarelli LR, Valentini G. "Pyruvate kinase deficiency: The genotype-phenotype association." Blood Rev. 2007, 23:217-31.

Zanella A, Fermo E, Bianchi P, Valentini G. "Red cell pyruvate kinase deficiency: molecular and clinical aspects." Br J Haematol. 2005;130(1):11-25.

Zhang, C., et al., "Synergistic anti-tumor activity of gemcitabine and ABT-737 in vitro and in vivo through disrupting the interaction of USP9X and Mcl-1", Molecular Cancer Therapeutics, (May 12, 2011).

Zhang, C., et al., "USP9X destabilizes pVHL and promotes cell proliferation", Oncotarget, Vol. 7, No. 37, pp. 60519-60534, (2016).

Zhang, Y & XIA, Y., Adenosine signaling in normal and sickle erythrocytes and beyond, Microbes Infect., 14(10) (2012).

Zhang, Y. et al., Detrimental effects of adenosine signaling in sickle cell disease, Nature Medicine, 17(1):79-87 (2011).

Zhang, Yongmin et al., "Organic reactions in chiral micelles. 7. The structural effects on the asymmetric oxidation of prochiral sulfides in chiral micelles", Chinese Journal of Chemistry, (1990), pp. 89-96.

Zhao, Y., et al., "Noncanonical regulation of alkylation damage resistance by the OTUD4 deubiquitinase", EMBO Journal, vol. 34, No. 12, pp. 1687-1703, (2015).

Zhi et al., Hybrid Antibacterals. DNA Polymerase—Topoisomerase Inhibitors. J. Med. Chem., published on Web Jan. 5, 2006., vol. 49, pp. 1455-1465, especially p. 1456. Scheme 3, compound 4; p. 1457, Scheme 4, compound 13, p. 1462.

Zhou, L., et al., "The Scaffold Protein KSR1, A Novel Therapeutic Target for the Treatment of Merlin-Deficient Tumors", Oncogene 35(26), pp. 3443-3453, (Jun. 2016).

Zhou, ZH et al., Phosphorus, Sulfur and Silicon and the Related Elements (1999), 152, pp. 45-52. Chemical Abstract No. 132: 180853

Zhu, Tong et al., Polymer-Supported Synthesis of Pyridone-Focused Libraries as Inhibitors of Anaplastic Lymphoma Kinase, Journal of Combinatorial Chemistry, 8(3), pp. 401-409.

Clinical Trial Study—NCT04000165 "A Dose-Finding Study of AG-348 in Sickle Cell Disease", ClinicalTrials.gov, Jun. 27, 2019, 9 pages.

Kalfa, T.A et al., "Phase 1 Single (SAD) and Multiple Ascending Dose (MAD) Studies of the Safety, Tolerability, Pharmacokinetics (PK) and Pharmacodynamics (PD) of FT-4202, an Allosteric Activator of Pyruvate Kinase-R, in Healthy and Sickle Cell Disease Subjects", Blood, American Society of Hematology, Nov. 13, 2019, p. 3, vol. 134.

National Center for Biotechnology Information. PubChem Substance Record for SID 377251214, SCHEMBL20511283, Source: SureChEMBL. https://pubchem.ncbi.nlm.nih.gov/substance/377251214. Accessed Nov. 3, 2020. Available Dec. 15, 2018. (Year: 2018).

Supplemental European Search Report for EP Application 20 86 4351, Aug. 2, 2023, 10 pages.

U.S. Appl. No. 16/576,720, filed Sep. 19, 2019, 47 pages.

Qian et al., "Drug-polymer solubility and miscibility: Stability consideration and practical challenges in amorphous solid dispersion development", J. Pharm. Sci., Jul. 2010, vol. 99, No. 7, pp. 2941-2947.

Surechembl, "Open Patent Data", 2 pages, downloaded Oct. 31, 2023 from https://www.surechembl.org/knowledgebase/75969.

Schroeder et al., "Etavopivat, a Pyruvate Kinase Activator in Red Blood Cells, for the Treatment of Sickle Cell Disease", The Journal of Pharmacology and Experimental Therapeutics, Mar. 2022, vol. 380, pp. 210-219.

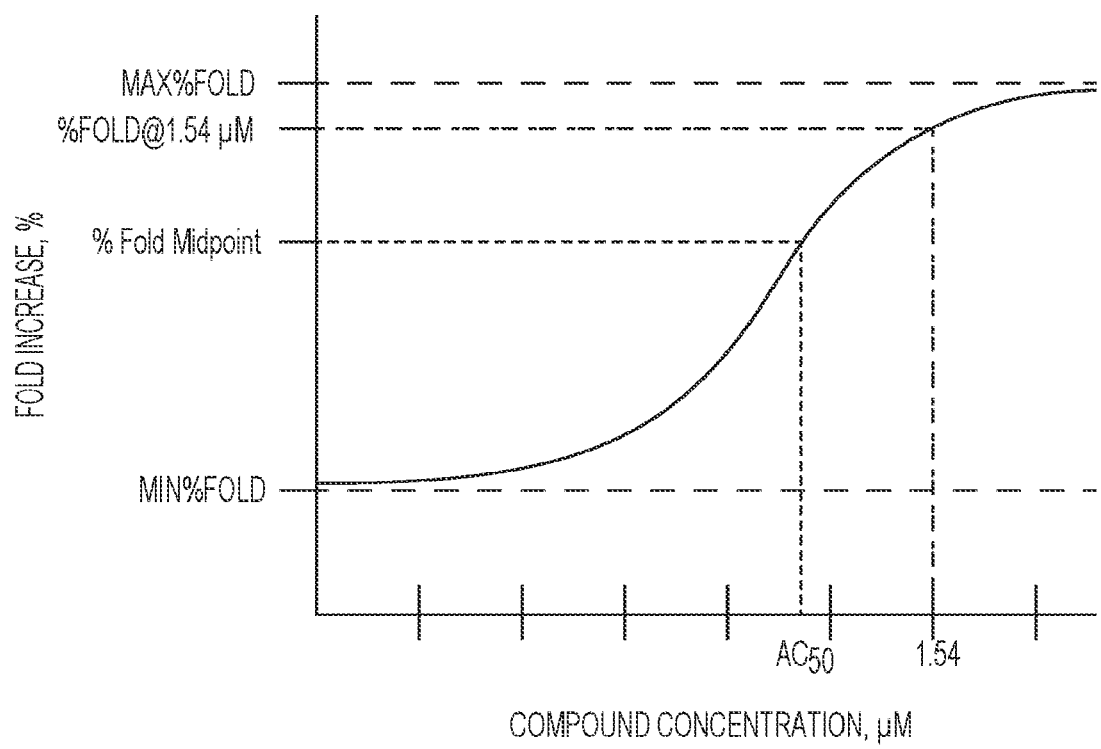

PYRROLOPYRROLE COMPOSITIONS AS PYRUVATE KINASE (PKR) ACTIVATORS

CROSS REFERENCE TO RELATED APPLICATIONS

This application is a continuation of U.S. patent application Ser. No. 17/239,364, filed Apr. 23, 2021, which is a continuation of U.S. patent application Ser. No. 16/496,279, filed Sep. 20, 2019, which is the U.S. national phase of International Application No. PCT/US2018/023405, filed Mar. 20, 2018, which claims the benefit of U.S. Provisional Patent Application No. 62/473,751, filed on Mar. 20, 2017, each of which is incorporated by reference in its entirety.

TECHNICAL FIELD

The present disclosure is directed to modulating pyruvate kinase, including novel compounds useful as PKR activators.

BACKGROUND

Pyruvate Kinase (PK) converts phosphoenolpyruvate (PEP) and adenosine diphosphate (ADP) to pyruvate and adenosine triphosphate (ATP), respectively, which is the final step in glycolysis. In humans, four PK isoforms are expressed by two structural genes. The PKLR gene encodes PKR and PKL tissue specific isoforms expressed in erythroid cells and liver, respectively. The PKM gene codes for isoforms PKM1, expressed in brain and skeletal muscle, and PKM2 (M2-type pyruvate kinase), expressed in fetal and most adult tissues except erythroid cells (Takenaka et al, Eur J Biochem 1991, 198:101).

Mutations in the PKLR gene can lead to pyruvate kinase deficiency (PKD), an autosomal recessive disorder, which is the most frequent enzymatic defect of the glycolytic pathway in erythrocytes. Over 200 different mutations have been identified on the structural PKLR gene (Bianchi et al, Blood Cells Mol Dis 2000, 26:47). Generally, most PKD patients are heterozygous with two different mutant alleles, but homozygous mutations have also been described (Diez et al. Blood 2005, 106:1851). Clinical symptoms of PKD vary considerably from mild to severe anemia. Mutations can reduce PK enzymatic activity or decrease PK protein stability. Pathological manifestations are usually observed when enzyme activity falls below 25% normal PK activity, and severe disease has been associated with a high degree of reticulocytosis (Miwa et al, Am J Hematol 51:122). Although the global incidence of PKD is unknown, it has been estimated at 51 cases per million in North America (Beutler et al, Blood 2000, 95:3585).

Currently, there is no definitive treatment for severe PKD (Cazzola, Haematologica 2005, 90:1). Although splenectomy can be clinically useful in patients with severe disease, in some cases, allogeneic hematopoietic transplantation is required (Tanphaichitr et al, Bone Marrow Transplant 2000, 26:689). In these patients, hematopoietic stem cell (HSC) gene therapy might be a good and more effective treatment. Gene therapy strategies for PKD have been addressed in animal models demonstrating that introduction of the correct version of the human PKLR gene into hematopoietic stem cells using retroviral vectors alleviates the disease (Meza et al, Hum Gene Ther 2007, 18:502). Although bone marrow transplant (BMT) or gene therapy strategies would be definitive treatments of the disease, important adverse effects are associated with both approaches (Aiuti et al, Gene Ther 2007, 14:1555).

There remains a need for strategies to improve the treatment of diseases related to PKR, such as PKD, including the discovery/development of PKR activating small molecules. PKR exists in both a dimeric and tetrameric state, but functions most efficiently as a tetramer. Small molecules have been shown to be capable of shifting the equilibrium of PKR to the tetrameric (most active) form, providing a mechanistic rationale for their use as therapy for PKD-associated hemolytic anemia. Thus, there is a need for PKR activating compounds, useful for treating diseases and disorders associated with modulation of PKR and/or PKM2.

SUMMARY

Compounds that activate PKR are disclosed herein. PKR Activating Compounds disclosed herein can increase the activity of wild-type and mutant PK enzymes in biochemical assays disclosed herein (e.g., Example 47). Data from PKR Activating Compounds herein illustrate the potential for these compounds to restore glycolytic pathway activity in patients with PK deficiency, with the goal of providing clinical benefit. Compounds disclosed herein are useful in the treatment of diseases or disorders associated with pyruvate kinase function. For example, the PKR Activating Compounds disclosed can be useful in the treatment of diseases, including but not limited to, PKD, sickle cell disease (SCD) (e.g., sickle cell anemia), and thalassemia (e.g., beta-thalassemia). In other embodiments, the compounds can be useful in the treatment of other indications related to pyruvate kinase modulation.

One aspect of the present disclosure relates to compounds of Formula I (e.g., compounds of Formula (I) identified as PKR Activating Compounds using the Luminescence Assay Protocol of Example 47):

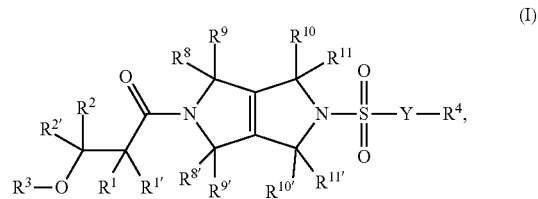

and pharmaceutically acceptable salts thereof,
wherein:
Y is a bond, —(CR$^5$R$^{5'}$)$_t$—, —NR$^5$(CR$^5$R$^{5'}$)$_t$—, or —O—;
each R$^1$, R$^{1'}$, R$^2$, and R$^{2'}$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_4$-C$_8$)cycloalkenyl, heterocyclyl, aryl, heteroaryl, halogen, —CN, —OR$^5$, —SR$^5$, —NO$_2$, —NR$^5$R$^{5'}$, —S(O)$_2$R$^5$, —S(O)$_2$NR$^5$R$^{5'}$, —S(O)R$^5$, —S(O)NR$^5$R$^{5'}$, —NR$^5$S(O)$_2$R$^{5'}$, —NR$^5$S(O)R$^{5'}$, —C(O)R$^5$, or —C(O)OR$^5$,
wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —R$^5$, —OR$^5$, —SR$^5$, —NO$_2$, —NR$^5$R$^{5'}$, —S(O)$_2$R$^5$, —S(O)$_2$NR$^5$R$^{5'}$, —S(O)R$^5$, —S(O)NR$^5$R$^{5'}$, —NR$^5$S(O)$_2$R$^{5'}$, —NR$^5$S(O)R$^{5'}$, —C(O)R$^5$, and —C(O)OR$^5$;

or $R^1$ and $R^{1'}$, or $R^2$ and $R^{2'}$, together with the atom to which they are attached, can combine to form a —$(C_3-C_8)$cycloalkyl ring, heterocycle, $(C_5-C_8)$spirocycle or 5- to 8-membered spiroheterocycle;

or $R^1$ and $R^2$, together with the atoms to which they are attached, can combine to form a —$(C_3-C_8)$cycloalkyl or a 3- to 8-membered heterocycle;

$R^3$ is independently —H, —$(C_1-C_6)$alkyl, —$(C_2-C_6)$alkenyl, —$(C_2-C_6)$alkynyl, —$(C_3-C_8)$cycloalkyl, —$(C_4-C_8)$cycloalkenyl, heterocyclyl, aryl, heteroaryl, —$S(O)_2R^5$, —$S(O)_2NR^5R^{5'}$, —$S(O)R^5$, —$S(O)NR^5R^{5'}$, —$C(O)R^5$, or —$C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, and —$C(O)OR^5$;

or $R^2$ and $R^3$, together with the atoms to which they are attached, can combine to form a 5- to 8-membered heterocyclic ring;

or $R^1$ and $R^3$, together with the atoms to which they are attached, can combine to form a 5- to 8-membered heterocyclic ring;

$R^4$ is —H, —$(C_1-C_6)$alkyl, —$(C_2-C_6)$alkenyl, —$(C_2-C_6)$alkynyl, —$(C_3-C_8)$cycloalkyl, —$(C_4-C_8)$cycloalkenyl, heterocyclyl, aryl, heteroaryl, halogen, —CN, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, or —$C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, and —$C(O)OR^5$;

each $R^5$ and $R^{5'}$ is independently, at each occurrence, —H, —$(C_1-C_6)$alkyl, —$(C_2-C_6)$alkenyl, —$(C_2-C_6)$alkynyl, —$(C_3-C_8)$cycloalkyl, —$(C_4-C_8)$cycloalkenyl, heterocyclyl, aryl, heteroaryl, halogen, —CN, —$OR^6$, —$SR^6$, —$NO_2$, —$NR^6R^{6'}$, —$S(O)_2R^6$, —$S(O)_2NR^6R^{6'}$, —$S(O)R^6$, —$S(O)NR^6R^{6'}$, —$NR^6S(O)_2R^{6'}$, —$NR^6S(O)R^{6'}$, —$C(O)R^6$, or —$C(O)OR^6$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^6$, —$OR^6$, —$SR^6$, —$NO_2$, —$NR^6R^{6'}$, —$S(O)_2R^6$, —$S(O)_2NR^6R^{6'}$, —$S(O)R^6$, —$S(O)NR^6R^{6'}$, —$NR^6S(O)_2R^{6'}$, —$NR^6S(O)R^{6'}$, —$C(O)R^6$, and —$C(O)OR^6$;

or two $R^5$ on adjacent atoms together with the atoms to which they are attached form an aryl ring optionally substituted with one or more $R^6$; or two $R^5$ on adjacent atoms together with the atoms to which they are attached form a heteroaryl ring optionally substituted with one or more $R^6$; or two $R^5$ on adjacent atoms together with the atoms to which they are attached form a $(C_3-C_8)$cycloalkyl ring optionally substituted with one or more $R^6$; or two $R^5$ on adjacent atoms together with the atoms to which they are attached form a heterocycloalkyl ring optionally substituted with one or more $R^6$;

or two $R^{5'}$ on adjacent atoms together with the atoms to which they are attached form an aryl ring optionally substituted with one or more $R^6$; or two $R^{5'}$ on adjacent atoms together with the atoms to which they are attached form a heteroaryl ring optionally substituted with one or more $R^6$; or two $R^{5'}$ on adjacent atoms together with the atoms to which they are attached form a $(C_3-C_8)$cycloalkyl ring optionally substituted with one or more $R^6$; or two $R^{5'}$ on adjacent atoms together with the atoms to which they are attached form a heterocycloalkyl ring optionally substituted with one or more $R^6$;

each $R^6$ and $R^{6'}$ is independently, at each occurrence, —H, —$(C_1-C_6)$alkyl, —$(C_2-C_6)$alkenyl, —$(C_2-C_6)$alkynyl, —$(C_3-C_8)$cycloalkyl, —$(C_4-C_8)$cycloalkenyl, heterocyclyl, aryl, heteroaryl, halogen, —CN, —$OR^7$, —$SR^7$, —$NO_2$, —$NR^7R^{7'}$, —$S(O)_2R^7$, —$S(O)_2NR^7R^{7'}$, —$S(O)R^7$, —$S(O)NR^7R^{7'}$, —$NR^7S(O)_2R^{7'}$, —$NR^7S(O)R^{7'}$, —$C(O)R^7$, or —$C(O)OR^7$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^7$, —$OR^7$, —$SR^7$, —$NO_2$, —$NR^7R^{7'}$, —$S(O)_2R^7$, —$S(O)_2NR^7R^{7'}$, —$S(O)R^7$, —$S(O)NR^7R^{7'}$, —$NR^7S(O)_2R^{7'}$, —$NR^7S(O)R^{7'}$, —$C(O)R^7$, and —$C(O)OR^7$;

each $R^7$ and $R^{7'}$ is independently, at each occurrence, —H, —$(C_1-C_6)$alkyl, —$(C_2-C_6)$alkenyl, —$(C_2-C_6)$alkynyl, —$(C_3-C_8)$cycloalkyl, —$(C_4-C_8)$cycloalkenyl, heterocyclyl, aryl, heteroaryl, halogen, —CN, —OH, —SH, —$NO_2$, —$NH_2$, —$S(O)_2H$, —$S(O)_2NH_2$, —$S(O)H$, —$S(O)NH_2$, —$NHS(O)_2H$, —$NHS(O)H$, —$C(O)H$, or —$C(O)OH$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —OH, —SH, —$NO_2$, —$NH_2$, —$S(O)_2H$, —$S(O)_2NH_2$, —$S(O)H$, —$S(O)NH_2$, —$NHS(O)_2H$, —$NHS(O)H$, —$C(O)H$, and —$C(O)OH$;

each $R^8$, $R^{8'}$, $R^9$, $R^{9'}$, $R^{10}$, $R^{10'}$, $R^{11}$, and $R^{11'}$ is independently, at each occurrence, —H, —$(C_1-C_6)$alkyl, —$(C_2-C_6)$alkenyl, —$(C_2-C_6)$alkynyl, —$(C_3-C_8)$cycloalkyl, or —$(C_4-C_8)$cycloalkenyl, wherein each alkyl, alkenyl, alkynyl, cycloalkyl and cycloalkenyl, is optionally substituted with one or more substituents selected from the group consisting of oxo, halogen, —CN, —OH, —SH, —$NO_2$, —$NH_2$, —$S(O)_2H$, —$S(O)_2NH_2$, —$S(O)H$, —$S(O)NH_2$, —$NHS(O)_2H$, —$NHS(O)H$, —$C(O)H$, or and —$C(O)OH$; and t is 0, 1, 2, or 3.

Unless otherwise indicated herein, each occurrence of $R^7$ and $R^{7'}$ disclosed herein for each of $R^6$, $R^{6'}$, $R^8$, $R^{8'}$, $R^9$, $R^{9'}$, $R^{10}$, $R^{10'}$, $R^{11}$, and $R^{11'}$ is independently selected from any of the possible recited values of $R^7$ and $R^{7'}$. For example, the value $R^7$ may have a different value for each of $R^6$, $R^{6'}$, $R^8$, $R^{8'}$, $R^9$, $R^{9'}$, $R^{10}$, $R^{10'}$, $R^{11}$, and $R^{11'}$ unless otherwise indicated herein.

The present disclosure also provides compounds of Formula (I) and pharmaceutically acceptable salts thereof, wherein:

Y is a bond;

$R^1$ is selected from the group consisting of —H, —$(C_1-C_6)$alkyl, 6-membered aryl, and 6-membered heteroaryl;

$R^{1'}$ is selected from the group consisting of —H and —($C_1$-$C_6$)alkyl;

or $R^1$ and $R^{1'}$, together with the atom to which they are attached, can combine to form a —($C_3$-$C_8$)cycloalkyl or a 3- to 8-membered heterocycle;

each $R^2$ and $R^{2'}$ is independently selected from the group consisting of —H and —($C_1$-$C_6$)alkyl;

$R^3$ is —H or —($C_1$-$C_6$)alkyl;

or $R^1$ and $R^3$, together with the atoms to which they are attached, can combine to form a 5- to 8-membered heterocyclic ring, optionally fused to an aryl or heteroaryl ring;

$R^4$ is 6- to 10-membered aryl or 6- to 10-membered heteroaryl, each optionally substituted with one or more substituents selected from the group consisting of oxo, halogen, —CN, —$R^5$, —$OR^5$, or —$NR^5R^{5'}$;

each $R^5$ and $R^{5'}$ is independently, at each occurrence, —H, —($C_1$-$C_6$)alkyl optionally substituted with one or more halogen, —$OR^6$, or —$NR^6R^{6'}$;

or two $R^5$ on adjacent atoms of $R^4$ together with the atoms to which they are attached optionally form a 5- or 6-membered heterocycloalkyl ring optionally substituted with one or more $R^6$;

each $R^6$ is independently, at each occurrence, —H, —($C_1$-$C_6$)alkyl, —($C_2$-$C_6$)alkenyl, —($C_2$-$C_6$)alkynyl, —($C_3$-$C_8$)cycloalkyl, —($C_4$-$C_8$)cycloalkenyl, heterocyclyl, aryl, heteroaryl, halogen, —CN, —$OR^7$, —$SR^7$, —$NO_2$, —$NR^7R^{7'}$, —$S(O)_2R^7$, —$S(O)_2NR^7R^{7'}$, —$S(O)R^7$, —$S(O)NR^7R^{7'}$, —$NR^7S(O)_2R^{7'}$, —$NR^7S(O)R^{7'}$, —$C(O)R^7$, or —$C(O)OR^7$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^7$, —$OR^7$, —$SR^7$, —$NO_2$, —$NR^7R^{7'}$, —$S(O)_2R^7$, —$S(O)_2NR^7R^{7'}$, —$S(O)R^7$, —$S(O)NR^7R^{7'}$, —$NR^7S(O)_2R^{7'}$, —$NR^7S(O)R^{7'}$, —$C(O)R^7$, and —$C(O)OR^7$;

each $R^7$ and $R^{7'}$ is independently, at each occurrence, —H, —($C_1$-$C_6$)alkyl, —($C_2$-$C_6$)alkenyl, —($C_2$-$C_6$)alkynyl, —($C_3$-$C_8$)cycloalkyl, —($C_4$-$C_8$)cycloalkenyl, heterocyclyl, aryl, heteroaryl, halogen, —CN, —OH, —SH, —$NO_2$, —$NH_2$, —$S(O)_2H$, —$S(O)_2NH_2$, —$S(O)H$, —$S(O)NH_2$, —$NHS(O)_2H$, —$NHS(O)H$, —$C(O)H$, or —$C(O)OH$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —OH, —SH, —$NO_2$, —$NH_2$, —$S(O)_2H$, —$S(O)_2NH_2$, —$S(O)H$, —$S(O)NH_2$, —$NHS(O)_2H$, —$NHS(O)H$, —$C(O)H$, and —$C(O)$OH;

each $R^8$, $R^{8'}$, $R^9$, $R^{9'}$, $R^{10}$, $R^{10'}$, $R^{11}$, and $R^{11'}$ is independently, at each occurrence, —H or —($C_1$-$C_6$)alkyl optionally substituted with one or more substituents selected from the group consisting of oxo, halogen, —CN, —OH, —SH, —$NO_2$, —$NH_2$, —$S(O)_2H$, —$S(O)_2NH_2$, —$S(O)H$, —$S(O)NH_2$, —$NHS(O)_2H$, —$NHS(O)H$, —$C(O)H$, or and —$C(O)OH$.

For example, the present disclosure relates to compounds of Formula I and pharmaceutically acceptable salts thereof, wherein:

Y is a bond;

each $R^1$ and $R^{1'}$ is independently selected from the group consisting of —H, —($C_1$-$C_6$)alkyl, aryl, and heteroaryl, wherein each alkyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, and —$C(O)OR^5$;

or $R^1$ and $R^{1'}$, together with the atom to which they are attached, can combine to form a —($C_3$-$C_8$)cycloalkyl ring, heterocycle, ($C_5$-$C_8$)spirocycle or 5- to 8-membered spiroheterocycle;

each $R^2$ and $R^{2'}$ is independently selected from the group consisting of —H and —($C_1$-$C_6$)alkyl, optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, and —$C(O)OR^5$;

$R^3$ is independently —H, —($C_1$-$C_6$)alkyl, —($C_2$-$C_6$)alkenyl, —($C_2$-$C_6$)alkynyl, —($C_3$-$C_8$)cycloalkyl, —($C_4$-$C_8$)cycloalkenyl, heterocyclyl, aryl, heteroaryl, —$S(O)_2R^5$, —$S(O)_2NR^5R^{5'}$, —$S(O)R^5$, —$S(O)NR^5R^{5'}$, —$C(O)R^5$, or —$C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, and —$C(O)OR^5$;

or $R^1$ and $R^3$, together with the atoms to which they are attached, can combine to form a 5- to 8-membered heterocyclic ring, optionally fused to an aryl or heteroaryl ring;

$R^4$ is 6- to 10-membered aryl or 6- to 10-membered heteroaryl, each optionally substituted with one or more substituents selected from the group consisting of oxo, halogen, —CN, —$R^5$, —$OR^5$ or —$NR^5R^{5'}$;

each $R^5$ and $R^{5'}$ is independently, at each occurrence, —H, —($C_1$-$C_6$)alkyl, —$OR^6$, or —$NR^6R^{6'}$;

or any two $R^5$ on adjacent atoms of $R^4$, together with the atoms to which they are attached form a 5- or 6-membered heterocycloalkyl ring optionally substituted with one or more $R^6$;

each $R^6$ is independently, at each occurrence, —H or —($C_1$-$C_6$)alkyl; and each $R^8$, $R^{8'}$, $R^9$, $R^{9'}$, $R^{10}$, $R^{10'}$, $R^{11}$, and $R^{11'}$ is independently, at each occurrence, —H.

In some PKR Activating Compounds, $R^4$ is 6-membered aryl or heteroaryl substituted with two —$R^5$, selected from the group consisting of —$OR^6$ and —$NR^6R^{6'}$, on adjacent atoms of $R^4$, that together with the atoms to which they are attached form a heterocycloalkyl ring fused to $R^4$ that is optionally substituted with one or more $R^6$, selected from the group consisting of —H and —($C_1$-$C_6$)alkyl.

In another aspect, the disclosure provides pharmaceutical compositions comprising a compound of Formula I and a pharmaceutically acceptable carrier.

In another aspect, the disclosure provides methods of treating a disease or disorder associated with modulation of pyruvate kinase (PKR) which comprises administering to a patient in need thereof an effective amount of a compound of Formula I.

The present disclosure also provides methods of treating a disease associated with decreased activity of PKR in a subject in need thereof which comprises administering to the subject an effective amount of a compound of Formula I.

Another aspect of the present disclosure is a method of activating PKR, comprising contacting PKR with an effective amount of a compound of Formula I.

Further aspects of the present disclosure include: methods of increasing the lifetime of red blood cells; methods of regulating 2,3-diphosphoglycerate levels in blood; and methods of regulating ATP levels in blood; each of the foregoing methods comprising administering to a subject in need thereof an effective amount of a compound of Formula I.

Another aspect of the present disclosure provides methods of treating hereditary non-spherocytic hemolytic anemia comprising administering to a subject in need thereof an effective amount of a compound of Formula I.

Also provided herein are methods of treating a disease or disorder associated with increased 2,3 diphosphoglycerate levels comprising administering to a subject in need thereof an effective amount of a compound of Formula I.

Another aspect of the disclosure provided herein includes methods of treating a disease or disorder associated with decreased ATP levels comprising administering to a subject in need thereof an effective amount of a compound of Formula I.

A further aspect of the present disclosure includes methods of treating sickle cell anemia comprising administering to a subject in need thereof a therapeutically effective amount of any of Formula I.

A further aspect of the present disclosure includes methods of treating hemolytic anemia comprising administering to a subject in need thereof a therapeutically effective amount of a compound of Formula I.

Another aspect of the present disclosure includes methods of treating beta thalassemia comprising administering to a subject in need thereof a therapeutically effective amount of a compound of Formula I.

BRIEF DESCRIPTION OF THE DRAWING

FIG. 1 shows an exemplary dose-response curve for compounds disclosed herein. Dose-response curves may be generated using the standard four parameter fit algorithm of ActivityBase XE Runner to determine MAX % Fold, MIN % Fold, slope and $AC_{50}$. MAX % Fold is the highest % fold increase observed at any concentration of compound, and MIN % Fold is the lowest % fold increase observed at any concentration of compound. The $AC_{50}$ value for a compound is the concentration (µM) corresponding to the midway between the maximum and minimum values of the four parameter logistic curve fit (i.e., at which the % fold increase along the four parameter logistic curve fit is halfway between MAX % Fold and MIN % Fold (% Fold Midpoint). Another useful parameter for evaluating compounds of this disclosure is % Fold@ 1.54 µM, which is the % fold increase at a compound concentration of 1.5 µM (e.g., 1.54 µM). X-axis and y-axis not necessarily to scale.

DETAILED DESCRIPTION

The present disclosure relates to compounds and compositions that are capable of activating the activity of PKR and/or PKM2. The disclosure features methods of treating a disease or disorder in which PKR and/or PKM2 plays a role by administering to a patient in need thereof a therapeutically effective amount of a compound of Formula (I), or a pharmaceutically acceptable salt thereof. The methods of the present disclosure can be used in the treatment of a variety of PKR and/or PKM2 dependent diseases and disorders by activating the activity of PKR and/or PKM2 enzymes. Activation of PKR and PKM2 provides a novel approach to the treatment of diseases including, but not limited to, PKD, SCD (e.g., sickle cell anemia), and thalassemia (e.g., beta-thalassemia. In some embodiments, the PKR Activating Compounds disclosed herein can be useful for the treatment of hereditary blood disorders related to pyruvate kinase activity, including PKD and SCD.

In a first aspect of the disclosure, compounds of Formula (I) are described:

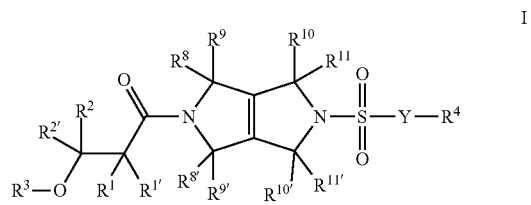

and pharmaceutically acceptable salts, thereof, wherein Y, $R^1$, $R^{1'}$, $R^2$, $R^{2'}$, $R^3$, $R^4$, $R^8$, $R^{8'}$, $R^9$, $R^{9'}$, $R^{10}$, $R^{10'}$, $R^{11}$, and $R^{11'}$ are as described herein above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents in place of one or more hydrogen atoms. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$)alkyl, ($C_1$-$C_6$) alkyl, ($C_1$-$C_6$)alkoxy, ($C_1$-$C_6$)haloalkyl, ($C_1$-$C_6$)haloalkoxy, —O—($C_2$-$C_6$)alkenyl, —O—($C_2$-$C_6$)alkynyl, ($C_2$-$C_6$)alkenyl, ($C_2$-$C_6$)alkynyl, —OP(O)(OH)$_2$, —OC(O)($C_1$-$C_6$)alkyl, —C(O)($C_1$-$C_6$)alkyl, —OC(O)O($C_1$-$C_6$)alkyl, —NH$_2$, —NH(($C_1$-$C_6$)alkyl), —N(($C_1$-$C_6$)alkyl)$_2$, —NHC(O)($C_1$-$C_6$)alkyl, —C(O)NH($C_1$-$C_6$)alkyl, —S(O)$_2$($C_1$-$C_6$)alkyl, —S(O)NH($C_1$-$C_6$)alkyl, and S(O)N(($C_1$-$C_6$)alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Unless otherwise specifically defined, the term "aryl" refers to cyclic, aromatic hydrocarbon groups that have 1 to 3 aromatic rings having a total of 5 to 14 ring atoms, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, -halogen, —O—($C_1$-$C_6$)alkyl, ($C_1$-$C_6$)alkyl, —O—($C_2$-$C_6$)alkenyl, —O—($C_2$-$C_6$)alkynyl, ($C_2$-$C_6$)alkenyl, ($C_2$-$C_6$)alkynyl, —OH, —OP(O)(OH)$_2$, —OC(O)($C_1$-$C_6$)alkyl, —C(O)($C_1$-$C_6$)alkyl, —OC(O)O($C_1$-$C_6$)alkyl, —NH$_2$, NH(($C_1$-$C_6$)alkyl), N(($C_1$-$C_6$)alkyl)$_2$, —S(O)$_2$—($C_1$-$C_6$)alkyl, —S(O)NH($C_1$-$C_6$)alkyl, and —S(O)N(($C_1$-$C_6$)alkyl)$_2$. The substituents can themselves be optionally substituted. Furthermore, when containing two fused rings the aryl groups herein defined may have an unsaturated or partially saturated ring fused with a fully unsaturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or polycyclic aromatic radical of 5 to 24 ring atoms, containing one or more ring heteroatoms selected from the group consisting of N, O, and S, the remaining ring atoms being C. Heteroaryl as herein defined also means a bicyclic heteroaromatic group wherein the heteroatom is selected from the group consisting of N, O, and S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1λ$^2$-pyrrolo[2,1-b]pyrimidine, dibenzo[b,d] thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two fused rings the heteroaryl groups herein defined may have an unsaturated or partially saturated ring fused with a fully unsaturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

"Halogen" or "halo" refers to fluorine, chlorine, bromine, or iodine.

"Alkyl" refers to a straight or branched chain saturated hydrocarbon containing 1-12 carbon atoms. Examples of a ($C_1$-$C_6$)alkyl group include, but are not limited to, methyl, ethyl, propyl, butyl, pentyl, hexyl, isopropyl, isobutyl, sec-butyl, tert-butyl, isopentyl, neopentyl, and isohexyl. An alkyl group may be substituted by one or more substituents.

"Alkoxy" refers to a straight or branched chain saturated hydrocarbon containing 1-12 carbon atoms containing a terminal "O" in the chain, e.g., —O(alkyl). Examples of alkoxy groups include without limitation, methoxy, ethoxy, propoxy, butoxy, t-butoxy, or pentoxy groups.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

"Cycloalkyl" or "carbocyclyl" means monocyclic or polycyclic saturated rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A $C_3$-$C_8$ cycloalkyl is a cycloalkyl group containing between 3 and 8 carbon atoms. A cycloalkyl group can be fused (e.g., decalin) or bridged (e.g., norbornane). A cycloalkyl group may be substituted by one or more substituents.

"Heterocyclyl" or "heterocycloalkyl" means 5- to 7-membered monocyclic or 7- to 10-membered polycyclic rings containing carbon and heteroatoms taken from oxygen, nitrogen, or sulfur, where such rings are either saturated or partially unsaturated. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "hydroxyalkyl" means an alkyl group as defined above, where the alkyl group is substituted with one or more OH groups. Examples of hydroxyalkyl groups include HO—$CH_2$—, HO—$CH_2$—$CH_2$— and $CH_3$—CH(OH)—.

The term "haloalkyl" as used herein refers to an alkyl group, as defined herein, which is substituted with one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted with one or more halogen. Examples of haloalkoxy groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., —C≡N.

"Spirocycloalkyl" or "spirocyclyl" means carbogenic bicyclic ring systems with both rings connected through a single atom. The ring can be different in size and nature, or identical in size and nature. Examples include spiropentane, spirohexane, spiroheptane, spirooctane, spirononane, or spirodecane. One or both of the rings in a spirocycle can be fused to another carbocyclic, heterocyclic, aromatic, or heteroaromatic ring. A ($C_5$-$C_{12}$)spirocycloalkyl is a spirocycle containing between 5 and 12 carbon atoms. One or more of the carbon atoms can be substituted with a heteroatom.

The term "spiroheterocycloalkyl" or "spiroheterocyclyl" is understood to mean a spirocycle wherein at least one of the rings is a heterocycle (e.g., at least one of the rings is furanyl, morpholinyl, or piperadinyl).

The term "isomer" refers to compounds that have the same composition and molecular weight but differ in physical and/or chemical properties. The structural difference may be in constitution (e.g., geometric isomers) or in the ability to rotate a plane of polarized light (stereoisomers). With regard to stereoisomers, the compounds of Formula (I) may have one or more asymmetric carbon atoms and may occur as racemates, racemic mixtures or as individual enantiomers or diastereomers.

The disclosure also includes pharmaceutical compositions comprising an effective amount of a disclosed compound and a pharmaceutically acceptable carrier.

"Pharmaceutically acceptable salts" are well known in the art. For example, S. M. Berge et al., describe pharmaceutically acceptable salts in detail in J. Pharmaceutical Sciences, 1977, 66, 1-19, incorporated herein by reference. Representative pharmaceutically acceptable salts include, e.g., water-soluble and water-insoluble salts, such as acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. The compounds of Formula I may form salts which are also within the scope of this disclosure. Reference to a compound of Formula I herein is understood to include reference to salts thereof, unless otherwise indicated.

A "patient" or "subject" is a mammal, e.g., a human, mouse, rat, guinea pig, dog, cat, horse, cow, pig, or non-human primate, such as a monkey, chimpanzee, baboon, or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent, or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound, a pharmaceutically acceptable salt of a disclosed compound or a composition to a subject, a pharmaceutically acceptable salt of a compound, or a composition to a subject, which can form an equivalent amount of active compound within the subject's body.

The term "cancer" includes, but is not limited to, the following cancers: bladder cancer, breast cancer (e.g., ductal carcinoma), cervical cancer (e.g., squamous cell carcinoma), colorectal cancer (e.g., adenocarcinoma), esophageal cancer (e.g., squamous cell carcinoma), gastric cancer (e.g., adenocarcinoma, medulloblastoma, colon cancer, choriocarcinoma, squamous cell carcinoma), head and neck cancer, hematologic cancer (e.g., acute lymphocytic anemia, acute myeloid leukemia, acute lymphoblastic B cell leukemia, anaplastic large cell lymphoma, B-cell lymphoma, Burkitt's lymphoma, chronic lymphocytic leukemia, chronic eosinophilic leukemia/hypereosinophilic syndrome, chronic myeloid leukemia, Hodgkin's lymphoma, mantle cell lymphoma, multiple myeloma, T-cell acute lymphoblastic leukemia), lung cancer (e.g., bronchioloalveolar adenocarcinoma, mesothelioma, mucoepidermoid carcinoma, small-cell lung cancer, non-small cell lung cancer, adenocarcinoma, squamous cell carcinoma), liver cancer (e.g., hepatocellular carcinoma), lymphoma, neurological cancer (e.g., glioblastoma, neuroblastoma, neuroglioma), ovarian (e.g., adenocarcinoma), pancreatic cancer (e.g., ductal carcinoma), prostate cancer (e.g., adenocarcinoma), renal cancer (e.g., renal cell carcinoma, clear cell renal carcinoma), sarcoma (e.g., chondrosarcoma, Ewings sarcoma, fibrosarcoma, multipotential sarcoma, osteosarcoma, rhabdomyosarcoma, synovial sarcoma), skin cancer (e.g, melanoma, epidermoid carcinoma, squamous cell carcinoma), thyroid cancer (e.g., medullary carcinoma), and uterine cancer.

Unless otherwise indicated, "PKR Activating Compound" as used herein refers to a compound having one or more of the following characteristics when tested according to the Luminescence Assay Protocol of Example 47 below: (1) an $AC_{50}$ value of less than 40 µM; (2) a maximum % Fold (MAX % Fold) value of greater than 75%; and/or (3) a % Fold value at 1.54 µM compound concentration (% Fold@ 1.54 µM) of at least 75%. In some embodiments, the Luminescence Assay Protocol of Example 47 is performed with wild type (wt) PKR, G332S mutant form of PKR or R510Q mutant form of PKR. In some embodiments, the PKR Activating Compound is a compound of Formula (I). In some embodiments, the PKR Activating Compound has: (1) an $AC_{50}$ value of less than 0.1 µM, 0.1-1.0 µM, or 1.01-40 µM; (2) a MAX % Fold of 75%-250%, 251-500%, or 75%-500%; and/or (3) a % Fold@1.54 µM of 75%-250%, 251-500%, or 75%-500%. In some embodiments, a PKR Activating Compound has (1) an $AC_{50}$ value of less than 1.0 µM; (2) a MAX % Fold of 75%-500%; and/or (3) a % Fold@ 1.54 µM of 75%-500%. In some embodiments, a PKR Activating Compound has (1) an $AC_{50}$ value of less than 1.0 µM; (2) a MAX % Fold of 75%-500%; and/or (3) a % Fold@1.54 µM of 75%-500%, obtained in the Luminescence Assay Protocol with any one or more of wild type PKR (wt), G332S mutant form of PKR, or R510Q mutant form of PKR. In some embodiments, the PKR Activating Compound has (1) an $AC_{50}$ value of less than 1.0 µM; (2) a MAX % Fold of 75%-500%; and/or (3) a % Fold@ 1.54 µM of 75%-500%, obtained in the Luminescence Assay Protocol with wild type PKR (wt). In some embodiments, the PKR Activating Compound has (1) an $AC_{50}$ value of less than 1.0 µM; (2) a MAX % Fold of 75%-500%; and/or (3) a % Fold@1.54 µM of 75%-500%, obtained in the Luminescence Assay Protocol with any one or both of G332S mutant form of PKR or R510Q mutant form of PKR.

It should be understood that all stereoisomeric forms are included within the present disclosure, including mixtures thereof.

The compounds of the disclosure may contain asymmetric or chiral centers, and, therefore, exist in different stereoisomeric forms. It is intended that all stereoisomeric forms of the compounds of the disclosure, such as those which may exist due to asymmetric carbons on various substituents, including enantiomeric forms (which may exist even in the absence of asymmetric carbons), rotameric forms, atropisomers, and diastereomeric forms, as well as mixtures thereof, including racemic mixtures, form part of the present disclosure. The assay results may reflect the data collected for the racemic form, the enantiomerically pure form, or any other form in terms of stereochemistry. Individual stereoisomers of the compounds of the disclosure may, for example, be substantially free of other isomers, or may be admixed, for example, as racemates or with all other, or other selected, stereoisomers. In some embodiments of the disclosure, the compounds of Formula (I) are enantiomers. In some embodiments, the compounds are the (S)-enantiomer. In other embodiments the compounds are the (R)-enantiomer. In some embodiments, the compounds of Formula (I) may be (+) or (−) enantiomers.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g., substituted biaryls) and are considered as part of this disclosure. Enantiomers can also be separated by use of a chiral HPLC column.

In addition, unless otherwise indicated, the present disclosure embraces all geometric and positional isomers (such as, for example, 4-pyridyl and 3-pyridyl). For example, if a compound of the disclosure incorporates a double bond or a fused ring, both the cis- and trans-forms, as well as mixtures, are embraced within the scope of the disclosure. If the compound contains a double bond, the substituent may be in the E or Z configuration, unless otherwise indicated. If the compound contains a disubstituted cycloalkyl, the cycloalkyl substituent may have a cis- or trans configuration, unless otherwise indicated.

Compounds of the disclosure, and pharmaceutically acceptable salts and stereoisomers, thereof may exist in their tautomeric form (for example, as an amide or imino ether). Moreover, all keto-enol and imine-enamine forms of the compounds are included in the disclosure. All such tautomeric forms are contemplated herein as part of the present disclosure.

The use of the terms "salt" and the like, is intended to equally apply to the salt of enantiomers, stereoisomers, rotamers, tautomers, positional isomers, and racemates of the inventive compounds.

The present disclosure relates to compounds or pharmaceutically acceptable salts thereof, capable of activating PKR and/or PKM2, which are useful for the treatment of diseases and disorders associated with modulation of a PKR and/or PKM2 enzyme. The disclosure further relates to compounds, or pharmaceutically acceptable salts thereof, which are useful for activating PKR and/or PKM2.

Compounds of the Disclosure

In one aspect of the disclosure, compounds of Formula (I) are provided:

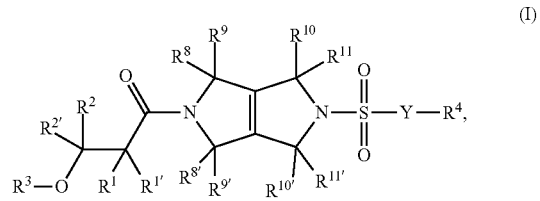

(I)

and pharmaceutically acceptable salts thereof, wherein Y, $R^1$, $R^{1'}$, $R^2$, $R^{2'}$, $R^3$, $R^4$, $R^8$, $R^{8'}$, $R^9$, $R^{9'}$, $R^{10}$, $R^{10'}$, $R^{11}$, and $R^{11'}$ are as defined above and described in classes and subclasses herein, both singly and in combination.

Unless otherwise indicated herein, each occurrence of $R^7$ and $R^{7'}$ disclosed herein for each of $R^6$, $R^{6'}$, R8, $R^{8'}$, $R^9$, $R^{9'}$, $R^{10}$, $R^{10'}$, $R^{11}$, and $R^{11'}$ is independently selected from any of the possible recited values of $R^7$ and $R^{7'}$. For example, the value $R^7$ may have a different for each of $R^6$, $R^{6'}$, $R^8$, $R^{8'}$, $R^9$, $R^{9'}$, $R^{10}$, $R^{10'}$, $R^{11}$, and $R^{11'}$ unless otherwise indicated herein.

In some embodiments, the compounds of Formula I have an $AC_{50}$ value≤40 μM for PKR activity determined by a luminescence assay (e.g., that described in Example 47, below). In some embodiments, the compounds of Formula I have an $AC_{50}$ value≤1.0 μM for PKR activity determined by a luminescence assay (e.g., that described in Example 47, below). In some embodiments, the compounds of Formula I have an $AC_{50}$ value≤0.1 μM for PKR activity determined by a luminescence assay (e.g., that described in Example 47, below).

In some embodiments, the compounds of Formula I are of the Formula (Ia):

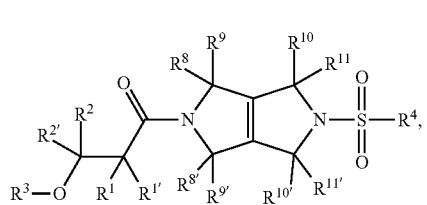

(Ia)

and pharmaceutically acceptable salts thereof, wherein $R^1$, $R^{1'}$, $R^2$, $R^{2'}$, $R^3$, $R^4$, $R^8$, $R^{8'}$, $R^9$, $R^{9'}$, $R^{10}$, $R^{10'}$, $R^{11}$, and $R^{11'}$ are as defined above and described in classes and subclasses herein, both singly and in combination.

In some embodiments, the compounds of Formula I are of the Formula (Ib):

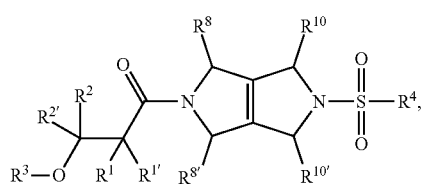

(Ib)

and pharmaceutically acceptable salts thereof, wherein $R^1$, $R^{1'}$, $R^2$, $R^{2'}$, $R^3$, $R^4$, $R^8$, $R^{8'}$, $R^{10}$, and $R^{10'}$ are as defined above and described in classes and subclasses herein, both singly and in combination.

In some embodiments, the compounds of Formula I are of the Formula (Ic):

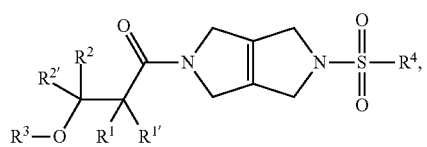

(Ic)

and pharmaceutically acceptable salts thereof, wherein $R^1$, $R^{1'}$, $R^2$, $R^{2'}$, $R^3$, and $R^4$ are as defined above and described in classes and subclasses herein, both singly and in combination.

In some embodiments, compounds of Formula (Ic) are provided, wherein:
each $R^1$, $R^{1'}$, $R^2$, and $R^{2'}$ is independently —H, —($C_1$-$C_6$)alkyl, aryl, or heteroaryl, wherein each alkyl, aryl, or heteroaryl is optionally substituted with one or more —$OR^5$;
or $R^1$ and $R^{1'}$, together with the atom to which they are attached, can combine to form a —($C_3$-$C_8$)cycloalkyl ring;

$R^3$ is —H or —($C_1$-$C_6$)alkyl;
or $R^1$ and $R^3$, together with the atoms to which they are attached, can combine to form a 5- to 8-membered heterocyclic ring, optionally fused to an aryl ring;
$R^4$ is aryl or heteroaryl, wherein each aryl or heteroaryl is optionally substituted with one or more substituents selected from the group consisting of —$R^5$ and —$OR^5$;
each $R^5$ is independently —H or —($C_1$-$C_6$)alkyl, wherein each alkyl is optionally substituted with one or more halogen;
or two $R^5$ on adjacent atoms together with the atoms to which they are attached form a heterocycloalkyl ring optionally substituted with one or more $R^6$; and
each $R^6$ is —($C_1$-$C_6$)alkyl.

In some embodiments, compounds of Formula (Ic) are provided, wherein:
each $R^1$, $R^{1'}$, $R^2$, and $R^{2'}$ is independently —H, phenyl, pyridyl, ethyl, or methyl optionally substituted with —$OR^5$;
or $R^1$ and $R^{1'}$, together with the atom to which they are attached, can combine to form a cyclopropyl ring;
$R^3$ is —H or methyl;
or $R^1$ and $R^3$, together with the atoms to which they are attached, can combine to form a tetrahydrofuran, tetrahydropyran, 2,3-dihydrobenzofuran, or morpholine;
$R^4$ is phenyl, pyridyl, benzothiazolyl, benzofuranyl, or benzoxazolyl, wherein each phenyl, pyridyl, or benzoxazolyl is optionally substituted with one or two substituents selected from the group consisting of —$R^5$ and —$OR^5$;
each $R^5$ is independently —H or methyl optionally substituted with two or more halogen;
or two $R^5$ on adjacent atoms together with the atoms to which they are attached form a heterocycloalkyl ring, comprising two heteroatoms selected from the group consisting of O and N, optionally substituted with one or two $R^6$; and
each $R^6$ is methyl.

In some embodiments, the compounds of Formula I are of the Formula (Id-1):

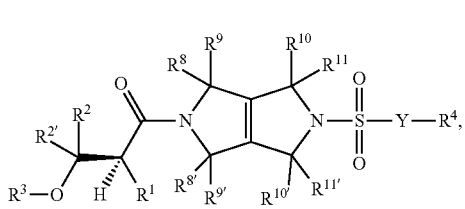

(Id-1)

and pharmaceutically acceptable salts thereof, wherein Y, $R^4$, $R^8$, $R^{8'}$, $R^9$, $R^{9'}$, $R^{10}$, $R^{10'}$, $R^{11}$, and $R^{11'}$ are as defined above and described in classes and subclasses herein, both singly and in combination; and
$R^1$ is —($C_1$-$C_6$)alkyl, —($C_2$-$C_6$)alkenyl, —($C_2$-$C_6$)alkynyl, —($C_3$-$C_8$)cycloalkyl, —($C_4$-$C_8$)cycloalkenyl, heterocyclyl, aryl, heteroaryl, halogen, —CN, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^5$, —$NR^5S(O)R^5$, —$C(O)R^5$, or —$C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —S(O)$_2$NR$^5$R$^{5'}$, —S(O)R$^5$, —S(O)NR$^5$R$^{5'}$, —NR$^5$S(O)$_2$R$^{5'}$, —NR$^5$S(O)R$^{5'}$, —C(O)R$^5$, and —C(O)OR$^5$;

each R$^2$ and R$^{2'}$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_4$-C$_8$)cycloalkenyl, heterocyclyl, aryl, heteroaryl, halogen, —CN, —OR$^5$, —SR$^5$, —NO$_2$, —NR$^5$R$^{5'}$, —S(O)$_2$R$^5$, —S(O)$_2$NR$^5$R$^{5'}$, —S(O)R$^5$, —S(O)NR$^5$R$^{5'}$, —NR$^5$S(O)$_2$R$^{5'}$, NR$^5$S(O)R$^{5'}$, —C(O)R$^5$, or —C(O)OR$^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —R$^5$, —OR$^5$, —SR$^5$, —NO$_2$, —NR$^5$R$^{5'}$, —S(O)$_2$R$^5$, —S(O)$_2$NR$^5$R$^{5'}$, —S(O)R$^5$, —S(O)NR$^5$R$^{5'}$, —NR$^5$S(O)$_2$R$^{5'}$, —NR$^5$S(O)R$^{5'}$, —C(O)R$^5$, and —C(O)OR$^5$;

or R$^2$ and R$^{2'}$, together with the atom to which they are attached, can combine to form —(C$_3$-C$_8$)cycloalkyl ring, heterocycle, (C$_5$-C$_8$)spirocycle or 5- to 8-membered spiroheterocycle;

or R$^1$ and R$^2$, together with the atoms to which they are attached, can combine to form a —(C$_3$-C$_8$)cycloalkyl or a 3- to 8-membered heterocycle;

R$^3$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_4$-C$_8$)cycloalkenyl, heterocyclyl, aryl, heteroaryl, —S(O)$_2$R$^5$, —S(O)$_2$NR$^5$R$^{5'}$, —S(O)R$^5$, —S(O)NR$^5$R$^{5'}$, —C(O)R$^5$, or —C(O)OR$^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —R$^5$, —OR$^5$, —SR$^5$, —NO$_2$, —NR$^5$R$^{5'}$, —S(O)$_2$R$^5$, —S(O)$_2$NR$^5$R$^{5'}$, —S(O)R$^5$, —S(O)NR$^5$R$^{5'}$, —NR$^5$S(O)$_2$R$^{5'}$, —NR$^5$S(O)R$^{5'}$, —C(O)R$^5$, and —C(O)OR$^5$;

or R$^2$ and R$^3$, together with the atoms to which they are attached, can combine to form a 5- to 8-membered heterocyclic ring; and or R$^1$ and R$^3$, together with the atoms to which they are attached, can combine to form a 5- to 8-membered heterocyclic ring, optionally fused to an aryl or heteroaryl ring.

In some embodiments, the compounds of Formula (Id-1) are of the Formula (Ia-1):

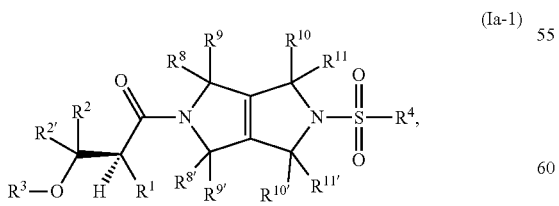

(Ia-1)

and pharmaceutically acceptable salts thereof, wherein R$^1$, R$^2$, R$^{2'}$, R$^3$, R$^4$, R$^8$, R$^{8'}$, R$^9$, R$^{9'}$, R$^{10}$, R$^{10'}$, R$^{11}$, and R$^{11'}$ are as defined above and described in classes and subclasses herein, both singly and in combination.

In some embodiments, the compounds of Formula (Id-1) are of the Formula (Ib-1):

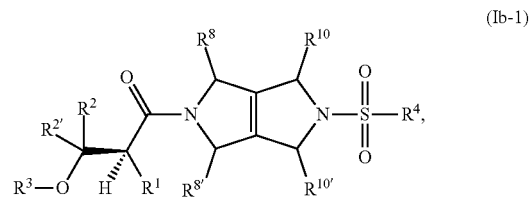

(Ib-1)

and pharmaceutically acceptable salts thereof, wherein R$^1$, R$^2$, R$^{2'}$, R$^3$, R$^4$, R$^8$, R$^{8'}$, R$^{10}$, and R$^{10'}$ are as defined above and described in classes and subclasses herein, both singly and in combination.

In some embodiments, the compounds of Formula (Id-1) are of the Formula (Ic-1):

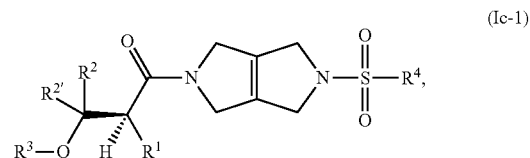

(Ic-1)

and pharmaceutically acceptable salts thereof, wherein R$^1$, R$^2$, R$^{2'}$, R$^3$, and R$^4$ are as defined above and described in classes and subclasses herein, both singly and in combination.

In some embodiments, the compounds of Formula I are of the Formula (Id-2):

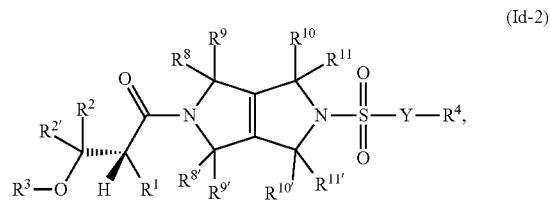

(Id-2)

and pharmaceutically acceptable salts, thereof, wherein Y, R$^4$, R$^8$, R$^{8'}$, R$^9$, R$^{9'}$, R$^{10}$, R$^{10'}$, R$^{11}$, and R$^{11'}$ are as defined above and described in classes and subclasses herein, both singly and in combination; and R$^1$ is —(C$_1$-C$_6$)alkyl, —(C$_2$-C$_6$)alkenyl, —(C$_2$-C$_6$)alkynyl, —(C$_3$-C$_8$)cycloalkyl, —(C$_4$-C$_8$)cycloalkenyl, heterocyclyl, aryl, heteroaryl, halogen, —CN, —OR$^5$, —SR$^5$, —NO$_2$, —NR$^5$R$^{5'}$, —S(O)$_2$R$^5$, —S(O)$_2$NR$^5$R$^{5'}$, —S(O)R$^5$, —S(O)NR$^5$R$^{5'}$, —NR$^5$S(O)$_2$R$^{5'}$, —NR$^5$S(O)R$^{5'}$, —C(O)R$^5$, or —C(O)OR$^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —R$^5$, —OR$^5$, —SR$^5$, —NO$_2$, —NR$^5$R$^{5'}$, —S(O)$_2$R$^5$, —S(O)$_2$NR$^5$R$^{5'}$, —S(O)R$^5$, —S(O)NR$^5$R$^{5'}$, —NR$^5$S(O)$_2$R$^{5'}$, —NR$^5$S(O)R$^{5'}$, —C(O)R$^5$, and —C(O)OR$^5$;

each R$^2$ and R$^{2'}$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_4$-C$_8$)cycloalkenyl, heterocyclyl, aryl, heteroaryl, halogen, —CN, —OR$^5$, —SR$^5$, —NO$_2$, —NR$^5$R$^{5'}$, —S(O)$_2$R$^5$, —S(O)$_2$NR$^5$R$^{5'}$, —S(O)R$^5$, —S(O)NR$^5$R$^{5'}$, —NR$^5$S(O)$_2$R$^{5'}$, NR$^5$S(O)R$^{5'}$, —C(O)R$^5$, or —C(O)OR$^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —R$^5$, —OR$^5$, —SR$^5$, —NO$_2$, —NR$^5$R$^{5'}$, —S(O)$_2$R$^5$, —S(O)$_2$NR$^5$R$^{5'}$, —S(O)R$^5$, —S(O)NR$^5$R$^{5'}$, —NR$^5$S(O)$_2$R$^{5'}$, —NR$^5$S(O)R$^{5'}$, —C(O)R$^5$, and —C(O)OR$^5$;

or R$^2$ and R$^{2'}$, together with the atom to which they are attached, can combine to form —(C$_3$-C$_8$)cycloalkyl ring, heterocycle, (C$_5$-C$_8$)spirocycle or 5- to 8-membered spiroheterocycle;

or R$^1$ and R$^2$, together with the atoms to which they are attached, can combine to form a —(C$_3$-C$_8$)cycloalkyl or a 3- to 8-membered heterocycle;

R$^3$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_4$-C$_8$)cycloalkenyl, heterocyclyl, aryl, heteroaryl, —S(O)$_2$R$^5$, —S(O)$_2$NR$^5$R$^{5'}$, —S(O)R$^5$, —S(O)NR$^5$R$^{5'}$, —C(O)R$^5$, or —C(O)OR$^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —R$^5$, —OR$^5$, —SR$^5$, —NO$_2$, —NR$^5$R$^{5'}$, —S(O)$_2$R$^5$, —S(O)$_2$NR$^5$R$^{5'}$, —S(O)R$^5$, —S(O)NR$^5$R$^{5'}$, —NR$^5$S(O)$_2$R$^{5'}$, —NR$^5$S(O)R$^{5'}$, —C(O)R$^5$, and —C(O)OR$^5$;

or R$^2$ and R$^3$, together with the atoms to which they are attached, can combine to form a 5- to 8-membered heterocyclic ring; and or R$^1$ and R$^3$, together with the atoms to which they are attached, can combine to form a 5- to 8-membered heterocyclic ring, optionally fused to an aryl or heteroaryl ring.

In some embodiments, the compounds of Formula (Id-2) are of the Formula (Ia-2):

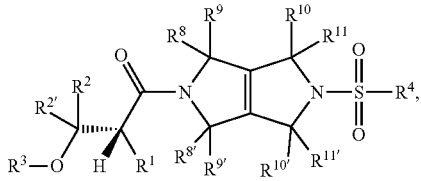
(Ia-2)

and pharmaceutically acceptable salts thereof, wherein R$^1$, R$^2$, R$^{2'}$, R$^3$, R$^4$, R$^8$, R$^{8'}$, R$^9$, R$^{9'}$, R$^{10}$, R$^{10'}$, R$^{11}$, and R$^{11'}$ are as defined above and described in classes and subclasses herein, both singly and in combination.

In some embodiments, the compounds of Formula (Id-2) are of the Formula (Ib-2):

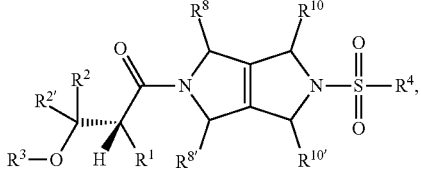
(Ib-2)

and pharmaceutically acceptable salts thereof, wherein R$^1$, R$^2$, R$^{2'}$, R$^3$, R$^4$, R$^8$, R$^{8'}$, R$^{10}$ and R$^{10'}$ are as defined above and described in classes and subclasses herein, both singly and in combination.

In some embodiments, the compounds of Formula (Id-2) are of the Formula (Ic-2):

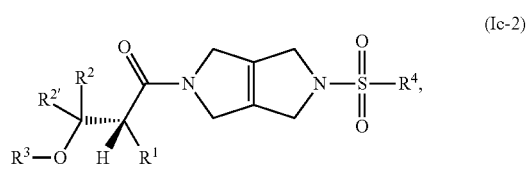
(Ic-2)

and pharmaceutically acceptable salts thereof, wherein R$^1$, R$^2$, R$^{2'}$, R$^3$, and R$^4$ are as defined above and described in classes and subclasses herein, both singly and in combination.

In some embodiments of Formula (I), (Ia), (Ib), and (Ic), R$^1$ and R$^{1'}$ are each independently hydrogen, optionally substituted —(C$_1$-C$_6$)alkyl (e.g., methyl optionally substituted with —OR$^5$, or ethyl), optionally substituted aryl (e.g., phenyl), or optionally substituted heteroaryl (e.g., pyridyl), or R$^1$ and R$^{1'}$ are taken together with the atoms to which they are attached to form an optionally substituted —(C$_3$-C$_4$)cycloalkyl (e.g., cyclopropyl). In some embodiments, R$^1$ and R$^{1'}$ are both hydrogen. In some embodiments, R$^1$ and R$^{1'}$ are both optionally substituted —(C$_1$-C$_6$)alkyl. In some embodiments, one of R$^1$ and R$^{1'}$ is optionally substituted —(C$_1$-C$_6$)alkyl, optionally substituted aryl, or optionally substituted heteroaryl. In some embodiments, one of R$^1$ and R$^{1'}$ is optionally substituted aryl or optionally substituted heteroaryl. In some embodiments, one of R$^1$ and R$^{1'}$ is hydrogen. In some embodiments, one of R$^1$ and R$^{1'}$ is optionally substituted —(C$_1$-C$_6$)alkyl. In some embodiments, one of R$^1$ and R$^{1'}$ is optionally substituted aryl. In some embodiments, one of R$^1$ and R$^{1'}$ is optionally substituted heteroaryl. In some embodiments, R$^1$ and R$^{1'}$ are taken together with the atoms to which they are attached to form an optionally substituted —(C$_3$-C$_4$)cycloalkyl.

In some embodiments of Formula (Id-1), (Ia-1), (Ib-1), (Ic-1), (Id-2), (Ia-2), (Ib-2), and (Ic-2), R$^1$ is optionally substituted —(C$_1$-C$_6$)alkyl (e.g., methyl optionally substituted with —OR$^5$, or ethyl), optionally substituted aryl (e.g., phenyl), or optionally substituted heteroaryl (e.g., pyridyl). In some embodiments, R$^1$ is optionally substituted —(C$_1$-C$_6$)alkyl. In some embodiments, R$^1$ is optionally substituted aryl. In some embodiments, R$^1$ is optionally substituted heteroaryl.

In some embodiments of Formula (I), (Ia), (Ib), (Ic), (Id-1), (Ia-1), (Ib-1), (Ic-1), (Id-2), (Ia-2), (Ib-2), and (Ic-2), R$^2$ and R$^{2'}$ are each independently hydrogen or optionally substituted —(C$_1$-C$_6$)alkyl (e.g., methyl). In some embodiments, R$^2$ and R$^{2'}$ are both hydrogen. In some embodiments, R$^2$ and R$^{2'}$ are both optionally substituted —(C$_1$-C$_6$)alkyl. In some embodiments, one of R$^2$ and R$^{2'}$ is hydrogen. In some embodiments, one of R$^2$ and R$^{2'}$ is optionally substituted —(C$_1$-C$_6$)alkyl.

In some embodiments of Formula (I), (Ia), (Ib), (Ic), (Id-1), (Ia-1), (Ib-1), (Ic-1), (Id-2), (Ia-2), (Ib-2), and (Ic-2), R$^3$ is hydrogen or optionally substituted —(C$_1$-C$_6$)alkyl (e.g., methyl). In some embodiments, R$^3$ is hydrogen. In some embodiments, R$^3$ is optionally substituted —(C$_1$-C$_6$)alkyl.

In some embodiments of Formula (I), (Ia), (Ib), and (Ic), $R^3$ and one of $R^1$ or $R^{1'}$ are taken together with the atoms to which they are attached to form an optionally substituted 5-6-membered heterocyclic ring, optionally fused to an aryl ring (e.g., tetrahydrofuran, tetrahydropyran, 2,3-dihydrobenzofuran, or morpholine). In some embodiments, $R^3$ and $R^1$ combine to form an optionally substituted heterocyclic ring selected from the group consisting of tetrahydrofuran, tetrahydropyran, morpholine, dioxane, and 2,3-dihydrobenzofuran.

In some embodiments of Formula (Id-1), (Ia-1), (Ib-1), (Ic-1), (Id-2), (Ia-2), (Ib-2), and (Ic-2), $R^3$ and $R^1$ are taken together with the atoms to which they are attached to form an optionally substituted 5-6-membered heterocyclic ring (e.g., tetrahydrofuran, tetrahydropyran, 2,3-dihydrobenzofuran, or morpholine). In some embodiments, $R^3$ and $R^1$ combine to form an optionally substituted heterocyclic ring selected from the group consisting of tetrahydrofuran, tetrahydropyran, morpholine, dioxane, and 2,3-dihydrobenzofuran.

In some embodiments of Formula (I), (Ia), (Ib), and (Ic), $R^1$ and $R^{1'}$ are each independently hydrogen or optionally substituted phenyl or pyridyl; $R^2$ and $R^{2'}$ are each independently hydrogen; and $R^3$ is hydrogen or optionally substituted $-(C_1-C_6)$alkyl. In some embodiments, $R^1$ and $R^{1'}$ are each independently hydrogen or optionally substituted phenyl or pyridyl; $R^2$ and $R^{2'}$ are each independently hydrogen; and $R^3$ is hydrogen. In some embodiments, one of $R^1$ and $R^{1'}$ is hydrogen and the other is optionally substituted phenyl; $R^2$ and $R^{2'}$ are each independently hydrogen; and $R^3$ is hydrogen or optionally substituted $-(C_1-C_6)$alkyl. In some embodiments, one of $R^1$ and $R^{1'}$ is hydrogen and the other is optionally substituted pyridyl; $R^2$ and $R^{2'}$ are each independently hydrogen; and $R^3$ is hydrogen or optionally substituted $-(C_1-C_6)$alkyl. In some embodiments, $R^1$ and $R^{1'}$ are each independently hydrogen or optionally substituted phenyl or pyridyl; $R^2$ and $R^{2'}$ are each independently hydrogen or optionally substituted $-(C_1-C_6)$alkyl; and $R^3$ is hydrogen. In some embodiments, one of $R^1$ and $R^{1'}$ is hydrogen and the other is optionally substituted phenyl; $R^2$ and $R^{2'}$ are each independently hydrogen or optionally substituted $-(C_1-C_6)$alkyl; and $R^3$ is hydrogen. In some embodiments, one of $R^1$ and $R^{1'}$ is hydrogen and the other is optionally substituted pyridyl; $R^2$ and $R^{2'}$ are each independently hydrogen or optionally substituted $-(C_1-C_6)$alkyl; and $R^3$ is hydrogen.

In some embodiments of Formula (Id-1), (Ia-1), (Ib-1), (Ic-1), (Id-2), (Ia-2), (Ib-2), and (Ic-2), $R^1$ is optionally substituted phenyl or pyridyl; $R^2$ and $R^{2'}$ are each independently hydrogen; and $R^3$ is hydrogen or optionally substituted $-(C_1-C_6)$alkyl. In some embodiments, $R^1$ is optionally substituted phenyl or pyridyl; $R^2$ and $R^{2'}$ are each independently hydrogen; and $R^3$ is hydrogen. In some embodiments, $R^1$ is optionally substituted phenyl or pyridyl; $R^2$ and $R^{2'}$ are each independently hydrogen or optionally substituted $-(C_1-C_6)$alkyl; and $R^3$ is hydrogen. In some embodiments, $R^1$ is optionally substituted phenyl; $R^2$ and $R^{2'}$ are each independently hydrogen or optionally substituted $-(C_1-C_6)$alkyl; and $R^3$ is hydrogen. In some embodiments, $R^1$ is optionally substituted pyridyl; $R^2$ and $R^{2'}$ are each independently hydrogen or optionally substituted $-(C_1-C_6)$alkyl; and $R^3$ is hydrogen.

In some embodiments of Formula (I), (Ia), (Ib), (Ic), (Id-1), (Ia-1), (Ib-1), (Ic-1), (Id-2), (Ia-2), (Ib-2), and (Ic-2), $R^4$ is optionally substituted aryl (e.g., phenyl) or heteroaryl (e.g., pyridyl, benzofuranyl, benzoxazolyl, or benzothiazolyl). In some embodiments, the aryl or heteroaryl is optionally substituted with one or more substituents selected from the group consisting of oxo, halogen, $-CN$, $-R^5$, $-OR^5$, $-SR^5$, $-NO_2$, $-NR^5R^{5'}$, $-S(O)_2R^5$, $-S(O)_2NR^5R^{5'}$, $-S(O)R^5$, $-S(O)NR^5R^{5'}$, $-NR^5S(O)_2R^{5'}$, $-NR^5S(O)R^{5'}$, $-C(O)R^5$, and $-C(O)OR^5$. In some embodiments, the aryl or heteroaryl is optionally substituted with one or more substituents selected from the group consisting of halogen, oxo, $-CN$, $-R^5$, $-OR^5$, $-S(O)_2NR^5R^{5'}$, $-S(O)NR^5R^{5'}$, and $-C(O)R^5$. In some embodiments, aryl or heteroaryl is optionally substituted with one or more substituents selected from the group consisting of $-R^5$ and $-OR^5$.

In some embodiments, $R^4$ is aryl or heteroaryl optionally substituted with one or more $-R^5$ or $-OR^5$, or two $R^5$ on adjacent atoms, together with the atoms to which they are attached, form a heterocycloalkyl ring, optionally substituted with one or more $R^6$. In some embodiments, $R^4$, including any substitution thereof, is selected from the group consisting of:

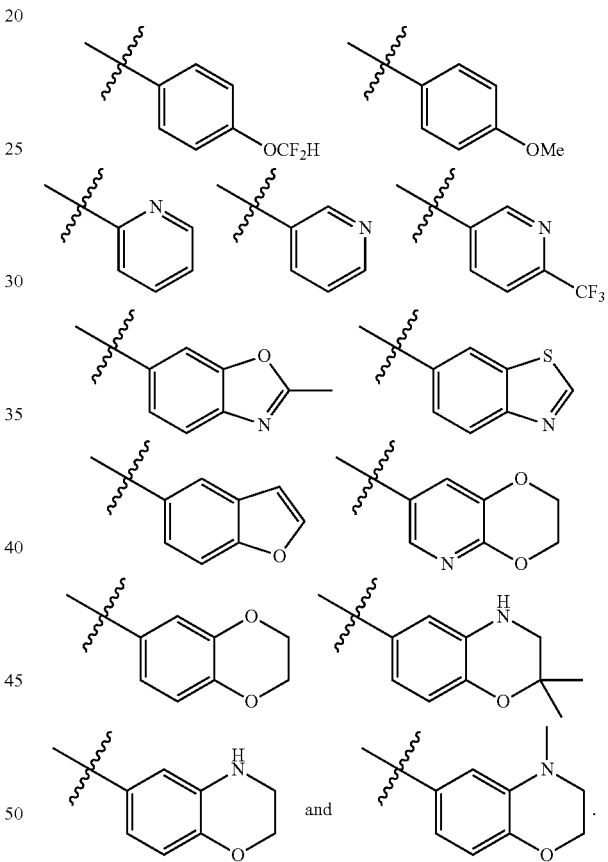

In some embodiments, $R^4$ is 6-membered aryl or heteroaryl substituted with two $-R^5$, selected from the group consisting of $-OR^6$ and $-NR^6R^{6'}$, on adjacent atoms of $R^4$, that together with the atoms to which they are attached form a heterocycloalkyl ring fused to $R^4$ that is optionally substituted with one or more $R^6$, selected from the group consisting of $-H$ and $-(C_1-C_6)$alkyl.

In some embodiments, each $R^5$ is independently $-H$, $-(C_1-C_6)$alkyl (e.g., methyl, optionally substituted with one or more halogen), halogen, $-CN$, $-OR^6$, $-SR^6$, $-NO_2$, $-NR^6R^{6'}$, $-S(O)_2R^6$, $-S(O)_2NR^6R^{6'}$, $-S(O)R^6$, $-S(O)NR^6R^{6'}$, $-NR^6S(O)_2R^{6'}$, $-NR^6S(O)R^{6'}$, $-C(O)R^6$, or $-C(O)OR^6$. In some embodiments, each $R^5$ is independently $-H$ or optionally substituted $-(C_1-C_6)$alkyl.

In some embodiments, two $R^5$ on adjacent atoms, together with the atoms to which they are attached, form an aryl ring optionally substituted with one or more $R^6$. In some embodiments, two $R^5$ on adjacent atoms, together with the atoms to which they are attached, form a heteroaryl ring optionally substituted with one or more $R^6$. In some embodiments, two $R^5$ on adjacent atoms together with the atoms to which they are attached form a $(C_3-C_8)$cycloalkyl ring optionally substituted with one or more $R^6$. In some embodiments, two $R^5$ on adjacent atoms together with the atoms to which they are attached form a heterocycloalkyl ring optionally substituted with one or more $R^6$.

In some embodiments, each $R^6$ is independently —H, —$(C_1-C_6)$alkyl (e.g., methyl), halogen, —CN, —$OR^7$, —$SR^7$, —$NO_2$, —$NR^7R^{7'}$, —$S(O)_2R^7$, —$S(O)_2NR^7R^{7'}$, —$S(O)R^7$, —$S(O)NR^7R^{7'}$, —$NR^7S(O)_2R^{7'}$, —$NR^7S(O)R^{7'}$, —$C(O)R^7$, or —$C(O)OR^7$. In some embodiments, $R^6$ is —$(C_1-C_6)$alkyl.

In some embodiments, Y is a bond.
In some embodiments, Y is —$CR^5R^{5'}$—.
In some embodiments, Y is —$NR^5(CR^5R^{5'})_t$—.
In some embodiments, Y is —O—.

Nonlimiting examples of the compounds of the disclosure include:

| Example | Structure | Name |
|---|---|---|
| 1 | 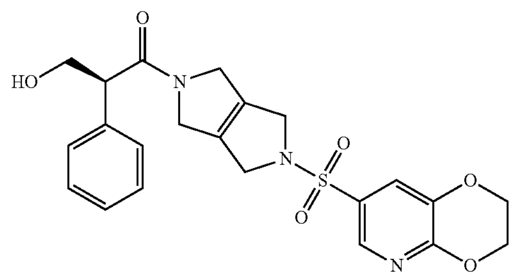 [SMILES: O=C([C@H](CO)c1ccccc1)N1CC2=C(C1)CN(S(=O)(=O)c1cnc3c(c1)OCCO3)C2] | (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one |
| 2 | 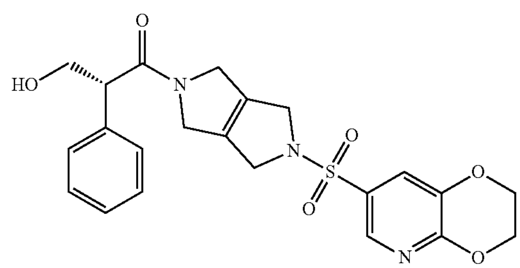 [SMILES: O=C([C@@H](CO)c1ccccc1)N1CC2=C(C1)CN(S(=O)(=O)c1cnc3c(c1)OCCO3)C2] | (R)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one |
| 3[a] | 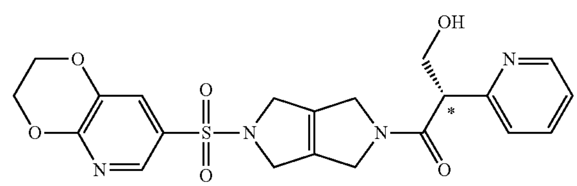 | (R or S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-(pyridin-2-yl)propan-1-one |
| 4[a] | 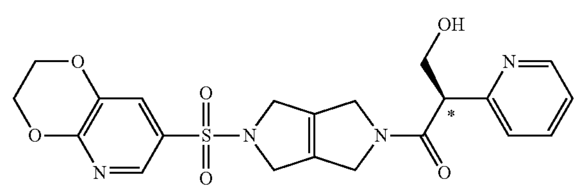 [SMILES: O=C([C@@H](CO)c1ccccn1)N1CC2=C(C1)CN(S(=O)(=O)c1cnc3c(c1)OCCO3)C2] | (S or R)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-(pyridin-2-yl)propan-1-one |
| 5[b] | 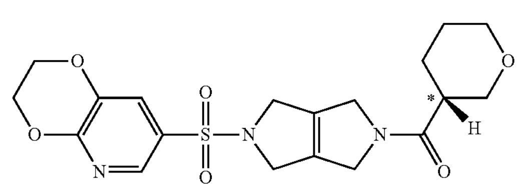 [SMILES: O=C([C@@H]1CCCOC1)N1CC2=C(C1)CN(S(=O)(=O)c1cnc3c(c1)OCCO3)C2] | (R or S)-(5-((2,3-dihydro-[1,4]dioxino[2,3-b]pyridin-7-yl)sulfonyl)-3,4,5,6-tetrahydropyrrolo[3,4-c]pyrrol-2(1H)-yl)(tetrahydro-2H-pyran-3-yl)methanone |
| 6[b] | 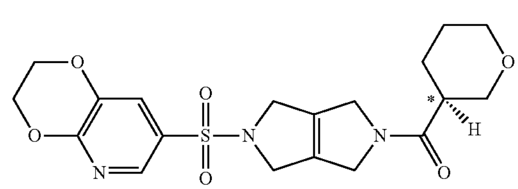 [SMILES: O=C([C@H]1CCCOC1)N1CC2=C(C1)CN(S(=O)(=O)c1cnc3c(c1)OCCO3)C2] | (S or R)-(5-((2,3-dihydro-[1,4]dioxino[2,3-b]pyridin-7-yl)sulfonyl)-3,4,5,6-tetrahydropyrrolo[3,4-c]pyrrol-2(1H)-yl)(tetrahydro-2H-pyran-3-yl)methanone |

| Example | Structure | Name |
| --- | --- | --- |
| 7 | 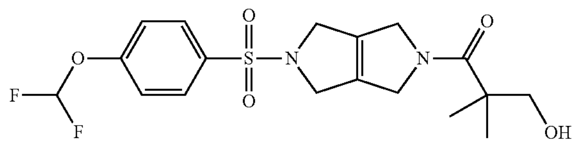 [SMILES: CC(C)(CO)C(=O)N1CC2=C(C1)CN(S(=O)(=O)c1ccc(OC(F)F)cc1)C2] | 1-(5-((4-(difluoromethoxy)phenyl)sulfonyl)-3,4,5,6-tetrahydropyrrolo[3,4-c]pyrrol-2(1H)-yl)-3-hydroxy-2,2-dimethylpropan-1-one |
| 8 | 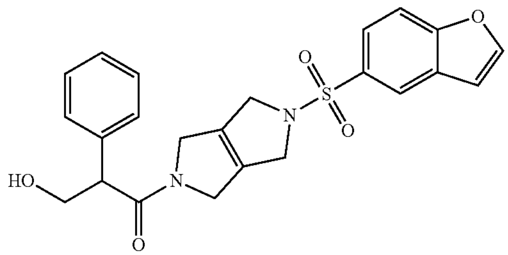 [SMILES: O=C(C(CO)c1ccccc1)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-3-hydroxy-2-phenylpropan-1-one |
| 9 | 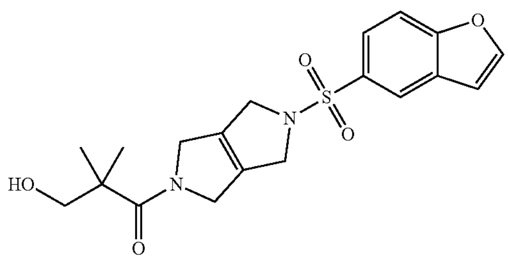 [SMILES: CC(C)(CO)C(=O)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-3-hydroxy-2,2-dimethylpropan-1-one |
| 10 | 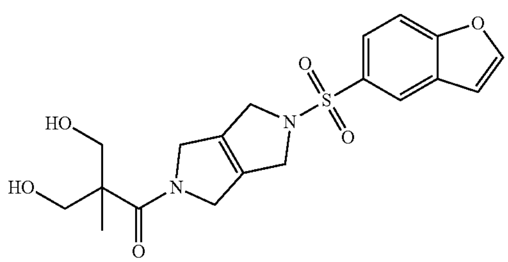 [SMILES: CC(CO)(CO)C(=O)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-3-hydroxy-2-(hydroxymethyl)-2-methylpropan-1-one |
| 11 | 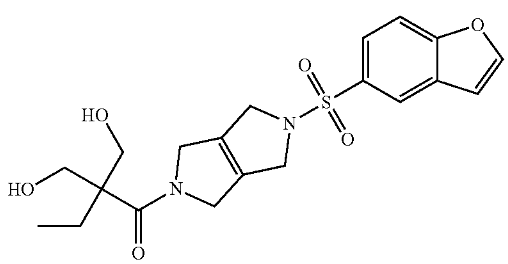 [SMILES: CCC(CO)(CO)C(=O)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-2,2-bis(hydroxymethyl)butan-1-one |
| 12 | 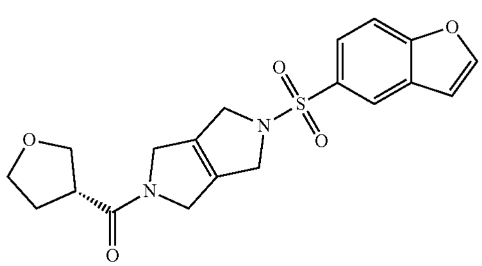 [SMILES: O=C([C@@H]1CCOC1)N1CC2=C(C1)CN(S(=O)(=O)c1ccc3occc3c1)C2] | (R)-(5-(benzofuran-5-ylsulfonyl)-3,4,5,6-tetrahydropyrrolo[3,4-c]pyrrol-2(1H)-yl)(tetrahydrofuran-3-yl)methanone |

| Example | Structure | Name |
|---|---|---|
| 13 | 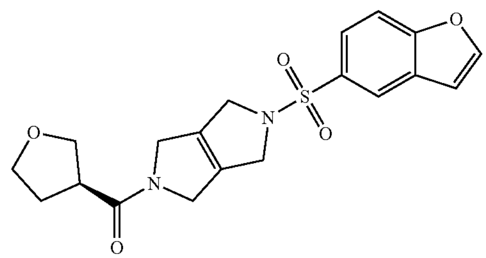 [SMILES: O=C([C@H]1CCOC1)N1CC2=C(C1)CN(S(=O)(=O)c1ccc3occc3c1)C2] | (S)-(5-(benzofuran-5-ylsulfonyl)-3,4,5,6-tetrahydropyrrolo[3,4-c]pyrrol-2(1H)-yl)(tetrahydrofuran-3-yl)methanone |
| 14 | 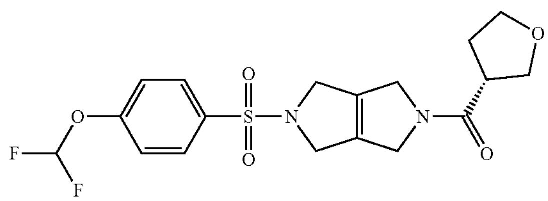 [SMILES: O=C([C@@H]1CCOC1)N1CC2=C(C1)CN(S(=O)(=O)c1ccc(OC(F)F)cc1)C2] | (R)-(5-((4-(difluoromethoxy)phenyl)sulfonyl)-3,4,5,6-tetrahydropyrrolo[3,4-c]pyrrol-2(1H)-yl)(tetrahydrofuran-3-yl)methanone |
| 15 | 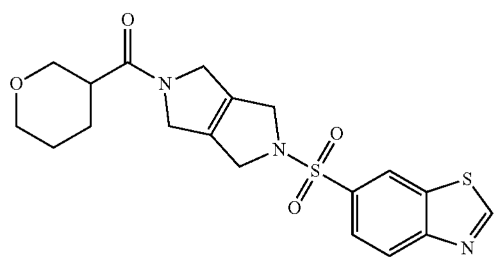 [SMILES: O=C(C1CCCOC1)N1CC2=C(C1)CN(S(=O)(=O)c1ccc3ncsc3c1)C2] | (5-(benzo[d]thiazol-6-ylsulfonyl)-3,4,5,6-tetrahydropyrrolo[3,4-c]pyrrol-2(1H)-yl)(tetrahydro-2H-pyran-3-yl)methanone |
| 16 | 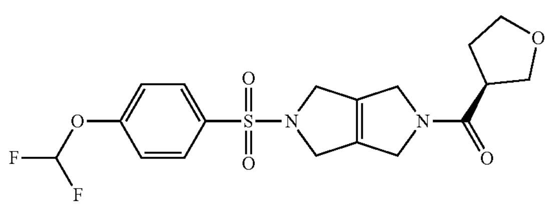 [SMILES: O=C([C@H]1CCOC1)N1CC2=C(C1)CN(S(=O)(=O)c1ccc(OC(F)F)cc1)C2] | (S)-(5-((4-(difluoromethoxy)phenyl)sulfonyl)-3,4,5,6-tetrahydropyrrolo[3,4-c]pyrrol-2(1H)-yl)(tetrahydrofuran-3-yl)methanone |
| 17 | 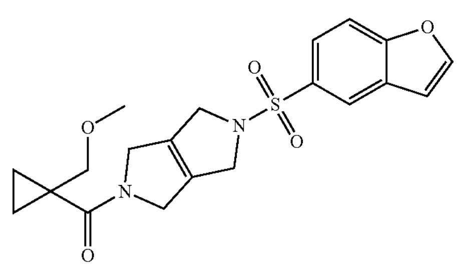 [SMILES: COCC1(C(=O)N2CC3=C(C2)CN(S(=O)(=O)c2ccc4occc4c2)C3)CC1] | (5-(benzofuran-5-ylsulfonyl)-3,4,5,6-tetrahydropyrrolo[3,4-c]pyrrol-2(1H)-yl)(1-(methoxymethyl)cyclopropyl)methanone |
| 18 | 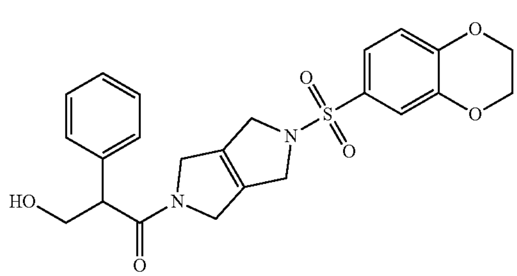 [SMILES: O=C(C(CO)c1ccccc1)N1CC2=C(C1)CN(S(=O)(=O)c1ccc3c(c1)OCCO3)C2] | 1-(5-((2,3-dihydrobenzo[b][1,4]dioxin-6-yl)sulfonyl)-3,4,5,6-tetrahydropyrrolo[3,4-c]pyrrol-2(1H)-yl)-3-hydroxy-2-phenylpropan-1-one |

-continued

| Example | Structure | Name |
|---|---|---|
| 19 | 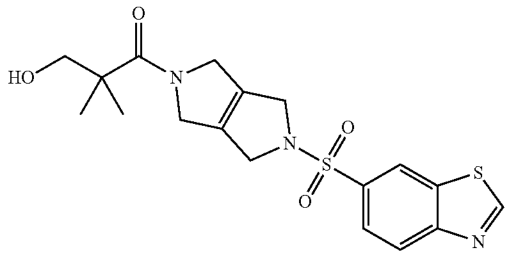 [SMILES: CC(C)(CO)C(=O)N1CC2=C(C1)CN(S(=O)(=O)c1ccc3ncsc3c1)C2] | 1-(5-(benzo[d]thiazol-6-ylsulfonyl)-3,4,5,6-tetrahydropyrrolo[3,4-c]pyrrol-2(1H)-yl)-3-hydroxy-2,2-dimethylpropan-1-one |
| 20 | 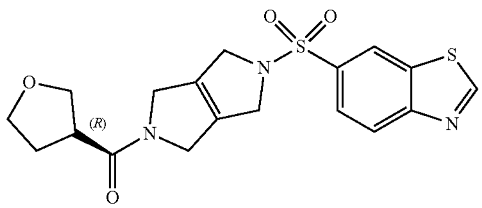 | (R)-(5-(benzo[d]thiazol-6-ylsulfonyl)-3,4,5,6-tetrahydropyrrolo[3,4-c]pyrrol-2(1H)-yl)(tetrahydrofuran-3-yl)methanone |
| 21 | 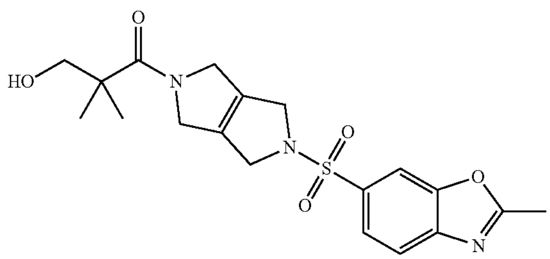 [SMILES: Cc1nc2ccc(S(=O)(=O)N3CC4=C(CN(C(=O)C(C)(C)CO)C4)C3)cc2o1] | 3-hydroxy-2,2-dimethyl-1-(5-((2-methylbenzo[d]oxazol-6-yl)sulfonyl)-3,4,5,6-tetrahydropyrrolo[3,4-c]pyrrol-2(1H)-yl)propan-1-one |
| 22 | 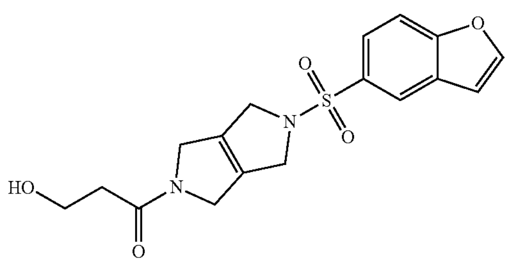 [SMILES: O=C(CCO)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-3-hydroxypropan-1-one |
| 23 | 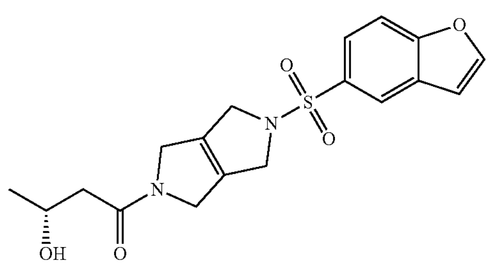 [SMILES: C[C@@H](O)CC(=O)N1CC2=C(C1)CN(S(=O)(=O)c1ccc3occc3c1)C2] | (R)-1-(5-(benzofuran-5-ylsulfonyl)-3,4,5,6-tetrahydropyrrolo[3,4-c]pyrrol-2(1H)-yl)-3-hydroxybutan-1-one |
| 24 | 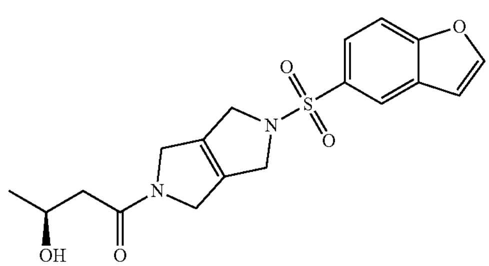 [SMILES: C[C@H](O)CC(=O)N1CC2=C(C1)CN(S(=O)(=O)c1ccc3occc3c1)C2] | (S)-1-(5-(benzofuran-5-ylsulfonyl)-3,4,5,6-tetrahydropyrrolo[3,4-c]pyrrol-2(1H)-yl)-3-hydroxybutan-1-one |

-continued

| Example | Structure | Name |
| --- | --- | --- |
| 25 | 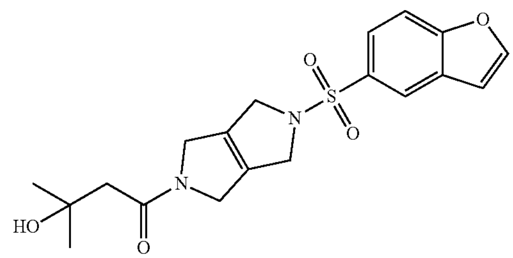 [SMILES: CC(C)(O)CC(=O)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-3-hydroxy-3-methylbutan-1-one |
| 26 | (+/−) | (2S,3R and 2R,3S)-1-(5-((4-(difluoromethoxy)phenyl)sulfonyl)-3,4,5,6-tetrahydropyrrolo[3,4-c]pyrrol-2(1H)-yl)-3-hydroxy-2-phenylbutan-1-one |
| 27 | (+/−) | (2R,3R and 2S,3S)-1-(5-((4-(difluoromethoxy)phenyl)sulfonyl)-3,4,5,6-tetrahydropyrrolo[3,4-c]pyrrol-2(1H)-yl)-3-hydroxy-2-phenylbutan-1-one |
| 28 | 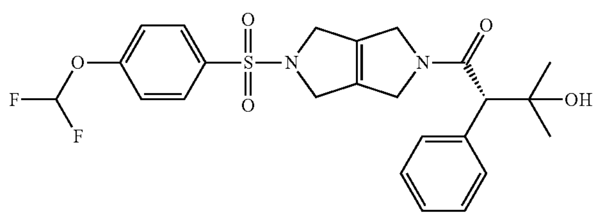 [SMILES: CC(C)(O)[C@@H](C(=O)N1CC2=C(C1)CN(S(=O)(=O)c1ccc(OC(F)F)cc1)C2)c1ccccc1] | (S)-1-(5-((4-(difluoromethoxy)phenyl)sulfonyl)-3,4,5,6-tetrahydropyrrolo[3,4-c]pyrrol-2(1H)-yl)-3-hydroxy-3-methyl-2-phenylbutan-1-one |
| 29 | 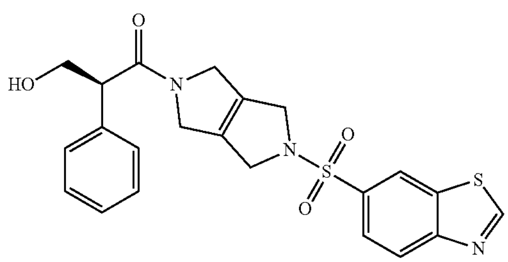 [SMILES: O=C([C@H](CO)c1ccccc1)N1CC2=C(C1)CN(S(=O)(=O)c1ccc3ncsc3c1)C2] | (S)-1-(5-(benzo[d]thiazol-6-ylsulfonyl)-3,4,5,6-tetrahydropyrrolo[3,4-c]pyrrol-2(1H)-yl)-3-hydroxy-2-phenylpropan-1-one |
| 30 | 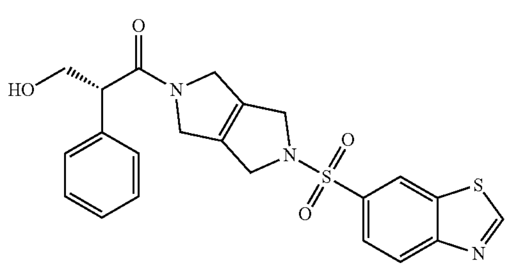 [SMILES: O=C([C@@H](CO)c1ccccc1)N1CC2=C(C1)CN(S(=O)(=O)c1ccc3ncsc3c1)C2] | (R)-1-(5-(benzo[d]thiazol-6-ylsulfonyl)-3,4,5,6-tetrahydropyrrolo[3,4-c]pyrrol-2(1H)-yl)-3-hydroxy-2-phenylpropan-1-one |

| Example | Structure | Name |
|---|---|---|
| 31 | 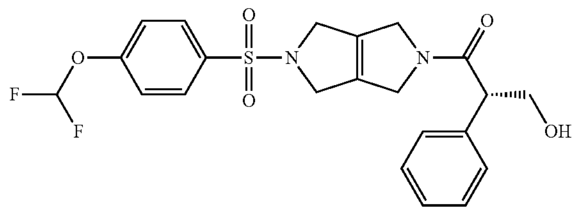 [SMILES: O=C([C@H](CO)c1ccccc1)N1CC2=C(C1)CN(S(=O)(=O)c1ccc(OC(F)F)cc1)C2] | (S)-1-(5-((4-(difluoromethoxy)phenyl)sulfonyl)-3,4,5,6-tetrahydropyrrolo[3,4-c]pyrrol-2(1H)-yl)-3-hydroxy-2-phenylpropan-1-one |
| 32 | 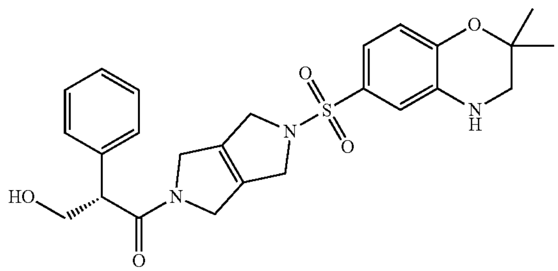 [SMILES: CC1(C)CNc2cc(S(=O)(=O)N3CC4=C(CN(C(=O)[C@H](CO)c5ccccc5)C4)C3)ccc2O1] | (S)-1-(5-((2,2-dimethyl-3,4-dihydro-2H-benzo[b][1,4]oxazin-6-yl)sulfonyl)-3,4,5,6-tetrahydropyrrolo[3,4-c]pyrrol-2(1H)-yl)-3-hydroxy-2-phenylpropan-1-one |
| 33[c] | 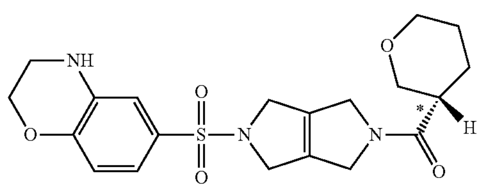 [SMILES: O=C([C@H]1CCCOC1)N1CC2=C(C1)CN(S(=O)(=O)c1ccc3c(c1)NCCO3)C2] | (S or R)-(5-((3,4-dihydro-2H-benzo[b][1,4]oxazin-6-yl)sulfonyl)-3,4,5,6-tetrahydropyrrolo[3,4-c]pyrrol-2(1H)-yl)(tetrahydro-2H-pyran-3-yl)methanone |
| 34[c] | 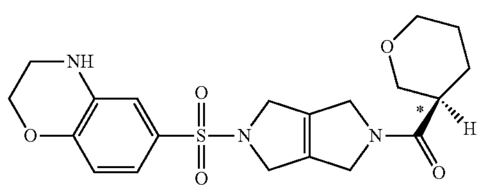 [SMILES: O=C([C@@H]1CCCOC1)N1CC2=C(C1)CN(S(=O)(=O)c1ccc3c(c1)NCCO3)C2] | (R or S)-(5-((3,4-dihydro-2H-benzo[b][1,4]oxazin-6-yl)sulfonyl)-3,4,5,6-tetrahydropyrrolo[3,4-c]pyrrol-2(1H)-yl)(tetrahydro-2H-pyran-3-yl)methanone |
| 35 | 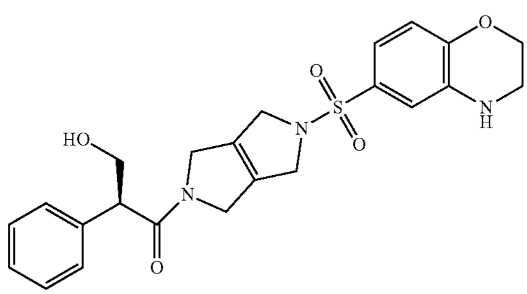 [SMILES: O=C([C@H](CO)c1ccccc1)N1CC2=C(C1)CN(S(=O)(=O)c1ccc3c(c1)NCCO3)C2] | (S)-1-(5-((3,4-dihydro-2H-benzo[b][1,4]oxazin-6-yl)sulfonyl)-3,4,5,6-tetrahydropyrrolo[3,4-c]pyrrol-2(1H)-yl)-3-hydroxy-2-phenylpropan-1-one |
| 36 | 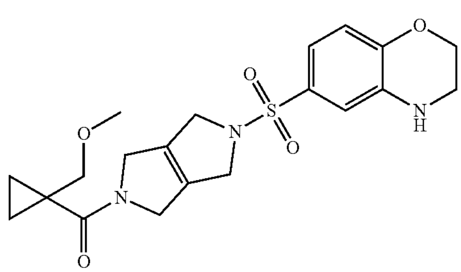 [SMILES: COCC1(C(=O)N2CC3=C(C2)CN(S(=O)(=O)c2ccc4c(c2)NCCO4)C3)CC1] | (5-((3,4-dihydro-2H-benzo[b][1,4]oxazin-6-yl)sulfonyl)-3,4,5,6-tetrahydropyrrolo[3,4-c]pyrrol-2(1H)-yl)(1-(methoxymethyl)cyclopropyl)methanone |

-continued

| Example | Structure | Name |
|---|---|---|
| 37 | 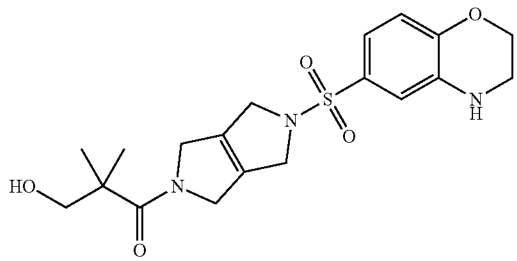 [SMILES: CC(C)(CO)C(=O)N1CC2=C(C1)CN(S(=O)(=O)c1ccc3c(c1)NCCO3)C2] | 1-(5-((3,4-dihydro-2H-benzo[b][1,4]oxazin-6-yl)sulfonyl)-3,4,5,6-tetrahydropyrrolo[3,4-c]pyrrol-2(1H)-yl)-3-hydroxy-2,2-dimethylpropan-1-one |
| 38 | 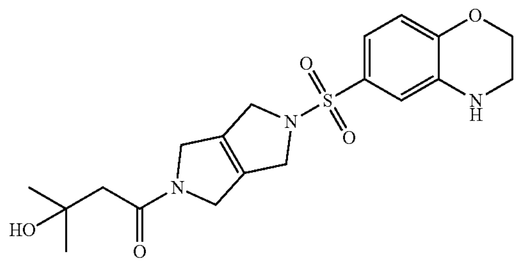 [SMILES: CC(C)(O)CC(=O)N1CC2=C(C1)CN(S(=O)(=O)c1ccc3c(c1)NCCO3)C2] | 1-(5-((3,4-dihydro-2H-benzo[b][1,4]oxazin-6-yl)sulfonyl)-3,4,5,6-tetrahydropyrrolo[3,4-c]pyrrol-2(1H)-yl)-3-hydroxy-3-methylbutan-1-one |
| 39 | 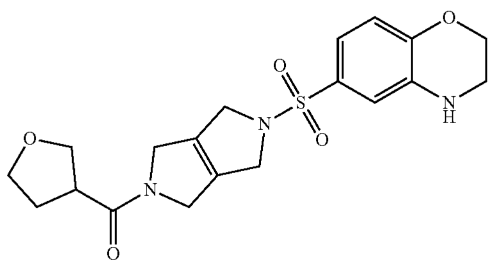 [SMILES: O=C(C1CCOC1)N1CC2=C(C1)CN(S(=O)(=O)c1ccc3c(c1)NCCO3)C2] | (5-((3,4-dihydro-2H-benzo[b][1,4]oxazin-6-yl)sulfonyl)-3,4,5,6-tetrahydropyrrolo[3,4-c]pyrrol-2(1H)-yl)(tetrahydrofuran-3-yl)methanone |
| 40 | 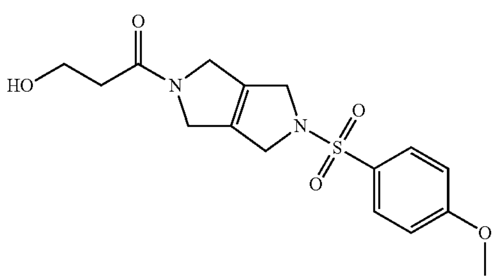 [SMILES: COc1ccc(S(=O)(=O)N2CC3=C(CN(C(=O)CCO)C3)C2)cc1] | 3-hydroxy-1-(5-((4-methoxyphenyl)sulfonyl)-3,4,5,6-tetrahydropyrrolo[3,4-c]pyrrol-2(1H)-yl)propan-1-one |
| 41[d] | 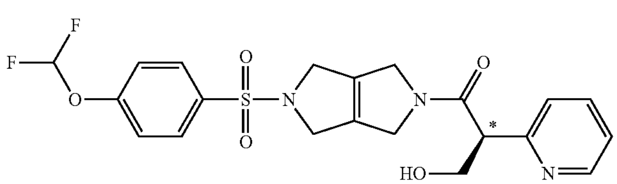 [SMILES: O=C([C@H](CO)c1ccccn1)N1CC2=C(C1)CN(S(=O)(=O)c1ccc(OC(F)F)cc1)C2] | (S or R)-1-(5-((4-(difluoromethoxy)phenyl)sulfonyl)-3,4,5,6-tetrahydropyrrolo[3,4-c]pyrrol-2(1H)-yl)-3-hydroxy-2-(pyridin-2-yl)propan-1-one |
| 42[d] | 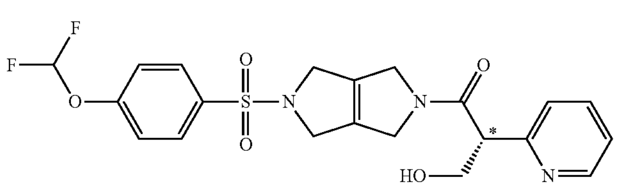 [SMILES: O=C([C@@H](CO)c1ccccn1)N1CC2=C(C1)CN(S(=O)(=O)c1ccc(OC(F)F)cc1)C2] | (R or S)-1-(5-((4-(difluoromethoxy)phenyl)sulfonyl)-3,4,5,6-tetrahydropyrrolo[3,4-c]pyrrol-2(1H)-yl)-3-hydroxy-2-(pyridin-2-yl)propan-1-one |

| Example | Structure | Name |
|---|---|---|
| 43 | 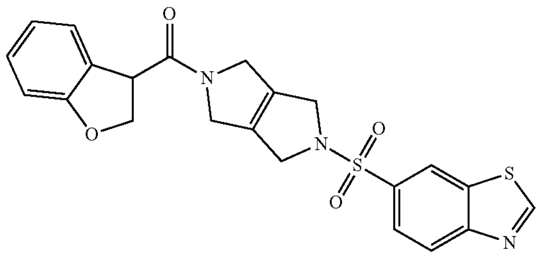 [SMILES: O=C(C1COc2ccccc21)N1CC2=C(C1)CN(S(=O)(=O)c1ccc3ncsc3c1)C2] | (5-(benzo[d]thiazol-6-ylsulfonyl)-3,4,5,6-tetrahydropyrrolo[3,4-c]pyrrol-2(1H)-yl)(2,3-dihydrobenzofuran-3-yl)methanone |
| 44[e] | 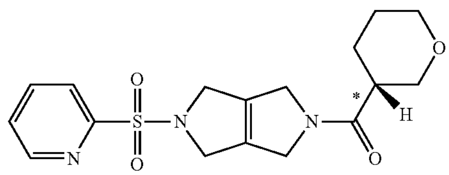 [SMILES: O=C([C@@H]1CCCOC1)N1CC2=C(C1)CN(S(=O)(=O)c1ccccn1)C2] | (R or S)-(5-(pyridin-2-ylsulfonyl)-3,4,5,6-tetrahydropyrrolo[3,4-c]pyrrol-2(1H)-yl)(tetrahydro-2H-pyran-3-yl)methanone |
| 45[e] | 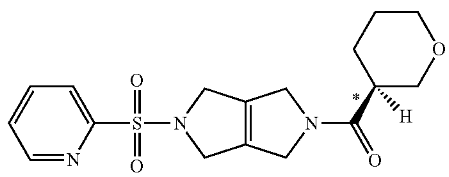 [SMILES: O=C([C@H]1CCCOC1)N1CC2=C(C1)CN(S(=O)(=O)c1ccccn1)C2] | (S or R)-(5-(pyridin-2-ylsulfonyl)-3,4,5,6-tetrahydropyrrolo[3,4-c]pyrrol-2(1H)-yl)(tetrahydro-2H-pyran-3-yl)methanone |
| 46 | 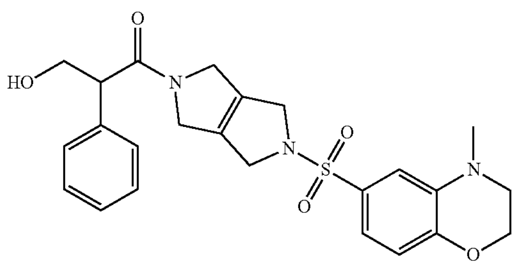 [SMILES: CN1CCOc2ccc(S(=O)(=O)N3CC4=C(CN(C(=O)C(CO)c5ccccc5)C4)C3)cc21] | 3-hydroxy-1-(5-((4-methyl-3,4-dihydro-2H-benzo[b][1,4]oxazin-6-yl)sulfonyl)-3,4,5,6-tetrahydropyrrolo[3,4-c]pyrrol-2(1H)-yl)-2-phenylpropan-1-one |
| 47 | 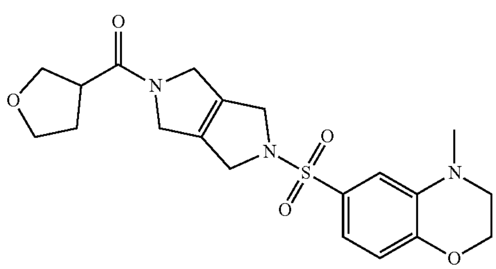 [SMILES: CN1CCOc2ccc(S(=O)(=O)N3CC4=C(CN(C(=O)C5CCOC5)C4)C3)cc21] | (5-((4-methyl-3,4-dihydro-2H-benzo[b][1,4]oxazin-6-yl)sulfonyl)-3,4,5,6-tetrahydropyrrolo[3,4-c]pyrrol-2(1H)-yl)(tetrahydrofuran-3-yl)methanone |
| 48 | 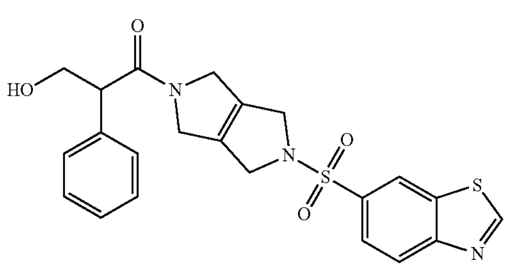 [SMILES: O=C(C(CO)c1ccccc1)N1CC2=C(C1)CN(S(=O)(=O)c1ccc3ncsc3c1)C2] | 1-(5-(benzo[d]thiazol-6-ylsulfonyl)-3,4,5,6-tetrahydropyrrolo[3,4-c]pyrrol-2(1H)-yl)-3-hydroxy-2-phenylpropan-1-one |

| Example | Structure | Name |
|---|---|---|
| 49 | 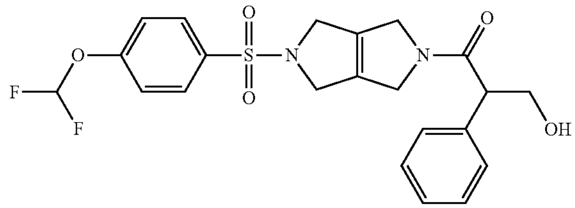 | 1-(5-((4-(difluoromethoxy)phenyl)sulfonyl)-3,4,5,6-tetrahydropyrrolo[3,4-c]pyrrol-2(1H)-yl)-3-hydroxy-2-phenylpropan-1-one |
| 50 | 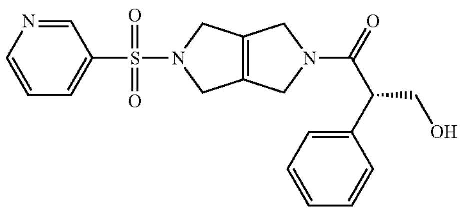 [SMILES: O=C([C@H](CO)c1ccccc1)N1CC2=C(C1)CN(S(=O)(=O)c1cccnc1)C2] | (2S)-3-hydroxy-2-phenyl-1-[5-(pyridine-3-sulfonyl)-1H,2H,3H,4H,5H,6H-pyrrolo[3,4-c]pyrrol-2-yl]propan-1-one |
| 51 | 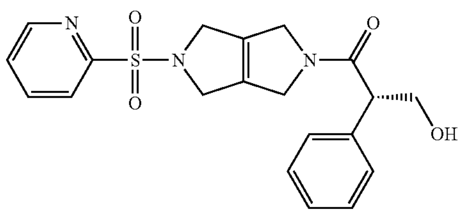 [SMILES: O=C([C@H](CO)c1ccccc1)N1CC2=C(C1)CN(S(=O)(=O)c1ccccn1)C2] | (2S)-3-hydroxy-2-phenyl-1-[5-(pyridine-2-sulfonyl)-1H,2H,3H,4H,5H,6H-pyrrolo[3,4-c]pyrrol-2-yl]propan-1-one |
| 52 | 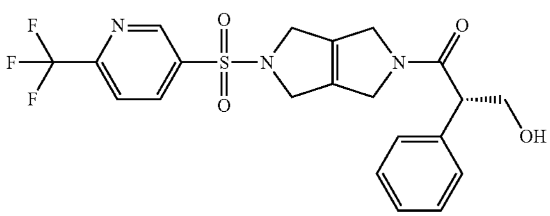 [SMILES: O=C([C@H](CO)c1ccccc1)N1CC2=C(C1)CN(S(=O)(=O)c1ccc(C(F)(F)F)nc1)C2] | (2S)-3-hydroxy-2-phenyl-1-(5-{[6-(trifluoromethyl)pyridin-3-yl]sulfonyl}-1H,2H,3H,4H,5H,6H-pyrrolo[3,4-c]pyrrol-2-yl)propan-1-one |
| 53 | 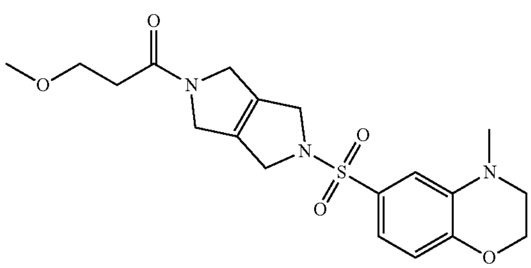 [SMILES: COCCC(=O)N1CC2=C(C1)CN(S(=O)(=O)c1ccc3c(c1)N(C)CCO3)C2] | 3-methoxy-1-(5-((4-methyl-3,4-dihydro-2H-benzo[b][1,4]oxazin-6-yl)sulfonyl)-3,4,5,6-tetrahydropyrrolo[3,4-c]pyrrol-2(1H)-yl)propan-1-one |
| 54 | 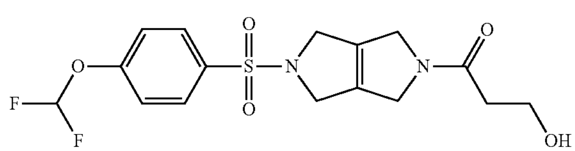 [SMILES: O=C(CCO)N1CC2=C(C1)CN(S(=O)(=O)c1ccc(OC(F)F)cc1)C2] | 1-(5-((4-(difluoromethoxy)phenyl)sulfonyl)-3,4,5,6-tetrahydropyrrolo[3,4-c]pyrrol-2(1H)-yl)-3-hydroxypropan-1-one |
| 55 | 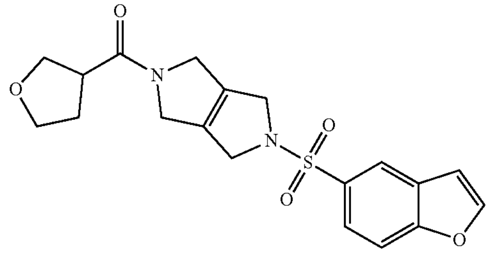 [SMILES: O=C(C1CCOC1)N1CC2=C(C1)CN(S(=O)(=O)c1ccc3occc3c1)C2] | (5-(benzofuran-5-ylsulfonyl)-3,4,5,6-tetrahydropyrrolo[3,4-c]pyrrol-2(1H)-yl)(tetrahydrofuran-3-yl)methanone |

| Example | Structure | Name |
|---|---|---|
| 56 | 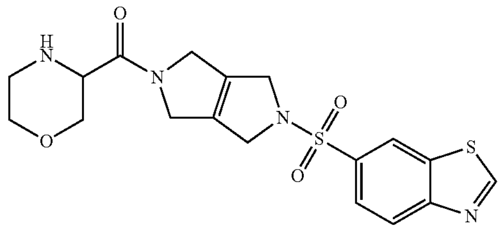 [SMILES: O=C(C1COCCN1)N1CC2=C(C1)CN(S(=O)(=O)c1ccc3ncsc3c1)C2] | (5-(benzo[d]thiazol-6-ylsulfonyl)-3,4,5,6-tetrahydropyrrolo[3,4-c]pyrrol-2(1H)-yl)(morpholin-3-yl)methanone |
| 57 | 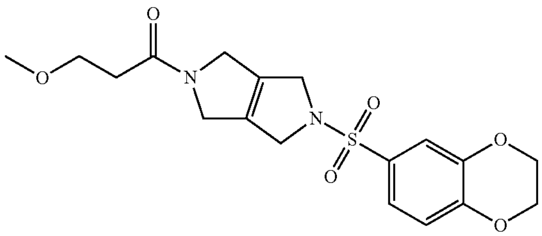 [SMILES: COCCC(=O)N1CC2=C(C1)CN(S(=O)(=O)c1ccc3c(c1)OCCO3)C2] | 1-(5-((2,3-dihydrobenzo[b][1,4]dioxin-6-yl)sulfonyl)-3,4,5,6-tetrahydropyrrolo[3,4-c]pyrrol-2(1H)-yl)-3-methoxypropan-1-one |
| 58 | 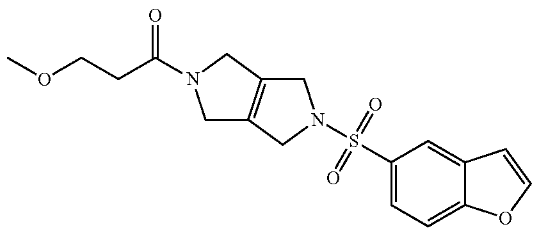 [SMILES: COCCC(=O)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-3-methoxypropan-1-one |

[a]Compounds 3 and 4 are enantiomers, but absolute stereochemistry is undetermined (*);
[b]Compounds 5 and 6 are enantiomers, but absolute stereochemistry is undetermined (*);
[c]Compounds 33 and 34 are enantiomers, but absolute stereochemistry is undetermined (*);
[d]Compounds 41 and 42 are enantiomers, but absolute stereochemistry is undetermined (*);
[e]Compounds 44 and 45 are enantiomers, but absolute stereochemistry is undetermined (*).

Method of Synthesizing the Compounds

The compounds of the present disclosure may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles of chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). When a compound is desired as a single enantiomer or diastereomer, it may be obtained by stereospecific synthesis or by resolution of the final product or of any convenient intermediate. For example, enantiomerically pure compounds of Formula (I) can be prepared using enantiomerically pure chiral building blocks. Alternatively, racemic mixtures of the final compounds or a racemic mixture of an advanced intermediate can be subjected to chiral purification as described herein below to deliver the desired enantiomerically pure intermediates or final compounds. In the instances where an advanced intermediate is purified into its individual enantiomers, each individual enantiomer can be carried on separately to deliver the final enantiomerically pure compounds of Formula (I). Resolution of the final product, an intermediate, or a starting material may be effected by any suitable method known in the art. See, for example, "Stereochemistry of Organic Compounds" by E. L. Eliel, S. H. Wilen, and L. N. Mander (Wiley-Interscience, 1994). The absolute stereochemistry of compounds obtained by chiral resolution or chiral purification may or may not be determined. Enantiomerically pure compounds with undetermined absolute stereochemistry have been drawn as a single enantiomer chosen arbitrarily and are marked with an asterisk (*) at the chiral carbon herein.

The compounds described herein may be made from commercially available starting materials or synthesized using known organic, inorganic, and/or enzymatic processes.

Preparation of Compounds

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereof as appreciated by those skilled in the art. Preferred methods include but are not limited to those methods described in the synthetic examples below.

It should be understood that in the description and formula shown above, the various groups Y, $R^1$, $R^{1'}$, $R^2$, $R^{2'}$, $R^3$, $R^4$, $R^8$, $R^{8'}$, $R^9$, $R^{9'}$, $R^{10}$, $R^{10'}$, $R^{11}$, $R^{11'}$ and other variables are as defined above, except where otherwise indicated.

Methods of Identifying and Characterizing PKR Activating Compounds

In certain embodiments, specific PKR Activating Compounds (including compounds of Formula (I), as well as additional examples of such compounds) can be identified using the Luminescence Assay Protocol described in Example 47. The PKR Activating Compounds can be selected by obtaining and analyzing data from a dose-response curve for a compound in accordance with the Luminescence Assay Protocol. FIG. 1 shows an exemplary dose-response curve for compounds disclosed herein. The values of $AC_{50}$ and MAX % Fold are independent of each other (i.e., the value of one does not affect the other). In some embodiments, PKR Activating Compounds can be selected based on the % Fold increase at a given concentration of compound (e.g., 1.54 µM) in the Luminescence Assay Protocol. The % Fold increase at a given concentration is a value which will be impacted by both the potency ($AC_{50}$) and activity (MAX % Fold).

In some embodiments, the PKR Activating Compound can be selected as a compound of Formula (I) having a % Fold value at 1.54 µM concentration of compound (% Fold@ 1.54 µM) of at least 75% (e.g., 75%-500%, 75%-250%, or 250%-500%) in an assay (e.g., the Luminescence Assay of Example 47) using a PKR enzyme (e.g., wild type PKR enzyme, or a clinically relevant mutant PKR, such as PKR G332S or PKR R510Q).

In some embodiments, PKR Activating Compounds have a % Fold@ 1.54 µM of at least 75% (e.g., 75%-500% or 250%-500%) obtained using the Luminescence Assay Protocol of Example 47. PKR Activating Compounds can be identified in accordance with Example 47 by a method comprising the steps of (a) incubating a mixture of phosphoenolpyruvic acid (PEP) and PKR enzyme (e.g., wild type PKR or a clinically relevant PKR mutant enzyme) with a test compound at a concentration of 1.54 µM; (b) adding adenosine-5'-diphosphate (ADP) and a kinase luminescence reporter composition (e.g., Kinase Glo Plus) to the mixture in step (a) under conditions effective to induce luminescence in the presence of a test compound that is a PKR Activating Compound; (c) measuring the luminescence values of the mixture obtained in step (b); (d) determining the % Fold@ 1.54 µM value for the test compound; and (e) identifying the test compound as a PKR Activating Compound when the test compound has a % Fold@ 1.54 µM value of at least 75% (e.g., 75-500%, or 250-500%).

Methods of Using the Disclosed Compounds

In another aspect, the present disclosure relates to a method of activating PKR, including methods of treating a disease or disorder in a patient by administering a therapeutically effective amount of a PKR Activating Compound disclosed herein. For example, the method can comprise administering to a patient in need thereof a therapeutically effective amount of a compound of Formula (I). In some embodiments, the disease or disorder is selected from the group consisting of PKD, SCD (e.g., sickle cell anemia), and thalassemia (e.g., beta-thalassemia). A method of treating a patient diagnosed with a disease, selected from the group consisting of PKD, SCD, and thalassemia, comprises administering a therapeutically effective amount of a compound disclosed herein, including a therapeutically effective amount of a PKR Activating Compound of Formula (I). A method of treating PKD comprises administering a therapeutically effective amount of a compound disclosed herein, including a PKR Activating Compound of Formula (I). A method of treating SCD comprises administering a therapeutically effective amount of a compound disclosed herein, including a PKR Activating Compound of Formula (I). A method of treating thalassemia comprises administering a therapeutically effective amount of a compound disclosed herein, including a PKR Activating Compound of Formula (I).

In other embodiments, the method comprises administering a therapeutically effective amount of a compound of Formula (I) for the treatment of a patient diagnosed with a condition selected from the group consisting of: hereditary non-spherocytic hemolytic anemia, hemolytic anemia (e.g., chronic hemolytic anemia caused by phosphoglycerate kinase deficiency), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases. In some embodiments, the disease or disorder is hereditary non-sperocytic hemolytic anemia. In some embodiments, the disease or disorder is SCD (e.g., sickle cell anemia) or thalassemia (e.g., beta-thalassemia). In some embodiments, the disease or disorder is hemolytic anemia (e.g., in a patient diagnosed with PKD). In some embodiments, the disease or disorder is beta thalassemia. In some embodiments, the disease or disorder is SCD.

Another aspect of the disclosure relates to of the use of a PKR Activating Compound for treating a disease or disorder associated with modulation of PKR and/or PKM2. The present disclosure also relates to the use of an activator of PKR and/or PKM2 for the preparation of a medicament used in the treatment of a disease or condition, wherein the medicament comprises a compound of Formula (I). In other embodiments, the present disclosure relates to the use of an activator of PKR and/or PKM2 for the preparation of a medicament used in the treatment of a disease or condition mediated by PKR and/or PKM2, wherein the medicament comprises a compound of Formula (I). The method can comprise administering to a patient in need of a treatment for diseases or disorders associated with modulation of PKR and/or PKM2 an effective amount of the compositions and/or compounds of Formula (I). The method can comprise the use of a PKR Activating Compound and/or a compound of Formula (I) in the preparation of a medicament for the treatment of diseases or disorders associated with modulation (e.g., activation) of PKR and/or PKM2.

In another aspect, the present disclosure is directed to of the use of a PKR Activating Compound treating a disease or disorder associated with activation of PKR and/or PKM2. The use can comprise administering to a patient in need of a treatment for diseases or disorders associated with modulation of PKR and/or PKM2 an effective amount of the compositions and/or compounds of Formula (I). In some embodiments, the disease or disorder is selected from the group consisting of SCD, sickle cell anemia, thalassemia (e.g., beta-thalassemia), hereditary non-spherocytic hemolytic anemia, hemolytic anemia (e.g., chronic hemolytic anemia caused by phosphoglycerate kinase deficiency), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases.

In another aspect, the present disclosure is directed to a method of activating PKR and/or PKM2. The method involves administering to a patient in need thereof an effective amount of a compound of Formula (I).

In another aspect, the present disclosure is directed to a method of increasing the lifetime of red blood cells in a patient or ex vivo using an effective amount of a PKR Activating Compound, such as a compound of Formula (I), or to the use of a PKR Activating Compound, such as a compound of Formula (I), in the preparation of a medicament or a composition (e.g., reagent) for increasing the lifetime of red blood cells in a patient or ex vivo using an effective amount of a PKR Activating Compound, such as the compound Formula (I).

In another aspect, the present disclosure is directed to a method of regulating 2,3-diphosphoglycerate levels in blood in a patient or ex vivo using an effective amount of a PKR Activating Compound, such as a compound Formula (I), or to the use of a PKR Activating Compound, such as a compound Formula (I), in the preparation of a medicament or a composition (e.g., reagent) for regulating 2,3-diphosphoglycerate levels in blood in a patient or ex vivo.

In another aspect, the present disclosure is directed to a method of regulating ATP levels in blood in a patient or ex vivo using an effective amount of a PKR Activating Compound, such as a compound Formula (I), or to the use of a PKR Activating Compound, such as a compound Formula (I), in the preparation of a medicament or a composition (e.g., reagent) for regulating ATP levels in blood in a patient or ex vivo.

In another aspect, the present disclosure relates to a method of treating a disease or disorder associated with decreased activity of PKR and/or PKM2 in a subject in need thereof, the method comprising administering to a patient in need thereof an effective amount of a compound of Formula (I). In some embodiments, the disease or disorder is selected from the group consisting of PKD, SCD, sickle cell anemia, thalassemia (e.g., beta-thalassemia), hereditary non-spherocytic hemolytic anemia, hemolytic anemia (e.g., chronic hemolytic anemia caused by phosphoglycerate kinase deficiency), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases.

In another embodiment, the present disclosure relates to a compound of Formula (I) or a pharmaceutical composition comprising a compound of the present disclosure and a pharmaceutically acceptable carrier used for the treatment of SCD, sickle cell anemia, thalassemia (e.g., beta-thalassemia), hereditary non-spherocytic hemolytic anemia, hemolytic anemia (e.g., chronic hemolytic anemia caused by phosphoglycerate kinase deficiency), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases.

Another aspect of the disclosure is directed to pharmaceutical compositions comprising a compound of Formula (I) and a pharmaceutically acceptable carrier.

In another aspect, the present disclosure relates to a method of treating cancer. The method comprises administering to a patient in need of a treatment for cancer an effective amount of a compound of Formula (I), or a pharmaceutically acceptable salt thereof.

In another aspect, the present disclosure relates to a method for the manufacture of a medicament for treating a disease or condition mediated by PKR and/or PKM2, wherein the medicament comprises a compound of Formula (I). Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The pharmaceutical acceptable carrier may further include an excipient, diluent, or surfactant. Illustrative pharmaceutical compositions are tablets and gelatin capsules comprising a compound of the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection. Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds. The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety. The disclosed compounds can be also formulated as a suppository that can be prepared from fatty emulsions or suspensions; using polyalkylene glycols such as propylene glycol, as the carrier.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

The compounds of the present disclosure can be administered in effective amounts to treat a disease or disorder in subjects. The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

The following numbered embodiments, while non-limiting, are exemplary of certain aspects of the present disclosure:

1. A compound of the Formula I:

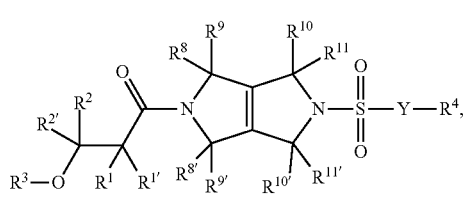

(I)

or a pharmaceutically acceptable salt thereof,
wherein:
Y is a bond, $-(CR^5R^{5'})_t-$, $-NR^5(CR^5R^{5'})_t-$, or $-O-$;

each $R^1$, $R^{1'}$, $R^2$, and $R^{2'}$ is independently $-H$, $-(C_1-C_6)$alkyl, $-(C_2-C_6)$alkenyl, $-(C_2-C_6)$alkynyl, $-(C_3-C_8)$cycloalkyl, $-(C_4-C_8)$cycloalkenyl, heterocyclyl, aryl, heteroaryl, halogen, $-CN$, $-OR^5$, $-SR^5$, $-NO_2$, $-NR^5R^{5'}$, $-S(O)_2R^5$, $-S(O)_2NR^5R^{5'}$, $-S(O)R^5$, $-S(O)NR^5R^{5'}$, $-NR^5S(O)_2R^{5'}$, $-NR^5S(O)R^{5'}$, $-C(O)R^5$, or $-C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, $-CN$, $-R^5$, $-OR^5$, $-SR^5$, $-NO_2$, $-NR^5R^{5'}$, $-S(O)_2R^5$, $-S(O)_2NR^5R^{5'}$, $-S(O)R^5$, $-S(O)NR^5R^{5'}$, $-NR^5S(O)_2R^{5'}$, $-NR^5S(O)R^{5'}$, $-C(O)R^5$, and $-C(O)OR^5$;

or $R^1$ and $R^{1'}$, or $R^2$ and $R^{2'}$, together with the atom to which they are attached, can combine to form $-(C_3-C_8)$cycloalkyl ring, heterocycle, $(C_5-C_8)$spirocycle or 5- to 8-membered spiroheterocycle;

or $R^1$ and $R^2$, together with the atoms to which they are attached, can combine to form a $-(C_3-C_8)$cycloalkyl or a 3- to 8-membered heterocycle;

$R^3$ is independently $-H$, $-(C_1-C_6)$alkyl, $-(C_2-C_6)$alkenyl, $-(C_2-C_6)$alkynyl, $-(C_3-C_8)$cycloalkyl, $-(C_4-C_8)$cycloalkenyl, heterocyclyl, aryl, heteroaryl, $-S(O)_2R^5$, $-S(O)_2NR^5R^{5'}$, $-S(O)R^5$, $-S(O)NR^5R^{5'}$, $-C(O)R^5$, or $-C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, $-CN$, $-R^5$, $-OR^5$, $-SR^5$, $-NO_2$, $-NR^5R^{5'}$, $-S(O)_2R^5$, $-S(O)_2NR^5R^{5'}$, $-S(O)R^5$, $-S(O)NR^5R^{5'}$, $-NR^5S(O)_2R^{5'}$, $-NR^5S(O)R^{5'}$, $-C(O)R^5$, and $-C(O)OR^5$;

or $R^2$ and $R^3$, together with the atoms to which they are attached, can combine to form a 5- to 8-membered heterocyclic ring;

or $R^1$ and $R^3$, together with the atoms to which they are attached, can combine to form a 5- to 8-membered heterocyclic ring, optionally fused to an aryl or heteroaryl ring;

$R^4$ is $-H$, $-(C_1-C_6)$alkyl, $-(C_2-C_6)$alkenyl, $-(C_2-C_6)$alkynyl, $-(C_3-C_8)$cycloalkyl, $-(C_4-C_8)$cycloalkenyl, heterocyclyl, aryl, heteroaryl, halogen, $-CN$, $-OR^5$, $-SR^5$, $-NO_2$, $-NR^5R^{5'}$, $-S(O)_2R^5$, $-S(O)_2NR^5R^{5'}$, $-S(O)R^5$, $-S(O)NR^5R^{5'}$, $-NR^5S(O)_2R^{5'}$, $-NR^5S(O)R^{5'}$, $-C(O)R^5$, or $-C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, $-CN$, $-R^5$, $-OR^5$, $-SR^5$, $-NO_2$, $-NR^5R^{5'}$, $-S(O)_2R^5$, $-S(O)_2NR^5R^{5'}$, $-S(O)R^5$, $-S(O)NR^5R^{5'}$, $-NR^5S(O)_2R^{5'}$, $-NR^5S(O)R^{5'}$, $-C(O)R^5$, and $-C(O)OR^5$;

each $R^5$ and $R^{5'}$ is independently, at each occurrence, $-H$, $-(C_1-C_6)$alkyl, $-(C_2-C_6)$alkenyl, $-(C_2-C_6)$alkynyl, $-(C_3-C_8)$cycloalkyl, $-(C_4-C_8)$cycloalkenyl, heterocyclyl, aryl, heteroaryl, halogen, $-CN$, $-OR^6$, $-SR^6$, $-NO_2$, $-NR^6R^{6'}$, $-S(O)_2R^6$, $-S(O)_2NR^6R^{6'}$, $-S(O)R^6$, $-S(O)NR^6R^{6'}$, $-NR^6S(O)_2R^{6'}$, $-NR^6S(O)R^{6'}$, $-C(O)R^6$, or $-C(O)OR^6$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —R$^6$, —OR$^6$, —SR$^6$, —NO$_2$, —NR$^6$R$^{6'}$, —S(O)$_2$R$^6$, —S(O)$_2$NR$^6$R$^{6'}$, —S(O)R$^6$, —S(O)NR$^6$R$^{6'}$, —NR$^6$S(O)$_2$R$^{6'}$, —NR$^6$S(O)R$^{6'}$, —C(O)R$^6$, and —C(O)OR$^6$;

or two R$^5$ on adjacent atoms together with the atoms to which they are attached form an aryl ring optionally substituted with one or more R$^6$; or two R$^5$ on adjacent atoms together with the atoms to which they are attached form a heteroaryl ring optionally substituted with one or more R$^6$; or two R$^5$ on adjacent atoms together with the atoms to which they are attached form a (C$_3$-C$_8$)cycloalkyl ring optionally substituted with one or more R$^6$; or two R$^5$ on adjacent atoms together with the atoms to which they are attached form a heterocycloalkyl ring optionally substituted with one or more R$^6$;

or two R$^{5'}$ on adjacent atoms together with the atoms to which they are attached form an aryl ring optionally substituted with one or more R$^6$; or two R$^{5'}$ on adjacent atoms together with the atoms to which they are attached form a heteroaryl ring optionally substituted with one or more R$^6$; or two R$^{5'}$ on adjacent atoms together with the atoms to which they are attached form a (C$_3$-C$_8$)cycloalkyl ring optionally substituted with one or more R$^6$; or two R$^{5'}$ on adjacent atoms together with the atoms to which they are attached form a heterocycloalkyl ring optionally substituted with one or more R$^6$;

each R$^6$ and R$^{6'}$ is independently, at each occurrence, —H, —(C$_1$-C$_6$)alkyl, —(C$_2$-C$_6$)alkenyl, —(C$_2$-C$_6$)alkynyl, —(C$_3$-C$_8$)cycloalkyl, —(C$_4$-C$_8$)cycloalkenyl, heterocyclyl, aryl, heteroaryl, halogen, —CN, —OR$^7$, —SR$^7$, —NO$_2$, —NR$^7$R$^{7'}$, —S(O)$_2$R$^7$, —S(O)$_2$NR$^7$R$^{7'}$, —S(O)R$^7$, —S(O)NR$^7$R$^{7'}$, —NR$^7$S(O)$_2$R$^{7'}$, —NR$^7$S(O)R$^{7'}$, —C(O)R$^7$, or —C(O)OR$^7$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —R$^7$, —OR$^7$, —SR$^7$, —NO$_2$, —NR$^7$R$^{7'}$, —S(O)$_2$R$^7$, —S(O)$_2$NR$^7$R$^{7'}$, —S(O)R$^7$, —S(O)NR$^7$R$^{7'}$, —NR$^7$S(O)$_2$R$^{7'}$, —NR$^7$S(O)R$^{7'}$, —C(O)R$^7$, and —C(O)OR$^7$;

each R$^7$ and R$^{7'}$ is independently, at each occurrence, —H, —(C$_1$-C$_6$)alkyl, —(C$_2$-C$_6$)alkenyl, —(C$_2$-C$_6$)alkynyl, —(C$_3$-C$_8$)cycloalkyl, —(C$_4$-C$_8$)cycloalkenyl, heterocyclyl, aryl, heteroaryl, halogen, —CN, —OH, —SH, —NO$_2$, —NH$_2$, —S(O)$_2$H, —S(O)$_2$NH$_2$, —S(O)H, —S(O)NH$_2$, —NHS(O)$_2$H, —NHS(O)H, —C(O)H, or —C(O)OH, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —OH, —SH, —NO$_2$, —NH$_2$, —S(O)$_2$H, —S(O)$_2$NH$_2$, —S(O)H, —S(O)NH$_2$, —NHS(O)$_2$H, —NHS(O)H, —C(O)H, and —C(O)OH;

each R$^8$, R$^{8'}$, R$^9$, R$^{9'}$, R$^{10}$, R$^{10'}$, R$^{11}$, and R$^{11'}$ is independently, at each occurrence, —H, —(C$_1$-C$_6$)alkyl, —(C$_2$-C$_6$)alkenyl, —(C$_2$-C$_6$)alkynyl, —(C$_3$-C$_8$)cycloalkyl, or —(C$_4$-C$_8$)cycloalkenyl, wherein each alkyl, alkenyl, alkynyl, cycloalkyl and cycloalkenyl, is optionally substituted with one or more substituents selected from the group consisting of oxo, halogen, —CN, —R$^7$, —OR$^7$, —SR$^7$, —NO$_2$, —NR$^7$R$^{7'}$, —S(O)$_2$R$^7$, —S(O)$_2$NR$^7$R$^{7'}$, —S(O)R$^7$, —S(O)NR$^7$R$^{7'}$, —NR$^7$S(O)$_2$R$^{7'}$, —NR$^7$S(O)R$^{7'}$, —C(O)R$^7$, and —C(O)OR$^7$;

and t is 0, 1, 2, or 3.

2. The compound of embodiment 1, having Formula (Ia):

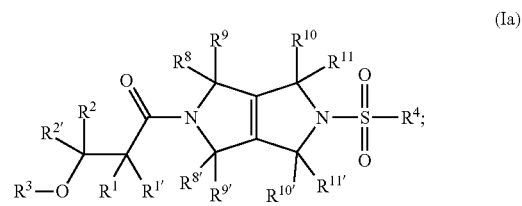

or a pharmaceutically acceptable salt thereof.

3. The compound of embodiment 1 or 2, having Formula (Ib):

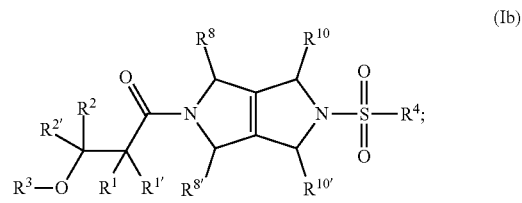

or a pharmaceutically acceptable salt thereof.

4. The compound of any one of embodiments 1-3, having Formula (Ic):

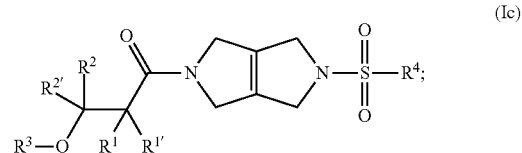

or a pharmaceutically acceptable salt thereof.

5. The compound of any one of embodiments 1-4, wherein R$^1$ and R$^{1'}$ are each independently hydrogen, optionally substituted —(C$_1$-C$_6$)alkyl, optionally substituted aryl, or optionally substituted heteroaryl, or wherein R$^1$ and R$^{1'}$, taken together with the atoms to which they are attached, form an optionally substituted —(C$_3$-C$_4$)cycloalkyl.

6. The compound of any one of embodiments 1-5, wherein R$^2$ and R$^{2'}$ are each independently hydrogen or optionally substituted —(C$_1$-C$_6$)alkyl.

7. The compound of any one of embodiments 1-6, wherein R$^3$ is hydrogen or optionally substituted —(C$_1$-C$_6$)alkyl.

8. The compound of any one of embodiments 1-7, wherein R$^3$ is hydrogen.

9. The compound of any one of embodiments 1-4, wherein R$^3$ and one of R$^1$ or R$^{1'}$, taken together with the atoms to which they are attached, form an optionally substituted 5-6-membered heterocyclic ring.

10. The compound of any one of embodiments 1-4, wherein R$^1$ and R$^{1'}$ are each independently hydrogen or optionally substituted phenyl or pyridyl; $R^2$ and $R^{2'}$ are each independently hydrogen; and $R^3$ is hydrogen or optionally substituted —$(C_1-C_6)$alkyl.

11. The compound of any one of embodiments 1-4, wherein $R^1$ and $R^{1'}$ are each independently hydrogen or optionally substituted phenyl or pyridyl; $R^2$ and $R^{2'}$ are each independently hydrogen; and $R^3$ is hydrogen.

12. The compound of any one of embodiments 1-4, wherein $R^4$ is optionally substituted aryl or heteroaryl.

13. The compound of embodiment 12, wherein the aryl or heteroaryl is optionally substituted with one or more substituents selected from the group consisting of oxo, halogen, —CN, —$R^5$, —$OR^5$, —$S(O)_2NR^5R^{5'}$, —$S(O)NR^5R^{5'}$, and —$C(O)R^5$.

14. The compound of embodiment 12, wherein two $R^5$ on adjacent atoms together with the atoms to which they are attached form an aryl ring optionally substituted with one or more $R^6$.

15. The compound of embodiment 12, wherein two $R^5$ on adjacent atoms together with the atoms to which they are attached form a heteroaryl ring optionally substituted with one or more $R^6$.

16. The compound of embodiment 12, wherein two $R^5$ on adjacent atoms together with the atoms to which they are attached form a $(C_3-C_8)$cycloalkyl ring optionally substituted with one or more $R^6$.

17. The compound of embodiment 12, wherein two $R^5$ on adjacent atoms together with the atoms to which they are attached form a heterocycloalkyl ring optionally substituted with one or more $R^6$.

18. The compound of embodiment 1, wherein Y is —$CR^5R^{5'}$—.

19. The compound of embodiment 1, wherein Y is —$NR^5(CR^5R^{5'})_t$—.

20. The compound of embodiment 1, wherein Y is —O—.

21. A compound of the Formula (Id-1):

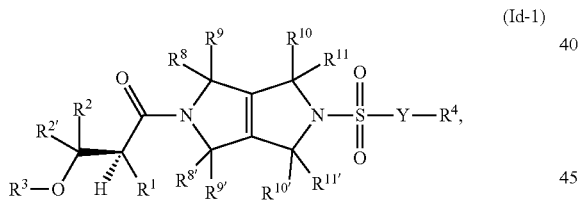

(Id-1)

or a pharmaceutically acceptable salt thereof,
wherein:
Y is a bond, —$(CR^5R^{5'})_t$—, —$NR^5(CR^5R^{5'})_t$—, or —O—;
$R^1$ is —$(C_1-C_6)$alkyl, —$(C_2-C_6)$alkenyl, —$(C_2-C_6)$alkynyl, —$(C_3-C_8)$cycloalkyl, —$(C_4-C_8)$cycloalkenyl, heterocyclyl, aryl, heteroaryl, halogen, —CN, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, or —$C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, and —$C(O)OR^5$;

each $R^2$ and $R^{2'}$ is independently —H, —$(C_1-C_6)$alkyl, —$(C_2-C_6)$alkenyl, —$(C_2-C_6)$alkynyl, —$(C_3-C_8)$cycloalkyl, —$(C_4-C_8)$cycloalkenyl, heterocyclyl, aryl, heteroaryl, halogen, —CN, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, or —$C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, and —$C(O)OR^5$; or $R^2$ and $R^{2'}$, together with the atom to which they are attached, can combine to form —$(C_3-C_8)$cycloalkyl ring, heterocycle, $(C_5-C_8)$spirocycle or 5- to 8-membered spiroheterocycle;

or $R^1$ and $R^2$, together with the atoms to which they are attached, can combine to form a —$(C_3-C_8)$cycloalkyl or a 3- to 8-membered heterocycle;

$R^3$ is independently —H, —$(C_1-C_6)$alkyl, —$(C_2-C_6)$alkenyl, —$(C_2-C_6)$alkynyl, —$(C_3-C_8)$cycloalkyl, —$(C_4-C_8)$cycloalkenyl, heterocyclyl, aryl, heteroaryl, —$S(O)_2R^5$, —$S(O)_2NR^5R^{5'}$, —$S(O)R^5$, —$S(O)NR^5R^{5'}$, —$C(O)R^5$, or —$C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, and —$C(O)OR^5$;

or $R^2$ and $R^3$, together with the atoms to which they are attached, can combine to form a 5- to 8-membered heterocyclic ring;

or $R^1$ and $R^3$, together with the atoms to which they are attached, can combine to form a 5- to 8-membered heterocyclic ring, optionally fused to an aryl or heteroaryl ring;

$R^4$ is —H, —$(C_1-C_6)$alkyl, —$(C_2-C_6)$alkenyl, —$(C_2-C_6)$alkynyl, —$(C_3-C_8)$cycloalkyl, —$(C_4-C_8)$cycloalkenyl, heterocyclyl, aryl, heteroaryl, halogen, —CN, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, or —$C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^{5'}$, —$NR^5S(O)R^{5'}$, —$C(O)R^5$, and —$C(O)OR^5$;

each $R^5$ and $R^{5'}$ is independently, at each occurrence, —H, —$(C_1-C_6)$alkyl, —$(C_2-C_6)$alkenyl, —$(C_2-C_6)$alkynyl, —$(C_3-C_8)$cycloalkyl, —$(C_4-C_8)$cycloalkenyl, heterocyclyl, aryl, heteroaryl, halogen, —CN, —$OR^6$, —$SR^6$, —$NO_2$, —$NR^6R^{6'}$, —$S(O)_2R^6$, —$S(O)_2NR^6R^{6'}$, —$S(O)R^6$, —$S(O)NR^6R^{6'}$, —$NR^6S(O)_2R^{6'}$, —$NR^6S(O)R^{6'}$, —$C(O)R^6$, or —$C(O)OR^6$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^6$, —$OR^6$, —$SR^6$, —$NO_2$, —$NR^6R^{6'}$, —S(O)₂R⁶, —S(O)₂NR⁶R⁶', —S(O)R⁶, —S(O)NR⁶R⁶', —NR⁶S(O)₂R⁶', —NR⁶S(O)R⁶', —C(O)R⁶, and —C(O)OR⁶;

or two R⁵ on adjacent atoms together with the atoms to which they are attached form an aryl ring optionally substituted with one or more R⁶; or two R⁵ on adjacent atoms together with the atoms to which they are attached form a heteroaryl ring optionally substituted with one or more R⁶; or two R⁵ on adjacent atoms together with the atoms to which they are attached form a (C₃-C₈)cycloalkyl ring optionally substituted with one or more R⁶; or two R⁵ on adjacent atoms together with the atoms to which they are attached form a heterocycloalkyl ring optionally substituted with one or more R⁶;

or two R⁵' on adjacent atoms together with the atoms to which they are attached form an aryl ring optionally substituted with one or more R⁶; or two R⁵' on adjacent atoms together with the atoms to which they are attached form a heteroaryl ring optionally substituted with one or more R⁶; or two R⁵' on adjacent atoms together with the atoms to which they are attached form a (C₃-C₈)cycloalkyl ring optionally substituted with one or more R⁶; or two R⁵' on adjacent atoms together with the atoms to which they are attached form a heterocycloalkyl ring optionally substituted with one or more R⁶;

each R⁶ and R⁶' is independently, at each occurrence, —H, —(C₁-C₆)alkyl, —(C₂-C₆)alkenyl, —(C₂-C₆)alkynyl, —(C₃-C₈)cycloalkyl, —(C₄-C₈)cycloalkenyl, heterocyclyl, aryl, heteroaryl, halogen, —CN, —OR⁷, —SR⁷, —NO₂, —NR⁷R⁷', —S(O)₂R⁷, —S(O)₂NR⁷R⁷', —S(O)R⁷, —S(O)NR⁷R⁷', —NR⁷S(O)₂R⁷', —NR⁷S(O)R⁷', —C(O)R⁷, or —C(O)OR⁷, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —R⁷, —OR⁷, —SR⁷, —NO₂, —NR⁷R⁷', —S(O)₂R⁷, —S(O)₂NR⁷R⁷', —S(O)R⁷, —S(O)NR⁷R⁷', —NR⁷S(O)₂R⁷', —NR⁷S(O)R⁷', —C(O)R⁷, and —C(O)OR⁷;

each R⁷ and R⁷' is independently, at each occurrence, —H, —(C₁-C₆)alkyl, —(C₂-C₆)alkenyl, —(C₂-C₆)alkynyl, —(C₃-C₈)cycloalkyl, —(C₄-C₈)cycloalkenyl, aryl, heterocyclyl, aryl, heteroaryl, halogen, —CN, —OH, —SH, —NO₂, —NH₂, —S(O)₂H, —S(O)₂NH₂, —S(O)H, —S(O)NH₂, —NHS(O)₂H, —NHS(O)H, —C(O)H, or —C(O)OH, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —OH, —SH, —NO₂, —NH₂, —S(O)₂H, —S(O)₂NH₂, —S(O)H, —S(O)NH₂, —NHS(O)₂H, —NHS(O)H, —C(O)H, and —C(O)OH;

each R⁸, R⁸', R⁹, R⁹', R¹⁰, R¹⁰', R¹¹, and R¹¹' is independently, at each occurrence, —H, —(C₁-C₆)alkyl, —(C₂-C₆)alkenyl, —(C₂-C₆)alkynyl, —(C₃-C₈)cycloalkyl, or —(C₄-C₈)cycloalkenyl, wherein each alkyl, alkenyl, alkynyl, cycloalkyl and cycloalkenyl, is optionally substituted with one or more substituents selected from the group consisting of oxo, halogen, —CN, —R⁷, —OR⁷, —SR⁷, —NO₂, —NR⁷R⁷', —S(O)₂R⁷, —S(O)₂NR⁷R⁷', —S(O)R⁷, —S(O)NR⁷R⁷', —NR⁷S(O)₂R⁷', —NR⁷S(O)R⁷', —C(O)R⁷, and —C(O)OR⁷;

and
t is 0, 1, 2, or 3.

22. The compound of embodiment 21, having Formula (Ia-1):

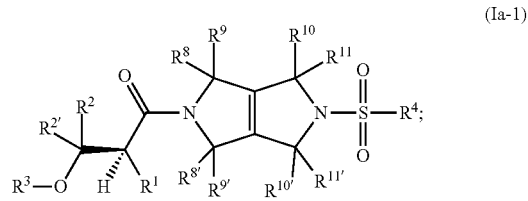

or a pharmaceutically acceptable salt thereof.

23. The compound of embodiments 21 or 22, having Formula (Ib-1):

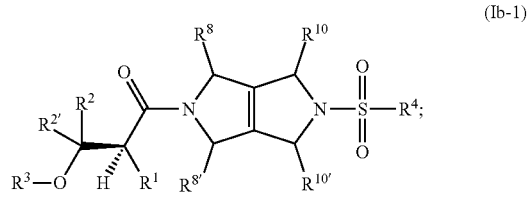

or a pharmaceutically acceptable salt thereof.

24. The compound of any one of embodiments 21-23, having Formula (Ic-1):

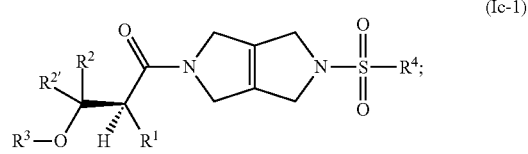

or a pharmaceutically acceptable salt thereof.

25. The compound of any one of embodiments 21-24, wherein R¹ is optionally substituted —(C₁-C₆)alkyl, optionally substituted aryl, or optionally substituted heteroaryl.

26. The compound of any one of embodiments 21-25, wherein R² and R²' are each independently hydrogen or optionally substituted —(C₁-C₆)alkyl.

27. The compound of any one of embodiments 21-26, wherein R³ is hydrogen or optionally substituted —(C₁-C₆)alkyl.

28. The compound of any one of embodiments 21-27, wherein R³ is hydrogen.

29. The compound of any one of embodiments 21-24, wherein R³ and R¹ taken together with the atoms to which they are attached, form an optionally substituted 5-6-membered heterocyclic ring.

30. The compound of any one of embodiments 21-24, wherein R¹ is optionally substituted phenyl or pyridyl; R² and R²' are each independently hydrogen; and R³ is hydrogen or optionally substituted —(C₁-C₆)alkyl.

31. The compound of any one of embodiments 21-24, wherein R¹ is optionally substituted phenyl or pyridyl; R² and R²' are each independently hydrogen; and R³ is hydrogen.

32. The compound of any one of embodiments 21-31, wherein $R^4$ is optionally substituted aryl or heteroaryl.

33. The compound of embodiment 32, wherein the aryl or heteroaryl is optionally substituted with one or more substituents selected from the group consisting of oxo, halogen, —CN, —$R^5$, —$OR^5$, —$S(O)_2NR^5R^{5'}$, —$S(O)NR^5R^{5'}$, and —$C(O)R^5$.

34. The compound of embodiment 32, wherein two $R^5$ on adjacent atoms together with the atoms to which they are attached form an aryl ring optionally substituted with one or more $R^6$.

35. The compound of embodiment 32, wherein two $R^5$ on adjacent atoms together with the atoms to which they are attached form a heteroaryl ring optionally substituted with one or more $R^6$.

36. The compound of embodiment 32, wherein two $R^5$ on adjacent atoms together with the atoms to which they are attached form a ($C_3$-$C_8$)cycloalkyl ring optionally substituted with one or more $R^6$.

37. The compound of embodiment 32, wherein two $R^5$ on adjacent atoms together with the atoms to which they are attached form a heterocycloalkyl ring optionally substituted with one or more $R^6$.

38. The compound of embodiment 21, wherein Y is —$CR^5R^{5'}$—.

39. The compound of embodiment 21, wherein Y is —$NR^5(CR^5R^{5'})_t$—.

40. The compound of embodiment 21, wherein Y is —O—.

41. A compound of the Formula (Id-2):

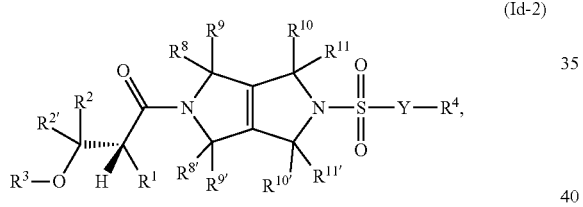

(Id-2)

or a pharmaceutically acceptable salt thereof,
wherein:
Y is a bond, —$(CR^5R^{5'})_t$—, —$NR^5(CR^5R^{5'})_t$—, or —O—;
$R^1$ is —($C_1$-$C_6$)alkyl, —($C_2$-$C_6$)alkenyl, —($C_2$-$C_6$)alkynyl, —($C_3$-$C_8$)cycloalkyl, —($C_4$-$C_8$)cycloalkenyl, heterocyclyl, aryl, heteroaryl, halogen, —CN, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^5$, —$NR^5S(O)R^5$, —$C(O)R^5$, or —$C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^5$, —$NR^5S(O)R^5$, —$C(O)R^5$, and —$C(O)OR^5$;
each $R^2$ and $R^{2'}$ is independently —H, —($C_1$-$C_6$)alkyl, —($C_2$-$C_6$)alkenyl, —($C_2$-$C_6$)alkynyl, —($C_3$-$C_8$)cycloalkyl, —($C_4$-$C_8$)cycloalkenyl, heterocyclyl, aryl, heteroaryl, halogen, —CN, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^5$, —$NR^5S(O)R^5$, —$C(O)R^5$, or —$C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^5$, —$NR^5S(O)R^5$, —$C(O)R^5$, and —$C(O)OR^5$; or $R^2$ and $R^{2'}$, together with the atom to which they are attached, can combine to form —($C_3$-$C_8$)cycloalkyl ring, heterocycle, ($C_5$-$C_8$)spirocycle or 5- to 8-membered spiroheterocycle;
or $R^1$ and $R^2$, together with the atoms to which they are attached, can combine to form a —($C_3$-$C_8$)cycloalkyl or a 3- to 8-membered heterocycle;
$R^3$ is independently —H, —($C_1$-$C_6$)alkyl, —($C_2$-$C_6$)alkenyl, —($C_2$-$C_6$)alkynyl, —($C_3$-$C_8$)cycloalkyl, —($C_4$-$C_8$)cycloalkenyl, heterocyclyl, aryl, heteroaryl, —$S(O)_2R^5$, —$S(O)_2NR^5R^{5'}$, —$S(O)R^5$, —$S(O)NR^5R^{5'}$, —$C(O)R^5$, or —$C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^5$, —$NR^5S(O)R^5$, —$C(O)R^5$, and —$C(O)OR^5$;
or $R^2$ and $R^3$, together with the atoms to which they are attached, can combine to form a 5- to 8-membered heterocyclic ring;
or $R^1$ and $R^3$, together with the atoms to which they are attached, can combine to form a 5- to 8-membered heterocyclic ring, optionally fused to an aryl or heteroaryl ring;
$R^4$ is —H, —($C_1$-$C_6$)alkyl, —($C_2$-$C_6$)alkenyl, —($C_2$-$C_6$)alkynyl, —($C_3$-$C_8$)cycloalkyl, —($C_4$-$C_8$)cycloalkenyl, heterocyclyl, aryl, heteroaryl, halogen, —CN, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^5$, —$NR^5S(O)R^5$, —$C(O)R^5$, or —$C(O)OR^5$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^5$, —$OR^5$, —$SR^5$, —$NO_2$, —$NR^5R^{5'}$, —$S(O)_2R^5$, —$S(O)_2NR^5R^{5'}$, —$S(O)R^5$, —$S(O)NR^5R^{5'}$, —$NR^5S(O)_2R^5$, —$NR^5S(O)R^5$, —$C(O)R^5$, and —$C(O)OR^5$;
each $R^5$ and $R^{5'}$ is independently, at each occurrence, —H, —($C_1$-$C_6$)alkyl, —($C_2$-$C_6$)alkenyl, —($C_2$-$C_6$)alkynyl, —($C_3$-$C_8$)cycloalkyl, —($C_4$-$C_8$)cycloalkenyl, heterocyclyl, aryl, heteroaryl, halogen, —CN, —$OR^6$, —$SR^6$, —$NO_2$, —$NR^6R^{6'}$, —$S(O)_2R^6$, —$S(O)_2NR^6R^{6'}$, —$S(O)R^6$, —$S(O)NR^6R^{6'}$, —$NR^6S(O)_2R^6$, —$NR^6S(O)R^6$, —$C(O)R^6$, or —$C(O)OR^6$, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —$R^6$, —$OR^6$, —$SR^6$, —$NO_2$, —$NR^6R^{6'}$, —$S(O)_2R^6$, —$S(O)_2NR^6R^{6'}$, —$S(O)R^6$, —$S(O)NR^6R^{6'}$, —$NR^6S(O)_2R^6$, —$NR^6S(O)R^6$, —$C(O)R^6$, and —$C(O)OR^6$;
or two $R^5$ on adjacent atoms together with the atoms to which they are attached form an aryl ring optionally substituted with one or more $R^6$; or two $R^5$ on adjacent atoms together with the atoms to which they are attached form a heteroaryl ring optionally substituted with one or more R⁶; or two R⁵ on adjacent atoms together with the atoms to which they are attached form a (C₃-C₈)cycloalkyl ring optionally substituted with one or more R⁶; or two R⁵ on adjacent atoms together with the atoms to which they are attached form a heterocycloalkyl ring optionally substituted with one or more R⁶;

or two R⁵' on adjacent atoms together with the atoms to which they are attached form an aryl ring optionally substituted with one or more R⁶; or two R⁵' on adjacent atoms together with the atoms to which they are attached form a heteroaryl ring optionally substituted with one or more R⁶; or two R⁵' on adjacent atoms together with the atoms to which they are attached form a (C₃-C₈)cycloalkyl ring optionally substituted with one or more R⁶; or two R⁵' on adjacent atoms together with the atoms to which they are attached form a heterocycloalkyl ring optionally substituted with one or more R⁶;

each R⁶ and R⁶' is independently, at each occurrence, —H, —(C₁-C₆)alkyl, —(C₂-C₆)alkenyl, —(C₂-C₆)alkynyl, —(C₃-C₈)cycloalkyl, —(C₄-C₈)cycloalkenyl, heterocyclyl, aryl, heteroaryl, halogen, —CN, —OR⁷, —SR⁷, —NO₂, —NR⁷R⁷', —S(O)₂R⁷, —S(O)₂NR⁷R⁷', —S(O)R⁷, —S(O)NR⁷R⁷', —NR⁷S(O)₂R⁷', —NR⁷S(O)R⁷', —C(O)R⁷, or —C(O)OR⁷, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —R⁷, —OR⁷, —SR⁷, —NO₂, —NR⁷R⁷', —S(O)₂R⁷, —S(O)₂NR⁷R⁷', —S(O)R⁷, —S(O)NR⁷R⁷', —NR⁷S(O)₂R⁷', —NR⁷S(O)R⁷', —C(O)R⁷, and —C(O)OR⁷;

each R⁷ and R⁷' is independently, at each occurrence, —H, —(C₁-C₆)alkyl, —(C₂-C₆)alkenyl, —(C₂-C₆)alkynyl, —(C₃-C₈)cycloalkyl, —(C₄-C₈)cycloalkenyl, heterocyclyl, aryl, heteroaryl, halogen, —CN, —OH, —SH, —NO₂, —NH₂, —S(O)₂H, —S(O)₂NH₂, —S(O)H, —S(O)NH₂, —NHS(O)₂H, —NHS(O)H, —C(O)H, or —C(O)OH, wherein each alkyl, alkenyl, alkynyl, cycloalkyl, cycloalkenyl, heterocyclyl, aryl, or heteroaryl is optionally substituted with one or more substituents selected from the group consisting of oxo, halogen, —CN, —OH, —SH, —NO₂, —NH₂, —S(O)₂H, —S(O)₂NH₂, —S(O)H, —S(O)NH₂, —NHS(O)₂H, —NHS(O)H, —C(O)H, and —C(O)OH;

each R⁸, R⁸', R⁹, R⁹', R¹⁰, R¹⁰', R¹¹, and R¹¹' is independently, at each occurrence, —H, —(C₁-C₆)alkyl, —(C₂-C₆)alkenyl, —(C₂-C₆)alkynyl, —(C₃-C₈)cycloalkyl, or —(C₄-C₈)cycloalkenyl, wherein each alkyl, alkenyl, alkynyl, cycloalkyl and cycloalkenyl, is optionally substituted with one or more substituents selected from the group consisting of oxo, halogen, —CN, —R⁷, —OR⁷, —SR⁷, —NO₂, —NR⁷R⁷', —S(O)₂R⁷, —S(O)₂NR⁷R⁷', —S(O)R⁷, —S(O)NR⁷R⁷', —NR⁷S(O)₂R⁷', —NR⁷S(O)R⁷', —C(O)R⁷, and —C(O)OR⁷;

and t is 0, 1, 2, or 3.

42. The compound of embodiment 41, having Formula (Ia-2):

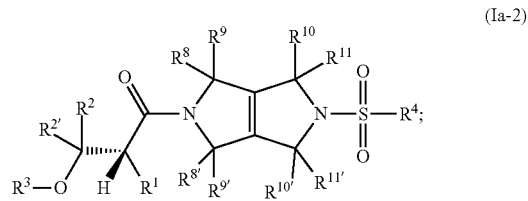

or a pharmaceutically acceptable salt thereof.

43. The compound of embodiment 41 or 42, having Formula (Ib-2):

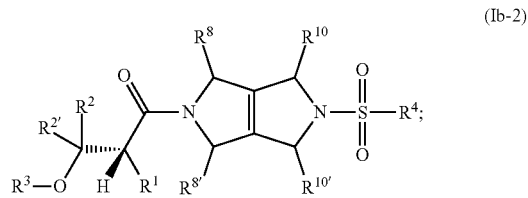

or a pharmaceutically acceptable salt thereof.

44. The compound of any one of embodiments 41-43, having Formula (Ic-2):

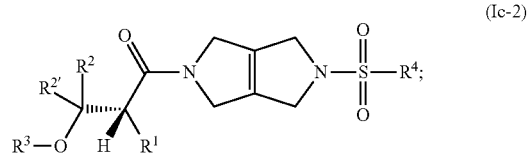

or a pharmaceutically acceptable salt thereof.

45. The compound of any one of embodiments 41-44, wherein R¹ is optionally substituted —(C₁-C₆)alkyl, optionally substituted aryl, or optionally substituted heteroaryl.

46. The compound of any one of embodiments 41-45, wherein R² and R²' are each independently hydrogen or optionally substituted —(C₁-C₆)alkyl.

47. The compound of any one of embodiments 41-46, wherein R³ is hydrogen or optionally substituted —(C₁-C₆)alkyl.

48. The compound of any one of embodiments 41-47, wherein R³ is hydrogen.

49. The compound of any one of embodiments 41-44, wherein R³ and R¹ taken together with the atoms to which they are attached, form an optionally substituted 5-6-membered heterocyclic ring.

50. The compound of any one of embodiments 41-44, wherein R¹ is optionally substituted phenyl or pyridyl; R² and R²' are each independently hydrogen; and R³ is hydrogen or optionally substituted —(C₁-C₆)alkyl.

51. The compound of any one of embodiments 41-44, wherein R¹ is optionally substituted phenyl or pyridyl; R² and R²' are each independently hydrogen; and R³ is hydrogen.

52. The compound of any one of embodiments 41-51, wherein R⁴ is optionally substituted aryl or heteroaryl.

53. The compound of embodiment 52, wherein the aryl or heteroaryl is optionally substituted with one or more substituents selected from the group consisting of oxo, halogen, —CN, —$R^5$, —$OR^5$, —$S(O)_2NR^5R^{5'}$, —$S(O)NR^5R^{5'}$, and —$C(O)R^5$.

54. The compound of embodiment 52, wherein two $R^5$ on adjacent atoms together with the atoms to which they are attached form an aryl ring optionally substituted with one or more $R^6$.

55. The compound of embodiment 52, wherein two $R^5$ on adjacent atoms together with the atoms to which they are attached form a heteroaryl ring optionally substituted with one or more $R^6$.

56. The compound of embodiment 52, wherein two $R^5$ on adjacent atoms together with the atoms to which they are attached form a ($C_3$-$C_8$)cycloalkyl ring optionally substituted with one or more $R^6$.

57. The compound of embodiment 52, wherein two $R^5$ on adjacent atoms together with the atoms to which they are attached form a heterocycloalkyl ring optionally substituted with one or more $R^6$.

58. The compound of embodiment 41, wherein Y is —$CR^5R^{5'}$—.

59. The compound of embodiment 41, wherein Y is —$NR^5(CR^5R^{5'})_t$—.

60. The compound of embodiment 41, wherein Y is —O—.

61. A compound selected from the group consisting of:

| Example | Structure | Name |
|---|---|---|
| 1 | 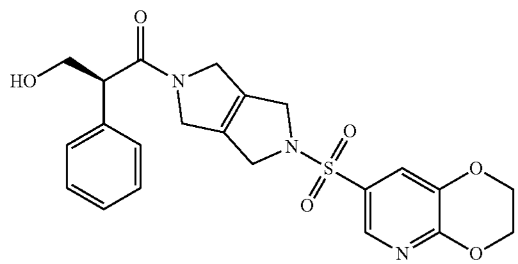 [SMILES: O=C([C@H](CO)c1ccccc1)N1CC2=C(C1)CN(S(=O)(=O)c1cnc3c(c1)OCCO3)C2] | (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one |
| 2 | 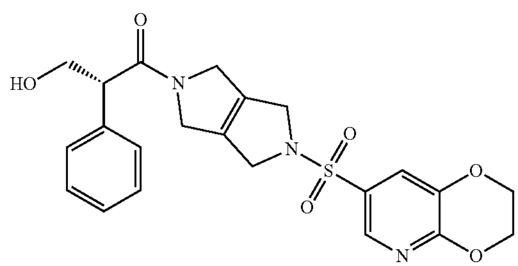 [SMILES: O=C([C@@H](CO)c1ccccc1)N1CC2=C(C1)CN(S(=O)(=O)c1cnc3c(c1)OCCO3)C2] | (R)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one |
| 3 | 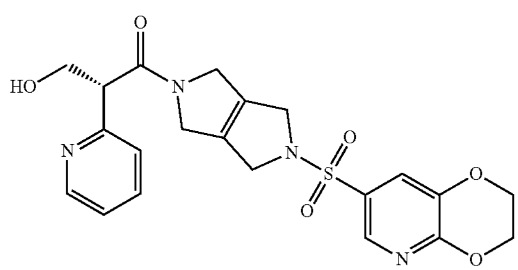 [SMILES: O=C([C@@H](CO)c1ccccn1)N1CC2=C(C1)CN(S(=O)(=O)c1cnc3c(c1)OCCO3)C2] | (R)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-(pyridin-2-yl)propan-1-one |
| 4 | 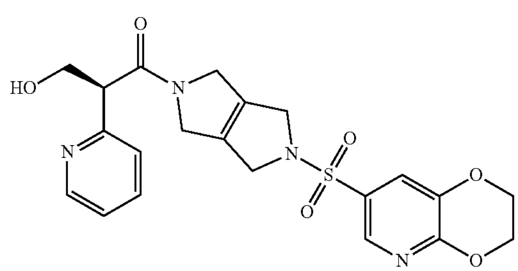 [SMILES: O=C([C@H](CO)c1ccccn1)N1CC2=C(C1)CN(S(=O)(=O)c1cnc3c(c1)OCCO3)C2] | (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-(pyridin-2-yl)propan-1-one |

| Example | Structure | Name |
| --- | --- | --- |
| 5 | 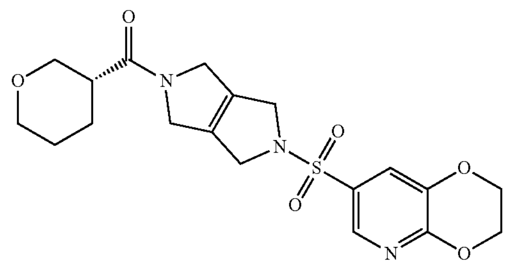 [SMILES: O=C([C@@H]1CCCOC1)N1CC2=C(C1)CN(S(=O)(=O)c1cnc3c(c1)OCCO3)C2] | (R)-(5-((2,3-dihydro-[1,4]dioxino[2,3-b]pyridin-7-yl)sulfonyl)-3,4,5,6-tetrahydropyrrolo[3,4-c]pyrrol-2(1H)-yl)(tetrahydro-2H-pyran-3-yl)methanone |
| 6 | 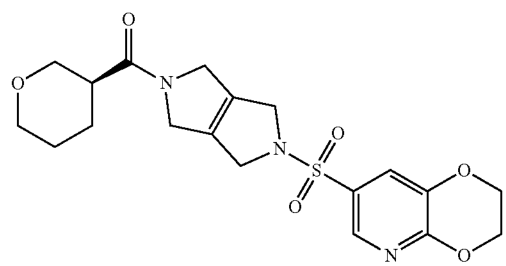 [SMILES: O=C([C@H]1CCCOC1)N1CC2=C(C1)CN(S(=O)(=O)c1cnc3c(c1)OCCO3)C2] | (S)-(5-((2,3-dihydro-[1,4]dioxino[2,3-b]pyridin-7-yl)sulfonyl)-3,4,5,6-tetrahydropyrrolo[3,4-c]pyrrol-2(1H)-yl)(tetrahydro-2H-pyran-3-yl)methanone |
| 7 | 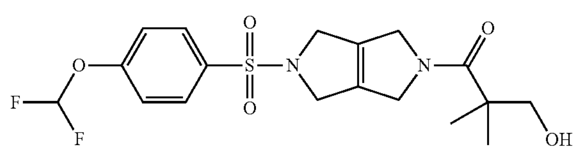 | 1-(5-((4-(difluoromethoxy)phenyl)sulfonyl)-3,4,5,6-tetrahydropyrrolo[3,4-c]pyrrol-2(1H)-yl)-3-hydroxy-2,2-dimethylpropan-1-one |
| 8 | 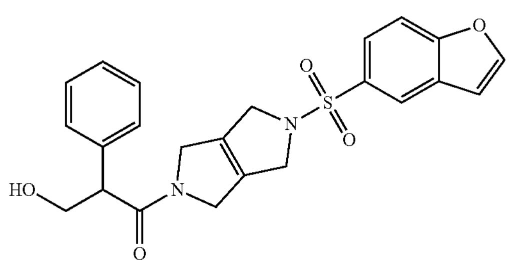 [SMILES: O=C(C(CO)c1ccccc1)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-3-hydroxy-2-phenylpropan-1-one |
| 9 | 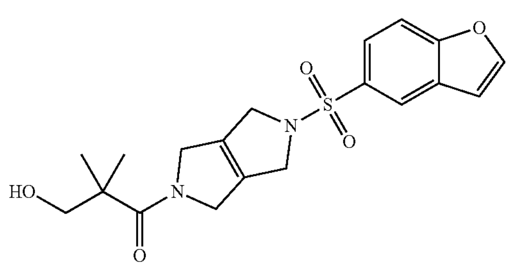 [SMILES: CC(C)(CO)C(=O)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-3-hydroxy-2,2-dimethylpropan-1-one |
| 10 | 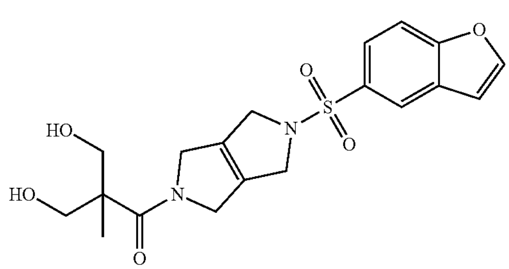 [SMILES: CC(CO)(CO)C(=O)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-3-hydroxy-2-(hydroxymethyl)-2-methylpropan-1-one |

-continued

| Example | Structure | Name |
|---|---|---|
| 11 | 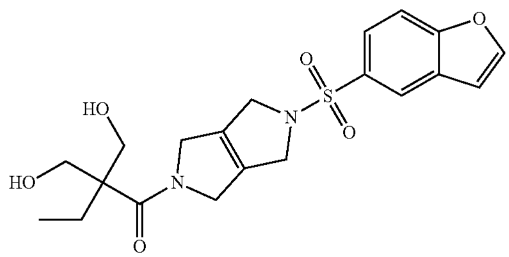 [SMILES: CCC(CO)(CO)C(=O)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-2,2-bis(hydroxymethyl)butan-1-one |
| 12 | 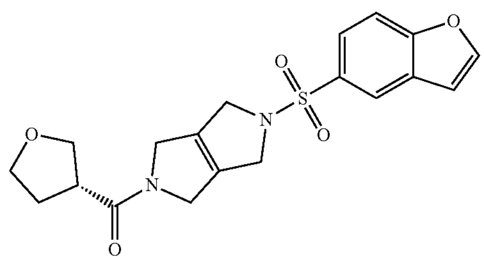 [SMILES: O=C([C@@H]1CCOC1)N1CC2=C(C1)CN(S(=O)(=O)c1ccc3occc3c1)C2] | (R)-(5-(benzofuran-5-ylsulfonyl)-3,4,5,6-tetrahydropyrrolo[3,4-c]pyrrol-2(1H)-yl)(tetrahydrofuran-3-yl)methanone |
| 13 | 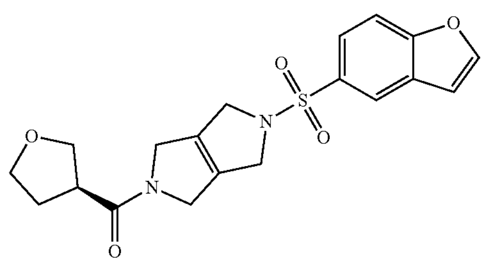 [SMILES: O=C([C@H]1CCOC1)N1CC2=C(C1)CN(S(=O)(=O)c1ccc3occc3c1)C2] | (S)-(5-(benzofuran-5-ylsulfonyl)-3,4,5,6-tetrahydropyrrolo[3,4-c]pyrrol-2(1H)-yl)(tetrahydrofuran-3-yl)methanone |
| 14 | 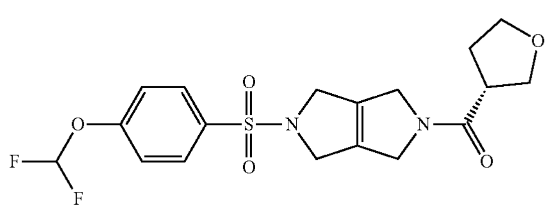 [SMILES: O=C([C@@H]1CCOC1)N1CC2=C(C1)CN(S(=O)(=O)c1ccc(OC(F)F)cc1)C2] | (R)-(5-((4-(difluoromethoxy)phenyl)sulfonyl)-3,4,5,6-tetrahydropyrrolo[3,4-c]pyrrol-2(1H)-yl)(tetrahydrofuran-3-yl)methanone |
| 15 | 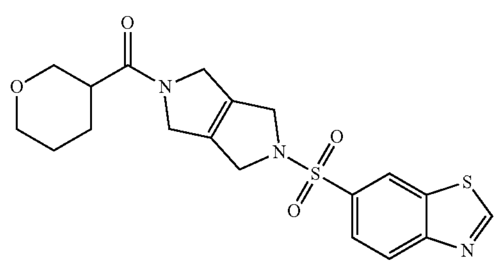 [SMILES: O=C(C1CCCOC1)N1CC2=C(C1)CN(S(=O)(=O)c1ccc3ncsc3c1)C2] | (5-(benzo[d]thiazol-6-ylsulfonyl)-3,4,5,6-tetrahydropyrrolo[3,4-c]pyrrol-2(1H)-yl)(tetrahydro-2H-pyran-3-yl)methanone |
| 16 | 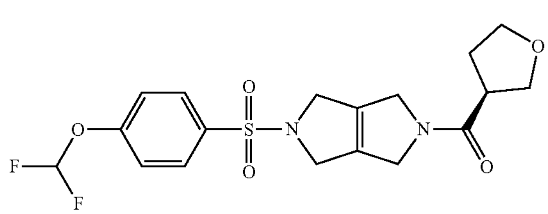 [SMILES: O=C([C@H]1CCOC1)N1CC2=C(C1)CN(S(=O)(=O)c1ccc(OC(F)F)cc1)C2] | (S)-(5-((4-(difluoromethoxy)phenyl)sulfonyl)-3,4,5,6-tetrahydropyrrolo[3,4-c]pyrrol-2(1H)-yl)(tetrahydrofuran-3-yl)methanone |

-continued

| Example | Structure | Name |
|---|---|---|
| 17 | 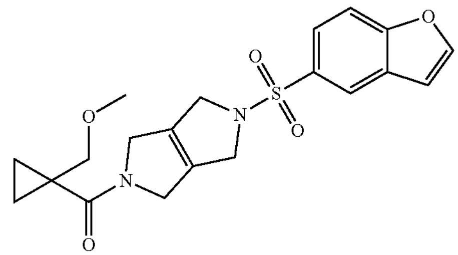 [SMILES: COCC1(C(=O)N2CC3=C(C2)CN(S(=O)(=O)c2ccc4occc4c2)C3)CC1] | (5-(benzofuran-5-ylsulfonyl)-3,4,5,6-tetrahydropyrrolo[3,4-c]pyrrol-2(1H)-yl)(1-(methoxymethyl)cyclopropyl)methanone |
| 18 | 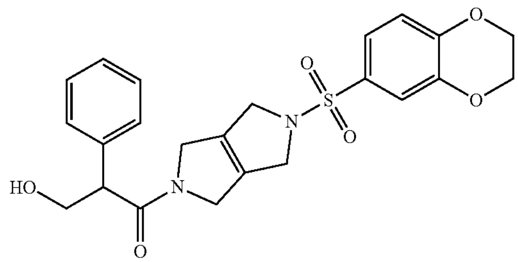 [SMILES: O=C(C(CO)c1ccccc1)N1CC2=C(C1)CN(S(=O)(=O)c1ccc3c(c1)OCCO3)C2] | 1-(5-((2,3-dihydrobenzo[b][1,4]dioxin-6-yl)sulfonyl)-3,4,5,6-tetrahydropyrrolo[3,4-c]pyrrol-2(1H)-yl)-3-hydroxy-2-phenylpropan-1-one |
| 19 | 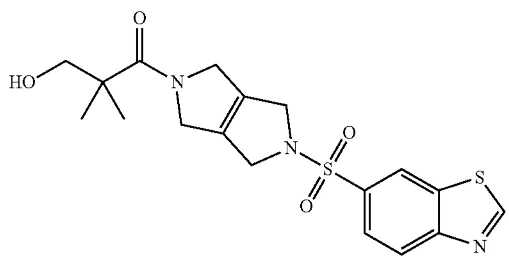 [SMILES: CC(C)(CO)C(=O)N1CC2=C(C1)CN(S(=O)(=O)c1ccc3ncsc3c1)C2] | 1-(5-(benzo[d]thiazol-6-ylsulfonyl)-3,4,5,6-tetrahydropyrrolo[3,4-c]pyrrol-2(1H)-yl)-3-hydroxy-2,2-dimethylpropan-1-one |
| 20 | 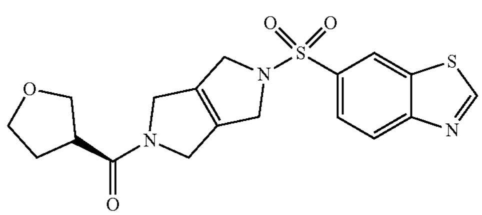 | (R)-(5-(benzo[d]thiazol-6-ylsulfonyl)-3,4,5,6-tetrahydropyrrolo[3,4-c]pyrrol-2(1H)-yl)(tetrahydrofuran-3-yl)methanone |
| 21 | 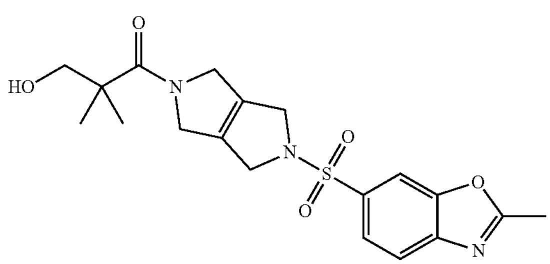 [SMILES: Cc1nc2ccc(S(=O)(=O)N3CC4=C(CN(C(=O)C(C)(C)CO)C4)C3)cc2o1] | 3-hydroxy-2,2-dimethyl-1-(5-((2-methylbenzo[d]oxazol-6-yl)sulfonyl)-3,4,5,6-tetrahydropyrrolo[3,4-c]pyrrol-2(1H)-yl)propan-1-one |
| 22 | 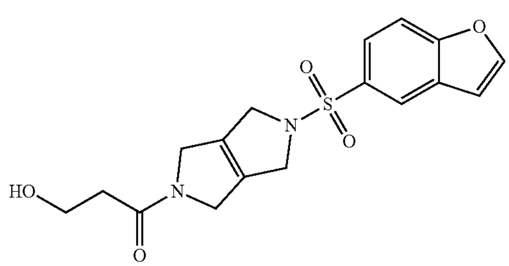 [SMILES: O=C(CCO)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-3-hydroxypropan-1-one |

| Example | Structure | Name |
|---|---|---|
| 23 | 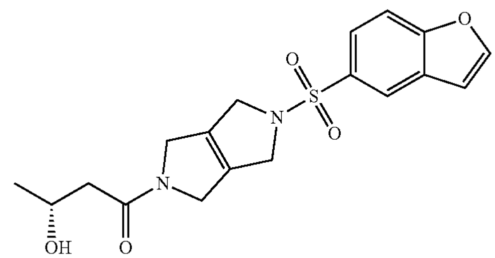 [SMILES: C[C@@H](O)CC(=O)N1CC2=C(C1)CN(S(=O)(=O)c1ccc3occc3c1)C2] | (R)-1-(5-(benzofuran-5-ylsulfonyl)-3,4,5,6-tetrahydropyrrolo[3,4-c]pyrrol-2(1H)-yl)-3-hydroxybutan-1-one |
| 24 | 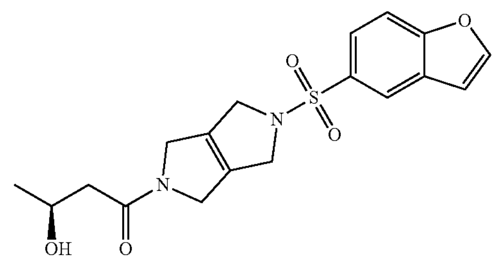 [SMILES: C[C@H](O)CC(=O)N1CC2=C(C1)CN(S(=O)(=O)c1ccc3occc3c1)C2] | (S)-1-(5-(benzofuran-5-ylsulfonyl)-3,4,5,6-tetrahydropyrrolo[3,4-c]pyrrol-2(1H)-yl)-3-hydroxybutan-1-one |
| 25 | 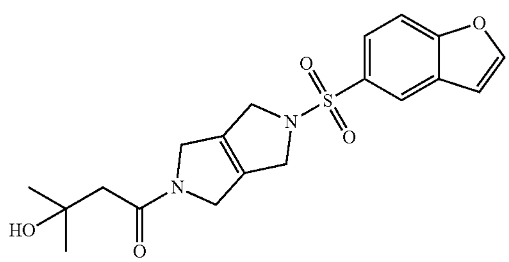 [SMILES: CC(C)(O)CC(=O)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-3-hydroxy-3-methylbutan-1-one |
| 26 | 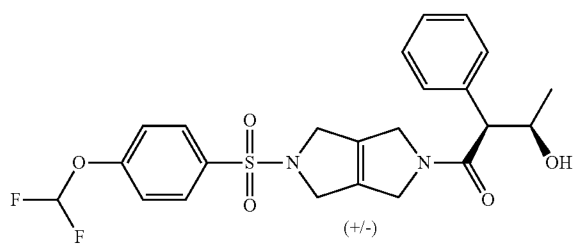 [SMILES: C[C@@H](O)[C@@H](C(=O)N1CC2=C(C1)CN(S(=O)(=O)c1ccc(OC(F)F)cc1)C2)c1ccccc1] | (2S,3R and 2R,3S)-1-(5-((4-(difluoromethoxy)phenyl)sulfonyl)-3,4,5,6-tetrahydropyrrolo[3,4-c]pyrrol-2(1H)-yl)-3-hydroxy-2-phenylbutan-1-one |
| 27 | 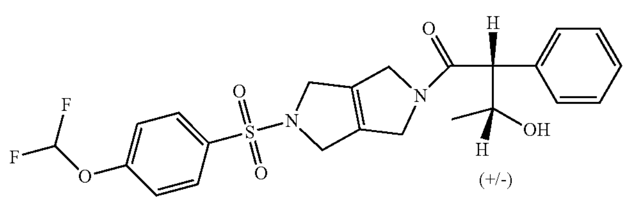 [SMILES: C[C@@H](O)[C@H](C(=O)N1CC2=C(C1)CN(S(=O)(=O)c1ccc(OC(F)F)cc1)C2)c1ccccc1] | (2R,3R and 2S,3S)-1-(5-((4-(difluoromethoxy)phenyl)sulfonyl)-3,4,5,6-tetrahydropyrrolo[3,4-c]pyrrol-2(1H)-yl)-3-hydroxy-2-phenylbutan-1-one |
| 28 | 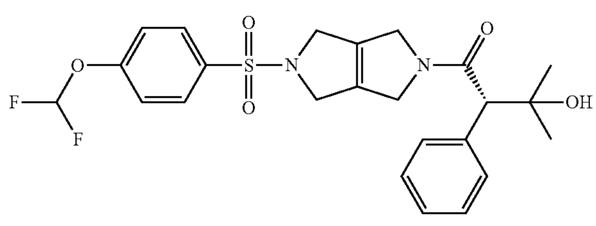 [SMILES: CC(C)(O)[C@@H](C(=O)N1CC2=C(C1)CN(S(=O)(=O)c1ccc(OC(F)F)cc1)C2)c1ccccc1] | (S)-1-(5-((4-(difluoromethoxy)phenyl)sulfonyl)-3,4,5,6-tetrahydropyrrolo[3,4-c]pyrrol-2(1H)-yl)-3-hydroxy-3-methyl-2-phenylbutan-1-one |

-continued

| Example | Structure | Name |
|---|---|---|
| 29 | 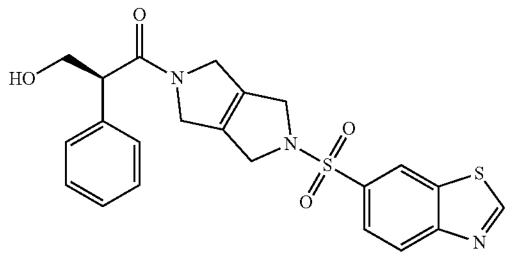 [SMILES: O=C([C@H](CO)c1ccccc1)N1CC2=C(C1)CN(S(=O)(=O)c1ccc3ncsc3c1)C2] | (S)-1-(5-(benzo[d]thiazol-6-ylsulfonyl)-3,4,5,6-tetrahydropyrrolo[3,4-c]pyrrol-2(1H)-yl)-3-hydroxy-2-phenylpropan-1-one |
| 30 | 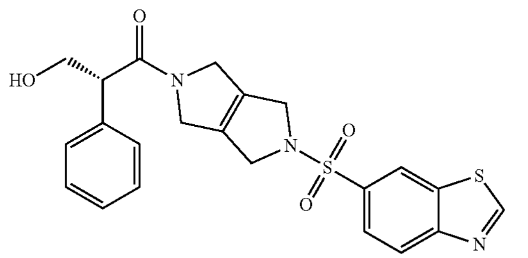 [SMILES: O=C([C@@H](CO)c1ccccc1)N1CC2=C(C1)CN(S(=O)(=O)c1ccc3ncsc3c1)C2] | (R)-1-(5-(benzo[d]thiazol-6-ylsulfonyl)-3,4,5,6-tetrahydropyrrolo[3,4-c]pyrrol-2(1H)-yl)-3-hydroxy-2-phenylpropan-1-one |
| 31 | 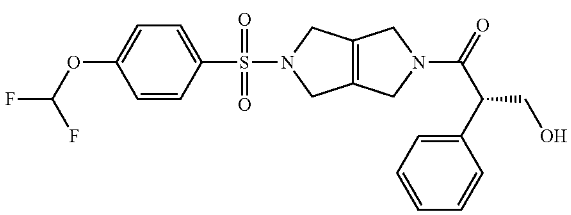 [SMILES: O=C([C@H](CO)c1ccccc1)N1CC2=C(C1)CN(S(=O)(=O)c1ccc(OC(F)F)cc1)C2] | (S)-1-(5-((4-(difluoromethoxy)phenyl)sulfonyl)-3,4,5,6-tetrahydropyrrolo[3,4-c]pyrrol-2(1H)-yl)-3-hydroxy-2-phenylpropan-1-one |
| 32 | 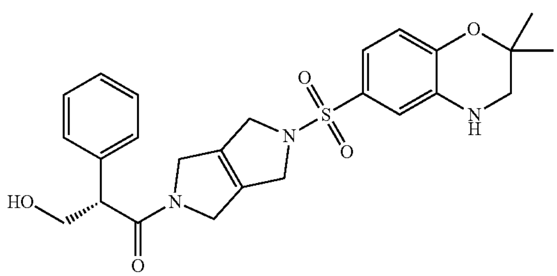 [SMILES: CC1(C)CNc2cc(S(=O)(=O)N3CC4=C(CN(C(=O)[C@H](CO)c5ccccc5)C4)C3)ccc2O1] | (S)-1-(5-((2,2-dimethyl-3,4-dihydro-2H-benzo[b][1,4]oxazin-6-yl)sulfonyl)-3,4,5,6-tetrahydropyrrolo[3,4-c]pyrrol-2(1H)-yl)-3-hydroxy-2-phenylpropan-1-one |
| 33 | 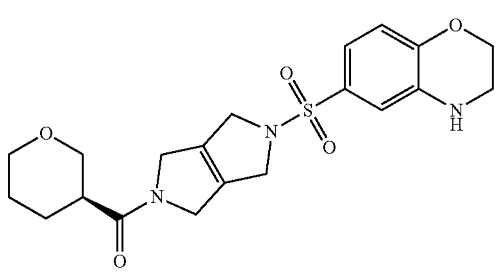 [SMILES: O=C([C@H]1CCCOC1)N1CC2=C(C1)CN(S(=O)(=O)c1ccc3c(c1)NCCO3)C2] | (S)-(5-((3,4-dihydro-2H-benzo[b][1,4]oxazin-6-yl)sulfonyl)-3,4,5,6-tetrahydropyrrolo[3,4-c]pyrrol-2(1H)-yl)(tetrahydro-2H-pyran-3-yl)methanone |
| 34 | 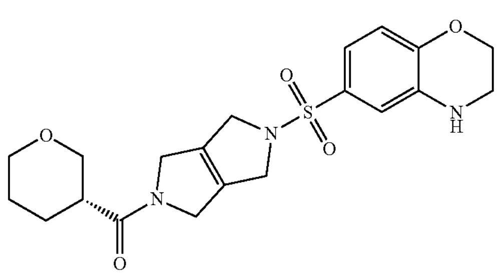 [SMILES: O=C([C@@H]1CCCOC1)N1CC2=C(C1)CN(S(=O)(=O)c1ccc3c(c1)NCCO3)C2] | (R)-(5-((3,4-dihydro-2H-benzo[b][1,4]oxazin-6-yl)sulfonyl)-3,4,5,6-tetrahydropyrrolo[3,4-c]pyrrol-2(1H)-yl)(tetrahydro-2H-pyran-3-yl)methanone |

| Example | Structure | Name |
|---|---|---|
| 35 | 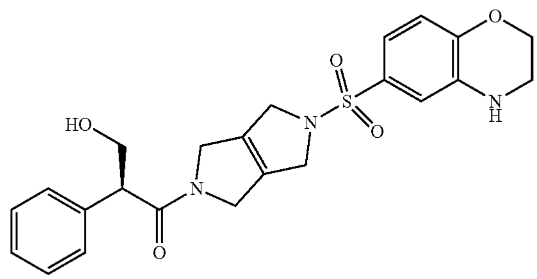 [SMILES: O=C([C@H](CO)c1ccccc1)N1CC2=C(C1)CN(S(=O)(=O)c1ccc3c(c1)NCCO3)C2] | (S)-1-(5-((3,4-dihydro-2H-benzo[b][1,4]oxazin-6-yl)sulfonyl)-3,4,5,6-tetrahydropyrrolo[3,4-c]pyrrol-2(1H)-yl)-3-hydroxy-2-phenylpropan-1-one |
| 36 | 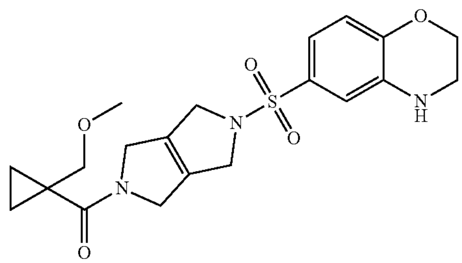 [SMILES: COCC1(C(=O)N2CC3=C(C2)CN(S(=O)(=O)c2ccc4c(c2)NCCO4)C3)CC1] | (5-((3,4-dihydro-2H-benzo[b][1,4]oxazin-6-yl)sulfonyl)-3,4,5,6-tetrahydropyrrolo[3,4-c]pyrrol-2(1H)-yl)(1-(methoxymethyl)cyclopropyl)methanone |
| 37 | 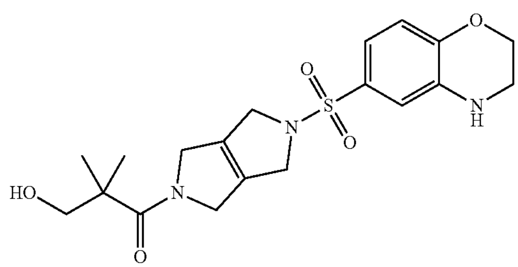 [SMILES: CC(C)(CO)C(=O)N1CC2=C(C1)CN(S(=O)(=O)c1ccc3c(c1)NCCO3)C2] | 1-(5-((3,4-dihydro-2H-benzo[b][1,4]oxazin-6-yl)sulfonyl)-3,4,5,6-tetrahydropyrrolo[3,4-c]pyrrol-2(1H)-yl)-3-hydroxy-2,2-dimethylpropan-1-one |
| 38 | 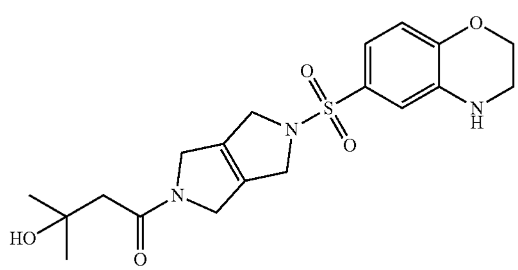 [SMILES: CC(C)(O)CC(=O)N1CC2=C(C1)CN(S(=O)(=O)c1ccc3c(c1)NCCO3)C2] | 1-(5-((3,4-dihydro-2H-benzo[b][1,4]oxazin-6-yl)sulfonyl)-3,4,5,6-tetrahydropyrrolo[3,4-c]pyrrol-2(1H)-yl)-3-hydroxy-3-methylbutan-1-one |
| 39 | 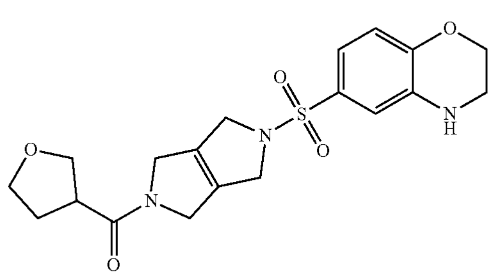 [SMILES: O=C(C1CCOC1)N1CC2=C(C1)CN(S(=O)(=O)c1ccc3c(c1)NCCO3)C2] | (5-((3,4-dihydro-2H-benzo[b][1,4]oxazin-6-yl)sulfonyl)-3,4,5,6-tetrahydropyrrolo[3,4-c]pyrrol-2(1H)-yl)(tetrahydrofuran-3-yl)methanone |

| Example | Structure | Name |
|---|---|---|
| 40 | 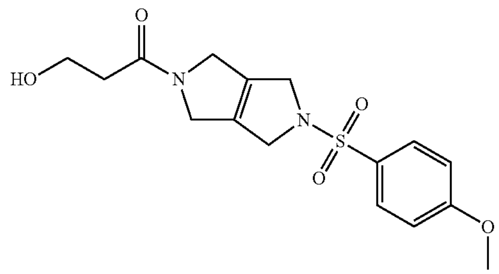 [SMILES: COc1ccc(S(=O)(=O)N2CC3=C(CN(C(=O)CCO)C3)C2)cc1] | 3-hydroxy-1-(5-((4-methoxyphenyl)sulfonyl)-3,4,5,6-tetrahydropyrrolo[3,4-c]pyrrol-2(1H)-yl)propan-1-one |
| 41 | 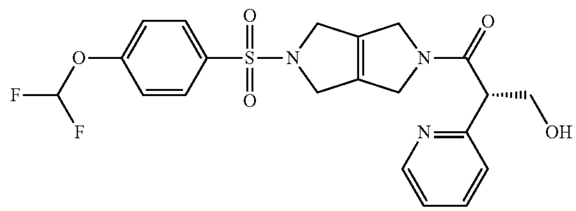 [SMILES: O=C([C@H](CO)c1ccccn1)N1CC2=C(C1)CN(S(=O)(=O)c1ccc(OC(F)F)cc1)C2] | (S)-1-(5-((4-(difluoromethoxy)phenyl)sulfonyl)-3,4,5,6-tetrahydropyrrolo[3,4-c]pyrrol-2(1H)-yl)-3-hydroxy-2-(pyridin-2-yl)propan-1-one |
| 42 | 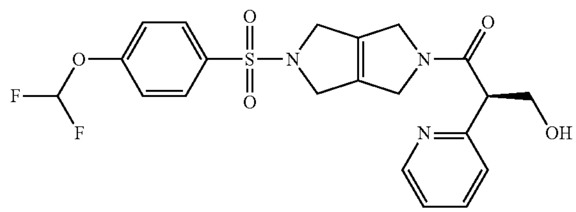 [SMILES: O=C([C@@H](CO)c1ccccn1)N1CC2=C(C1)CN(S(=O)(=O)c1ccc(OC(F)F)cc1)C2] | (R)-1-(5-((4-(difluoromethoxy)phenyl)sulfonyl)-3,4,5,6-tetrahydropyrrolo[3,4-c]pyrrol-2(1H)-yl)-3-hydroxy-2-(pyridin-2-yl)propan-1-one |
| 43 | 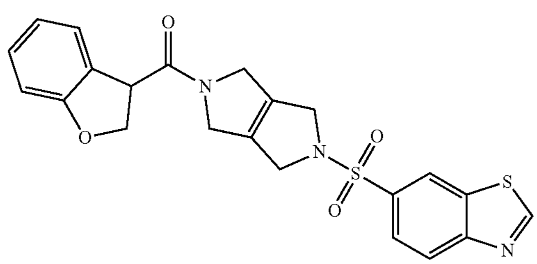 [SMILES: O=C(C1COc2ccccc21)N1CC2=C(C1)CN(S(=O)(=O)c1ccc3ncsc3c1)C2] | (5-(benzo[d]thiazol-6-ylsulfonyl)-3,4,5,6-tetrahydropyrrolo[3,4-c]pyrrol-2(1H)-yl)(2,3-dihydrobenzofuran-3-yl)methanone |
| 44 | 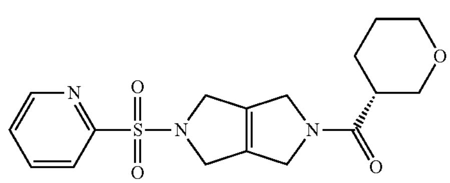 [SMILES: O=C([C@@H]1CCCOC1)N1CC2=C(C1)CN(S(=O)(=O)c1ccccn1)C2] | (R)-(5-(pyridin-2-ylsulfonyl)-3,4,5,6-tetrahydropyrrolo[3,4-c]pyrrol-2(1H)-yl)(tetrahydro-2H-pyran-3-yl)methanone |
| 45 | 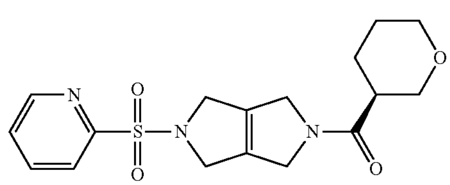 [SMILES: O=C([C@H]1CCCOC1)N1CC2=C(C1)CN(S(=O)(=O)c1ccccn1)C2] | (S)-(5-(pyridin-2-ylsulfonyl)-3,4,5,6-tetrahydropyrrolo[3,4-c]pyrrol-2(1H)-yl)(tetrahydro-2H-pyran-3-yl)methanone |
| 46 | 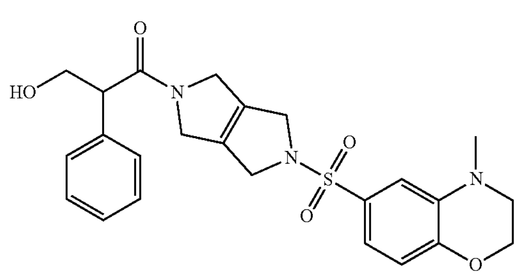 [SMILES: CN1CCOc2ccc(S(=O)(=O)N3CC4=C(CN(C(=O)C(CO)c5ccccc5)C4)C3)cc21] | 3-hydroxy-1-(5-((4-methyl-3,4-dihydro-2H-benzo[b][1,4]oxazin-6-yl)sulfonyl)-3,4,5,6-tetrahydropyrrolo[3,4-c]pyrrol-2(1H)-yl)-2-phenylpropan-1-one |

| Example | Structure | Name |
|---|---|---|
| 47 | 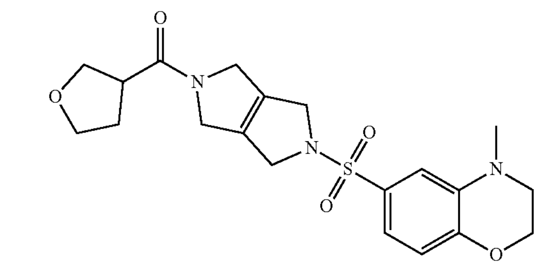 [SMILES: CN1CCOc2ccc(S(=O)(=O)N3CC4=C(CN(C(=O)C5CCOC5)C4)C3)cc21] | (5-((4-methyl-3,4-dihydro-2H-benzo[b][1,4]oxazin-6-yl)sulfonyl)-3,4,5,6-tetrahydropyrrolo[3,4-c]pyrrol-2(1H)-yl)(tetrahydrofuran-3-yl)methanone |
| 48 | 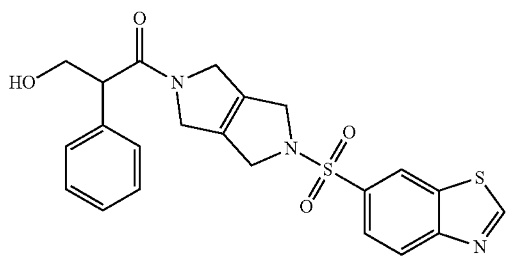 [SMILES: O=C(C(CO)c1ccccc1)N1CC2=C(C1)CN(S(=O)(=O)c1ccc3ncsc3c1)C2] | 1-(5-(benzo[d]thiazol-6-ylsulfonyl)-3,4,5,6-tetrahydropyrrolo[3,4-c]pyrrol-2(1H)-yl)-3-hydroxy-2-phenylpropan-1-one |
| 49 | 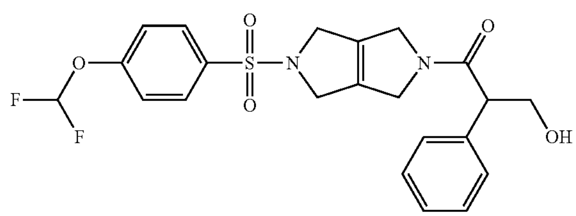 | 1-(5-((4-(difluoromethoxy)phenyl)sulfonyl)-3,4,5,6-tetrahydropyrrolo[3,4-c]pyrrol-2(1H)-yl)-3-hydroxy-2-phenylpropan-1-one |
| 50 | 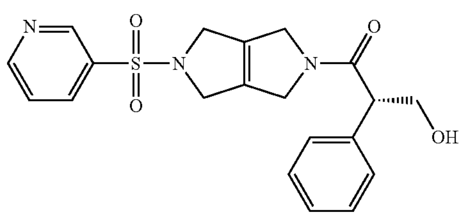 [SMILES: O=C([C@H](CO)c1ccccc1)N1CC2=C(C1)CN(S(=O)(=O)c1cccnc1)C2] | (2S)-3-hydroxy-2-phenyl-1-[5-(pyridine-3-sulfonyl)-1H,2H,3H,4H,5H,6H-pyrrolo[3,4-c]pyrrol-2-yl]propan-1-one |
| 51 | 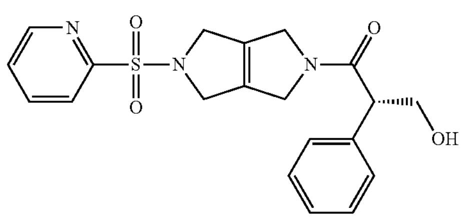 [SMILES: O=C([C@H](CO)c1ccccc1)N1CC2=C(C1)CN(S(=O)(=O)c1ccccn1)C2] | (2S)-3-hydroxy-2-phenyl-1-[5-(pyridine-2-sulfonyl)-1H,2H,3H,4H,5H,6H-pyrrolo[3,4-c]pyrrol-2-yl]propan-1-one |
| 52 | 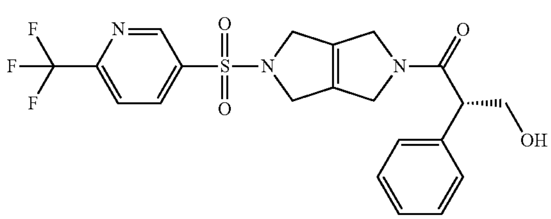 [SMILES: O=C([C@H](CO)c1ccccc1)N1CC2=C(C1)CN(S(=O)(=O)c1ccc(C(F)(F)F)nc1)C2] | (2S)-3-hydroxy-2-phenyl-1-(5-{[6-(trifluoromethyl)pyridin-3-yl]sulfonyl}-1H,2H,3H,4H,5H,6H-pyrrolo[3,4-c]pyrrol-2-yl)propan-1-one |

| Example | Structure | Name |
|---|---|---|
| 53 | 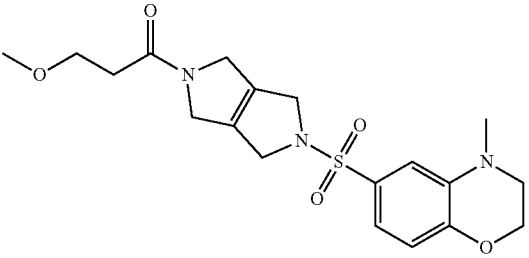 [SMILES: COCCC(=O)N1CC2=C(C1)CN(S(=O)(=O)c1ccc3c(c1)N(C)CCO3)C2] | 3-methoxy-1-(5-((4-methyl-3,4-dihydro-2H-benzo[b][1,4]oxazin-6-yl)sulfonyl)-3,4,5,6-tetrahydropyrrolo[3,4-c]pyrrol-2(1H)-yl)propan-1-one; and |
| 54 | 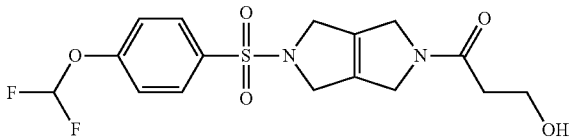 | 1-(5-((4-(difluoromethoxy)phenyl)sulfonyl)-3,4,5,6-tetrahydropyrrolo[3,4-c]pyrrol-2(1H)-yl)-3-hydroxypropan-1-one. |
| 55 | 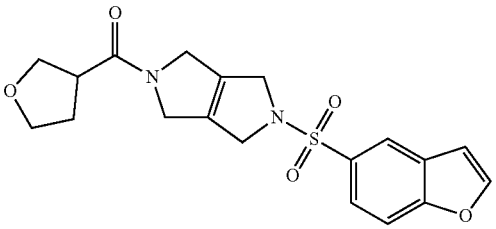 [SMILES: O=C(C1CCOC1)N1CC2=C(C1)CN(S(=O)(=O)c1ccc3occc3c1)C2] | (5-(benzofuran-5-ylsulfonyl)-3,4,5,6-tetrahydropyrrolo[3,4-c]pyrrol-2(1H)-yl)(tetrahydrofuran-3-yl)methanone |
| 56 | 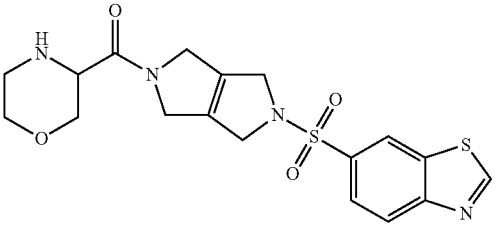 [SMILES: O=C(C1COCCN1)N1CC2=C(C1)CN(S(=O)(=O)c1ccc3ncsc3c1)C2] | (5-(benzo[d]thiazol-6-ylsulfonyl)-3,4,5,6-tetrahydropyrrolo[3,4-c]pyrrol-2(1H)-yl)(morpholin-3-yl)methanone |
| 57 | 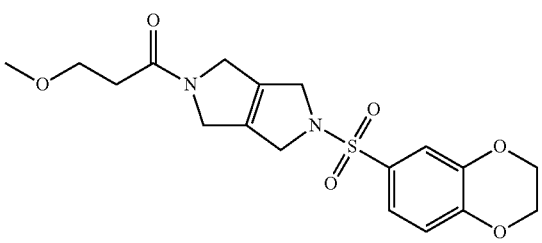 [SMILES: COCCC(=O)N1CC2=C(C1)CN(S(=O)(=O)c1ccc3c(c1)OCCO3)C2] | 1-(5-((2,3-dihydrobenzo[b][1,4]dioxin-6-yl)sulfonyl)-3,4,5,6-tetrahydropyrrolo[3,4-c]pyrrol-2(1H)-yl)-3-methoxypropan-1-one |
| 58 | 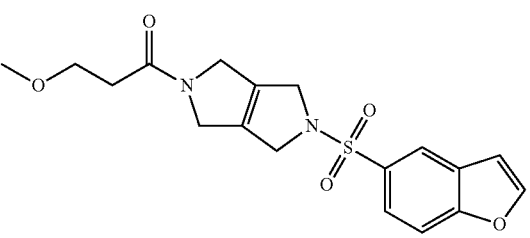 [SMILES: COCCC(=O)N1CC2=C(C1)CN(S(=O)(=O)c1ccc3occc3c1)C2] | 1-(5-(benzofuran-5-ylsulfonyl)-3,4,5,6-tetrahydropyrrolo[3,4-c]pyrrol-2(1H)-yl)-3-methoxypropan-1-one |

62. A pharmaceutical composition comprising a compound of any one of embodiments 1-61 and a pharmaceutically acceptable carrier.

63. A method of treating a disease or disorder associated with modulation of pyruvate kinase (PKR), comprising administering to a patient in need thereof an effective amount of a compound of any one of embodiments 1-61 or a composition of embodiment 62.

64. A method of treating a disease associated with decreased activity of PKR in a subject in need thereof, comprising administering to the subject an effective amount of a compound of any one of embodiments 1-61 or a composition of embodiment 62.

65. A method of activating PKR, comprising administering to a subject in need thereof an effective amount of a compound of any one of embodiments 1-61 or a composition of embodiment 62.
66. A method of increasing the lifetime of red blood cells comprising administering to a subject in need thereof an effective amount of a compound of any one of embodiments 1-61 or a composition of embodiment 62.
67. A method of regulating 2,3-diphosphoglycerate levels in blood comprising administering to a subject in need thereof an effective amount of a compound of any one of embodiments 1-61 or a composition of embodiment 62.
68. A method of regulating ATP levels in blood comprising administering to a subject in need thereof an effective amount of a compound of any one of embodiments 1-61 or a composition of embodiment 62.
69. A method of treating hereditary non-spherocytic hemolytic anemia comprising administering to a subject in need thereof an effective amount of a compound of any one of embodiments 1-61 or a composition of embodiment 62.
70. A method of treating a disease or disorder associated with increased 2,3-diphosphoglycerate levels comprising administering to a subject in need thereof an effective amount of a compound of any one of embodiments 1-61 or a composition of embodiment 62.
71. A method of a treating disease or disorder associated with decreased ATP levels comprising administering to a subject in need thereof an effective amount of a compound of any one of embodiments 1-61 or a composition of embodiment 62.
72. The method of any of embodiments 63-64 or 70-71, wherein the disease or disorder is selected from the group consisting of sickle cell disease, sickle cell anemia, thalassemia (e.g., beta-thalassemia), hereditary non-spherocytic hemolytic anemia, hemolytic anemia (e.g., chronic hemolytic anemia caused by phosphoglycerate kinase deficiency), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), and anemia of chronic diseases.
73. A method of treating a disease or disorder comprising administering to a patient in need thereof an effective amount of a compound of any one of embodiments 1-61 or a composition of embodiment 62.
74. The method of embodiment 73, wherein the disease or disorder is selected from the group consisting of sickle cell disease, sickle cell anemia, thalassemia (e.g., beta-thalassemia), hereditary non-spherocytic hemolytic anemia, hemolytic anemia (e.g., chronic hemolytic anemia caused by phosphoglycerate kinase deficiency), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), and anemia of chronic diseases.
75. The method of embodiment 74, wherein the disease or disorder is sickle cell anemia.
76. The method of embodiment 74, wherein the disease or disorder is hemolytic anemia.
77. The method of embodiment 74, wherein the disease or disorder is beta thalassemia.
78. A PKR Activating Compound having a % Fold@ 1.54 µM of at least 75%, according to the Luminescence Assay Protocol of Example 47.
79. The PKR Activating Compound of embodiment 78 having a % Fold@ 1.54 µM of 75-500%.
80. The PKR Activating Compound of embodiment 79 having a % Fold@ 1.54 µM of 250-500%.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims The following are illustrative, but non-limiting, examples of certain embodiments of the present disclosure. The synthetic schemes are presented for the synthesis of certain compounds herein disclosed.

Definitions used in the following Schemes and elsewhere herein are:
ACN acetonitrile
AcOH acetic acid
AIBN azobisisobutyronitrile
$AlCl_3$ trichloroaluminum
$Boc_2O$ di-tert-butyl dicarbonate
$NaBH_4$ sodium borohydride
BOP ammonium 4-(3-(pyridin-3-ylmethyl)ureido)benzenesulfinate
Brine saturated aqueous sodium chloride solution
$CDCl_3$ deuterated chloroform
δ chemical shift
DCM dichloromethane or methylene chloride
DCE dichloroethane
DIEA N,N-diisopropylethylamine
DMA N,N-dimethylacetamide
DMF N,N-dimethylformamide
DMSO dimethylsulfoxide
DMT dimercaptotriazine
EDCI N1-((ethylimino)methylene)-N3,N3-dimethylpropane-1,3-diamine hydrochloride
equiv equivalents
EtOAc, EA ethyl acetate
EtOH ethanol
h hour
HCl hydrochloric acid
$^1H$ NMR proton nuclear magnetic resonance
HOAc acetic acid
HATU 2-(3H-[1,2,3]triazolo[4,5-b]pyridin-3-yl)-1,1,3,3-tetramethylisouronium hexafluorophosphate
HBTU O-(Benzotriazol-yl)N,N,N',N'-tetramethyluronium hexafluorophosphate
HOBT 1H-benzo[d][1,2,3]triazol-1-ol hydrate
HPLC high performance liquid chromatography
Hz hertz
KOAc potassium acetate
LCMS liquid chromatography/mass spectrometry
LDA lithium diisopropylamide
(M+1) mass+1
m-CPBA m-chloroperbenzoic acid
MeOH methanol
min minute(s)
n-BuLi n-butyl lithium
NCS N-chlorosuccinimide NaH sodium hydride
NaHCO$_3$ sodium bicarbonate
NaOH sodium hydroxide
Na$_2$SO$_4$ sodium sulfate
Pd$_2$(dba)$_3$ tris(dibenzylideneacetone)dipalladium(0)
PFA paraformaldehyde
PTLC preparative thin layer chromatography
RT room temperature
Rt retention time
SFC supercritical fluid chromatography
SPE solid phase extraction
TEA triethylamine
TFAA trifluoroacetic anhydride
TMSCN trimethylsilyl cyanide
THF tetrahydrofuran
TLC thin layer chromatography
Xantphos 4,5-Bis(diphenylphosphino)-9,9-dimethylxanthene
ZnI$_2$ zinc iodide Materials Unless otherwise noted, all materials were obtained from commercial suppliers and were used without further purification. Anhydrous solvents were obtained from Sigma-Aldrich (Milwaukee, WI) and used directly. All reactions involving air- or moisture-sensitive reagents were performed under a nitrogen atmosphere.

Intermediate 1: 2-[2H,3H-[1,4]dioxino[2,3-b]pyridine-7-sulfonyl]-1H,2H,3H,4H,5H,6H-pyrrolo[3,4-c]pyrrole

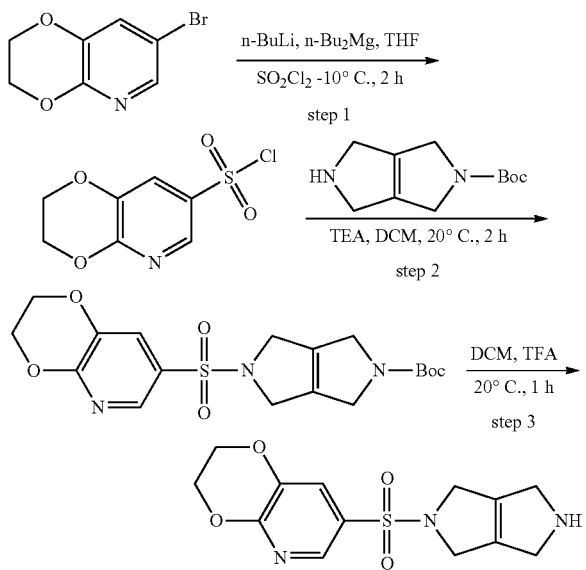

Step 1. 2H,3H-[1,4]dioxino[2,3-b]pyridine-7-sulfonyl Chloride

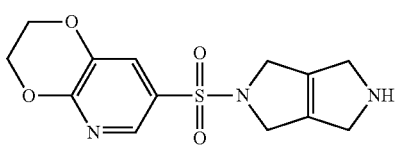 [SMILES: O=S(=O)(c1cnc2c(c1)OCCO2)N1CC2=C(CNC2)C1]

Into a 100 mL round-bottom flask purged and maintained with an inert atmosphere of nitrogen was placed a solution of n-BuLi in hexane (2.5 M, 2 mL, 5.0 mmol, 0.54 equiv) and a solution of n-Bu$_2$Mg in heptanes (1.0 M, 4.8 mL, 4.8 mmol, 0.53 equiv). The resulting solution was stirred for 10 min at RT (20° C.). This was followed by the dropwise addition of a solution of 7-bromo-2H,3H-[1,4]dioxino[2,3-b]pyridine (2 g, 9.26 mmol, 1.00 equiv) in tetrahydrofuran (16 mL) with stirring at −10° C. in 10 min. The resulting mixture was stirred for 1 h at −10° C. The reaction mixture was slowly added to a solution of thionyl chloride (16 mL) at −10° C. The resulting mixture was stirred for 0.5 h at −10° C. The reaction was then quenched by the careful addition of 30 mL of saturated ammonium chloride solution at 0° C. The resulting mixture was extracted with 3×50 mL of dichloromethane. The organic layers were combined, dried over anhydrous sodium sulfate, filtered and concentrated under vacuum. The residue was purified by silica gel column chromatography, eluting with ethyl acetate/petroleum ether (1:3). This provided 1.3 g (60%) of 2H,3H-[1,4]dioxino[2,3-b]pyridine-7-sulfonyl chloride as a white solid. LCMS m/z: calculated for C$_7$H$_6$ClNO$_4$S: 235.64; found: 236 [M+H]$^+$.

Step 2. tert-Butyl 5-[2H,3H-[1,4]dioxino[2,3-b]pyridine-7-sulfonyl]-1H,2H,3H,4H,5H,6H-pyrrolo[3,4-c]pyrrole-2-carboxylate

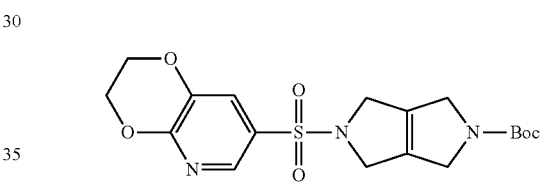

Into a 100-mL round-bottom flask was placed 2H,3H-[1,4]dioxino[2,3-b]pyridine-7-sulfonyl chloride (1.3 g, 5.52 mmol, 1.00 equiv), tert-butyl 1H,2H,3H,4H,5H,6H-pyrrolo[3,4-c]pyrrole-2-carboxylate (1.16 g, 5.52 mmol), dichloromethane (40 mL), and triethylamine (1.39 g, 13.74 mmol, 2.49 equiv). The solution was stirred for 2 h at 20° C., then diluted with 40 mL of water. The resulting mixture was extracted with 3×30 mL of dichloromethane. The organic layers were combined, dried over anhydrous sodium sulfate, filtered and concentrated under vacuum. The residue was purified by silica gel column chromatography, eluting with dichloromethane/methanol (10:1). This provided 1.2 g (53%) of tert-butyl 5-[2H,3H-[1,4]dioxino[2,3-b]pyridine-7-sulfonyl]-1H,2H,3H,4H,5H,6H-pyrrolo[3,4-c]pyrrole-2-carboxylate as a yellow solid. LCMS m/z: calculated for C$_{18}$H$_{23}$N$_3$O$_6$S: 409.46; found: 410 [M+H]$^+$.

Step 3. 2-[2H,3H-[1,4]dioxino[2,3-b]pyridine-7-sulfonyl]-1H,2H,3H,4H,5H,6H-pyrrolo[3,4-c]pyrrole Into a 100-mL round-bottom flask was placed tert-butyl 5-[2H,3H-[1,4]dioxino[2,3-b]pyridine-7-sulfonyl]-1H,2H,3H,4H,5H,6H-pyrrolo[3,4-c]pyrrole-2-carboxylate (1.2 g, 2.93 mmol, 1.00 equiv), dichloromethane (30 mL), and trifluoroacetic acid (6 mL). The solution was stirred for 1 h at 20° C. The resulting mixture was concentrated under vacuum. The residue was dissolved in 10 mL of methanol and the pH was adjusted to 8 with sodium bicarbonate (2 mol/L). The resulting solution was extracted with 3×10 mL of dichloromethane. The organic layers were combined, dried over anhydrous sodium sulfate, filtered and concentrated under vacuum. The crude product was purified by silica gel column chromatography, eluting with dichloromethane/methanol (10:1). This provided 650 mg (72%) of 2-[2H,3H-[1,4]dioxino[2,3-b]pyridine-7-sulfonyl]-1H,2H,3H,4H,5H,6H-pyrrolo[3,4-c]pyrrole as a yellow solid. LCMS m/z: calculated for $C_{13}H_{15}N_3O_4S$: 309.34; found: 310 $[M+H]^+$.

Intermediate 2: 2-((2,3-dihydrobenzo[b][1,4]dioxin-6-yl)sulfonyl)-1,2,3,4,5,6-hexahydropyrrolo[3,4-c]pyrrole

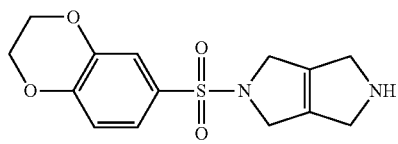 [SMILES: O=S(=O)(c1ccc2c(c1)OCCO2)N1CC2=C(CNC2)C1]

Prepared as described for Intermediate 1 (step 2 and step 3), using the appropriate synthetic precursors.

Step 2: tert-butyl 5-(2,3-dihydro-1,4-benzodioxine-6-sulfonyl)-1H,2H,3H,4H,5H,6H-pyrrolo[3,4-c]pyrrole-2-carboxylate This resulted in 170 mg (98%) of tert-butyl 5-(2,3-dihydro-1,4-benzodioxine-6-sulfonyl)-1H,2H,3H,4H,5H,6H-pyrrolo[3,4-c]pyrrole-2-carboxylate as a brown solid. LCMS: m/z=409 $[M+H]^+$.

Step 3: 2-(2,3-dihydro-1,4-benzodioxine-6-sulfonyl)-1H,2H,3H,4H,5H,6H-pyrrolo[3,4-c]pyrrole This resulted in 200 mg (91%) of 2-(2,3-dihydro-1,4-benzodioxine-6-sulfonyl)-1H,2H,3H,4H,5H,6H-pyrrolo[3,4-c]pyrrole as brown oil. LCMS: m/z=309 $[M+H]^+$.

Intermediates 3 and 4. (S)-3-hydroxy-2-phenylpropanoic Acid and (R)-3-hydroxy-2-phenylpropanoic Acid

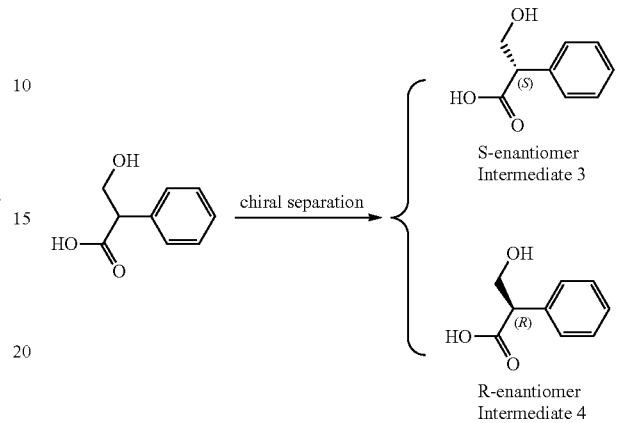

Materials 3-Hydroxy-2-phenylpropanoic acid (1 g) was separated by Prep-SFC with the following conditions: Instrument Name: SHIMADZU LC-20AD, LC parameters: Pump Mode: Binary gradient, Start Conc. of Pump B: 100.0%, Total Flow: 170 mL/min, Phase A, Phase B: MeOH (0.1% HAC), Column Name: CHIRALPAK AD-H, Length: 100 mm, Internal Diameter: 4.6 mm, Particle Size: 5 μm, Column Temp: 20° C., PDA Model: SPD-M20A, Wavelength: from 190 nm to 500 nm. This provided peak 1: (Rt=5.76 min) 380 mg of (S)-3-hydroxy-2-phenylpropanoic acid as a white solid, and peak 2: (Rt=6.87 min) 370 mg of (R)-3-hydroxy-2-phenylpropanoic acid as a white solid.

$^1$H NMR (300 MHz, DMSO-$d_6$): δ ppm 12.31 (br s, 1H), 7.40-7.20 (m, 5H), 4.94 (br s, 1H), 3.92 (t, J=9 Hz, 1H), 3.67-3.54 (m, 2H). S-enantiomer: $\alpha_D^{16.7}=-110$ (C 0.02, water); [literature: −79] R-enantiomer: $\alpha_D^{16.7}=+125$ (C 0.02, water).

Intermediate 5: 1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-2-(pyridin-2-yl)ethan-1-one

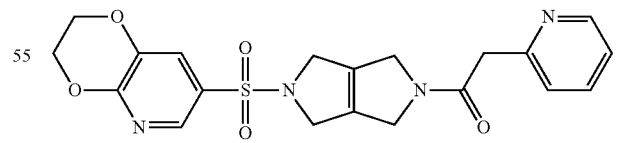

Prepared according to the reaction conditions described for Example 1 from the appropriate reagents. 1-(5-((2,3-Dihydro-[1,4]dioxino[2,3-b]pyridin-7-yl)sulfonyl)-3,4,5,6-tetrahydropyrrolo[3,4-c]pyrrol-2(1H)-yl)-2-(pyridin-2-yl)ethan-1-one was isolated as a white solid (300 mg, 76%). LC-MS: m/z: calculated for $C_{20}H_{20}N_4O_5S$: 428.12; found 429.10 $[M+H]^+$.

Intermediate 6: 1-(5-((4-(difluoromethoxy)phenyl)sulfonyl)-3,4,5,6-tetrahydropyrrolo[3,4-c]pyrrol-2(1H)-yl)-2-(pyridin-2-yl)ethan-1-one

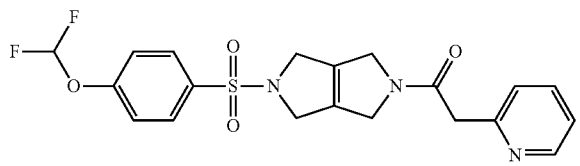 [SMILES: O=C(Cc1ccccn1)N1CC2=C(C1)CN(S(=O)(=O)c1ccc(OC(F)F)cc1)C2]

Prepared according to the reaction conditions described for Example 7 from the appropriate reagents. The crude material was purified by prep-HPLC: Column: SunFire Prep C18 5 μm 19*150 mm; mobile phase: water (contains 0.1% TFA) and CH$_3$CN with a gradient of 43% to 73% CH$_3$CN in 7 min; detector UV wavelength: 220 nm. This resulted in 25.6 mg (21%) of 1-(5-((4-(difluoromethoxy)phenyl)sulfonyl)-3,4,5,6-tetrahydropyrrolo[3,4-c]pyrrol-2(1H)-yl)-2-(pyridin-2-yl)ethan-1-one as a white solid.

$^1$H NMR (300 MHz, DMSO-d$_6$, ppm): δ 8.50-8.51 (d, J=4.2 Hz, 1H), 7.84-7.89 (m, 2H), 7.71-7.76 (t, J=7.5 Hz, 1H), 7.44-7.46 (d, J=8.1 Hz, 1H), 7.23-7.29 (m, 3H), 6.37-6.85 (t, J=72.6 Hz, 1H), 4.40 (br, 2H), 3.97-4.14 (br, 6H), 3.90-3.94 (br, 2H). LC-MS m/z: Calculated for C$_{20}$H$_{19}$F$_2$N$_3$O$_4$S: 435.11; found: 436 [M+H]$^+$.

Intermediate 7: 2-(Benzofuran-5-ylsulfonyl)-1,2,3,4,5,6-hexahydropyrrolo[3,4-c]pyrrole Hydrochloride

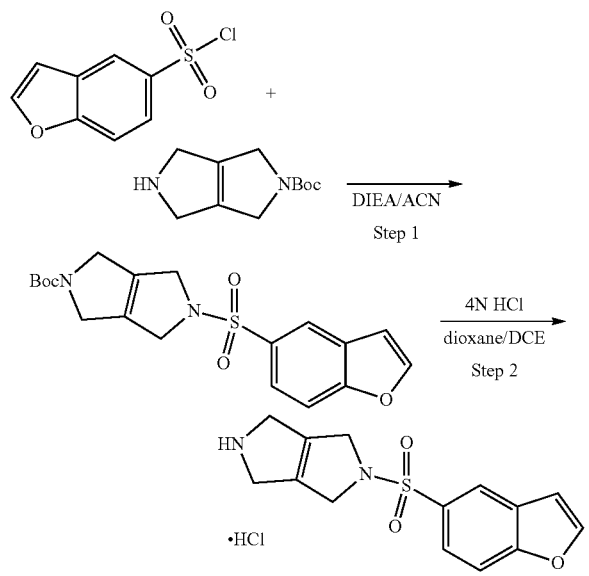

Step 1. tert-Butyl 5-(benzofuran-5-ylsulfonyl)-3,4,5,6-tetrahydropyrrolo[3,4-c]pyrrole-2(1H)-carboxylate To a solution of tert-butyl 3,4,5,6-tetrahydropyrrolo[3,4-c]pyrrole-2(1H)-carboxylate (0.7 g, 3.33 mmol) in acetonitrile (20 mL) and DIEA (1.70 mL, 9.76 mmol) was added benzofuran-5-sulfonyl chloride (17.48 ml, 3.50 mmol) in 1,4 dioxane (17 mL). The resulting mixture was stirred at RT overnight. The reaction mixture was worked up with saturated ammonium chloride solution and EtOAc. The combined organics were washed with brine, dried over Na$_2$SO$_4$, filtered, and concentrated under reduced pressure to provide tert-butyl 5-(benzofuran-5-ylsulfonyl)-3,4,5,6-tetrahydropyrrolo[3,4-c]pyrrole-2(1H)-carboxylate (1.3 g, 3.33 mmol, 100%) as an oil. LCMS: m/z=413 [M+Na]$^+$.

Step 2. 2-(Benzofuran-5-ylsulfonyl)-1,2,3,4,5,6-hexahydropyrrolo[3,4-c]pyrrole Hydrochloride Tert-butyl 5-(benzofuran-5-ylsulfonyl)-3,4,5,6-tetrahydropyrrolo[3,4-c]pyrrole-2(1H)-carboxylate (1.3 g, 3.33 mmol) was dissolved in a mixture of methanol (3.0 mL), DCE (10.0 mL) and 4 M HCl in 1,4-dioxane (5.0 mL). The reaction was heated at 50° C. for 2 h. The solvents were evaporated under reduced pressure and the reaction mixture was azeotropically dried with toluene and dried further under vacuum overnight to provide 2-(benzofuran-5-ylsulfonyl)-1,2,3,4,5,6-hexahydropyrrolo[3,4-c]pyrrole hydrochloride (0.95 mg, 3.33 mmol, 100%). LCMS: m/z=291 [M+H]$^+$.

Intermediate 8: 1-(6-((3,4,5,6-Tetrahydropyrrolo[3,4-c]pyrrol-2(1H)-yl)sulfonyl)-2,3-dihydro-4H-benzo[b][1,4]oxazin-4-yl)ethan-1-one Hydrochloride

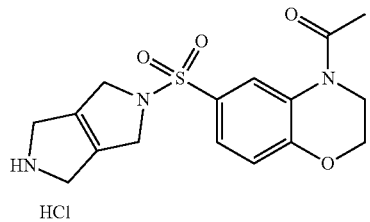 [SMILES: CC(=O)N1CCOc2ccc(S(=O)(=O)N3CC4=C(CNC4)C3)cc21 ; Cl]

Prepared as described for Intermediate 7, using the appropriate synthetic precursors. 94% overall yield. LCMS: m/z=350 [M+H]$^+$.

Intermediate 9: 2-(Pyridin-2-ylsulfonyl)-1,2,3,4,5,6-hexahydropyrrolo[3,4-c]pyrrole, Hydrochloride Salt

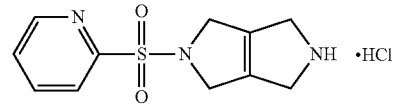 [SMILES: O=S(=O)(c1ccccn1)N1CC2=C(CNC2)C1 ; Cl]

Prepared as described for Intermediate 7, using the appropriate synthetic precursors.

Step 1. tert-Butyl 5-(pyridine-2-sulfonyl)-1H,2H,3H,4H,5H,6H-pyrrolo[3,4-c]pyrrole-2-carboxylate Isolated as a orange solid (570 mg, 36%). The material was used without further purification. LCMS: m/z=352 [M+H]$^+$.

Step 2. 2-(Pyridin-2-ylsulfonyl)-1,2,3,4,5,6-hexahydropyrrolo[3,4-c]pyrrole, Hydrochloride Salt Isolated as a white solid (467 mg, quantitative yield). LCMS: m/z=252 [M+H]$^+$.

Intermediate 10: 3-Hydroxy-2,2-dimethyl-1-(3,4,5,6-tetrahydropyrrolo[3,4-c]pyrrol-2(1H)-yl)propan-1-one Hydrochloride

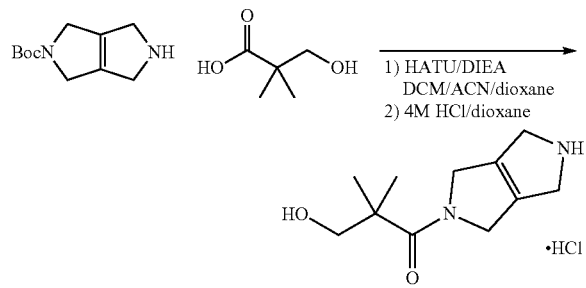

To a solution of tert-butyl 3,4,5,6-tetrahydropyrrolo[3,4-c]pyrrole-2(1H)-carboxylate (50.5 mg, 0.24 mmol) in DCM (1.2 mL) and DIEA (105 µL, 0.60 mmol) was added 3-hydroxy-2,2-dimethylpropanoic acid (28.4 mg, 0.240 mmol) in 1,4 dioxane (1.2 mL), followed by a solution of HATU (630 µl, 0.252 mmol) in acetonitrile (1.3 mL). The reaction mixture was stirred at RT for 3 hours and worked-up with 1 N NaOH (aqueous) and EtOAc. The resulting material was dissolved in DCM (0.9 mL) and 4 M HCl in 1,4-dioxane (0.36 mL) was added. The mixture was stirred at RT overnight. The reaction was concentrated, azeotropically dried with toluene and dried further under vacuum to give 3-hydroxy-2,2-dimethyl-1-(3,4,5,6-tetrahydropyrrolo[3,4-c]pyrrol-2(1H)-yl)propan-1-one hydrochloride (44.4 mg, 0.180 mmol, 75.0% yield).

Intermediate 11: (R)-(tetrahydrofuran-3-yl)(3,4,5,6-tetrahydropyrrolo[3,4-c]pyrrol-2(1H)-yl)methanone Hydrochloride Salt

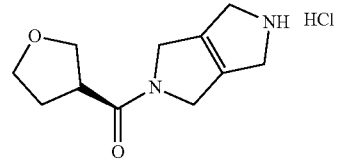

Prepared according to the procedure for Intermediate 10, using the appropriate synthetic precursors

Intermediate 12: 6-((3,4,5,6-Tetrahydropyrrolo[3,4-c]pyrrol-2(1H)-yl)sulfonyl)benzo[d]thiazole Hydrochloride

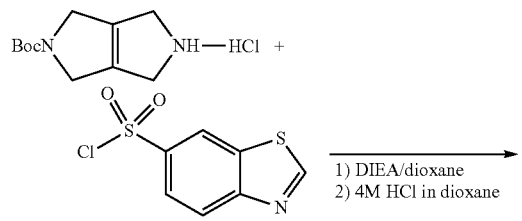

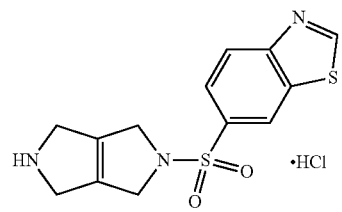

To a 50 mL round-bottomed flask was added tert-butyl 3,4,5,6-tetrahydropyrrolo[3,4-c]pyrrole-2(1H)-carboxylate hydrochloride (0.5 g, 2.026 mmol), DIEA (1.059 ml, 6.08 mmol), and dioxane (10 mL) to give a brown suspension. Benzo[d]thiazole-6-sulfonyl chloride (0.497 g, 2.128 mmol) was added. The reaction was heated at 50° C. with stirring for 2 hours. The volatiles were removed under reduced pressure. The residue was resuspended in dioxane (10 mL) and 4 M HCl in dioxane (5.07 ml, 20.26 mmol) was added. The reaction was heated at 50° C. with stirring for 2 hours. The volatiles were removed under reduced pressure to give 6-((3,4,5,6-tetrahydropyrrolo[3,4-c]pyrrol-2(1H)-yl)sulfonyl)benzo[d]thiazole hydrochloride (0.640 g, 1.865 mmol, 92%) as a brown oil that was used without further purification. LCMS: m/z=307.9 [M+H]$^+$.

Intermediate 13: 2-[[4-(difluoromethoxy)benzene]sulfonyl]-1H,2H,3H,4H,5H,6H-pyrrolo[3,4-c]pyrrole Hydrochloride

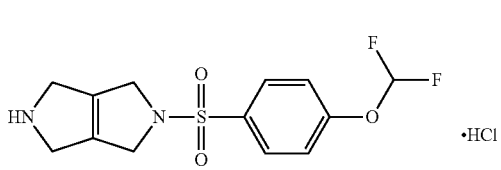 [SMILES: O=S(=O)(c1ccc(OC(F)F)cc1)N1CC2=C(CNC2)C1 ; Cl]

Prepared according to the procedure for Intermediate 12, using the appropriate synthetic precursors. Obtained 0.652 g (1.848 mmol, 91%). LCMS: m/z=317.1 [M+H]$^+$.

Intermediate 14: 2-((6-(trifluoromethyl)pyridin-3-yl)sulfonyl)-1,2,3,4,5,6-hexahydropyrrolo[3,4-c]pyrrole HCl Salt

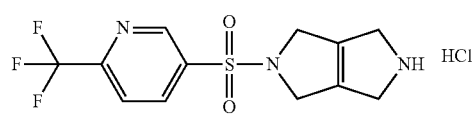

Prepared according to the procedure for Intermediate 12, using the appropriate synthetic precursors. LCMS: m/z=319.9 [M+H]$^+$.

Intermediate 15: 2,2-Dimethyl-6-[1H,2H,3H,4H,5H, 6H-pyrrolo[3,4-c]pyrrole-2-sulfonyl]-3,4-dihydro-2H-1,4-benzoxazine, TFA Salt

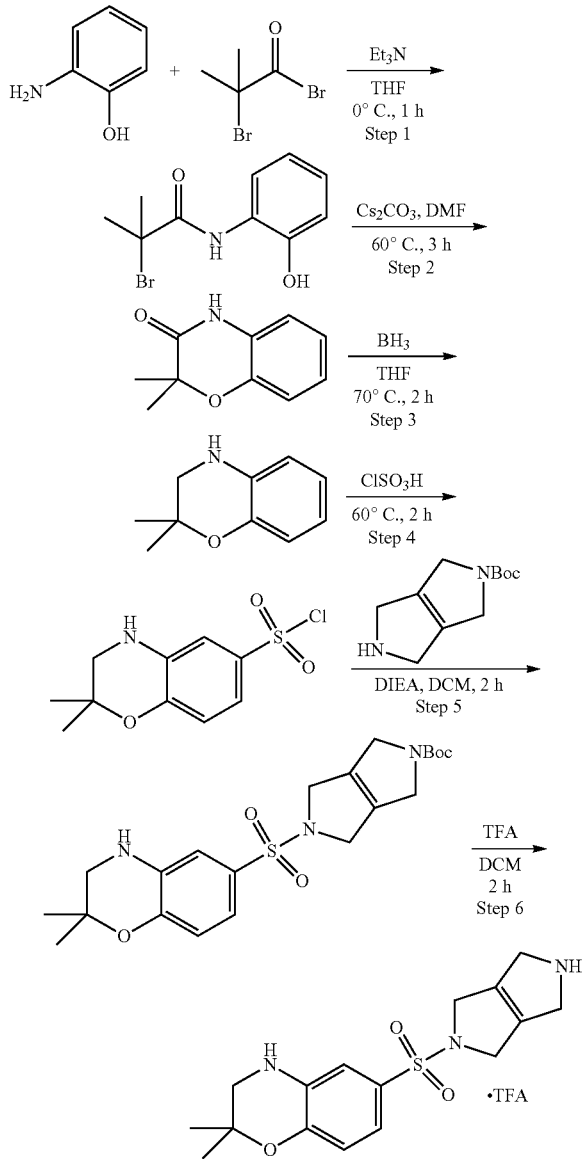

Step 1. 2-Bromo-N-(2-hydroxyphenyl)-2-methylpropanamide

To a 500-mL 3-necked round-bottom flask was added a mixture of 2-aminophenol (5 g, 45.82 mmol, 1.00 equiv), THF (150 mL) and TEA (5.1 g, 50.40 mmol). 2-Bromo-2-methylpropanoyl bromide (11.6 g, 50.46 mmol, 1.10 equiv) was then added dropwise. The solution was stirred for 1 h at 0° C. The reaction was then quenched by the addition of water (15 mL). The solution was extracted with ethyl acetate (3×200 mL), then the extract was washed with brine (2×150 mL) and dried over anhydrous sodium sulfate to provide 2-bromo-N-(2-hydroxyphenyl)-2-methylpropanamide (11.0 g, 93%) as a yellow oil. LCMS: m/z=259 [M+H]$^+$.

Step 2. 2,2-Dimethyl-3,4-dihydro-2H-1,4-benzoxazin-3-one

To a 250-mL 3-necked round-bottom flask was added 2-bromo-N-(2-hydroxyphenyl)-2-methylpropanamide (6 g, 23.25 mmol, 1.00 equiv), Cs$_2$CO$_3$ (9.85 g, 30.23 mmol, 1.30 equiv), and DMF (180 mL). The reaction mixture was stirred for 3 h at 60° C., then quenched by the addition of water (200 mL). The mixture was extracted with ethyl acetate (3×200 mL), and the extract was washed with brine (2×150 mL) and dried over anhydrous sodium sulfate to provide 2,2-dimethyl-3,4-dihydro-2H-1,4-benzoxazin-3-one (2.2 g, 53%) as a white solid. LCMS: m/z=178 [M+H]$^+$.

Step 3. 2,2-Dimethyl-3,4-dihydro-2H-1,4-benzoxazine

A mixture of 2,2-dimethyl-3,4-dihydro-2H-1,4-benzoxazin-3-one (2.76 g, 15.58 mmol, 1.00 equiv) and THF (10 mL) was prepared in a 100 mL 3-necked round-bottom flask. The mixture was cooled to 0° C., then BH$_3$·THF (1 M, 23.4 mL, 1.50 equiv) was added dropwise with stirring. The reaction mixture was stirred for 2 h at 70° C. The reaction was quenched by addition of methanol (4 mL), then concentrated under vacuum. The pH was adjusted to 6.0 with 1 N HCl aqueous solution and stirred for 30 minutes at RT. It was then neutralized with saturated aqueous sodium carbonate solution and the pH was adjusted to 8.0. The solution was extracted with ethyl acetate (50 mL), then the organic phase washed with brine (30 mL), dried over anhydrous sodium sulfate, filtered and concentrated under vacuum to provide 2,2-dimethyl-3,4-dihydro-2H-1,4-benzoxazine (2.90 g) as a colorless oil. The material was used without further purification. LCMS: m/z=164 [M+H]$^+$.

Step 4. 2,2-Dimethyl-3,4-dihydro-2H-1,4-benzoxazine-6-sulfonyl Chloride 2,2-Dimethyl-3,4-dihydro-2H-1,4-benzoxazine (500 mg, 3.06 mmol, 1.00 equiv) was placed in a 100-mL 3-necked round-bottom flask and cooled to 0° C. Sulfurochloridic acid (5 g, 42.91 mmol, 14.01 equiv) was added dropwise. The solution was stirred for 2 h at 60° C. The reaction was then quenched by the addition of water (50 mL) and extracted with dichloromethane (50 mL). The organic phase was washed with brine (3×20 mL), dried over anhydrous sodium sulfate and concentrated under vacuum to provide 2,2-dimethyl-3,4-dihydro-2H-1,4-benzoxazine-6-sulfonyl chloride (0.14 g, 17%) as a yellow oil.

Step 5. tert-Butyl 5-(2,2-dimethyl-3,4-dihydro-2H-1,4-benzoxazine-6-sulfonyl)-1H,2H,3H,4H,5H,6H-pyrrolo[3,4-c]pyrrole-2-carboxylate To a 25-mL round-bottom flask was added 2,2-dimethyl-3,4-dihydro-2H-1,4-benzoxazine-6-sulfonyl chloride (124 mg, 0.47 mmol, 1.00 equiv) and dichloromethane (2 mL), followed by addition of tert-butyl 1H,2H,3H,4H,5H,6H-pyrrolo[3,4-c]pyrrole-2-carboxylate (100 mg, 0.48 mmol, 1.00 equiv) and DIEA (110 mg, 0.85 mmol, 2.00 equiv). The solution was stirred for 2 h at 25° C. The reaction was then quenched by the addition of ethyl acetate (20 mL). The mixture was washed with brine (3×10 mL), dried over anhydrous sodium sulfate, filtered, and concentrated under vacuum. The residue was purified by flash chromatography on silica gel with dichloromethane/ethyl acetate (10:1) to provide tert-butyl 5-(2,2-dimethyl-3,4-dihydro-2H-1,4-benzoxazine-6-sulfonyl)-1H,2H,3H,4H,5H,6H-pyrrolo[3,4-c]pyrrole-2-carboxylate (0.102 g, 49%) as a light yellow oil. LCMS: m/z=436 [M+H]⁺.

Step 6. 2,2-Dimethyl-6-[1H,2H,3H,4H,5H,6H-pyrrolo[3,4-c]pyrrole-2-sulfonyl]-3,4-dihydro-2H-1,4-benzoxazine, TFA Salt To a solution of tert-butyl 5-(2,2-dimethyl-3,4-dihydro-2H-1,4-benzoxazine-6-sulfonyl)-1H,2H,3H,4H,5H,6H-pyrrolo[3,4-c]pyrrole-2-carboxylate (102 mg, 0.23 mmol, 1.00 equiv) in dichloromethane (3 mL) was added TFA (600 mg, 5.31 mmol, 23.00 equiv). The solution was stirred for 2 h at 25° C. under an atmosphere of nitrogen. The reaction mixture was concentrated under vacuum to provide 2,2-dimethyl-6-[1H,2H,3H,4H,5H,6H-pyrrolo[3,4-c]pyrrole-2-sulfonyl]-3,4-dihydro-2H-1,4-benzoxazine, TFA salt (85 mg) as a light yellow oil. The material was used without further purification. LCMS: m/z=336 [M+H]⁺.

Intermediates 17 and 18: (2R,3S and 2S,3R) 3-hydroxy-2-phenylbutanoic Acid and (2S,3S and 2R,3R) 3-hydroxy-2-phenylbutanoic Acid

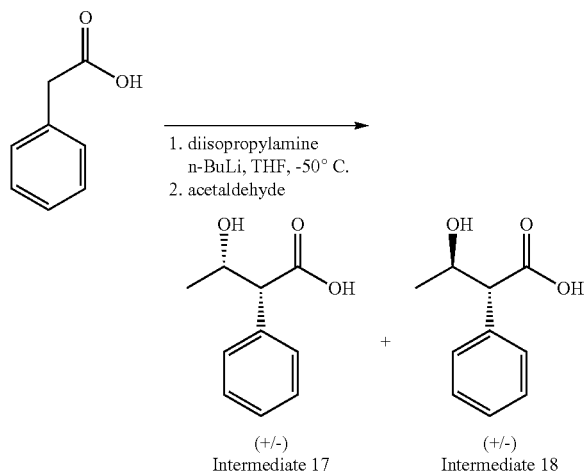

To a 250-mL 3-necked round-bottom flask purged and maintained with an inert atmosphere of nitrogen were added 2-phenylacetic acid (2 g, 14.69 mmol, 1.00 equiv) and tetrahydrofuran (50 mL). LDA (3.00 equiv, 22 mL, 2 N in THF) was added with stirring at −50° C. The reaction mixture was stirred for 1 h at −50° C., then acetaldehyde (1.94 g, 3.00 equiv) was added. The reaction was stirred for 1 h at −50° C. and then 1 h at RT. 3 N Aqueous hydrogen chloride solution (3 N, 20 mL) was added and the mixture was extracted with ethyl acetate (2×100 mL). The organic phase was dried over anhydrous sodium sulfate, filtered and concentrated under vacuum. The residue was purified by a flash column chromatography on silica gel eluted with dichloromethane/methanol (10:1). This provided:

Intermediate 17: A mixture of (2R,3S and 2S,3R)-3-hydroxy-2-phenylbutanoic acid (stereochemical configuration assumed). Obtained 700 mg (3.89 mmol, 26%) as an oil. LCMS: m/z=222 [M+1]⁺.

Intermediate 18: A mixture of (2R,3R and 2S,3S)-3-hydroxy-2-phenylbutanoic acid (stereochemical configuration assumed). Obtained 700 mg (3.89 mmol, 26%) as a white solid. LCMS: m/z=222 [M+1]⁺.

Examples 1 and 2: (2S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (Example 1) and (2R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (Example 2)

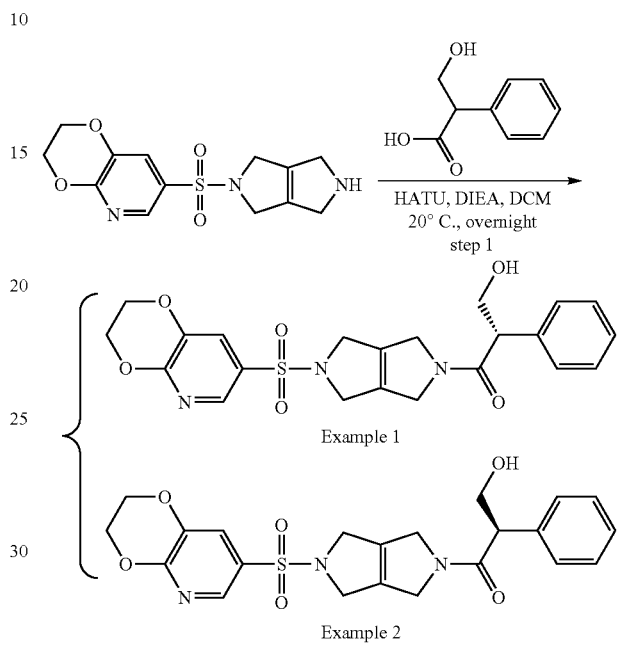

Into a 100 mL round-bottom flask was placed 2-[2H,3H-[1,4]dioxino[2,3-b]pyridine-7-sulfonyl]-1H,2H,3H,4H,5H,6H-pyrrolo[3,4-c]pyrrole (150 mg, 0.48 mmol, 1.00 equiv), 3-hydroxy-2-phenylpropanoic acid (97 mg, 0.58 mmol, 1.20 equiv), dichloromethane (10 mL), HATU (369 mg, 0.97 mmol, 2.00 equiv) and DIEA (188 mg, 1.46 mmol, 3.00 equiv). The resulting solution was stirred overnight at 20° C. The reaction mixture was diluted with 20 mL of water and was then extracted with 3×20 mL of dichloromethane. The organic layers were combined, dried over anhydrous sodium sulfate, filtered and concentrated under vacuum. The residue was purified by prep-TLC eluted with dichloromethane/methanol (20:1) and further purified by prep-HPLC (Column: XBridge C18 OBD Prep Column, 100 Å, 5 μm, 19 mm×250 mm; Mobile Phase A: water (10 mmol/L NH₄HCO₃), Mobile Phase B: MeCN; Gradient: 15% B to 45% B over 8 min; Flow rate: 20 mL/min; UV Detector: 254 nm). And then the two enantiomers were separated by prep-Chiral HPLC (Column, Daicel CHIRALPAK® IF, 2.0 cm×25 cm, 5 μm; mobile phase A: DCM, phase B: MeOH (hold 60% MeOH over 15 min); Flow rate: 16 ml/min; Detector, UV 254 & 220 nm). This resulted in peak 1 (Example 2, Rt: 8.47 min) 9.0 mg (4%) of (2R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one as a yellow solid. And peak 2 (Example 1, Rt: 11.83 min) 10.6 mg (5%) of (2S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one as a yellow solid.

Example 2 ¹H NMR (400 MHz, DMSO-d₆) δ 8.13 (d, J=2.0 Hz, 1H), 7.60 (d, J=2.0 Hz, 1H), 7.31-7.18 (m, 5H), 4.75 (t, J=5.2 Hz, 1H), 4.52-4.45 (m, 2H), 4.40-4.36 (m, 1H), 4.34-4.26 (m, 2H), 4.11-3.87 (m, 8H), 3.80-3.78 (m, 1H), 3.44-3.43 (m, 1H). LC-MS (ESI) m/z: calculated for $C_{22}H_{23}N_3O_6S$: 457.13; found: 458.0 [M+H]$^+$.

Example 1 $^1$H NMR (400 MHz, DMSO-d$_6$) δ 8.13 (d, J=2.0 Hz, 1H), 7.61 (d, J=2.0 Hz, 1H), 7.31-7.20 (m, 5H), 4.75 (t, J=5.2 Hz, 1H), 4.50-4.47 (m, 2H), 4.40-4.36 (m, 1H), 4.32-4.29 (m, 2H), 4.11-3.87 (m, 8H), 3.80-3.77 (m, 1H), 3.44-3.41 (m, 1H). LC-MS (ESI) m/z: calculated for $C_{22}H_{23}N_3O_6S$: 457.13; found: 458.0 [M+H]$^+$.

Examples 3 and 4: (2S or 2R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-(pyridin-2-yl)propan-1-one (Example 4) and (2R or 2S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-(pyridin-2-yl)propan-1-one (Example 3)

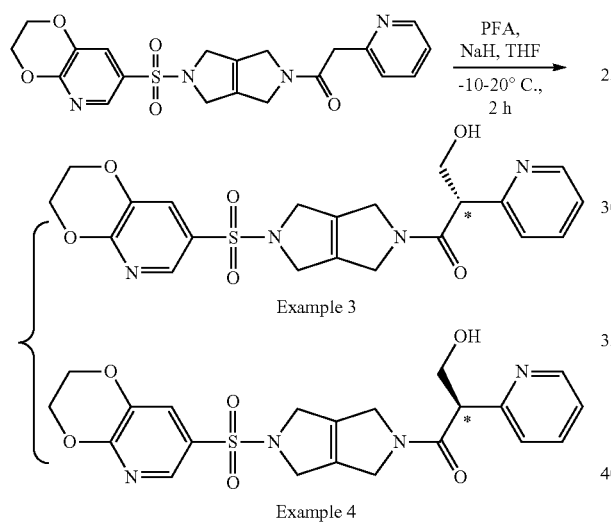

Into a 25 mL round-bottom flask was placed 1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-2-(pyridin-2-yl)ethan-1-one (80 mg, 0.17 mmol, 1.00 equiv) and tetrahydrofuran (10 mL). Sodium hydride (60% dispersion in mineral oil, 8 mg, 0.20 mmol, 1.18 equiv) was added. The solution was stirred for 10 min at 20° C., then a solution of paraformaldehyde (8.8 mg) in tetrahydrofuran (1 mL) was added dropwise with stirring at −10° C. The mixture was stirred for 2 h at 20° C., then concentrated under vacuum. The residue was purified by prep-HPLC (Column: XBridge C18 OBD Prep Column, 100 Å, 5 μm, 19 mm×250 mm; Mobile Phase A: water (0.05% NH$_3$·H$_2$O), Mobile Phase B: MeCN; Gradient: 20% B to 45% B over 8 min; Flow rate: 20 mL/min; UV Detector: 254 nm). The enantiomers were separated by prep-Chiral HPLC (Column, Daicel CHIRALPAK® ID, 2.0 cm×25 cm, 5 μm; mobile phase A: MeOH, phase B: DCM (hold 30% DCM over 23 min); Detector, Flow rate: 15 ml/min; Detector, UV 254 & 220 nm) to provide (2S or 2R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-(pyridin-2-yl)propan-1-one as a yellow solid (Example 4, Rt: 12.14 min., 19 mg, 24% yield), and (2R or 2S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-(pyridin-2-yl)propan-1-one as a yellow solid (Example 3, Rt: 18.44 min., 19.3 mg, 25% yield). Absolute stereochemistry was not determined (*).

(Example 4): $^1$H NMR (400 MHz, DMSO-d$_6$): δ 8.45-8.43 (m, 1H), 8.14 (d, J=2.4 Hz, 1H), 7.74-7.62 (m, 1H), 7.62 (d, J=2.4 Hz, 1H), 7.30-7.22 (m, 2H), 4.80 (t, J=5.20 Hz, 1H), 4.50-4.48 (m, 2H), 4.40-4.37 (m, 1H), 4.32-4.30 (m, 2H), 4.05-3.91 (m, 9H), 3.70-3.65 (m, 1H). LC-MS (ESI) m/z: calculated for $C_{21}H_{22}N_4O_6S$: 458.49; found: 459.0 [M+H]$^+$.

(Example 3): $^1$H NMR (400 MHz, DMSO-d$_6$): δ 8.45-8.43 (m, 1H), 8.14 (d, J=2.4 Hz, 1H), 7.74-7.62 (m, 1H), 7.61 (d, J=2.4 Hz, 1H), 7.30-7.22 (m, 2H), 4.80 (t, J=5.2 Hz, 1H), 4.50-4.48 (m, 2H), 4.40-4.37 (m, 1H), 4.32-4.30 (m, 2H), 4.05-3.91 (m, 9H), 3.70-3.65 (m, 1H). LC-MS (ESI) m/z: calculated for $C_{21}H_{22}N_4O_6S$: 458.49; found: 459.0 [M+H]$^+$.

Examples 5 and 6: (R or S)-(5-((2,3-dihydro-[1,4]dioxino[2,3-b]pyridin-7-yl)sulfonyl)-3,4,5,6-tetrahydropyrrolo[3,4-c]pyrrol-2(1H)-yl)(tetrahydro-2H-pyran-3-yl)methanone (Example 5) and (S or R)-(5-((2,3-dihydro-[1,4]dioxino[2,3-b]pyridin-7-yl)sulfonyl)-3,4,5,6-tetrahydropyrrolo[3,4-c]pyrrol-2(1H)-yl)(tetrahydro-2H-pyran-3-yl)methanone (Example 6)

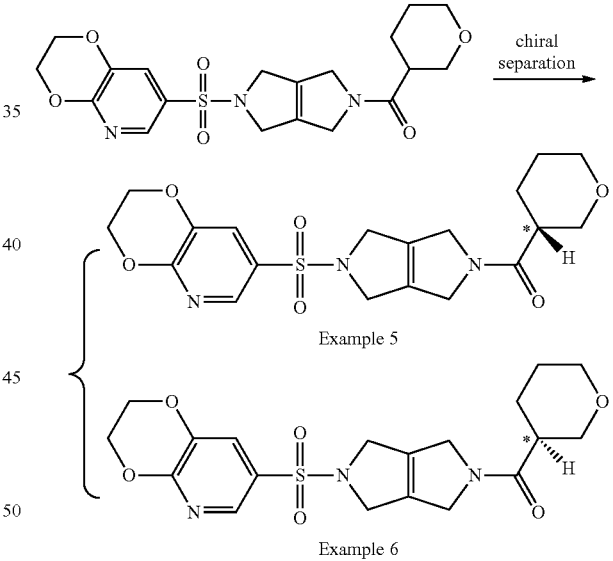

(5-((2,3-Dihydro-[1,4]dioxino[2,3-b]pyridin-7-yl)sulfonyl)-3,4,5,6-tetrahydropyrrolo[3,4-c]pyrrol-2(1H)-yl)(tetrahydro-2H-pyran-3-yl)methanone was prepared using the reaction conditions described for Example 1 from the appropriate reagents. The residue was purified by silica gel chromatography eluted with dichloromethane/methanol (20:1) and further purified by prep-HPLC (Column: XBridge BEH C18 OBD Prep Column, 130 Å, 5 μm, 19 mm×150 mm; Mobile phase: water (10 mmol NH$_4$HCO$_3$), MeCN (1% MeCN up to 40% over 8 min); Flow rate: 20 mL/min; Detector: 254 & 220 nm). The two enantiomers were separated by chiral-prep-HPLC (Column, Daicel CHIRALPAK® IB, 2.0 cm×25 cm, 5 μm; mobile phase A: DCM, phase B: Ethanol (hold 75% DCM over 13 min); Flow rate:

14 ml/min; Detector, UV 254 & 220 nm; Retention time: Example 5: 9.22 min, Example 6: 11.57 min) to provide (R or S)-(5-((2,3-dihydro-[1,4]dioxino[2,3-b]pyridin-7-yl)sulfonyl)-3,4,5,6-tetrahydropyrrolo[3,4-c]pyrrol-2(1H)-yl)(tetrahydro-2H-pyran-3-yl)methanone as a white solid (5.3 mg, 2%) and (S or R)-(5-((2,3-dihydro-[1,4]dioxino[2,3-b]pyridin-7-yl)sulfonyl)-3,4,5,6-tetrahydropyrrolo[3,4-c]pyrrol-2(1H)-yl)(tetrahydro-2H-pyran-3-yl)methanone as a white solid (4.9 mg, 2%). Absolute stereochemistry was not determined (*).

Example 5 $^1$H NMR (400 MHz, CDCl$_3$): δ 8.31 (s, 1H), 7.60 (s, 1H), 4.57-4.50 (m, 2H), 4.36-4.25 (m, 4H), 4.15-4.09 (m, 6H), 3.94-3.88 (m, 2H), 3.56-3.50 (m, 1H), 3.49-3.33 (m, 1H), 2.63-2.60 (m, 1H), 1.95-1.78 (m, 2H), 1.67-1.61 (m, 2H). LC-MS (ESI) m/z: calculated for $C_{19}H_{23}N_3O_6S$: 421.13; found: 422 [M+H]$^+$.

Example 6 $^1$H NMR (400 MHz, CDCl$_3$): δ 8.30 (s, 1H), 7.61 (s, 1H), 4.54-4.52 (m, 2H), 4.35-4.27 (m, 4H), 4.15-4.09 (m, 6H), 3.95-3.90 (m, 2H), 3.56-3.50 (m, 1H), 3.42-3.35 (m, 1H), 2.65-2.60 (m, 1H), 1.95-1.78 (m, 2H), 1.67-1.62 (m, 2H). LC-MS (ESI) m/z: calculated for $C_{19}H_{23}N_3O_6S$: 421.13; found: 422 [M+H]$^+$.

Example 7: 1-(5-[[4-(Difluoromethoxy)benzene]sulfonyl]-1H,2H,3H,4H,5H,6H-pyrrolo[3,4-c]pyrrol-2-yl)-3-hydroxy-2,2-dimethylpropan-1-one

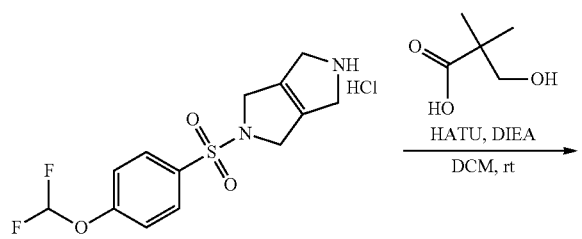

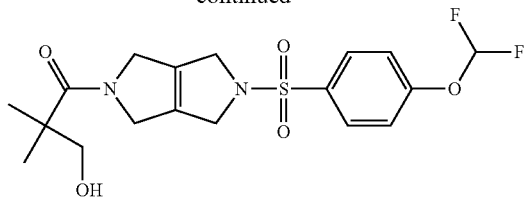

Example 7

Into a 50-mL round-bottom flask was placed 2-[[4-(difluoromethoxy)benzene]sulfonyl]-1H,2H,3H,4H,5H,6H-pyrrolo[3,4-c]pyrrole hydrochloride (113 mg, 0.32 mmol, 1.00 equiv), dichloromethane (10 mL), 3-hydroxy-2,2-dimethylpropanoic acid (41 mg, 0.35 mmol, 1.10 equiv), DIEA (123 mg, 0.95 mmol, 3.00 equiv) and HATU (241 mg, 0.63 mmol, 2.00 equiv). The solution was stirred for 2 h at room temperature, then concentrated under vacuum. The crude product was purified by Prep-HPLC (Waters I: column: Xbridge Prep C18 5 μm 19×150 mm; mobile phase gradient: CH$_3$CN/water (0.05% NH$_4$OH) from 32% to 47% in 7 minute run; detector UV wavelength: 254 nm.) to provide 25.3 mg (19%) of 1-(5-[[4-(difluoromethoxy)benzene]sulfonyl]-1H,2H,3H,4H,5H,6H-pyrrolo[3,4-c]pyrrol-2-yl)-3-hydroxy-2,2-dimethylpropan-1-one as a white solid.

$^1$H NMR (300 MHz, DMSO-d$_6$): δ ppm 7.89-7.92 (m, 2H), 7.39-7.42 (d, J=7.8 Hz, 2H), 7.17-7.66 (t, J=73.2 Hz, 1H), 4.68-4.72 (t, J=5.4 Hz, 1H), 3.90-4.50 (m, 8H), 3.40-3.42 (d, J=5.4 Hz, 2H), 1.09 (s, 6H). LC-MS (ESI) m/z: Calculated for $C_{18}H_{22}F_2N_2O_5S$: 416.12; found: 417 [M+H]$^+$.

The Examples in Table 1 below were prepared according to the procedures outlined above for Example 7, using the appropriate synthetic precursors.

TABLE 1

| Example | Structure, Name | LCMS | $^1$H NMR |
|---|---|---|---|
| 8 | 1-(5-(Benzofuran--5-ylsulfonyl)-3,4,5,6-tetrahydropyrrolo[3,4-c]pyrrol-2(1H)-yl)-3-hydroxy-2-phenylpropan-1-one | m/z: 439 | |
| 9 | 1-(5-(Benzofuran-5-ylsulfonyl)-3,4,5,6-tetrahydropyrrolo[3,4-c]pyrrol-2(1H)-yl)-3-hydroxy-2,2-dimethylpropan-1-one | m/z: 391 | |

TABLE 1-continued

| Example | Structure, Name | LCMS | ¹H NMR |
|---|---|---|---|
| 10 | 1-(5-(Benzofuran-5-ylsulfonyl)-3,4,5,6-tetrahydropyrrolo[3,4-c]pyrrol-2(1H)-yl)-3-hydroxy-2-(hydroxymethyl)-2-methylpropan-1-one | m/z: 407 | |
| 11 | 1-(5-(Benzofuran-5-ylsulfonyl)-3,4,5,6-tetrahydropyrrolo[3,4-c]pyrrol-2(1H)-yl)-2,2-bis(hydroxymethyl)butan-1-one | m/z: 421 | |
| 12 | 2-(1-Benzofuran-5-sulfonyl)-5-[(2R)-oxolane-3-carbonyl]-1H,2H,3H,4H,5H,6H-pyrrolo[3,4-c]pyrrole | m/z: 389.1 | |
| 13 | 2-(1-Benzofuran-5-sulfonyl)-5-[(3S)-oxolane-3-carbonyl]-1H,2H,3H,4H,5H,6H-pyrrolo[3,4-c]pyrrole | m/z : 389.1 | |
| 14 | (R)-(5-((4-(difluoromethoxy)phenyl)sulfonyl)-3,4,5,6-tetrahydropyrrolo[3,4-c]pyrrol-2(1H)-yl)(tetrahyrofuran-3-yl)methanone | m/z: 415 | (300 MHz, DMSO-d₆): δ ppm 7.89-7.94 (m, 2H),7.40-7.42 (d, 2H), 7.18-7.66 (t, J = 72 Hz, 1H) 3.83-4.29 (m, 9H), 3.62-3.74 (m, 3H), 3.06-3.16(m, 1H), 1.94-2.07 (m, 2H). |
| 15 | (5-(Benzo[d]thiazol-6-ylsulfonyl)-3,4,5,6-tetrahydropyrrolo[3,4-c]pyrrol-2(1H)-yl)(tetrahydro-2H-pyran-3-yl)methanone | m/z: 420 | (300 MHz, CDCl₃): δ ppm 9.22 (s, 1H), 8.54 (d, J = J = 1.2 Hz, 1H), 8.29 (d,8.7 Hz, 1H), 7.97 (dd, J = 8.7 Hz, J = 1.8 Hz, 1H), 4.24-4.12 (m, 8H), 3.94-3.90 (m, 2H), 3.54-3.41(m, 2H), 2.65-2.55 (m, 1H), 1.86-1.81 (m, 2H), 1.67-1.49 (m, 2H). |

TABLE 1-continued

| Example | Structure, Name | LCMS | ¹H NMR |
|---|---|---|---|
| 16 | (S)-(5-((4-(difluoromethoxy)phenyl)sulfonyl)-3,4,5,6-tetrahydropyrrolo[3,4-c]pyrrol-2(1H)-yl)(tetrahydrofuran-3-yl)methanone | m/z: 415 | (300 MHz, DMSO-$d_6$): δ ppm 7.95-7.98 (m, 2H), 7.35-7.42 (m, 2H), 6.79-7.28 (t, J = 72 Hz, 1H)3.80-4.32 (m, 14H),3.24-3.40 (m, 1H),2.22 (m, 2H). |
| 17 | (5-(benzofuran-5-ylsulfonyl)-3,4,5,6-tetrahydropyrrolo[3,4-c]pyrrol-2(1H)-yl)(1-(methoxymethyl)cyclopropyl)methanone | m/z: 403 | |
| 18 | 1-(5-((2,3-dihydrobenzo[b][1,4]dioxin-6-yl)sulfonyl)-3,4,5,6-tetrahydropyrrolo[3,4-c]pyrrol-2(1H)-yl)-3-hydroxy-2-phenylpropan-1-one | m/z: 457 | |

Example 19: 1-(5-(Benzo[d]thiazol-6-ylsulfonyl)-3,4,5,6-tetrahydropyrrolo[3,4-c]pyrrol-2(1H)-yl)-3-hydroxy-2,2-dimethylpropan-1-one

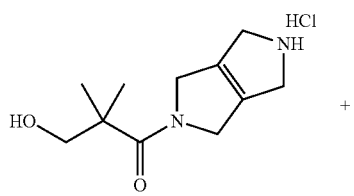

+

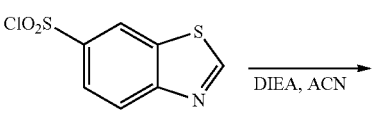

-continued

Example 19

To a 0.2 M solution of 3-hydroxy-2,2-dimethyl-1-(3,4,5,6-tetrahydropyrrolo[3,4-c]pyrrol-2(1H)-yl)propan-1-one hydrochloride (300 μl, 0.060 mmol) in $CH_3CN$ with 10% DIEA was added a 0.2 M solution of benzo[d]thiazole-6-sulfonyl chloride (300 μl, 0.06 mmol) in $CH_3CN$ with 3% DIEA. The reaction was agitated at RT for 5 hours, then concentrated and partitioned between ethyl acetate and aqueous NaOH (1 N). The organic phase was concentrated under reduced pressure and the crude material was purified by prep-HPLC to provide 1-(5-(benzo[d]thiazol-6-ylsulfonyl)-3,4,5,6-tetrahydropyrrolo[3,4-c]pyrrol-2(1H)-yl)-3-hydroxy-2,2-dimethylpropan-1-one (2.6 mg, 10% yield). LCMS: m/z 408 [M+H]$^+$.

The Examples in Table 2 below were prepared according to the procedure outlined above for Example 19, using the appropriate synthetic precursors.

TABLE 2

| Example | Structure, Name | LCMS |
|---|---|---|
| 20 | (R)-(5-(benzo[d]thiazol-6-ylsulfonyl)-3,4,5,6-tetrahydropyrrolo[3,4-c]pyrrol-2(1H)-yl)(tetrahydrofuran-3-yl)methanone | m/z: 406 |
| 21 | 3-Hydroxy-2,2-dimethyl-1-(5-((2-methylbenzo[d]oxazol-6-yl)sulfonyl)-3,4,5,6-tetrahydropyrrolo[3,4-c]pyrrol-2(1H)-yl)propan-1-one | m/z: 406 |
| 22 | 1-(5-(Benzofuran-5-ylsulfonyl)-3,4,5,6-tetrahydropyrrolo[3,4-c]pyrrol-2(1H)-yl)-3-hydroxypropan-1-one | m/z: 363 |
| 23 | (R)-1-(5-(benzofuran-5-ylsulfonyl)-3,4,5,6-tetrahydropyrrolo[3,4-c]pyrrol-2(1H)-yl)-3-hydroxybutan-1-one | m/z: 377 |
| 24 | (S)-1-(5-(benzofuran-5-ylfulfonyl)-3,4,5,6-tetrahydropyrrolo[3,4-c]pyrrol-2(1H)-yl)-3-hydroxybutan-1-one | m/z: 377 |

TABLE 2-continued

| Example | Structure, Name | LCMS |
|---|---|---|
| 25 | ![structure] (5-(Benzofuran-5-ylsulfonyl)-3,4,5,6-tetrahydropyrrolo[3,4-c]pyrrol-2(1H)-yl)(1-(methoxymethyl)cyclopropyl)methanone | m/z: 391.14 |

Example 26: (2S,3R and 2R,3S)-1-(5-[[4-(difluoromethoxy)benzene]sulfonyl]-1H,2H,3H,4H,5H,6H-pyrrolo[3,4-c]pyrrol-2-yl)-3-hydroxy-2-phenylbutan-1-one

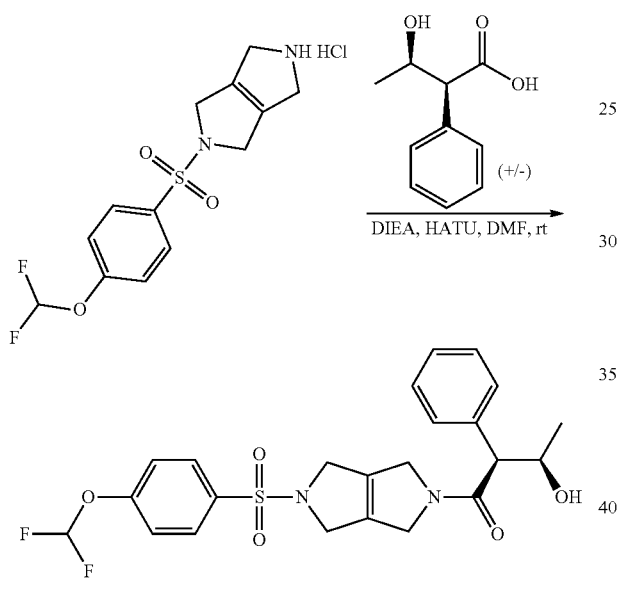

Example 26
(+/-)

To an 8-mL vial was added 2-((4-(difluoromethoxy)phenyl)sulfonyl)-1,2,3,4,5,6-hexahydropyrrolo[3,4-c]pyrrole hydrochloride (64 mg, 0.18 mmol, 1.00 equiv), DMF (1.50 mL), DIEA (58 mg, 0.45 mmol, 2.50 equiv), (2S,3R and 2R,3S)-3-hydroxy-2-phenylbutanoic acid (40 mg, 0.22 mmol, 1.20 equiv), and HATU (84 mg, 0.22 mmol, 1.20 equiv). The solution was stirred for 16 h at RT. The solution was diluted with 50 mL of ethyl acetate, washed with 4×15 mL of brine, dried over anhydrous sodium sulfate and concentrated under vacuum. The crude product was purified by prep-TLC (DCM/EA=1/2) to provide (2S,3R and 2R,3S)-1-(5-[[4-(difluoromethoxy)benzene]sulfonyl]-1H,2H,3H,4H,5H,6H-pyrrolo[3,4-c]pyrrol-2-yl)-3-hydroxy-2-phenylbutan-1-one as a white solid (41 mg, 47%). $^1$H NMR (300 MHz, CDCl$_3$): δ ppm 7.85-7.80 (m, 2H), 7.37-7.23 (m, 7H), 6.59 (t, J=72.6 Hz, 1H), 4.45-4.37 (m, 1H), 4.25-3.95 (m, 7H), 3.78-3.74 (m, 1H), 3.39 (d, J=3.9 Hz, 1H), 1.05 (d, J=6.3 Hz, 3H). LCMS: m/z=479.0 [M+H]$^+$.

The Examples in Table 3 below were prepared according to the procedure outlined above for Example 26, using the appropriate synthetic precursors.

TABLE 3

| Example | Structure, Name | LCMS | $^1$H NMR |
|---|---|---|---|
| 27 | ![structure] (2R,3R and 2S,3S)-1-(5-[[4-(difluoromethoxy)benzene]sulfonyl]-1H,2H,3H,4H,5H,6H-pyrrolo[3,4-c]pyrrol-2-yl)-3-hydroxy-2-phenylbutan-1-one (+/−) | m/z: 479 | (300 MHz, CDCl$_3$): δ ppm 7.84-7.81 (m, 2H), 7.35-7.26 (m, 7H), 6.59 (t, J = 72.6 Hz,1H), 4.35-3.97 (m, 8H), 3.76-3.71 (m, 1H), 3.36-3.34 (m, 1H), 1.06 (dd, J = 13.2 Hz, J = 6.3 Hz, 3H) |

TABLE 3-continued

| Example | Structure, Name | LCMS | ¹H NMR |
|---|---|---|---|
| 28 | (2S)-1-(5-[[4-(difluoromethoxy)benzene]sulfonyl]-1H,2H,3H,4H,5H,6H-pyrrolo[3,4-c]pyrrol-2-yl)-3-hydroxy-3-methyl-2-phenylbutan-1-one | m/z: 493 | (300 MHz, CDCl$_3$): δ ppm 7.83 (d, J = 8.7 Hz, 2H), 7.36-7.23 (m, 7H), 6.59 (t, J = 72.6 Hz, 1H), 4.28-3.85 (m, 8H), 3.32 (s, 1H), 1.39 (s, 3H), 0.92 (s, 3H) |
| 29 | (2S)-1-[5-(1,3-benzothiazole-6-sulfonyl)-1H,2H,3H,4H,5H,6H-pyrrolo[3,4-c]pyrrol-2-yl]-3-hydroxy-2-phenylpropan-1-one | m/z: 456 | (300 MHz, CDCl$_3$): δ ppm 9.20 (s, 1H), 8.49 (s, 1H), 8.25 (d, J = 6.6 Hz, 1H), 7.94 (d, J = 8.7Hz, 1H), 7.31-7.20 (m, 5H), 4.26-4.03 (m, 8H), 3.73-3.64 (m, 3H) |
| 30 | (2R)-1-[5-(1,3-benzothiazole-6-sulfonyl)-1H,2H,3H,4H,5H,6H-pyrrolo[3,4-c]pyrrol-2-yl]-3-hydroxy-2-phenylpropan-1-one | m/z: 456 | (300 MHz, CDCl$_3$): δ ppm 9.22 (s, 1H), 8.49 (s, 1H), 8.26 (d, J = 8.4 Hz, 1H), 7.94 (dd, J = 8.4 Hz, J = 1.8 Hz, 1H), 7.34-7.20 (m, 5H), 4.30-4.03 (m, 8H), 3.75-3.69 (m, 3H) |
| 31 | (2S)-1-(5-[[4-(difluoromethoxy)benzene]sulfonyl]-1H,2H,3H,4H,5H,6H-pyrrolo[3,4-c]pyrrol-2-yl)-3-hydroxy-2-phenylpropan-1-one | m/z: 465 | (300 MHz, DMSO-d$_6$): δ ppm 7.89-7.85 (m, 2H), 7.64-7.15 (m, 8H), 4.76 (t, J = 5.1Hz, 1H), 4.40-4.36 (m, 1H), 4.04-3.82 (m, 8H), 3.80-3.77 (m, 1H), 3.48-3.41 (m, 1H) |

Example 32: (2S)-1-[5-(2,2-dimethyl-3,4-dihydro-2H-1,4-benzoxazine-6-sulfonyl)-1H,2H,3H,4H,5H,6H-pyrrolo[3,4-c]pyrrol-2-yl]-3-hydroxy-2-phenyl-propan-1-one

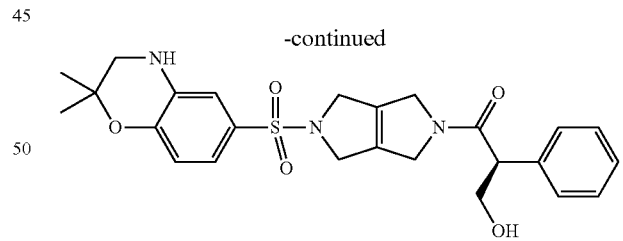

Example 32

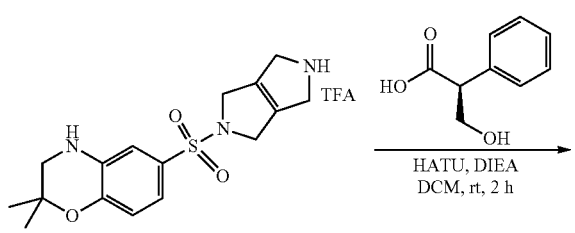

To a 25-mL round-bottom flask was added 2,2-dimethyl-6-[1H,2H,3H,4H,5H,6H-pyrrolo[3,4-c]pyrrole-2-sulfonyl]-3,4-dihydro-2H-1,4-benzoxazine TFA salt (112 mg, 0.25 mmol, 1.00 equiv), (2S)-3-hydroxy-2-phenylpropanoic acid (42 mg, 0.25 mmol, 1.00 equiv), HATU (80 mg, 0.21 mmol, 0.84 equiv), DCM (2.00 mL), and DIEA (58 mg, 0.45 mmol, 2.00 equiv). The solution was stirred for 2 h at 25° C., then extracted with 20 mL of ethyl acetate. The organic phase was washed with 20 mL of brine, dried over anhydrous sodium sulfate, and concentrated under vacuum. The residue was purified by silica gel column chromatography, eluting with dichloromethane/methanol (20/1) to provide (2S)-1-[5-(2,2-dimethyl-3,4-dihydro-2H-1,4-benzoxazine-6-sulfonyl)-1H,2H,3H,4H,5H,6H-pyrrolo[3,4-c]pyrrol-2-yl]-3-hydroxy-2-phenylpropan-1-one as a white solid (18.7 mg, 15%). $^1$H NMR (300 MHz, DMSO-$d_6$): δ ppm 7.29-7.28 (m, 5H), 7.04 (s, 1H), 6.90-6.85 (m, 1H), 6.76 (d, J=8.4 Hz, 1H), 6.35 (s, 1H), 4.85-4.70 (m, 1H), 4.50-4.30 (m, 1H), 3.97-3.93 (m, 8H), 3.90-3.80 (m, 1H), 3.35-3.50 (m, 1H), 3.02 (d, J=2.1 Hz, 2H), 1.24 (s, 6H). LCMS: m/z=484.0 [M+H]$^+$.

Examples 33 and 34: 6-(5-[[(3S or 3R)-oxan-3-yl]carbonyl]-1H,2H,3H,4H,5H,6H-pyrrolo[3,4-c]pyrrole-2-sulfonyl)-3,4-dihydro-2H-1,4-benzoxazine (Example 33) and 6-(5-[[(3R or 3S)-oxan-3-yl]carbonyl]-1H,2H,3H,4H,5H,6H-pyrrolo[3,4-c]pyrrole-2-sulfonyl)-3,4-dihydro-2H-1,4-benzoxazine (Example 34)

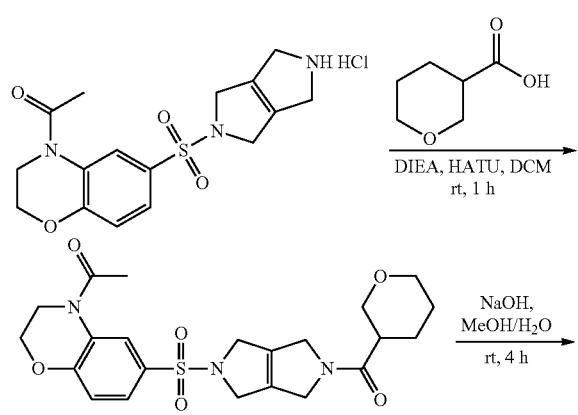

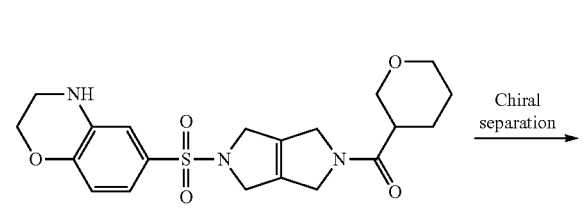

Example 33

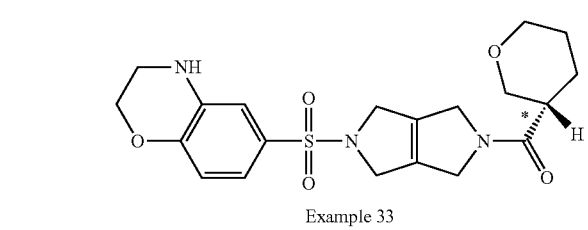

Example 34

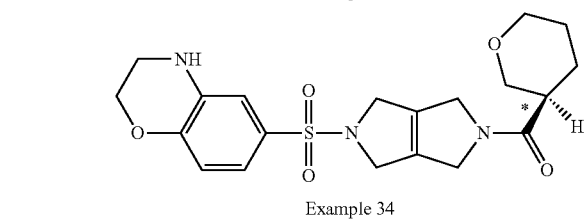

Step 1. 1-(6-[5-[(Oxan-3-yl)carbonyl]-1H,2H,3H,4H,5H,6H-pyrrolo[3,4-c]pyrrole-2-sulfonyl]-3,4-dihydro-2H-1,4-benzoxazin-4-yl)ethan-1-one

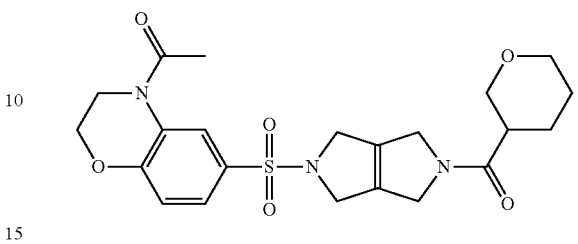

Into an 8-mL vial purged and maintained with an inert atmosphere of nitrogen was added oxane-3-carboxylic acid (62.4 mg, 0.48 mmol, 1.20 equiv), DIEA (154.8 mg, 1.20 mmol, 3.00 equiv), 1-(6-((3,4,5,6-tetrahydropyrrolo[3,4-c]pyrrol-2(1H)-yl)sulfonyl)-2,3-dihydro-4H-benzo[b][1,4]oxazin-4-yl)ethan-1-one hydrochloride salt (154.4 mg, 0.40 mmol, 1.00 equiv), HATU (167.2 mg, 0.44 mmol, 1.10 equiv), and dichloromethane (4 ml). The solution was stirred for 4 h at room temperature, then concentrated under vacuum. The crude product was purified by prep-TLC (DCM/MeOH=15/1) to provide 100 mg (54%) of 1-(6-[5-[(oxan-3-yl)carbonyl]-1H,2H,3H,4H,5H,6H-pyrrolo[3,4-c]pyrrole-2-sulfonyl]-3,4-dihydro-2H-1,4-benzoxazin-4-yl)ethan-1-one as a white solid. LCMS (ESI) m/z: Calculated for $C_{22}H_{27}N_3O_6S$: 461.16; found: 462.0 [M+H]$^+$.

Step 2. 6-[5-[(Oxan-3-yl)carbonyl]-1H,2H,3H,4H,5H,6H-pyrrolo[3,4-c]pyrrole-2-sulfonyl]-3,4-dihydro-2H-1,4-benzoxazine

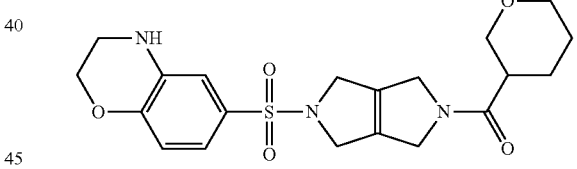

Into an 8-mL vial was placed 1-(6-[5-[(oxan-3-yl)carbonyl]-1H,2H,3H,4H,5H,6H-pyrrolo[3,4-c]pyrrole-2-sulfonyl]-3,4-dihydro-2H-1,4-benzoxazin-4-yl)ethan-1-one (92 mg, 0.20 mmol, 1.00 equiv) and a solution of sodium hydroxide (32 mg, 0.80 mmol, 4.00 equiv) in methanol (2 ml) and water (0.5 ml). The solution was stirred for 4 h at room temperature, then the pH was adjusted to 9 with hydrochloric acid (2 mol/L). The mixture was concentrated under vacuum. The residue was purified by a silica gel column chromatography, eluting with dichloromethane/methanol (50/1). The crude product (100 mg) was further purified by Prep-HPLC (Column: Xbridge Prep C18 5 μm 19×150 mm; mobile phase: water (contains 0.05% NH$_3$·H$_2$O) and CH$_3$CN with a gradient of 16% to 34% CH$_3$CN in 10 min; detector UV wave length 220 & 254 nm) to provide 80 mg (96%) of 6-[5-[(oxan-3-yl)carbonyl]-1H,2H,3H,4H,5H,6H-pyrrolo[3,4-c]pyrrole-2-sulfonyl]-3,4-dihydro-2H-1,4-benzoxazine as a white solid. LCMS (ESI) m/z: Calculated for $C_{20}H_{25}N_3O_5S$: 419.15; found: 420 [M+H]$^+$.

Step 3. Examples 33 and 34: 6-(5-[[(3S or 3R)-oxan-3-yl]carbonyl]-1H,2H,3H,4H,5H,6H-pyrrolo[3,4-c]pyrrole-2-sulfonyl)-3,4-dihydro-2H-1,4-benzoxazine and 6-(5-[[(3R or 3S)-oxan-3-yl]carbonyl]-1H,2H,3H,4H,5H,6H-pyrrolo[3,4-c]pyrrole-2-sulfonyl)-3,4-dihydro-2H-1,4-benzoxazine

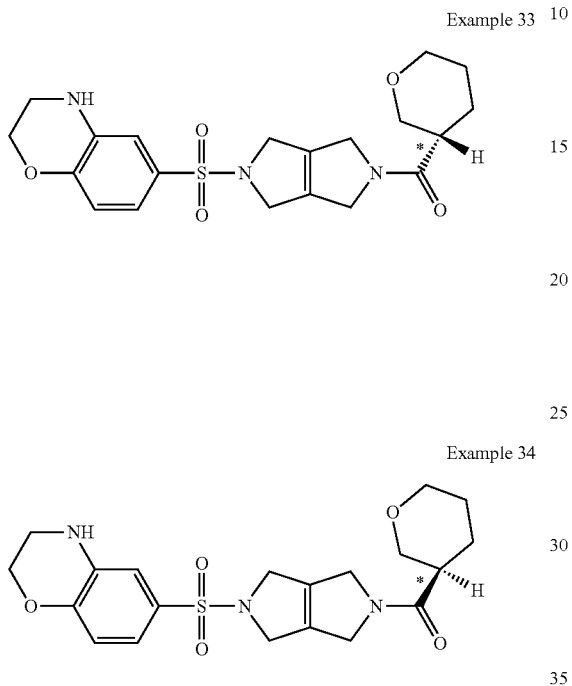

Example 33

Example 34

Chiral separation of racemic 6-[5-[(oxan-3-yl)carbonyl]-1H,2H,3H,4H,5H,6H-pyrrolo[3,4-c]pyrrole-2-sulfonyl]-3,4-dihydro-2H-1,4-benzoxazine (80 mg) was carried out by Chiral-Prep-HPLC (SHIMADZU LC-20AT: Column, CHIRALPAK IC; mobile phase, A: Ethanol [containing 0.1% DEA], Phase B: Methanol; detector UV wave length: 220 nm) to provide 22.3 mg (28%) of 6-(5-[[(3S or 3R)-oxan-3-yl]carbonyl]-1H,2H,3H,4H,5H,6H-pyrrolo[3,4-c]pyrrole-2-sulfonyl)-3,4-dihydro-2H-1,4-benzoxazine (Example 33) as a white solid, and 18.9 mg (24%) of 6-(5-[[(3S or 3R)-oxan-3-yl]carbonyl]-1H,2H,3H,4H,5H,6H-pyrrolo[3,4-c]pyrrole-2-sulfonyl)-3,4-dihydro-2H-1,4-benzoxazine (Example 34) as a white solid. Absolute stereochemistry was not determined (*).

Example 33. Prep chiral HPLC Rt=24.2 min. $^1$H NMR (300 MHz, CDCl$_3$): δ ppm 7.24-7.19 (m, 2H), 6.89 (d, J=6.6 Hz, 1H), 4.44-4.34 (d, 2H), 4.25-4.18 (m, 2H), 4.12 (s, 6H), 3.95-3.91 (m, 2H), 3.56-3.37 (m, 4H), 2.66-2.62 (m, 1H), 1.89-1.68 (m, 4H). LC-MS (ESI) m/z: Calculated for C$_{20}$H$_{25}$N$_3$O$_5$S: 419.15; found: 420 [M+H]$^+$.

Example 34 Prep chiral HPLC Rt=30.4 min. $^1$H NMR (300 MHz, CDCl$_3$): δ ppm 7.17-7.11 (m, 2H), 6.88 (d, J=8.1 Hz, 1H), 4.33-4.25 (m, 4H), 4.12 (s, 6H), 3.95-3.91 (m, 2H), 3.56-3.37 (m, 4H), 2.67-2.57 (m, 1H), 1.89-1.66 (m, 4H). LC-MS (ESI) m/z: Calculated for C$_{20}$H$_{25}$N$_3$O$_5$S: 419.15; found: 420 [M+H]$^+$.

The Examples in Table 4 below were prepared according to the procedures outlined above for Example 33 and 34, steps 1 and 2, using the appropriate synthetic precursors.

TABLE 4

| Example | Structure, Name | LCMS |
|---|---|---|
| 35 | (S)-1-(5-((3,4-dihydro-2H-benzo[b][1,4]oxazin-6-yl)sulfonyl)-3,4,5,6-tetrahydropyrrolo[3,4-c]pyrrol-2(1H)-yl)-3-hydroxy-2-phenylpropan-1-one | m/z: 456 |
| 36 | (5-((3,4-Dihydro-2H-benzo[b][1,4]oxazin-6-yl)sulfonyl)-3,4,5,6-tetrahydropyrrolo[3,4-c]pyrrol-2(1H)-yl)(1-(methoxy)cyclopropyl)methanone | m/z: 420 |
| 37 | 1-(5-((3,4-Dihydro-2H-benzo[b][1,4]oxazin-6-yl)sulfonyl)-3,4,5,6-tetrahydropyrrolo[3,4-c]pyrrol-2(1H)-yl)-3-hydroxy-2,2-dimethylpropan-1-one | m/z: 408 |
| 38 | 1-(5-((3,4-Dihydro-2H-benzo[b][1,4]oxazin-6-yl)sulfonyl)-3,4,5,6-tetrahyddropyrrolo[3,4-c]pyrrol-2(1H)-yl)-3-hydroxy-3-methylbutan-1-one | m/z: 408 |
| 39 | (R)-(5-((3,4-dihysro-2H-benzo[b][1,4]oxazin-6-yl)sulfonyl)-3,4,5,6-tetrahydropyrrolo[3,4-c]pyrrol-2(1H)-yl)(tetrahydrofuran-3-yl)methanone | m/z: 406 |

Examples 41 and 42: (S or R-)-1-(5-(4-(Difluoromethoxy)phenylsulfonyl)-4,5-dihydropyrrolo[3,4-c]pyrrol-2(1H,3H,4H)-yl)-3-hydroxy-2-(pyridin-2-yl)propan-1-one (Example 41) and (R or S)-1-(5-(4-(difluoromethoxy)phenylsulfonyl)-4,5-dihydropyrrolo[3,4-c]pyrrol-2(1H,3H,4H)-yl)-3-hydroxy-2-(pyridin-2-yl)propan-1-one (Example 42)

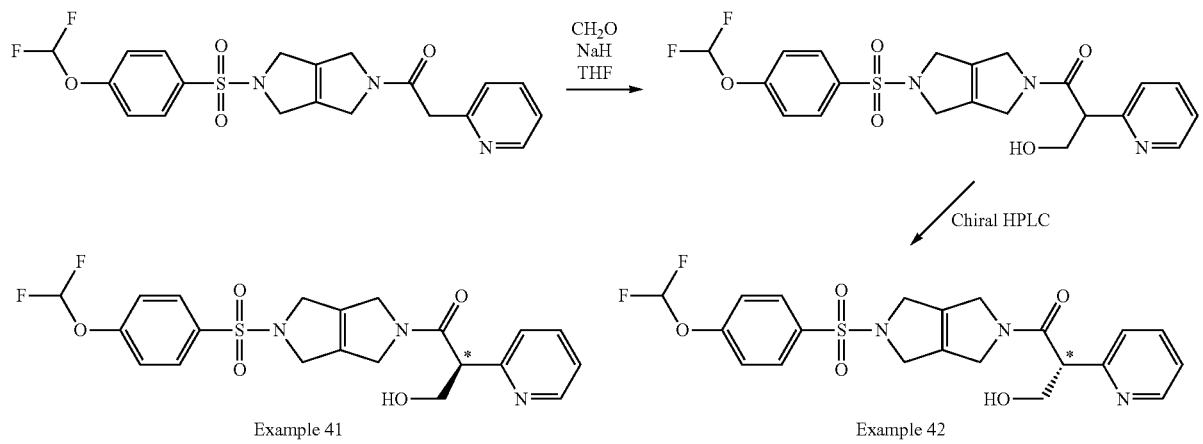

Example 41

Example 42

To a 100-mL 3-necked round-bottom flask was added 1-(5-[[4-(difluoromethoxy) benzene] sulfonyl]-1H,2H,3H,4H,5H,6H-pyrrolo[3,4-c]pyrrol-2-yl)-2-(pyridin-2-yl)ethan-1-one hydrochloride salt (80 mg, 0.18 mmol, 1.00 equiv) and sodium hydride (60% oil dispersion, 4.4 mg, 0.18 mmol, 1.00 equiv) in tetrahydrofuran (10 mL). The reaction mixture was cooled down to −10° C. and formaldehyde (5.5 mg, 0.18 mmol, 1.00 equiv, 0.2 mL in THF) was added dropwise. The mixture was stirred for 4 hours at 25° C., then quenched by addition of water (20 mL). The solution was extracted with dichloromethane (3×20 mL). The combined organic layers were evaporated under reduced pressure and the crude material was purified by Prep-HPLC with the following conditions: Column, X-bridge RP18, 5 μm, 19×150 mm; mobile phase: water (it contains 0.03% ammonia) and $CH_3CN$ with a gradient of 45% to 60% $CH_3CN$ in 5 min; flow rate: 20 mL/min; detector UV wavelength: 254 nm. This provided racemic 1-(5-(4-(difluoromethoxy)phenylsulfonyl)-4,5-dihydropyrrolo[3,4-c]pyrrol-2(1H,3H,4H)-yl)-3-hydroxy-2-(pyridin-2-yl)propan-1-one (76 mg, 89%) as a white solid. The enantiomers were separated by Chiral-Prep-HPLC (SHIMADZU LC-20AD) with the following conditions: Column, DAICEL chiral PAK OD-H, 20×250 mm, 5 μm; mobile phase: Phase A: ethanol, Phase B: methanol (containing 0.1% DEA) with isocratic elution of 60% ethanol; flow rate: 15 mL/min; detector wavelength: 220 nm. Absolute stereochemistry was not determined (*). This provided:

Example 41: (S or R)-1-(5-(4-(Difluoromethoxy)phenylsulfonyl)-4,5-dihydropyrrolo[3,4-c]pyrrol-2(1H,3H,4H)-yl)-3-hydroxy-2-(pyridin-2-yl)propan-1-one Isolated as a yellow solid (11.3 mg, 15%). $^1$H NMR (300 MHz, DMSO-$d_6$): δ ppm 8.45-8.47 (m, 1H), 7.90-7.87 (m, 2H), 7.70-7.75 (m, 1H), 7.37 (t, J=73.2 Hz, 1H), 7.23-7.37 (m, 4H), 4.70-4.85 (m, 1H), 4.37-4.42 (m, 1H), 4.03-4.06 (m, 9H), 3.70-3.72 (m, 1H). LCMS: m/z=466 [M+H]$^+$.

Example 42: (R or S)-1-(5-(4-(Difluoromethoxy)phenylsulfonyl)-4,5-dihydropyrrolo[3,4-c]pyrrol-2(1H,3H,4H)-yl)-3-hydroxy-2-(pyridin-2-yl)propan-1-one Isolated as a yellow solid (14.2 mg, 19%). $^1$H NMR (300 MHz, DMSO-$d_6$): δ ppm 8.45-8.47 (m, 1H), 7.90-7.87 (m, 2H), 7.70-7.75 (m, 1H), 7.31 (t, J=73.2 Hz, 1H), 7.23-7.31 (m, 4H), 4.70-4.85 (m, 1H), 4.38-4.42 (m, 1H), 4.03-4.06 (m, 9H), 3.69-3.72 (m, 1H). LCMS: m/z=466 [M+H]$^+$.

Example 43: (5-(Benzo[d]thiazol-6-ylsulfonyl)-3,4,5,6-tetrahydropyrrolo[3,4-c]pyrrol-2(1H)-yl)(2,3-dihydrobenzofuran-3-yl)methanone

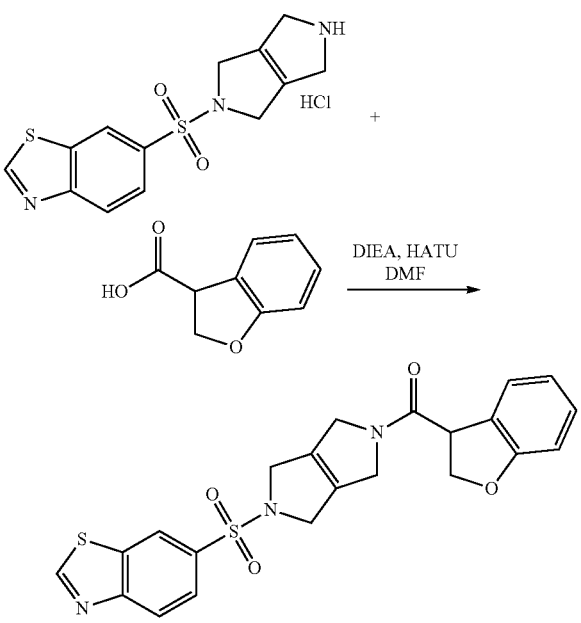

Example 43

To an 8-mL vial, purged and maintained with an inert atmosphere of nitrogen, was added 6-((3,4,5,6-tetrahydropyrrolo[3,4-c]pyrrol-2(1H)-yl)sulfonyl)benzo[d]thiazole hydrochloride (50 mg, 0.15 mmol, 1.00 equiv), 2,3-dihydro-1-benzofuran-3-carboxylic acid (29 mg, 0.18 mmol, 1.20 equiv), DIEA (68 mg, 0.53 mmol, 3.50 equiv), HATU (65 mg, 0.17 mmol, 1.20 equiv), and DMF (1.00 mL). The solution was stirred for 16 h at RT. Water (2 mL) was added dropwise. The solids were collected by filtration. The filter cake was washed with H$_2$O (0.5 mL) and MeOH (1.0 mL), and the filtrate was collected and dried under vacuum to provide (5-(benzo[d]thiazol-6-ylsulfonyl)-3,4,5,6-tetrahydropyrrolo[3,4-c]pyrrol-2(1H)-yl)(2,3-dihydrobenzofuran-3-yl)methanone (30 mg, 45%) as an off-white solid. $^1$H NMR (300 MHz, DMSO-d$_6$): δ ppm 9.66 (s, 1H), 8.84 (d, J=1.5 Hz, 1H), 8.32 (d, J=8.4 Hz, 1H), 7.99 (dd, J1=8.7 Hz, J2=1.8 Hz, 1H), 7.14-7.09 (m, 2H), 6.80-6.75 (m, 2H), 4.67-4.38 (m, 5H), 4.18 (s, 4H), 4.01 (m, 2H). LCMS: m/z=454 [M+H]$^+$.

Examples 44 and 45: (R or S)-(5-(pyridin-2-ylsulfonyl)-3,4,5,6-tetrahydropyrrolo[3,4-c]pyrrol-2(1H)-yl)(tetrahydro-2H-pyran-3-yl)methanone (Example 44) and (S or R)-(5-(pyridin-2-ylsulfonyl)-3,4,5,6-tetrahydropyrrolo[3,4-c]pyrrol-2(1H)-yl)(tetrahydro-2H-pyran-3-yl)methanone (Example 45)

To a 50-mL round-bottom flask was added 2-(pyridin-2-ylsulfonyl)-1,2,3,4,5,6-hexahydropyrrolo[3,4-c]pyrrole (100 mg, 0.40 mmol, 1.00 equiv), oxane-3-carboxylic acid (52 mg, 0.40 mmol, 1.00 equiv), HATU (302 mg, 0.79 mmol, 1.97 equiv), DCM (10 mL), and DIEA (154 mg, 1.19 mmol, 2.99 equiv). The solution was stirred overnight at 20° C. The mixture was diluted with 20 mL of DCM, washed with 2×20 mL of water, dried over anhydrous sodium sulfate, filtered, and concentrated under vacuum. The residue was purified by silica gel column chromatography, eluting with ethyl acetate/petroleum ether (10/1). The enantiomers were separated by prep-Chiral HPLC with the following conditions: column, Daicel CHIRALPAK® IA 21.2×250 mm, 5 μm; mobile phase, A=Hexane, phase B=EtOH (hold 50.0% EtOH over 42 min); flow rate, 20 mL/min; Detector, UV 254 & 220 nm. Absolute stereochemistry was not determined (*). This provided:

Example 44. (R or S)-(5-(pyridin-2-ylsulfonyl)-3,4,5,6-tetrahydropyrrolo[3,4-c]pyrrol-2(1H)-yl)(tetrahydro-2H-pyran-3-yl)methanone (Stereochemical Configuration Assumed)

Isolated as a white solid (12.1 mg, 8%). Prep-Chiral HPLC Rt=24.472 min. $^1$H NMR (400 MHz, CDCl$_3$): δ 8.73-8.69 (m, 1H), 8.03-7.88 (m, 2H), 7.56-7.42 (m, 1H), 4.43-4.26 (m, 6H), 4.16 (d, J=3.6 Hz, 2H), 3.98-3.87 (m, 2H), 3.54 (t, J=12.0 Hz, 1H), 3.50-3.34 (m, 1H), 2.68-2.49 (m, 1H), 1.96-1.76 (m, 2H), 1.69-1.48 (m, 2H). LCMS: m/z=364.0 [M+H]$^+$.

Example 45. (S or R)-(5-(pyridin-2-ylsulfonyl)-3,4,5,6-tetrahydropyrrolo[3,4-c]pyrrol-2(1H)-yl)(tetrahydro-2H-pyran-3-yl)methanone (Stereochemical Configuration Assumed)

Isolated as a white solid (7.3 mg, 5%). Prep-Chiral HPLC Rt=33.498 min. $^1$H NMR (400 MHz, CDCl$_3$): δ 8.75-8.67 (m, 1H), 8.04-7.88 (m, 2H), 7.58-7.39 (m, 1H), 4.43-4.26 (m, 6H), 4.18-4.16 (m, 2H), 4.00-3.89 (m, 2H), 3.54 (t, J=12.0 Hz, 1H), 3.48-3.29 (m, 1H), 2.69-2.48 (m, 1H), 1.95-1.76 (m, 2H), 1.72-1.58 (m, 2H). LCMS: m/z=364.2 [M+H]$^+$.

Example 46: 3-Hydroxy-1-(5-((4-methyl-3,4-dihydro-2H-benzo[b][1,4]oxazin-6-yl)sulfonyl)-3,4,5,6-tetrahydropyrrolo[3,4-c]pyrrol-2(1H)-yl)-2-phenylpropan-1-one

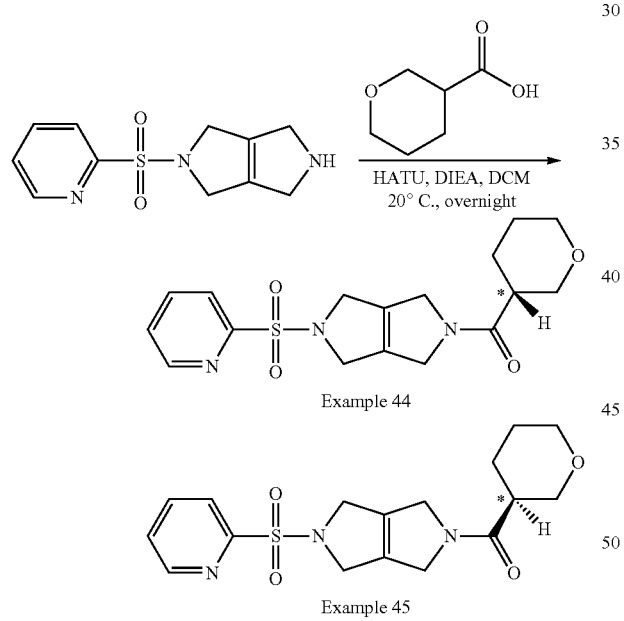

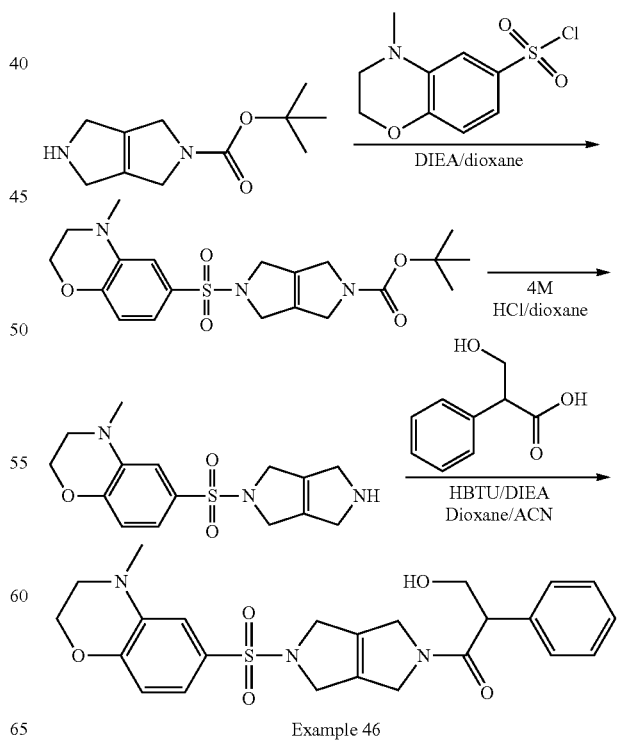

To a 1.5 mL vial was added a 0.2 M solution of tert-butyl 3,4,5,6-tetrahydropyrrolo[3,4-c]pyrrole-2(1H)-carboxylate hydrochloride (100 µL, 20 µmol) in dioxane and neat DIEA (10 µL, 57 µmol) to give a brown suspension. A 0.2 M solution of 4-methyl-3,4-dihydro-2H-benzo[b][1,4]oxazine-6-sulfonyl chloride (105 µL, 20 µmol) in dioxane was added. The reaction was heated at 50° C. with shaking for 2 hours. 4 M HCl in dioxane (50.0 µL, 0.200 mmol) was then added. The reaction was heated at 50° C. with shaking for an additional 2 hours. The volatiles were removed under reduced pressure. ACN (200 µL) was added to the vial. The vial was shaken for 15 minutes to resuspend the residue. Neat DIEA (25 µL, 0.143 mmol) and a 0.2 M solution of 3-hydroxy-2-phenylpropanoic acid (110 µL, 22 µmol) in dioxane was added to the vial, followed by a 0.2 M solution of HBTU (110 µL, 22 µmol) in ACN. The reaction was heated at 50° C. with shaking for an additional 2 hours. The volatiles were removed under reduced pressure. The residue was mixed with 1 N NaOH (0.5 mL) and extracted with 3:1 EtOAc/ACN (2×0.5 mL). The volatiles were removed under reduced pressure. The compound was purified using mass-triggered HPLC to give 3-hydroxy-1-(5-((4-methyl-3,4-dihydro-2H-benzo[b][1,4]oxazin-6-yl)sulfonyl)-3,4,5,6-tetrahydropyrrolo[3,4-c]pyrrol-2(1H)-yl)-2-phenylpropan-1-one. LCMS: m/z=470.2 [M+H]$^+$.

The Examples in Table 5 below were prepared according to the procedure outlined above for Example 46, using the appropriate synthetic precursors.

TABLE 5

| Example | Name | Structure | LCMS |
|---|---|---|---|
| 40 | 3-hydroxy-1-(5-((4-methoxyphenyl)sulfonyl)-3,4,5,6-tetrahydropyrrolo[3,4-c]pyrrol-2(1H)-yl)propan-1-one | 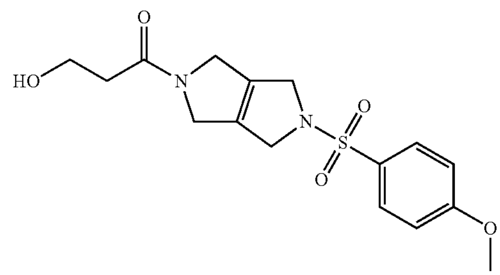 [SMILES: COc1ccc(S(=O)(=O)N2CC3=C(CN(C(=O)CCO)C3)C2)cc1] | |
| 47 | 4-Methyl-6-{[5-(oxolane-3-carbonyl)-1H,2H,3H,4H,5H,6H-pyrrolo[3,4-c]pyrrol-2-yl]sulfonyl}-3,4-dihydro-2H-1,4-benzoxazine | 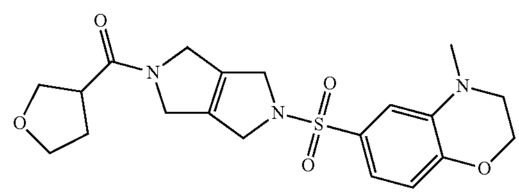 [SMILES: CN1CCOc2ccc(S(=O)(=O)N3CC4=C(CN(C(=O)C5CCOC5)C4)C3)cc21] | m/z: 420.2 |
| 48 | 1-[5-(1,3-Benzothiazole-6-sulfonyl)-1H,2H,3H,4H,5H,6H-pyrrolo[3,4-c]pyrrol-2-yl]-3-hydroxy-2-phenylpropan-1-one | 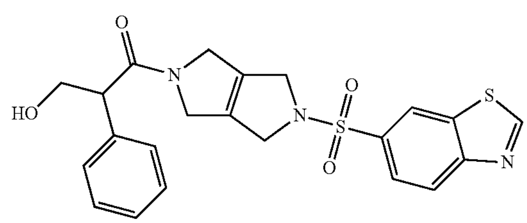 [SMILES: O=C(C(CO)c1ccccc1)N1CC2=C(C1)CN(S(=O)(=O)c1ccc3ncsc3c1)C2] | m/z: 456.1 |
| 49 | 1-{5-[4-(Difluoromethoxy)benzenesulfonyl]-1H,2H,3H,4H,5H,6H-pyrrolo[3,4-c]pyrrol-2-yl}-3-hydroxy-2-phenylpropan-1-one | 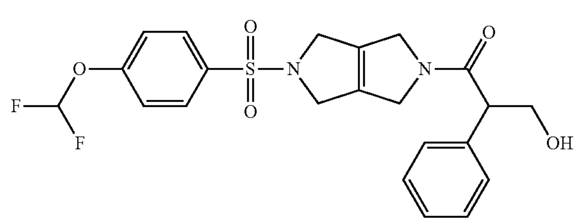 [SMILES: O=C(C(CO)c1ccccc1)N1CC2=C(C1)CN(S(=O)(=O)c1ccc(OC(F)F)cc1)C2] | m/z: 465.1 |
| 50 | (2S)-3-hydroxy-2-phenyl-1-[5-(pyridine-3-sulfonyl)-1H,2H,3H,4H,5H,6H-pyrrolo[3,4-c]pyrrol-2-yl]propan-1-one | 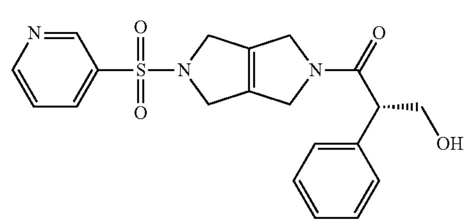 [SMILES: O=C([C@H](CO)c1ccccc1)N1CC2=C(C1)CN(S(=O)(=O)c1cccnc1)C2] | m/z: 400.3 |

TABLE 5-continued

| Example | Name | Structure | LCMS |
|---|---|---|---|
| 51 | (2S)-3-hydroxy-2-phenyl-1-[5-(pyridine-2-sulfonyl)-1H,2H,3H,4H,5H,6H-pyrrolo[3,4-c]pyrrol-2-yl]propan-1-one | 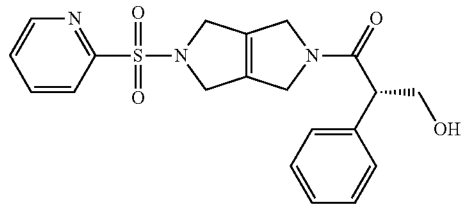 [SMILES: O=C([C@H](CO)c1ccccc1)N1CC2=C(C1)CN(S(=O)(=O)c1ccccn1)C2] | m/z: 400.3 |
| 52 | (2S)-3-hydroxy-2-phenyl-1-(5-{[6-(trifluoromethyl)pyridin-3-yl]sulfonyl}-1H,2H,3H,4H,5H,6H-pyrrolo[3,4-c]pyrrol-2-yl)propan-1-one | 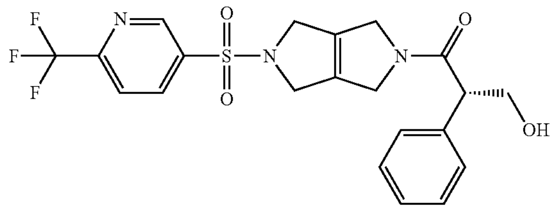 [SMILES: O=C([C@H](CO)c1ccccc1)N1CC2=C(C1)CN(S(=O)(=O)c1ccc(C(F)(F)F)nc1)C2] | m/z: 468.2 |
| 53 | 3-Methoxy-1-{5-[(4-methyl-3,4-dihydro-2H-1,4-benzoxazin-6-yl)sulfonyl]-1H,2H,3H,4H,5H,6H-pyrrolo[3,4-c]pyrrol-2-yl}propan-1-one | 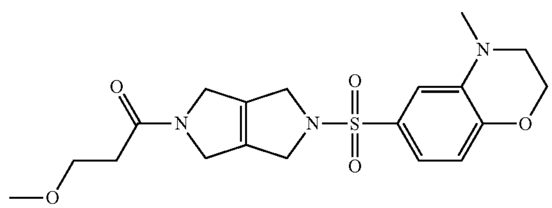 [SMILES: COCCC(=O)N1CC2=C(C1)CN(S(=O)(=O)c1ccc3c(c1)N(C)CCO3)C2] | m/z: 408.2 |
| 54 | 1-{5-[4-(Difluoromethoxy)benzenesulfonyl]-1H,2H,3H,4H,5H,6H-pyrrolo[3,4-c]pyrrol-2-yl}-3-hydroxypropan-1-one | 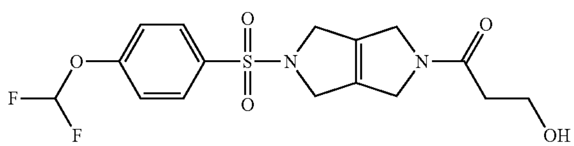 [SMILES: O=C(CCO)N1CC2=C(C1)CN(S(=O)(=O)c1ccc(OC(F)F)cc1)C2] | m/z: 391.1 |
| 55 | (5-(benzofuran-5-ylsulfonyl)-3,4,5,6-pyrrolo[3,4-c]pyrrol-2(1H)-yl)(tetrahydrofuran-3-yl)methanone | 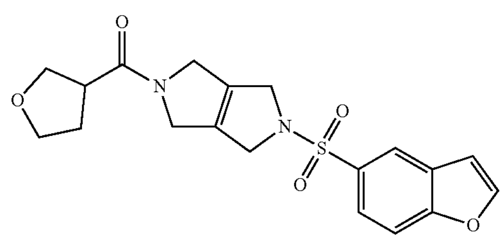 [SMILES: O=C(C1CCOC1)N1CC2=C(C1)CN(S(=O)(=O)c1ccc3occc3c1)C2] | |
| 56[a] | (5-(benzo[d]thiazol-6-ylsulfonyl)-3,4,5,6-tetrahydropyrrolo[3,4-c]pyrrol-2(1H)-yl)(morpholin-3-yl)methanone | 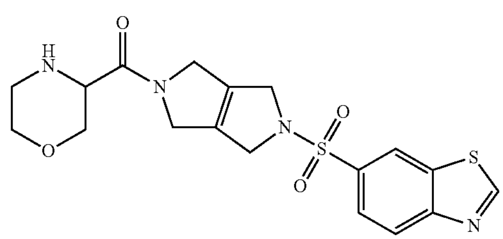 [SMILES: O=C(C1COCCN1)N1CC2=C(C1)CN(S(=O)(=O)c1ccc3ncsc3c1)C2] | |
| 57 | 1-(5-((2,3-dihydrobenzo[b][1,4]dioxin-6-yl)sulfonyl)-3,4,5,6-tetrahydropyrrolo[3,4-c]pyrrol-2(1H)-yl)-3-methoxypropan-1-one | 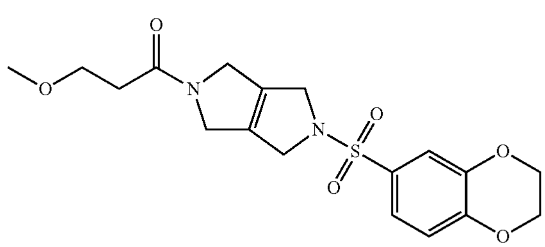 [SMILES: COCCC(=O)N1CC2=C(C1)CN(S(=O)(=O)c1ccc3c(c1)OCCO3)C2] | |

TABLE 5-continued

| Example | Name | Structure | LCMS |
|---|---|---|---|
| 58 | 1-(5-(benzofuran-5-ylsulfonyl)-3,4,5,6-tetrahydropyrrolo[3,4-c]pyrrol-2(1H)-yl)-3-methoxypropan-1-one | 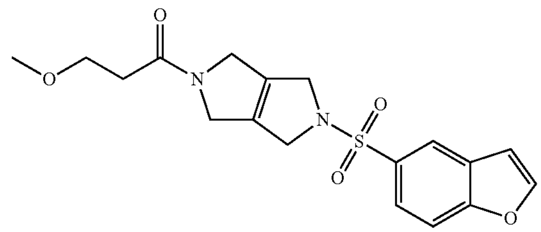 [SMILES: COCCC(=O)N1CC2=C(C1)CN(S(=O)(=O)c1ccc3occc3c1)C2] | |

[a]The morpholine moiety was protected with a Boc group on nitrogen throughout the synthesis of this molecule. The final step of the synthesis was deprotection of the Boc group (see step 2 in Example 46).

Example 47: PKR (wt/without FBP), PKR(G332S/with FBP), PKR(R510Q/without FBP)

Luminescence Assay Protocol

In some embodiments, a "PKR Activating Compound" refers to a compound having one or more characteristics when tested according to the following Luminescence Assay Protocol of Example 47 performed with wild type (wt) PKR and/or any one or more of G332S mutant form of PKR or R510Q mutant form of PKR: (1) an $AC_{50}$ value of less than 40 μM (e.g., compounds with $AC_{50}$ values of "+", "++", or "+++" in Table 6); (2) a maximum % Fold (MAX % Fold) value of greater than 75%; and/or (3) a % Fold value at 1.54 μM compound concentration (% Fold@ 1.54 μM) of at least 75%. In some embodiments, a PKR Activating Compound can have: (1) an $AC_{50}$ value of less than 0.1 μM (e.g., compounds with $AC_{50}$ values of "+++" in Table 6), 0.1-1.0 μM (e.g., compounds with $AC_{50}$ values of "++" in Table 6), or 1.01-40 μM (e.g., compounds with $AC_{50}$ values of "+" in Table 6); (2) a MAX % Fold of 75%-250%, 250-500%, or 75%-500%; and/or (3) a % Fold@1.54 μM of 75%-250%, 250-500%, or 75%-500%. In some embodiments, a PKR Activating Compound has (1) an $AC_{50}$ value of less than 1.0 μM; (2) a MAX % Fold of 75%-500%; and/or (3) a % Fold@ 1.54 μM of 75%-500%, obtained in the Luminescence Assay Protocol with any one or more of wild type PKR (wt), G332S mutant form of PKR, or R510Q mutant form of PKR. In some embodiments, the PKR Activating Compound has (1) an $AC_{50}$ value of less than 1.0 μM; (2) a MAX % Fold of 75%-500%; and/or (3) a % Fold@ 1.54 μM of 75%-500%, obtained in the Luminescence Assay Protocol with wild type PKR (wt). In some embodiments, the PKR Activating Compound has (1) an $AC_{50}$ value of less than 1.0 μM; (2) a MAX % Fold of 75%-500%; and/or (3) a % Fold@ 1.54 μM of 75%-500%, obtained in the Luminescence Assay Protocol with any one or both of G332S mutant form of PKR or R510Q mutant form of PKR.

The phosphorylation of Adenosine-5'-diphosphate (ADP) by various mutants of PKR was determined by the Kinase Glo Plus Assay (Promega) in the presence or absence of FBP [D-Fructose-1,6-diphosphate; BOC Sciences, CAS: 81028-91-3] as follows. Unless otherwise indicated, all reagents were purchased from Sigma-Aldrich. All reagents were prepared in buffer containing 50 mM Tris-HCl, 100 mM KCl, 5 mM $MgCl_2$, and 0.01% Triton X100, 0.03% BSA, and 1 mM DTT. Enzyme and PEP [Phospho(enol) pyruvic acid] were added at 2× to all wells of an assay-ready plate containing serial dilutions of test compounds or DMSO vehicle. Final enzyme concentrations for PKR(wt), PKR (R510Q), and PKR(G332S) were 0.8 nM, 0.8 nM, and 10 nM respectively. Final PEP concentration was 100 μM. The Enzyme/PEP mixture was incubated with compounds for 30 minutes at RT before the assay was initiated with the addition of 2×ADP [Adenosine-5'-diphosphate] and Kinase-GloPlus. Final concentration of ADP was 100 μM. Final concentration of KinaseGloPlus was 12.5%. For assays containing FBP, that reagent is added at 30 μM upon reaction initiation. Reactions were allowed to progress for 45 minutes at RT until luminescence was recorded by the BMG PHERAstar FS Multilabel Reader. All compounds were tested in triplicate at concentrations ranging from 42.5 μM to 2.2 nM in 0.83% DMSO.

Luminescence values were converted to % Fold increase by normalizing to the average of the DMSO control and multiplying by 100. Max, min, slope and $AC_{50}$ were determined by the standard four parameter fit algorithm of ActivityBase XE Runner. Compounds were evaluated with three parameters—$AC_{50}$, MAX % Fold, and % Fold@ 1.54 μM (FIG. 1). The $AC_{50}$ value for a compound is the concentration (μM) corresponding to the midway between the maximum and minimum values of the four parameter logistic curve fit (i.e., at which the % fold increase along the four parameter logistic curve fit is halfway between MAX % Fold and MIN % Fold (% Fold Midpoint)), MAX % Fold is the highest fold increase observed at any concentration of compound, and % Fold@ 1.54 μM is the fold increase at a compound concentration of 1.54 μM. The parameter % Fold@ 1.54 μM was selected to capture elements of both the $AC_{50}$ and MAX % Fold and to provide a ranking based on both potency and effect. The compound concentration of 1.54 μM was chosen as one that can optimally differentiate the set of compounds based on the range of activities observed.

As set forth in Tables 6 and 7 below, $AC_{50}$ values (columns A, D, G) are defined as follows: ≤0.1 μM (+++); >0.1 μM and ≤1.0 μM (++); >1.0 μM and ≤40 μM (+); >40 μM (0). Max % FOLD values (columns B, E, H) are defined as follows: ≤75% (+); >75% and ≤250% (++); >250% and ≤500% (+++). % Fold@ 1.54 μM values (columns C, F, I) are defined as follows: ≤75% (+); >75% and ≤250% (++); >250% and ≤500% (+++).

TABLE 6

Biological Data

| | PKRG332S Conditions[1] | | | PKRR510Q Conditions[1] | | | WT Conditions[1] | | |
|---|---|---|---|---|---|---|---|---|---|
| Example | A | B | C | D | E | F | G | H | I |
| 1 | ++ | ++ | ++ | +++ | +++ | +++ | +++ | ++ | ++ |
| 2 | + | ++ | ++ | + | +++ | ++ | + | ++ | ++ |

TABLE 6-continued

Biological Data

| Example | PKRG332S Conditions[1] | | | PKRR510Q Conditions[1] | | | WT Conditions[1] | | |
|---|---|---|---|---|---|---|---|---|---|
| | A | B | C | D | E | F | G | H | I |
| 3[a] | + | ++ | ++ | ++ | +++ | ++ | +++ | ++ | ++ |
| 4[a] | | | | + | ++ | ++ | + | ++ | ++ |
| 5[b] | + | ++ | ++ | + | +++ | ++ | ++ | ++ | ++ |
| 6[b] | 0 | | | 0 | | | + | ++ | ++ |
| 7 | +++ | | | ++ | | | ++ | ++ | ++ |
| 8 | | | | | | | +++ | +++ | +++ |
| 9 | | | | | | | +++ | ++ | ++ |
| 10 | | | | | | | +++ | +++ | ++ |
| 11 | | | | | | | ++ | +++ | ++ |
| 12 | | | | | | | ++ | +++ | ++ |
| 13 | | | | | | | ++ | +++ | ++ |
| 14 | ++ | ++ | ++ | + | +++ | ++ | ++ | +++ | +++ |
| 15 | 0 | ++ | ++ | + | +++ | ++ | ++ | ++ | ++ |
| 16 | ++ | ++ | ++ | + | +++ | ++ | ++ | +++ | ++ |
| 17 | | | | | | | ++ | ++ | ++ |
| 18 | 0 | ++ | ++ | +++ | ++ | ++ | | | |
| 19 | 0 | ++ | ++ | ++ | +++ | ++ | ++ | ++ | ++ |
| 20 | ++ | ++ | ++ | + | +++ | ++ | ++ | +++ | ++ |
| 21 | | | | | | | + | ++ | ++ |
| 22 | | | | | | | ++ | +++ | +++ |
| 23 | | | | | | | ++ | +++ | +++ |
| 24 | | | | | | | ++ | +++ | ++ |
| 25 | | | | | | | ++ | +++ | ++ |
| 26 | +++ | ++ | ++ | +++ | +++ | +++ | +++ | +++ | +++ |
| 27 | +++ | ++ | ++ | ++ | +++ | +++ | +++ | +++ | +++ |
| 28 | +++ | ++ | ++ | + | +++ | ++ | ++ | +++ | ++ |
| 29 | +++ | ++ | ++ | +++ | +++ | +++ | +++ | +++ | +++ |
| 30 | ++ | ++ | ++ | ++ | +++ | +++ | ++ | +++ | +++ |
| 31 | +++ | ++ | ++ | +++ | +++ | +++ | +++ | +++ | +++ |
| 32 | 0 | ++ | ++ | +++ | ++ | ++ | +++ | ++ | ++ |
| 33[c] | 0 | ++ | ++ | + | +++ | ++ | + | ++ | ++ |
| 34[c] | ++ | ++ | ++ | +++ | +++ | +++ | +++ | ++ | ++ |
| 35 | +++ | ++ | ++ | +++ | +++ | +++ | +++ | +++ | +++ |
| 36 | 0 | ++ | ++ | + | ++ | ++ | ++ | ++ | ++ |
| 37 | 0 | ++ | ++ | +++ | +++ | +++ | ++ | ++ | ++ |
| 38 | | | | | | | | | |
| 39 | +++ | ++ | ++ | ++ | +++ | +++ | ++ | +++ | +++ |
| 40 | | | | + | +++ | ++ | | | |
| 41[d] | +++ | ++ | ++ | +++ | +++ | +++ | +++ | +++ | +++ |
| 42[d] | +++ | ++ | ++ | +++ | +++ | +++ | +++ | +++ | +++ |
| 43 | ++ | ++ | ++ | + | +++ | +++ | ++ | +++ | +++ |
| 44[e] | + | ++ | ++ | 0 | ++ | ++ | + | ++ | ++ |
| 45[e] | ++ | ++ | ++ | + | +++ | ++ | ++ | +++ | ++ |
| 46 | 0 | ++ | ++ | 0 | ++ | ++ | +++ | ++ | ++ |
| 47 | 0 | ++ | ++ | + | +++ | ++ | ++ | ++ | ++ |
| 48 | +++ | ++ | ++ | +++ | +++ | +++ | +++ | +++ | +++ |
| 49 | +++ | ++ | ++ | +++ | +++ | +++ | +++ | +++ | +++ |
| 50 | ++ | ++ | ++ | ++ | +++ | +++ | ++ | +++ | +++ |
| 51 | ++ | ++ | ++ | +++ | +++ | +++ | +++ | +++ | +++ |
| 52 | ++ | ++ | ++ | + | +++ | ++ | ++ | ++ | ++ |
| 53 | 0 | ++ | ++ | + | ++ | ++ | ++ | ++ | ++ |
| 54 | | | | + | +++ | ++ | + | +++ | ++ |
| 55 | | | | | | | | | |
| 56 | 0 | ++ | ++ | + | ++ | ++ | | | |
| 57 | +++ | ++ | ++ | ++ | ++ | ++ | | | |
| 58 | +++ | ++ | ++ | ++ | +++ | ++ | | | |

[a] Compounds 3 and 4 are enantiomers, but absolute stereochemistry is undetermined;
[b] Compounds 5 and 6 are enantiomers, but absolute stereochemistry is undetermined;
[c] Compounds 33 and 34 are enantiomers, but absolute stereochemistry is undetermined;
[d] Compounds 41 and 42 are enantiomers, but absolute stereochemistry is undetermined;
[e] Compounds 44 and 45 are enantiomers, but absolute stereochemistry is undetermined.
[1] A - AC50 LUM KGP FBP $AC_{50}$ μM gmean;
B - AC50 LUM KGP FBP MAX % FOLD mean;
C - AC50 LUM KGP FBP % Fold @ 1.54 μM mean
D - AC50 LUM KGP woFBP $AC_{50}$ μM gmean;
E - AC50 LUM KGP woFBP MAX % FOLD mean;
F - AC50 LUM KGP woFBP % Fold @ 1.54 μM mean
G - AC50 LUM KGP woFBP $AC_{50}$ μM gmean;
H - AC50 LUM KGP woFBP MAX % FOLD mean;
I - AC50 LUM KGP woFBP % Fold @ 1.54 μM mean.

TABLE 7

Biological Data of Additional Compounds.

| Example | Structure | PKRG332S Conditions[1] A | PKRR510Q Conditions[1] D |
|---|---|---|---|
| 59 | [structure: bis-acyl octahydropyrrolo[3,4-c]pyrrole with two phenyl-CH(CH2OH)-C(O)- groups] | 0 | 0 |
| 60 | [structure: 2,3-dihydro-1,4-benzodioxin-6-ylsulfonyl-octahydropyrrolo[3,4-c]pyrrole with 3-phenyl-1H-pyrazol-4-carbonyl] | 0 | 0 |

[1] A-AC50 LUM KGP FBP $AC_{50}$ μM gmean; D-AC50 LUM KGP woFBP $AC_{50}$ μM gmean.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound of formula

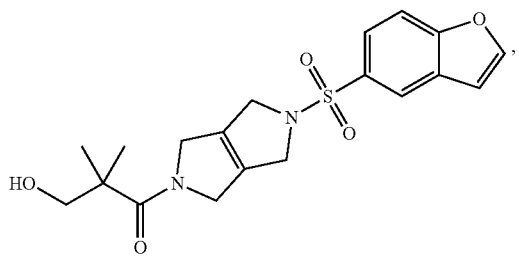 [SMILES: CC(C)(CO)C(=O)N1CC2=C(C1)CN(S(=O)(=O)c1ccc3occc3c1)C2]

or a pharmaceutically acceptable salt thereof.

2. A compound of formula

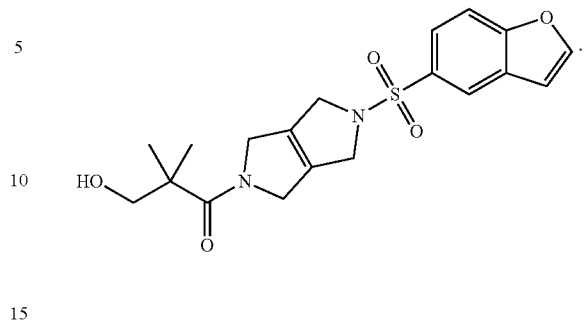

3. A pharmaceutical composition comprising the compound of claim 1, or a pharmaceutically acceptable salt thereof, and a pharmaceutically acceptable carrier.

4. A pharmaceutical composition comprising the compound of claim 2, and a pharmaceutically acceptable carrier.

* * * * *